(12) United States Patent
Florjancic et al.

(10) Patent No.: US 8,546,583 B2
(45) Date of Patent: *Oct. 1, 2013

(54) COMPOUNDS AS CANNABINOID RECEPTOR LIGANDS AND USES THEREOF

(75) Inventors: Alan S. Florjancic, Kenosha, WI (US); Michael J. Dart, Highland Park, IL (US); Keith B. Ryther, Round Lake Park, IL (US); Arturo Perez-Medrano, Grayslake, IL (US); William A. Carroll, Evanston, IL (US); Meena V. Patel, Green Oaks, IL (US); Karin Rosemarie Tietje, Mundelein, IL (US); Tongmei Li, Lake Bluff, IL (US); Teodozyj Kolasa, Lake Villa, IL (US); Megan E. Gallagher, Chicago, IL (US); Sridhar Peddi, Grayslake, IL (US); Jennifer M. Frost, Grayslake, IL (US); Derek W. Nelson, Highland Park, IL (US)

(73) Assignee: AbbVie Inc., North Chicago, IL (US)

( * ) Notice: Subject to any disclaimer, the term of this patent is extended or adjusted under 35 U.S.C. 154(b) by 500 days.

This patent is subject to a terminal disclaimer.

(21) Appl. No.: 11/755,434

(22) Filed: May 30, 2007

(65) Prior Publication Data

US 2008/0058335 A1   Mar. 6, 2008

Related U.S. Application Data

(60) Provisional application No. 60/809,712, filed on May 31, 2006.

(51) Int. Cl.
 *A61K 31/426* (2006.01)
 *A61K 31/427* (2006.01)
 *C07D 417/06* (2006.01)
 *C07D 417/14* (2006.01)
 *C07D 277/44* (2006.01)

(52) U.S. Cl.
 USPC ............. 548/195; 514/227.5; 514/239.5; 514/255.04; 514/326; 514/342; 514/371; 546/270.7; 546/169; 546/209; 544/58.7; 544/60; 544/133; 544/369

(58) Field of Classification Search
 USPC ........................................... 548/195
 See application file for complete search history.

(56) References Cited

U.S. PATENT DOCUMENTS

| | | | |
|---|---|---|---|
| 5,654,322 A | 8/1997 | Hirata et al. | |
| 6,559,186 B1 | 5/2003 | Campbell et al. | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 7,560,456 B2 | 7/2009 | Araki et al. | |
| 7,674,912 B2 | 3/2010 | Sams et al. | |
| 7,683,084 B2 | 3/2010 | Faghih et al. | |
| 7,872,006 B2 | 1/2011 | Moritani et al. | |
| 7,872,033 B2 | 1/2011 | Carroll et al. | |
| 7,875,639 B2 | 1/2011 | Florjancic et al. | |
| 7,875,640 B2 | 1/2011 | Kolasa et al. | |
| 2008/0242654 A1* | 10/2008 | Kolasa et al. | 514/210.2 |
| 2008/0287510 A1 | 11/2008 | Carroll et al. | |
| 2008/0312435 A1* | 12/2008 | Saito et al. | 544/133 |
| 2009/0082471 A1 | 3/2009 | Czarnik | |

(Continued)

FOREIGN PATENT DOCUMENTS

| | | |
|---|---|---|
| DE | 3533331 A1 | 3/1987 |
| EP | 0412404 | 1/1996 |

(Continued)

OTHER PUBLICATIONS

Golub et al., Science, vol. 286, Oct. 15, 1999, pp. 531-537.*

(Continued)

*Primary Examiner* — Laura L. Stockton
(74) *Attorney, Agent, or Firm* — Lisa V. Mueller; Michael Best & Friedrich LLP

(57) ABSTRACT

The present invention relates to compounds of formula (I), or pharmaceutical salts, prodrugs, salts of prodrugs, or combinations thereof,

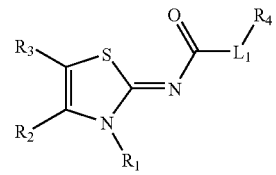

wherein $R_1$, $R_2$, $R_3$, $R_4$, and $L_1$ are defined in the specification, compositions comprising such compounds, and methods of treating conditions and disorders using such compounds and compositions. The present invention also relates to compounds of formula (II), or pharmaceutical salts, prodrugs, salts of prodrugs, or combinations thereof,

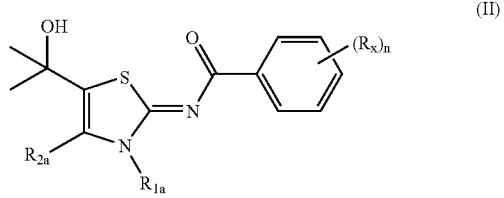

(II)

wherein $R_{1a}$, $R_{2a}$ and $(R_x)n$ are as defined in the specification, compositions comprising such compounds, and methods of treating conditions and disorders using such compounds and compositions.

5 Claims, No Drawings

(56) References Cited

U.S. PATENT DOCUMENTS

| | | | |
|---|---|---|---|
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |
| 2010/0063022 | A1 | 3/2010 | Carroll et al. |
| 2010/0069348 | A1 | 3/2010 | Carroll et al. |
| 2010/0069349 | A1 | 3/2010 | Carroll et al. |
| 2010/0093814 | A1 | 4/2010 | Florjancic et al. |
| 2010/0216760 | A1 | 8/2010 | Frost |

FOREIGN PATENT DOCUMENTS

| | | |
|---|---|---|
| EP | 0568096 A | 7/2002 |
| EP | 1219612 A | 7/2002 |
| EP | 1820504 A1 | 8/2007 |
| FR | 2796643 A | 1/2001 |
| WO | WO9507271 A1 | 3/1995 |
| WO | WO9710223 A1 | 3/1997 |
| WO | 2005058887 A | 6/2005 |
| WO | WO2005099353 A2 | 10/2005 |
| WO | WO2006008754 A1 | 1/2006 |
| WO | 2006051704 A | 5/2006 |
| WO | WO2006100208 A1 | 9/2006 |
| WO | WO2007140385 A2 | 12/2007 |
| WO | WO2007140439 A2 | 12/2007 |
| WO | WO2007140439 A3 | 1/2008 |
| WO | WO2007140385 A3 | 2/2008 |
| WO | WO2008079687 A1 | 7/2008 |
| WO | WO2008144360 A1 | 11/2008 |
| WO | WO2009048936 A1 | 4/2009 |
| WO | WO2009067613 A1 | 5/2009 |
| WO | WO2009114566 A1 | 9/2009 |

OTHER PUBLICATIONS

Arevalo-Martin, A., et al., "Therapeutic Action of Cannabinoids in a Murine Model of Multiple Sclerosis", Journal of Neuroscience, vol. 23, No. 7, pp. 2511-2516, 2003.
Baker, T.J., et al., "Regiospecific Vinyl Phosphateβ-Keto Phosphonate Rearrangements Initiated by Halogen-Metal Exchange", Journal of Organic Chemistry, vol. 63, No. 8, pp. 2613-2618, 1998.
Benito, C., et al., "A Glial Endogenous Cannabinoid System is Upregulated in the Brains of Macaques with Simian Immunodeficiency Virus-Induced Encephalitis", Journal of Neuroscience, vol. 25, No. 10, pp. 2530-2536, 2005.
Benito, C., et al., "Cannabinoid CB2 Receptors and Fatty Acid Amide Hydrolase Are Selectively Overexpressed in Neuritic Plaque-Associated Glia in Alzheimer's Disease Brains", Journal of Neuroscience, vol. 23, No. 35, pp. 11136-11141, 2003.
Bouchard, J.-F., et al., "Contribution of endocannabinoids in the endothelial protection afforded by ischemic preconditioning in the isolated rat heart", Life Sciences, vol. 72, pp. 1859-1870, 2003.
Boyle, W. J., et al., "Osteoclast differentiation and activation", Nature, vol. 423, pp. 337-342, 2003.
Brennan, T.J., et al., "Characterization of a rat model of incisional pain", Pain, vol. 64, pp. 493-501, 1996.
Buckley, N.E., et al., "Immunomodulation by cannabinoids is absent in mice deficient for the cannabinoid CB receptor", European Journal of Pharmacology, vol. 396, pp. 141-149, 2000.
Carlisle, S. J., et al., "Differential expression of the CB cannabinoid receptor by 2 rodent macrophages and macrophage-like cells in relation to cell activation", International Immunopharmacology, vol. 2, p. 69, 2002.
Carrier, E. J., et al., "Endocannabinoids in Neuroimmunology and Stress", Current Drug Targets—CNS & Neurological Disorders, vol. 4, pp. 657-665, 2005.

Casanova, M. L., et al., "Inhibition of skin tumor growth and angiogenesis in vivo by activation of cannibinoid receptors", Journal of Clinical Investigation, vol. 111, pp. 43-50, 2003.
Chaplan, S.R., et al., "Quantitative assessment of tactile allodynia in the rat paw", Journal of Neuroscience Methods, vol. 53, p. 55-63, 1994.
Cichewicz, D. L., et al., "Synergistic interactions between cannabinoid and opioid analgesics", Life Sciences, vol. 74, pp. 1317-1324, 2004.
Clayton, N., et al., "CB1 and CB2 cannabinoid receptors are implicated in inflammatory pain", Pain, vol. 96, pp. 253-260, 2002.
Dixon, W.J., "Efficient analysis of experimental observations", Annual Review of Pharmacology and Toxicology, vol. 20, p. 441-462, 1980.
Filippo, C. D., et al., "Cannabinoid CB2 receptor activation reduces mouse myocardial ischemia-reperfusion injury: involvement of cytokine/chemokines and PMN", Journal of Leukocyte Biology, vol. 75, pp. 453-459, 2004.
Galiègue, et al., "Expression of central and peripheral cannabinoid receptors in human immune tissues and leukocyte subpopulations", European Journal of Biochemistry, vol. 232, pp. 54-61, 1995.
Golech, S. A., et al., "Human brain endothelium: coexpression and function of vannilloid and endocannabinoid receptors", Molecular Brain Research, vol. 132, pp. 87-92, 2004.
Grotenhermen, F., et al., "IACM $2^{nd}$ Conference on Cannabinoids in Medicine", Expert Opinion in Pharmacotherapy, vol. 4, No. 12, pp. 2367-2371, 2003.
Hanuš, L., et al., "HU-308: A specific agonist for $CB_2$, a peripheral cannabinoid receptor", Proceedings of the National Academy of Science, vol. 96, pp. 14228-14233, 1999.
Hargreaves, et al., "A new and sensitive method for measuring thermal nociception in cutaneous hyperalgesia", Pain, vol. 32, p. 77, 1988.
Hohmann, A. G., et al., "Selective Activation of Cannabinoid CB2 Receptors Suppresses Hyperalgesia Evoked by Intradermal Capsaicin", Journal of Pharmacology and Experimental Therapeutics, vol. 308, pp. 446-453, 2004.
Ibrahim, M. M., et al., "Activation of CB2 cannabinoid receptors by AM1241 inhibits experimental neuropathic pain: Pain inhibition by receptors not present I the CNS", Proceedings of the National Academy of Science, vol. 100, No. 18, pp. 10529-10533, 2003.
Idris, A.I., et al., "Regulation of bone mass, bone loss and osteoclast activity by cannabinoid receptors", Nature Medicine, vol. 11, No. 7, pp. 774-779, 2005.
Ihenetu, K., et al., "Inhibition of interleukin-8 release in the human colonic epithelial cell line HT-29 by cannabinoids", European Journal of Pharmacology, vol. 458, pp. 207-215, 2003.
Julien, B., et al., "Antifibrogenic Role of the Cannabinoid Receptor CB2 in the Liver", Gastroenterology, vol. 128, pp. 742-755, 2005.
Karsak, M., et al., "Cannabinoid receptor type 2 gene is associated with human osteoporosis", Human Molecular Genetics, vol. 14, No. 22, pp. 3389-3396, 2005.
Kim, S.H., et al., An experimental model for peripheral neuropathy produced by segmental spinal nerve litigation in the rat, vol. 50, p. 355-363, 1992.
Kreutzberg, G. W., "Microglia: a sensor for pathological events in the CNS", Trends in Neuroscience, vol. 19, pp. 312-318, 1996.
Lépicier, P., et al., "Endocannabinoids protect the rat isolated heart against ischaemia", British Journal of Pharmacology, vol. 139, pp. 805-815, 2003.
Lotersztajn, S., et al., "Hepatic Fibrosis: Molecular Mechanisms and Drug Targets", Annual Review of Pharmacology and Toxicology, vol. 45, pp. 605-628, 2005.
Malan, T. P., et al., "CB2 cannabinoid receptor-mediated peripheral antinociception", Pain, vol. 93, pp. 239-245, 2001.
Maresz, K., et al., "Modulation of the cannabinoid CB2 receptor in microglial cells in response to inflammatory stimuli", Journal of Neurochemistry, vol. 95, pp. 437-445, 2005.
Mathison, R., et al., "Effects of cannabinoid receptor-2 activation on accelerated gastrointestinal transit in lipopolysaccharide-treated rats", British Journal of Pharmacology, vol. 142, pp. 1247-1254, 2004.

Molina-Holgado, F., et al., "Endogenous Interleukin-1 Receptor Antagonist Mediates Anti-Inflammatory and Neuroprotective Actions of Cannabinoids in Neurons and Glia", Journal of Neuroscience, vol. 23, No. 16, pp. 6470-6474, 2003.
McKallip, R. J., et al., "Targeting CB2 cannabinoid receptors as a novel therapy to treat malignant lymphoblastic disease", Blood, vol. 15, No. 2, pp. 627-634, 2002.
Nackley, A. G., et al., "Selective activation of cannabinoid CB2 receptors suppresses spinal fos protein expression and pain behavior in a rat model of inflammation", Neuroscience, vol. 119, pp. 747-757, 2003.
Ni, X., et al., "Win 55212-2, a cannabinoid receptor agonist, attenuates leukocyte/endothelial interactions in an experimental autoimmune encephalomyelitis model", Multiple Scherlosis, vol. 10, pp. 158-164, 2004.
Núñez, E., et al., "Cannabinoid CB2 Receptors Are Expressed by Perivascular Microglial Cells in the Human Brain: An Immunohistochemical Study", Synapse, vol. 58, pp. 208-213, 2004.
Patel, J. J., et al., "Inhibition of guinea-pig and human sensory nerve activity and the cough reflex in guinea-pigs by cannabinoid (CB2) receptor activation", British Journal of Pharmacology, vol. 140, pp. 261-268, 2003.
Pertwee, R. G., "Cannabinoids and multiple sclerosis", Pharmacology & Therapeutics, vol. 95, pp. 165-174, 2002.
Quartilho, A., et al., "Inhibition of Inflammatory Hyperalgesia by Activation of Peripheral CB2 Cannabinoid Receptors", Anesthesiology, vol. 99, pp. 955-960, 2003.
Ralston, S. H., "Genetic determinants of susceptibility to osteoporosis", Current Opinion in Pharmacology, vol. 3, pp. 286-290, 2003.
Ramírez, B. G., et al., "Prevention of Alzheimer's Disease Pathology by Cannabinoids: Neuroprotection Mediated by Blockade of Microglial Activation", Journal of Neuroscience, vol. 25, No. 8, pp. 1904-1913, 2005.
Sánchez, C., et al., "Inhibition of Glioma Growth in Vivo by Selective Activation of the CB2 Cannabinoid Receptor1", Cancer Research, vol. 61, pp. 5784-5789, 2001.
Steffens, S., et al., "Low dose oral cannabinoid therapy reduces progression of atherosclerosis in mice", Nature, vol. 434, pp. 782-786, 2005.
Valenzano, K. J., et al., "Pharmacological and pharmacokinetic characterization of the cannabinoid receptor 2 agonist, GW405833, utilizing rodent models of acute and chronic pain, anxiety, ataxia and catalepsy", Neuropharmacology, vol. 48, pp. 658-672, 2005.
Warhurst, A. C., et al., "Interferon γ induces differential upregulation of α and β chemokine secretion in colonic epithelial cell lines", Gut, vol. 42, pp. 208-213, 1998.
Walter, L., et al., "Cannabinoids and neuroinflammation", Pharmacology, vol. 141, pp. 775-785, 2004.
Watkins, L. R., et al., "Glial activation: a driving force for pathological pain", Trends in Neuroscience, vol. 24, No. 8, p. 450, 2001.
Weyer, et al., "Blutzuckersenkende Chinolin-8-carboxamidoalkyl-benzolsulfonamidderivate", Arzneimittel-Forschung, vol. 24, p. 269, 1974.
Wright, K., et al., "Differential Expression of Cannabinoid Receptors in the Human Colon: Cannabinoids Promote Epithelial Wound Healing", Gastroenterology, vol. 129, pp. 437-453, 2005.
Yoshihara, S., et al., "Endogenous Cannabinoid Receptor Agonists Inhibit Neurogenic Inflammations in Guinea Pig Airways", Allergy and Immunology, vol. 138, pp. 80-87, 2005.
Yoshihara, S., et al., "Cannabinoid Receptor Agonists Inhibit Sensory Nerve Activation in Guinea Pig Airways", American Journal of Respiratory and Critical Care Medicine, vol. 170, pp. 941-946, 2004.
Yoshihara, S., et al., "The Cannabinoid Receptor Agonist WIN 55212-2 Inhibits Neurogenic Inflammations in Airway Tissues", Journal of Pharmacological Sciences, vol. 98, No. 1, pp. 77-82, 2005.
Zimmer, A., et al., "Increased mortality, hypoactivity, and hypoalgesia in cannabinoid CB1 receptor knockout mice", Proceedings of the National Academy of Science, vol. 96, pp. 5780-5785, 1999.
Ambartsumova, R.F. et al., "Effect of Various Factors on the Reaction of 2-Aminobenzothiazoles with Propylene Oxide", Chemistry of Heterocyclic Compounds, vol. 38, No. 8 (2002) pp. 994-999.

Werbel L.M. et al. "1-Alkyl-3-(3-alkyl-5-nitro-4-thiazolin-2-ylidene)-ureas and Related compounds as Schistosomicides", Journal of Medicinal Chemistry, vol. 15, No. 9 (1972) pp. 955-963.
International Search Report, European Patent Office (Nov. 27, 2008).
Gouldson et al, "Mutational analysis and molecular modeling of the antagonist SR144528 binding site on the human cannabinoid CB2 receptor; figures 4 and 5," European Journal of Pharmacology, vol. 401, pp. 17-25, 2000.
International Search Report for application No. PCT/US07/069921, Mailed on Nov. 27, 2007, 4 pages.
Opposition filed by "Asociacion de Industries Farmaceuticas Dominicanas Inc" for the Dominican Patent application Nr P2008-0060, received on Apr. 1, 2009, 8 pages.
Abreo, et al., "Novel 3-Pyridyl Ethers with Subnanomolar Affinity for Central Neuronal Nicotonic Acetylcholine Receptors," Journal of Medicinal Chemistry, 1996, vol. 39 (4), pp. 817-825.
Araki, et al., (2003): STN International HCAPLUS database, (Columbus, OH). Accession No. 2003-931334.
Arevalo-Martin, et al., "Therapeutic Action of Cannabinoids in a Murine Model of Multiple Sclerosis," Journal of Neuroscience, 2003, vol. 23 (7), pp. 2511-2516.
Bennett, et al., "A Peripheral Mononeuropathy in Rat that Produces Disorders of Pain Sensation like those Seen in Man," Pain, 1988, vol. 33 (1), pp. 87-107.
Berge, et al., "Pharmaceutical Salts," Journal of Pharmaceutical Sciences, 1977, vol. 66 (1), pp. 1-19.
Beylot, et al., "In Vivo Studies of Intrahepatic Metabolic Pathways," Diabetes Metabolism, 1997, vol. 23 (3), pp. 251-257.
Blagojevic, et al., "Role of heavy water in Boron Neutron Capture Therapy," Topics in Dosimetry & Treatment Planning for Neutron Capture Therapy, 1994, pp. 125-134.
Blake, et al., "Studies With Deuterated Drugs," Journal of Pharmaceutical Sciences, 1975, vol. 64 (3), pp. 367-391.
Bozidar, et al., "Transformations of 1,2,4-Thiadiazolo/2,3-X/Azines," Heterocycles, 1987, vol. 26 (3), pp. 689-697.
Bozidar, et al., "Transformations of 1-(2-Chloropyridyl-3)-4-ethoxycarbonyland 1-(2-Chloropyridyl-3)-4-ethoxycarbonylmethyl Thiosemicarbazides. Attempts to Prepare Pyrido [3,2-e]-1,2,4-thiadiazine," Monatshefte Fur Chemie, 1988, vol. 119, pp. 333-339.
Brickner, et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
CAPLUS Record of U.S. Patent Application Publication No. 2008/0058335 by Westheim, et al., 2007.
CAPLUS Record of U.S. Patent Application Publication No. 2008/0242654 by Kolasa et al., 2008.
Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Czajka, et al., "Effect of Deuterium Oxide on the Reproductive Potential of Mice," Annals of the New York Academy of Sciences, 1960, vol. 84, pp. 770-779.
Czajka, et al., "Physiological Effects of Deuterium on Dogs," American Journal of Physiology, 1961, vol. 201 (2), pp. 357-362.
Dart, et al (2007): STN International HCAPLUS database, Columbus (OH), Accession No. 2007:1396538.
Final Office Action mailed Sep. 14, 2011 for U.S. Appl. No. 12/274,105, filed Nov. 19, 2008.
Final Office Action mailed Feb. 15, 2011 for U.S. Appl. No. 12/120,969, filed May 15, 2008.
Final Office Action mailed Nov. 16, 2011 for U.S. Appl. No. 12/554,445, filed Sep. 4, 2009.
Final Office Action mailed Nov. 16, 2011 for U.S. Appl. No. 12/560,897, filed Sep. 16, 2009.
Final Office Action mailed Oct. 19, 2011 for U.S. Appl. No. 12/560,893, filed Sep. 16, 2009.
Final Office Action mailed Dec. 28, 2011 for U.S. Appl. No. 12/639,173, filed Dec. 16, 2009.
Florjancic, et al., (2009): Caplus Entry for WO2009067613, Accession No. 2009:649814.

Florjancic, et al., (2010): STN International HCAPLUS database, Columbus (OH), Accession No. 2010:478868.

Foster, et al., "Deuterium Isotope Effects in the Metabolism of Drugs and Xenobiotics: Implications for Drug Design," Advances in Drug Research, 1985, vol. 14, pp. 2-36.

Giron, D., "Applications of Thermal Analysis and Coupled Techniques in Pharmaceutical Industry," Journal of Thermal Analysis and Calorimetry, 2002, vol. 68, pp. 335-357.

Giron, D., "Investigations of Polymorphism and Pseudo-Polymorphism in Pharmaceuticals by Combined Thermoanalytical Techniques," The Journal of Thermal Analysis and Calorimetry, 2001, vol. 64, pp. 37-60.

Golub, et al., "Molecular Classification of Cancer: Class Discovery and Class Prediction by Gene Expression Monitoring," Science, 1999, vol. 286 (5439), pp. 531-537.

Greene, et al., "Protection for the Amino group," Protective Groups in Organic Synthesis, 1999, Third Edition, pp. 494-653.

Ibrahim, et al., "CB2 Cannabinoid Receptor Activation Produces Antinociception by Stimulating Peripheral Release of Endogenous Opioids," Proceedings of the National Academy of Science, 2005, vol. 102 (8), pp. 3093-3098.

International Search Report for Application No. PCT/US08/063648, mailed on Aug. 13, 2008, 3 pages.

International Search Report for Application No. PCT/US2009/056179, mailed on Jun. 9, 2010, 4 pages.

International Search Report for Application No. PCT/US2009/057088, mailed on Oct. 5, 2010, 4 pages.

International Search Report for Application No. PCT/US2009/068173, mailed on Feb. 5, 2010, 3 pages.

Joshi, et al., "Comparison of Antinociceptive Actoins of Standard Analgesics in Attenuating Capsaicin and Nerve-Injury-Induced Mechanical Hypersensitivty," Neuroscience, 2006, vol. 143, pp. 587-596.

Kato, et al., "Synthesis of Deuterated Mosapride Citrate," Journal of Labelled Compounds and Radiopharmaceuticals, 1995, vol. 36 (10), pp. 927-932.

Kushner, et al., "Pharmacological uses and perspectives of heavy water and deuterated compounds," Canadian Journal of Physiology and Pharmacology, 1999, vol. 77 (2), pp. 79-88.

Li, et al., "An Improved Synthesis of Pyran-3,5-Dione: Application to the Synthesis of Abt-598, A Potassium Channel Opener, Via Hantzsch Reaction," Journal of Organic Chemistry, 2006, vol. 71 (4), pp. 1725-1727.

Lizondo, et al., "Linezolid: Oxazolidinone antibacterial," Drugs of the Future, 1996, vol. 21 (11), pp. 1116-1123.

Maligres, et al., "Stereocontrolled Preparation of a Nonpeptidal (-)-Spirobicyclic NK-1 Receptor Antagonist," Journal of Organic Chemistry, 2002, vol. 67 (4), pp. 1093-1101.

Mallesham, et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Manaka, et al., "2-Acylimino-3H-thiazoline Derivatives: A Novel Template for Platelet GPIIb/IIIa Receptor Antagonists," Bioorganic & Medicinal Chemistry Letters, 2001, vol. 11, pp. 1031-1035.

Non-Final Office Action mailed Jun. 1, 2011 for U.S. Appl. No. 12/554,445, filed Sep. 4, 2009.

Non-Final Office Action mailed Jun. 1, 2011 for U.S. Appl. No. 12/560,897, filed Sep. 16, 2009.

Non-Final Office Action mailed Sep. 7, 2010 for U.S. Appl. No. 12/120,969, filed May 15, 2008.

Non-Final Office Action mailed Jan. 12, 2010 for U.S. Appl. No. 12/120,969, filed May 15, 2008.

Non-Final Office Action mailed May 17, 2011 for U.S. Appl. No. 12/560,893, filed Sep. 16, 2009.

Non-Final Office Action mailed Aug. 23, 2011 for U.S. Appl. No. 12/639,173, filed Dec. 16, 2009.

Non-Final Office Action mailed Jan. 27, 2011 for US. Appl. No. 12/274,105, filed Nov. 19, 2008.

Ohta, et al., "N-Alkyidenearylcarboxamides as a new Potent and Selective CB2 Cannabinoid Receptor Agonist with an Analgesic Action," Bioorganic and Medicinal Chemistry Letters, 2007, vol. 17 (22), pp. 6299-6304.

Poste, et al., "Lipid Vesicles as Carriers for Introducing Biologically Active Materials into Cells," Methods in Cell Biology, 1976, vol. 14, pp. 33-71.

Radulescu, et al., "Actes Du Colloque Franco-Roumain De Chimie Appliquee, 3Rd, Bacau, Romania," 2004, pp. 117-120.

Radulescu, et al., "Synthesis and Characteristics of Compact Condensed Heterocyclic System 2-Aminothiazolo[5,4-c]Pyridine," Revista de Chimie, 2004, vol. 55 (11), pp. 889-893.

Radulescu, et al., "The Comparative Study on the Synthesis Methods of a Heterocyclic System 2-Aminothiazolo[4,5-13]Pyricline," Revista de Chimie, 2005, vol. 56 (6), pp. 659-662.

Rautio, et al, "Prodrugs: Design and Clinical Applications," Nature Reviews Drug Discovery, 2008, vol. 7 (3), pp. 255-270.

Rodriquez-Spong, et al., "General Principles of Pharmaceutical Solid Polymorphism: A Supramolecular Perspective," Advanced Drug Delivery Reviews, 2004, vol. 56 (3), pp. 241-274.

Ross, et al., "Antianaphylactic agents. 1. 2-(Acylamino)oxazoles," Journal of Medicinal Chemistry, 1979, vol. 22(4), pp. 412-417.

Shilpi, et al., "The Synthesis and Antimicrobial Screening of Some Novel Aza-Imidoxy Compounds as Potential Chemotherapeutic Agents," Phosphorus Sulfur and Silicon, 2006, vol. 181 (7), pp. 1665-1673.

Smith, D., "Do Prodrugs Deliver?" Current Opinion in Drug Discovery and Development, 2007, vol. 10 (5), 550-559.

Souillac, et al, "Characterization of Delivery Systems, Differential Scanning Calorimetry," Encyclopedia of Controlled Drug Delivery, 1999, pp. 217-218.

Testa, B., "Prodrugs: Bridging Pharmacodynamic/Pharmacokinetic Gaps," Current Opinion in Chemical Biology, 2009, vol. 13 (3), pp. 338-344.

Thomson, J., "Physiological Effects of D20 in Mammals," Annals of the New York Academy of Sciences, 1960, vol. 84, pp. 736-744.

Wang, et al., Drug Delivery: Principles and Applications, John Wiley & Sons, Inc., 2005, pp. 136-137.

Widdowson, et al., "Palladium Catalysed Suzuki Reactions of Fluoroarenes," Chemical Communication (Camb), 2003, vol. 5, pp. 578-579.

Williams, et al., "Renin Inhibitors Containing Conformationally Restricted P1-P1 Dipeptide Mimetics," Journal of Medicinal Chemistry, 1991, vol. 34 (3), pp. 887-900.

* cited by examiner

COMPOUNDS AS CANNABINOID RECEPTOR LIGANDS AND USES THEREOF

This application claims priority to the provisional application Ser. No. 60/809,712 filed on May 31, 2006.

TECHNICAL FIELD

The present invention relates to compounds that are cannabinoid receptor ligands, compositions comprising such compounds, and methods of treating conditions and disorders using such compounds and compositions.

BACKGROUND $(-)$-$\Delta^9$-Tetrahydrocannabinol ($\Delta^9$-THC), the major psychoactive constituent of marijuana, exerts a broad range of therapeutic effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic side effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness ale considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY

One aspect of the invention is directed towards compounds of formula (I), or pharmaceutical salts, prod rigs, salts of prodrugs, or combinations thereof,

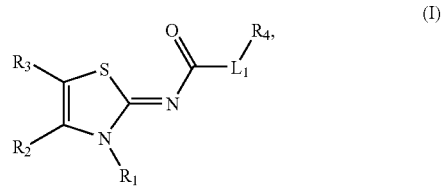

$R_1$ is alkoxyalkyl, alkoxyalkoxyalkyl, hydroxyalkyl, A, or A-alkylene-;

$R_2$ is hydrogen, alkoxy, alkoxyalkyl, alkoxycarbonyl, alkoxycarbonylalkyl, alkyl, alkyl-S(O)$_2$—, aryl, arylalkyl, arylalkenyl, azidoalkyl, cyano, cycloalkyl, halo, haloalkyl, heteroaryl, heterocycle, —(CR$_{21}$R$_{22}$)$_m$—OH, R$_a$R$_b$N—, R$_a$R$_b$N-alkyl-, R$_c$R$_d$NC(O)—, or R$_8$-R$_7$—;

$R_3$ is hydrogen, alkoxy, alkoxyalkyl, alkyl, alkylcarbonyl, alkyl-S(O)$_2$—, aryl, arylalkyl, arylalkenyl, cyano, cycloalkyl, halo, haloalkyl, heteroaryl, heterocycle, —(CR$_{31}$R$_{32}$)$_m$—OH, R$_a$R$_b$N—, R$_a$R$_b$N-alkyl-, or R$_8$-R$_7$—; or $R_2$ and $R_3$, together with the carbon atoms to which they are attached, form a 4-, 5-, 6-, or 7-membered monocyclic ring, optionally fused to a benzo or a monocyclic heteroaryl, said monocyclic ring contains zero, one, or two additional double bonds, zero or one oxygen atom, and zero or one nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, —OH, —O(alkyl), and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl;

with the proviso that when $R_2$ and $R_3$ are other than forming a ring with the carbon atoms to which they are attached, and $R_1$ is A or A-alkylene-, then $R_4$ is alkyl wherein the alkyl is optionally substituted with one substituent selected from the group consisting of alkoxy, alkoxycarbonyl, carboxy, halo, —OH, and $R_cR_fN$—; alkynyl, cycloalkyl, cycloalkenyl, aryl, cycloalkylalkyl, cycloalkenylalkyl, arylalkyl, or $R_{10}$-$L_2$-$R_9$— wherein $R_9$ is aryl, cycloalkyl, or cycloalkenyl;

$R_4$ is alkyl, alkynyl, cycloalkyl, cycloalkenyl, aryl, heteroaryl, heterocycle, cycloalkylalkyl, cycloalkenylalkyl, arylalkyl, heteroarylalkyl, heterocyclealkyl, or $R_{10}$-$L_2$-$R_9$—; wherein the alkyl group is optionally substituted with one substituent selected from the group consisting of alkoxy, alkoxycarbonyl, carboxy, halo, —OH, and $R_eR_fN$—;

$R_7$, $R_8$, $R_9$, and $R_{10}$ are each independently aryl, cycloalkyl, cycloalkenyl, heteroaryl, or heterocycle;

$R_a$ and $R_b$, at each occurrence, are each independently hydrogen, alkoxycarbonyl, alkyl, alkylcarbonyl, alkyl-S(O)$_2$—, or arylalkyl;

$R_c$ and $R_d$, are each independently hydrogen or alkyl;

$R_e$ and $R_f$, are each independently hydrogen, alkyl, or alkylcarbonyl;

A is a 4-, 5-, 6-, 7-, 8-, or 9-membered monocyclic heterocycle containing zero or one double bond, and one or two oxygen, and zero or one nitrogen as ring atoms, optionally fused with a monocyclic ring selected from benzo, cycloalkyl, cycloalkenyl, heterocycle and heteroaryl; wherein two non-adjacent atoms of each A can be optionally linked by an alkenylene bridge of 2, 3, or 4 carbon atoms, or optionally linked by an alkylene bridge of 1, 2, 3, or 4 carbon atoms; each A is independently unsubstituted or substituted with 1, 2, 3, 4, 5, or 6 substituents independently selected from the group consisting of oxo, alkyl, halo, —OH, —O(alkyl), and haloalkyl;

$L_1$ is a single bond or —NR$_g$—;

$L_2$ is a single bond, alkylene, or —O—;

$R_g$ is hydrogen or alkyl;

$R_{21}$, $R_{22}$, $R_{31}$, and $R_{32}$, at each occurrence, are each independently hydrogen, alkyl, haloalkyl, or halo; and m, at each occurrence, is independently 1, 2, 3, or 4.

Another aspect of the invention relates to compounds of formula (II), or pharmaceutical salts, prodrugs, salts of prodrugs, or combinations thereof,

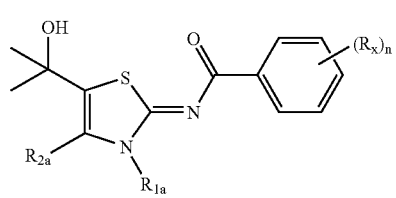

(II)

wherein $R_{1a}$ is alkyl, haloalkyl, or cycloalkylalkyl;

$R_{2a}$ is hydrogen or alkyl;

$R_x$ represents optional substituent of phenyl, selected from the group consisting of alkyl, alkoxy, cyano, halo, haloalkoxy, hydroxyl, and haloalkyl; and n is 1, 2, 3, 4, or 5

Also comprised in the present application are pharmaceutical compositions comprising a therapeutically effective amount of a compound of of the invention or a pharmaceutically acceptable salt thereof, in combination with a pharmaceutically acceptable carrier.

The present application also relates to a method of treating pain, nociceptive pain, and neuropathic pain in a mammal in need of such treatment comprising administering to the mammal a therapeutically effective amount of a compound of the invention or a pharmaceutically acceptable salt thereof.

Included in the present application is a method of treating a disorder selected from the group consisting of inflammatory disorders, immune disorders, neurological disorders, cancers of the immune system, respiratory disorders, and cardiovascular disorders in a mammal in need of such treatment comprising administering to the mammal a therapeutically effective amount of a compound of the invention or a pharmaceutically acceptable salt thereof.

Included in the present application is a method of providing neuroprotection in a mammal in need comprising administering to the mammal a therapeutically effective amount of a compound of the invention or a pharmaceutically acceptable salt thereof.

DEFINITION OF TERMS

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated from a reaction mixture.

All patents, patent applications, and literature references cited in the specification are herein incorporated by reference in their entirety. In the case of inconsistencies, the present disclosure, including definitions, will prevail.

As used in the specification and the appended claims, unless specified to the contrary, the following terms have the meaning indicated:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2, 3, or 4 carbon atoms and contains at least one carbon-carbon double. Representative examples of alkylene include, but are not limited to, —CH=CH— and —CH$_2$CH=CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, methoxymethyl, 2-methoxy-2-methylpropyl, and 3-methoxypropyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylcarbonyl" as used herein, means an allyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkylene group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —CH (C$_2$H$_5$), —CH(CH(CH$_3$)(C$_2$H$_5$))—, —C(H)(CH$_3$) CH$_2$CH$_2$—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH (CH$_3$)CH$_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkylene group, as defined herein. Representative examples of alkylsulfinylalkyl include, but are not limited to, methylsulfinylmethyl and ethylsulfinylmethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 1-propylpent-3-ynyl, 3-butynyl, 2-pentynyl, and 1-butynyl.

The term "aryl," as used herein, means phenyl, a bicyclic aryl or a tricyclic aryl. The bicyclic aryl is naphthyl, or a phenyl fused to a cycloalkyl, or a phenyl fused to a cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is exemplified by a bicyclic aryl fused to a monocyclic cycloalkyl, or a bicyclic aryl fused to a monocyclic cycloalkenyl, or a bicyclic aryl fused to a phenyl. Representative examples of tricyclic aryl ring include, but are not limited to, anthracene, phenanthrene, dihydroanthracenyl, fluorenyl, 1,2-dihydroacenaphthylenyl, and tetrahydrophenanthrenyl. The phenyl, bicyclic and tricyclic aryls are attached to the parent molecular moiety through any carbon atom contained within the phenyl, bicyclic and tricyclic aryls respectively.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 1-methyl-3-phenylpropyl, 2-methyl-1-phenylbutyl, 1-phenylpropyl, 3-phenylpropyl, and 2-naphth-2-ylethyl.

The term "azido" as used herein, means a —N$_3$ group,

The term "azidoalkyl" as used herein, means an azido group, as defined herein, appended to the parent molecular moiety through an alkylene group, as defined herein.

The term "carbonyl" as used herein, means a —C(O)— group.

the term "carboxy" as used herein, means a —CO$_2$H group.

The term "carboxyalkyl" as used herein, means a carboxy group, as defined herein, appended to the patent molecular moiety through an alkylene group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic or bicyclic ring system containing zero heteroatoms in the ring. The monocyclic cycloalkenyl has three-, four-, five-, six-, seven- or eight carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic ring systems include, but are not limited to, 2-cyclohexen-1-yl, 3-cyclohexen-1-yl, 2,4-cyclohexadien-1-yl and 3-cyclopenten-1-yl. Bicyclic ring systems are exemplified by a monocyclic cycloalkenyl ring fused to a monocyclic cycloalkyl ring, or a monocyclic cycloalkenyl ring fused to a monocyclic cycloalkenyl ring. Representative examples of bicyclic ring systems include, but are not limited to 3a,4,5,6,7,7a-hexahydro-1H-indenyl, 4,5,6,7-tetrahydro-3aH-indene, and octahydronaphthalenyl. The monocyclic or the bicyclic cycloalkenyl ring can be appended to the parent molecular moiety through any substitutable carbon atom within the monocyclic or the bicyclic cycloalkenyl.

The term "cycloalkenylalkyl" as used herein, means a cycloalkenyl group as defined herein, appended to the parent molecular moiety through an alkylene group, as defined herein.

The term "cycloalkyl" as used herein, means a monocyclic, or a bicyclic ring system, or a spirocyclic cycloalkyl. The monocyclic cycloalkyl is a carbocyclic ring system containing 3, 4, 5, 6, 7, or 8 carbon atoms, zero heteroatoms and zero double bonds. Examples of monocyclic ring systems include cyclopropyl, cyclobutyl, cyclopentyl, cyclohexyl, cycloheptyl, and cyclooctyl. Bicyclic ring systems are exemplified by a monocyclic cycloalkyl ring fused to a monocyclic cycloalkyl ring. Representative examples of bicyclic ring systems include, but are not limited to, bicyclo[4.1.0]heptane, bicyclo[6.1.0]nonane, octahydroindene, and decahydronaphthalene. Spirocyclic cycloalkyl is exemplified by a monocyclic cycloalkyl ring wherein two of the substituents on the same carbon atom of the ring, form a 4-, 5-, or 6-membered monocyclic cycloalkyl. An example of a spirocyclic cycloalkyl is spiro[2.5]octane. The monocyclic, bicyclic and spirocyclic cycloalkyl groups of the present invention can be appended to the parent molecular moiety through any substitutable carbon atom of the groups.

The term "cycloalkylalkyl" as used herein, means a cycloalkyl group, as defined herein, appended to the parent molecular moiety through an alkylene group, as defined herein. Representative examples of cycloalkylalkyl include, but are not limited to, cyclopentylmethyl, cyclohexylmethyl, cyclopropylmethyl, and 1-cyclopropylethyl.

The term "formyl" as used herein, means a —C(O))H group.

The term "formylalkyl" as used herein, means a formyl group, as defined herein, appended to the parent molecular moiety through an alkylene group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means an alkoxy group, as defined herein, in which one, two, three, four, five or six hydrogen atoms are replaced by halogen. Representative examples of haloalkoxy include, but are not limited to, trifluoromethoxy, difluoromethoxy, 2,2,2-trifluoroethoxy, and 2,2-difluoroethoxy.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2,2-difluoroethyl, trifluoromethyl, 2,2,2-trifluoroethyl, difluoromethyl, pentafluoroethyl, 2-chloro-3-fluoropentyl, and 2-iodoethyl.

The term "heteroaryl," as used herein, means a monocyclic heteroaryl or a bicyclic heteroaryl. The monocyclic heteroaryl is a 5 or 6 membered ring containing at least one heteroatom independently selected from the group consisting of O, N, and S. The 5-membered ring contains two double bonds and one, two, three, or four heteroatoms. The 6 membered ring contains three double bonds and one, two, three or four heteroatoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl include, but are not limited to, benzofuranyl, benzoxadiazolyl, 1,3-benzothiazolyl, benzimidazolyl, benzodioxolyl, benzothienyl, chromenyl, cinnolinyl, furopyridine, indolyl, indazolyl, isoindolyl, isoquinolinyl, naphthyridinyl, oxazolopyridine, quinolinyl, thienopyridine and thienopyridinyl. The monocyclic and the bicyclic heteroaryl groups are connected to the parent molecular moiety through any substitutable carbon atom or any substitutable nitrogen atom contained within the groups.

The term "heteroarylalkyl" as used herein, means a heteroaryl group as defined herein, appended to the parent molecular moiety through an alkylene group, as defined herein. An example of heteroarylalkyl is 3-thienylpropyl.

The term "heterocycle" or "heterocyclic" as used herein, refers to a monocyclic, bicyclic, tricyclic, or a spirocyclic ring system which contains at least one heteroatom. The monocyclic heterocycle is a 3, 4, 5, 6, 7, or 8-membered ring containing at least one heteroatom independently selected from the group consisting of O, N, and S. The 3 or 4 membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6, 7, or 8-membered ring contains zero, one, or two double bonds, and one, two, or three heteroatoms in the ring selected from the group consisting of O, N and S. Representative examples of monocyclic heterocycle include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle of the present invention is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Representative examples of bicyclic heterocycle include, but are not limited to, 1,3-benzodioxol-4-yl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. Spirocyclic heterocycle means a 4, 5-, 6-, 7-, or 8-membered monocyclic heterocycle ring wherein two of the substituents on the same carbon atom form a 4-, 5-, or 6-membered monocyclic cycloalkyl, wherein the cycloalkyl is optionally substituted with 1, 2, 3, 4, or 5 alkyl groups. One example of a spiroheterocycle is 5-oxaspiro[3,4]octane. The tricyclic heterocycle is a bicyclic heterocycle fused to a phenyl, or a bicyclic heterocycle fused to a monocyclic cycloalkyl, or a bicyclic heterocycle fused to a monocyclic cycloalkenyl, or a bicyclic heterocycle fused to a monocyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a6,7,8,9,9a-hexahydrodibenzo[b,d]thienyl. The monocyclic, bicyclic, tricyclic, and spirocyclic heterocycle groups are connected to the parent molecular moiety through any substitutable carbon atom or any substitutable nitrogen atom contained within the group.

The term "heterocyclealkyl" as used herein, means a heterocycle group as defined herein, appended to the parent molecular moiety through an alkylene group, as defined herein.

The term "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 3-hydroxy-3-methylbutyl, 2,3-dihydroxypentyl, and 2-ethyl-4-hydroxyheptyl.

The aryl, cycloalkyl, cycloalkenyl, heterocycle, or heteroaryl moieties of this invention, as a substituent, or as part of a substituent, is each independently unsubstituted or substituted with 1, 2, 3, 4, 5, or 6 substituents as described herein below, unless otherwise noted. The optional substituents are selected from the group consisting of alkenyl, alkoxy, alkoxyalkoxy, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfinyl, alkylsulfinylalkyl, alkyl-S(O)$_2$—, alkyl-S(O)$_2$-alkyl-, alkyl-S—, alkyl-S-alkyl-, alkynyl, carboxy, carboxyalkyl, cyano, cyanoalkyl, formyl, formylalkyl, halogen, haloalkyl, haloalkoxy, hydroxy, hydroxyalkyl, oxo, —SH, N(O)$_2$, NZ$_1$Z$_2$-alkylene-O—, —NZ$_1$Z$_2$, and (NZ$_3$Z$_4$)carbonyl. The exceptions are the cycloalkenyl, the aryl, the heteroaryl, and the heterocycle moieties as represented by R$_4$ and R$_9$ wherein the optional substituents are selected from the group consisting of alkenyl, alkoxy, alkoxyalkoxy, alkoxyalkoxyalkyl, alkoxyalkyl, alkyl, alkylcarbonyl, alkylcarbonylalkyl, alkylcarbonyloxy, alkyl-S—, alkyl-S-alkyl-, alkynyl, cyano, cyanoalkyl, formyl, formylalkyl, halogen, haloalkyl, haloalkoxy, hydroxy, hydroxyalkyl, oxo, —SH, N(O)$_2$, NZ$_1$Z$_2$-alkylene-O—, and —NZ$_1$Z$_2$.

The term "hydroxy-protecting group" or "O-protecting group" means a substituent which protects hydroxy groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "NZ$_1$Z$_2$" as used herein, means two groups, Z$_1$ and Z$_2$, which are appended to the parent molecular moiety through a nitrogen atom. Z$_1$ and Z$_2$ are each independently hydrogen, alkyl, alkoxyalkyl, alkylcarbonyl, haloalkyl, or formyl. In certain instances, Z$_1$ and Z$_2$ taken together with the nitrogen atom to which they are attached form a heterocyclic ring, optionally substituted with 1, 2, 3, or 4 substituents selected from alkyl, hydroxy and haloalkyl. Representative examples of NZ$_1$Z$_2$ include, but are not limited to, amino, methylamino, acetylamino, acetylmethylamino, phenylamino, benzylamino, azetidinyl, pyrrolidinyl and piperidinyl.

The term "NZ$_3$Z$_4$" as used herein, means two groups, Z$_3$ and Z$_4$, which are appended to the parent molecular moiety through a nitrogen atom. Z$_3$ and Z$_4$ are each independently hydrogen, alkyl, haloalkyl, phenyl or benzyl wherein the phenyl moiety is optionally substituted with 1, 2, 3, or 4 substituents selected from alkyl, hydroxy and haloalkyl. Representative examples of NZ$_3$Z$_4$ include, but are not limited to, amino, methylamino, phenylamino and benzylamino.

The term "oxo" as used herein, means a =O moiety.

The term "sulfinyl" as used herein, means a —S(O)— group.

The term "tautomer" as used herein means a proton shift from one atom of a compound to another atom of the same compound wherein two or more structurally distinct compounds are in equilibrium with each other.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I), for example, by hydrolysis in blood.

DETAILED DESCRIPTION

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

In compounds of formula (I), R$_1$ is alkoxyalkyl, alkoxyalkoxyalkyl, hydroxyalkyl, A, or A-alkylene- wherein A is as disclosed in the Summary. Embodiments of the present invention include compounds wherein R$_1$ is A or A-alkylene- wherein A is as disclosed in the Summary. Some examples of A are those that are represented by formula (i), (ii), (iii), (iv), (v) and (vi), wherein each ring is independently unsubstituted or substituted as described in the Summary. Certain examples of the optional substituents of A include, but are not limited to, alkyl such as C$_{1-6}$ alkyl, and oxo. The alkylene moiety of A-alkylene-, for example, is C$_1$-C$_6$ alkylene. Further example of the alkylene moiety of A-alkylene- is C$_1$-C$_3$ alkylene. Yet further example is C$_1$-C$_2$ alkylene.

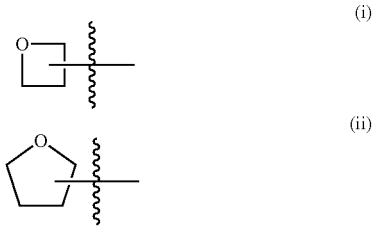

-continued

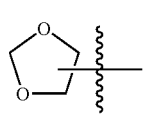
(iii)

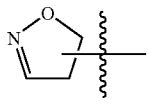
(iv)

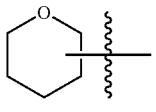
(v)

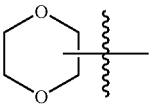
(vi)

Other examples of compounds of formula (I) include those wherein $R_1$ is alkoxyalkyl, alkoxyalkoxyalkyl, or hydroxyalkyl.

$R_2$ is hydrogen, alkoxy, alkoxyalkyl, alkoxycarbonyl, alkoxycarbonylalkyl, alkyl, alkyl-S(O)$_2$—, aryl, arylalkyl, arylalkenyl, azidoalkyl, cyano, cycloalkyl, halo, haloalkyl, heteroaryl, heterocycle, —(CR$_{21}$R$_{22}$)$_m$—OH, R$_a$R$_b$N—, R$_a$R$_b$N-alkyl-, R$_c$R$_d$NC(O)—, or R$_8$-R$_7$—; wherein R$_{21}$, R$_{22}$, m, R$_a$, R$_b$, R$_c$, R$_d$, R$_7$, and R$_8$ are as described in the Summary, and the optional substituents of aryl, cycloalkyl, heteroaryl and heterocycle moieties are as disclosed in the Definition of Terms. Certain examples of compounds of formula (I) include those wherein $R_2$ is hydrogen, alkoxycarbonyl, alkyl, aryl (for example, optionally substituted phenyl), halo, haloalkyl, or —(CR$_{21}$R$_{22}$)$_m$—OH; wherein R$_{21}$, R$_{22}$, and m are as described in the Summary, and the optional substituents of the aryl moiety are as disclosed in the Definition of Terms, for example, the optional substituents of the aryl moiety are selected from the group consisting of alkyl and halo. Included, but are not limited to, are compounds in which R$_{21}$ and R$_{22}$ are hydrogen and m is 1. Embodiments of the present invention include compounds in which $R_2$ is hydrogen or alkyl.

$R_3$ is hydrogen, alkoxy, alkoxyalkyl, alkyl, alkylcarbonyl, alkyl-S(O)$_2$—, aryl, arylalkyl, arylalkenyl, cyano, cycloalkyl, halo, haloalkyl, heteroaryl, heterocycle, —(CR$_{31}$R$_{32}$)$_m$—OH, R$_a$R$_b$N—, R$_a$R$_b$N-alkyl-, or R$_8$-R$_7$—; wherein R$_{31}$, R$_{32}$, m, R$_a$, and R$_b$, are as described in the Summary, and the optional substituents of aryl, cycloalkyl, heteroaryl and heterocycle moieties are as disclosed in the Definition of Terms. Examples of compounds of formula (I) include, but are not limited to, those wherein $R_3$ is hydrogen, alkyl (for example, methyl, tert-butyl), alkylcarbonyl, aryl (for example, phenyl), cycloalkyl (for example, cyclopropyl), halo, haloalkyl, heterocycle, or —(CR$_{31}$R$_{32}$)$_m$—OH, wherein R$_{31}$, R$_{32}$, and m are as disclosed in the Summary. The optional substituents of aryl, cycloalkyl, and heterocycle moieties are as disclosed in the Definition of Terms, for example, the optional substituents are selected from the group consisting of alkyl and halo. Non limiting examples of R$_{31}$ and R$_{32}$ (R$_{31}$ and R$_{32}$ can be the same or different) are alkyl (for example, methyl) or haloalkyl (for example, 2-iodoethyl or trifluoromethyl) m, for example, is 1. Embodiments of the present invention include compounds in which R$_3$ is alkyl (for example, methyl or tert-butyl) or —(CR$_{31}$R$_{32}$)$_m$—OH. Other examples include those wherein $R_3$ is —(CR$_{31}$R$_{32}$)$_m$—OH, wherein m is 1, and R$_{31}$ and R$_{32}$ are alkyl (such as, but not limited to, methyl) or haloalkyl (such as, but not limited to, trifluoromethyl).

In another embodiment, $R_2$ and $R_3$, together with the carbon atoms to which they are attached, form a 4-, 5-, 6-, or 7-membered monocyclic ring as described in the Summary. Embodiments of the present invention include compounds of formula (I) wherein $R_2$ and $R_3$, together with the carbon atoms to which they are attached, form a monocyclic ring as described in the Summary, containing zero heteroatoms in the ring. Formulae (vii), (viii), (ix), (x), (xi), (xii), (xiii), and (xiv) represent some of these rings that can be formed by $R_2$, $R_3$, together with the carbon atoms to which they are attached.

(vii)

(viii)

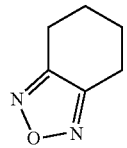
(ix)

(x)

(xi)

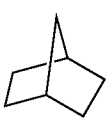
(xii)

(xiii)

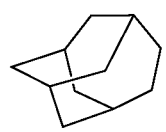
(xiv)

Yet other compounds of the present invention include those wherein $R_2$ and $R_3$, together with the carbon atoms to which they are attached, form a monocyclic ring as described in the Summary, containing zero or one additional double bond, zero oxygen atom and zero nitrogen atom as ring atoms; and two non-adjacent atoms of said monocyclic ring are linked by an alkenylene bridge of 2, 3, or 4 carbon atoms, or linked by an alkylene bridge of 1, 2, 3, or 4 carbon atoms. Examples include, but are not limited to, (xii), (xiii) and (xiv).

Yet other compounds of the present invention include those wherein $R_2$ and $R_3$, together with the carbon atoms to which they are attached, form a monocyclic ring as described in the Summary, containing zero or one additional double bond, and one oxygen atom and zero or one nitrogen atom as ring atoms. Examples of such monocyclic ring include, but are not limited to, formula (xv)-(xxix).

(xv)

(xvi)

(xvii)

(xviii)

(xix)

(xx)

(xxi)

(xxii)

(xxiii)

(xxiv)

(xxv)

(xxvi)

(xxvii)

(xxviii)

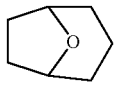
(xxix)

Each monocyclic ring formed by $R_2$, $R_3$, and the carbon atoms to which they are attached is independently unsubstituted or substituted as described in the Summary, for example, these rings can be independently unsubstituted or substituted with 1, 2, 3, 4, 5 or 6 substituents independently selected from alkyl such as $C_{1-6}$ alkyl, hydroxy, and oxo. Such rings are optionally fused with benzo or a monocyclic heteroaryl (for example, 1,3,4-oxadiazole, pyrrole, furan, and the like).

$R_4$ is alkyl, alkynyl, cycloalkyl, cycloalkenyl, aryl, heteroaryl, heterocycle, cycloalkylalkyl, cycloalkenylalkyl, arylalkyl, heteroarylalkyl, heterocyclealkyl, or $R_{10}$-$L_2$-$R_9$—; wherein the alkyl group is optionally substituted with one substituent selected from the group consisting of alkoxy, alkoxycarbonyl, carboxy, halo, —OH, and $R_eR_fN$—. In one embodiment, $R_4$ is optionally substituted aryl. In another embodiment, $R_4$ is optionally substituted phenyl. Examples of the optional substituents of $R_4$ include, but are not limited to, alkyl, alkoxy, cyano, halo, haloalkoxy, hydroxy, and haloalkyl. Other examples of compounds of formula (I) are those wherein $R_4$ is heteroaryl or heterocycle, each of which is optionally substituted as described in the Definition of Terms. Yet other examples are those wherein $R_4$ is alkyl optionally substituted with $R_eR_fN$— wherein $R_e$ and $R_f$ are as disclosed in the Summary. Further examples are those wherein $R_4$ is optionally substituted cycloalkyl wherein the optional substituents are as discussed in Definition of Terms.

$L_1$ is a single bond or —$NR_g$— wherein $R_g$ is hydrogen or alkyl. Certain compounds of the present invention include those wherein $L_1$ is a single bond. Yet others are those wherein $L_1$ is —$NR_g$— wherein $R_g$ is hydrogen or alkyl. Other examples include those wherein $L_1$ is —NH—.

It is appreciated that the present invention contemplates compounds of formula (I) with combinations of the above embodiments, including particular, more particular and preferred embodiments.

Accordingly, one aspect of the invention relates to a group of compounds of formula (I), or pharmaceutically acceptable salts thereof, wherein $R_1$ is A or A-alkenyl-, $R_2$ is hydrogen, alkoxycarbonyl, alkyl, aryl, halo, haloalkyl, or —$(CR_{21}R_{22})_m$—OH; $R_3$ is hydrogen, alkyl, aryl, cycloalkyl, halo, haloalkyl, heterocycle, or —$(CR_{31}R_{32})_m$—OH; $R_4$ is alkyl wherein the alkyl is optionally substituted with one substituent selected from the group consisting of alkoxy, alkoxycarbonyl, carboxy, halo, —OH, and $R_eR_fN$—, alkynyl, cycloalkyl, cycloalkenyl, aryl, cycloalkylalkyl, cycloalkenylalkyl, arylalkyl, or $R_{10}$-$L_2$-$R_9$—, wherein $R_9$ is aryl, cycloalkyl, or cycloalkenyl; and A, $L_1$, $R_{21}$, $R_{22}$, $R_{31}$, $R_{32}$, m, $R_e$, $R_f$, $L_2$, and $R_{10}$ are as disclosed in the Summary, and the optional substituents of the aryl, cycloalkyl, and cycloalkenyl moieties are as disclosed in the Definition of Terms. A, for example, is formula (i), (ii), (iii), (iv), (v), or (vi), wherein each ring is independently unsubstituted or substituted as described in the Summary. $R_{21}$ and $R_{22}$, for example, are hydrogen. m, for example, is 1 $R_{31}$ and $R_{32}$ are, for example, independently alkyl (such as methyl) or haloalkyl (such as 2-iodoethyl or trifluoromethyl). In one embodiment, $R_3$ is alkyl (for example, methyl or tert-butyl) or —$(CR_{31}R_{32})_m$—OH, and $R_2$ is hydrogen or alkyl wherein $R_{31}$, $R_{32}$ and m are as described in the Summary. Examples include those wherein $R_2$ is hydrogen or alkyl (for example, methyl), and $R_3$ is —$(CR_{31}R_{32})_m$—OH wherein m is 1, and $R_{31}$ and $R_{32}$ are alkyl (such as, but not limited to, methyl) or haloalkyl (such as, but not limited to, trifluoromethyl). Other examples include those wherein $R_2$ is hydrogen or alkyl (for example, methyl), and $R_3$ is alkyl (for example, tert-butyl). Yet other examples include those wherein $R_2$ is hydrogen or alkyl (for example, methyl), and $R_3$ is —$(CR_{31}R_{32})_m$—OH, wherein $R_{31}$ and $R_{32}$ are alkyl (for example, methyl), and m is 1. $R_4$, for example, is aryl, cycloalkyl, arylalkyl, cycloalkylalkyl, or $R_{10}$-$L_2$-$R_9$—, wherein $R_9$ is aryl or cycloalkyl. In other embodiments, $R_4$ is aryl or $R_{10}$-$L_2$-$R_9$—, wherein $R_9$ is aryl. The optional substituents of aryl and cycloalkyl moieties are as disclosed in the Definition of Terms. An example of the aryl moiety is phenyl. Other examples of the aryl moiety include, but are not limited to, naphthyl and 1,2-dihydroacenaphthylenyl. The optional substituents of aryl and cycloalkyl moieties are as disclosed in the Definition of Terms. Examples of the optional substituents of aryl and cycloalkyl moieties include, but are not limited to, alkyl, alkoxy, cyano, halo, haloalkoxy, hydroxy, and haloalkyl.

Another aspect of the invention provides a group of compounds of formula (I), or pharmaceutically acceptable salts thereof, wherein wherein $R_1$ is A or A-alkenyl-, $R_2$ and $R_3$, together with the carbon atoms to which they are attached form a monocyclic ring, and A, $R_4$, $L_1$, and said monocyclic ring are as described in the Summary. Some examples of A are as described herein above. Certain examples of the monocyclic ring formed by $R_2$, $R_3$, and the carbon atoms to which they are attached are represented by formulae (vii), (viii), and (x)-(xxix), each of which is optionally substituted with substituents as described in the Summary, and each of which is optionally fused with benzo or a monocyclic heteroaryl (for example, oxadiazole, furan or pyrrole). One example of such fused ring is represented by formula (ix). Examples of the optional substituents on the rings formed by $R_2$, $R_3$, and the carbon atoms to which they are attached include, but are not limited to, alkyl such as $C_{1-6}$ alkyl, hydroxy, and oxo.

Yet another aspect of the invention relates to a group of compounds of formula (I) or pharmaceutically acceptable salts thereof, wherein $R_1$ is alkoxyalkyl, alkoxyalkoxyalkyl, or hydroxyalkyl, $R_2$ and $R_3$, together with the carbon atoms to which they are attached, form a 4-, 5-, 6-, or 7-membered monocyclic ring, optionally fused to a benzo or a monocyclic heteroaryl, said monocyclic ring contains zero or one additional double bond, zero oxygen atom and zero nitrogen atom as ring atoms; two non-adjacent atoms of said monocyclic ring are linked by an alkenylene bridge of 2, 3, or 4 carbon atoms, or linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, —OH, —O(alkyl), and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl; and $R_4$, and $L_1$, are as described in the Summary. Some examples of the ring formed by $R_2$, $R_3$, and the carbon atoms to which they are attached are represented by formulae (xii), (xiii) and (xiv), each of which is optionally substituted as described in the Summary. Examples of the optional substituents include, but are not limited to, alkyl such as $C_{1-6}$ alkyl, hydroxy, and oxo.

A further aspect of the invention provides a group of compounds of formula (I) or pharmaceutically acceptable salts thereof, wherein $R_1$ is alkoxyalkyl, alkoxyalkoxyalkyl, or hydroxyalkyl, $R_2$ and $R_3$, together with the carbon atoms to which they are attached, form a 4-, 5-, 6-, or 7-membered monocyclic ring as described in the Summary, containing zero or one additional double bond, and one oxygen atom, and zero or one nitrogen atom as ring atoms; and $R_4$, and $L_1$, are as described in the Summary. Some examples of the monocyclic ring formed by $R_2$, $R_3$, and the carbon atoms to which they are attached are represented by formula (xv)-(xxix), each of which is optionally substituted as described in the Summary. Examples of the optional substituents include, but are not limited to, alkyl such as $C_{1-6}$ alkyl, hydroxy, and oxo.

For the above three groups of compounds of formula (I) described, $R_4$ is alkyl, alkynyl, or alkyl substituted with $NR_eR_f$, wherein $R_e$ and $R_f$ are as described in the Summary.

For the above three groups of compounds of formula (I) described, other examples of $R_4$ are aryl, arylalkyl, cycloalkyl, cycloalkylalkyl, or $R_{10}$-$L_2$-$R_9$— wherein $R_9$ is aryl or cycloalkyl, $L_2$ and $R_{10}$ are as disclosed in the Summary, and the optional substituents of the aryl moiety is as disclosed in the Definition of Terms. Embodiments of the present invention include compounds of formula (I) wherein $R_4$ is aryl or $R_{10}$-$L_2$-$R_9$—, wherein $R_9$ is aryl wherein the aryl moiety is optionally substituted as disclosed in the Definition of Terms. Preferably, $R_4$ is optionally substituted aryl. An example of the aryl moiety is phenyl. Other examples of the aryl moiety include naphthyl and 1,2-dihydroacenaphthylenyl. Examples of the optional substituents include, but are not limited to, alkyl, alkoxy, cyano, halo, haloalkoxy, hydroxy, and haloalkyl.

For the above three groups of compounds of formula (I) described, other examples of $R_4$ are heteroaryl, heterocycle, heteroarylalkyl, heterocyclealkyl, or $R_{10}$-$L_2$-$R_9$— wherein $R_9$ is heteroaryl or heterocycle, $L_2$ and $R_{10}$ are as disclosed in the Summary, and the optional substituents of the heteroaryl and heterocycle moieties are as disclosed in the Definition of Terms. Examples of the heteroaryl moiety include pyridinyl, thienyl, benzofuranyl, and quinolinyl. Examples of the heterocycle moiety include 3,4-dihydropyran-6-yl, tetrahydrofuranyl, tetrahydropyranyl, 1,3-benzodioxol-4-yl, and 2,3-dihydro-1-benzofuranyl. Examples of the optional substituents include, but are not limited to, alkyl, alkoxy, oxo, cyano, halo, haloalkoxy, hydroxy, and haloalkyl.

For all the foregoing embodiments described, examples of a subgroup include those wherein $L_1$ is a single bond. Yet other examples of a subgroup include those wherein $L_1$ is —$NR_g$— wherein $R_g$ is hydrogen or alkyl. Yet other examples of a subgroup include those wherein $L_1$ is —NH—.

A further aspect of the invention relates to compounds of formula (I) or pharmaceutically acceptable salts thereof wherein $L_1$ is a single bond; $R_1$ is alkoxyalkyl, alkoxyalkoxyalkyl, or hydroxyalkyl, $R_2$ is hydrogen or alkyl, $R_3$ is —$(CR_{31}R_{32})_m$—OH; $R_4$ is phenyl; $R_{31}$ and $R_{32}$ are methyl; and m is 1.

Yet a further aspect of the invention provides compounds of formula (II) or pharmaceutically acceptable salts thereof,

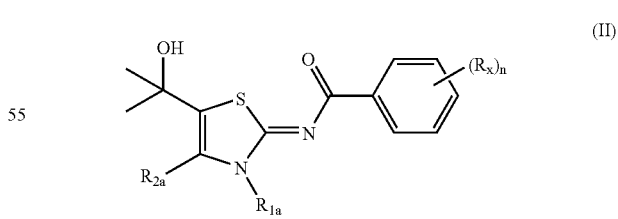

(II)

wherein
$R_{1a}$ is alkyl, haloalkyl, or cycloalkylalkyl;
$R_{2a}$ is hydrogen or alkyl;
$R_x$ represents optional substituent of phenyl, selected from the group consisting of alkyl, alkoxy, cyano, halo, haloalkoxy, hydroxyl, and haloalkyl; and
n is 1, 2, 3, 4, or 5.

In compounds of formula (II), $R_{2a}$ is hydrogen or alkyl such as $C_{1-6}$ alkyl. In one embodiment, $R_{2a}$ is hydrogen. In another embodiment, $R_{2a}$ is $C_{1-6}$ alkyl such as, but not limited to, methyl. $R_{1a}$ is cycloalkylalkyl wherein the cycloalkyl moiety is cyclopropyl, cyclobutyl, cyclopentyl or cyclohexyl, each of which is independently unsubstituted or substituted as described in the Definition of Terms. One example of the cycloalkyl moiety is cyclobutyl. Examples of the optional substituents of the cycloalkyl moiety include, but are not limited to, alkyl, haloalkyl, hydroxy, oxo, alkoxy, and haloalkoxy. In other embodiments, $R_{1a}$ is alkyl (such as, but not limited to, butyl). In yet another embodiment, $R_{1a}$ is haloalkyl.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers and mixtures of various ratio thereof and are included within the scope of this invention. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Abbreviations

Abbreviations which have been used in the descriptions of the Schemes and the Examples that follow are: DME for dimethoxyethane, DMF for N,N-dimethylformamide; EtOAc for ethyl acetate, EtOH for ethanol, HATU for O-(7-azabenzotriazol-1-yl)-N,N,N',N'-tetramethyluronium hexafluorophosphate, $Et_2O$ for diethyl ether, $Et_3N$ for triethylamine, HPLC for high pressure liquid chromatography, MeOH for methanol, min for minute or minutes DMSO for dimethylsulfoxide; TFA for trifluoroacetic acid, THF for tetrahydrofuran; Ts for p-$CH_3PhS(O)_2O$—; and Tf or triflate for $CF_3S(O)_2O$—.

Methods for Preparing Compounds

The compounds and processes of the present invention will be better understood in connection with the following synthetic Schemes and Examples which illustrate a means by which the compounds of the present invention can be prepared.

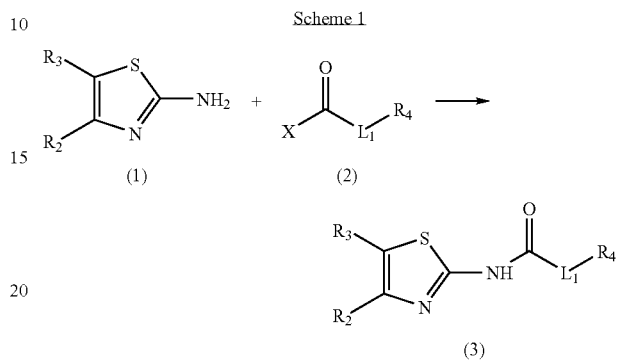

As shown in Scheme 1, compounds of formula (1) containing an amine group when treated with compounds of formula (2), wherein X is chloro or —OH under coupling conditions known to one skilled in the art, will provide compounds of formula (3). Typical conditions for the reaction of compounds of formula (2) wherein X is chloro and compounds of formula (1) include but are not limited to stirring an equimolar mixture of the compounds in solvents such as chloroform, dichloromethane or THF in the presence of a base such as but not limited to diisopropylethylamine at 0-30° C. for 8-24 hours. Acid coupling conditions of compounds of formula (2), wherein X is —OH and compounds of formula (1), include stirring an equimolar mixture of the compounds with a coupling reagent such as but not limited to bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU) along with a coupling auxiliary such as but not limited to 1-hydroxy-7-azabenzotriazole (HOAT) or 1-hydroxybenzotriazole hydrate (HOBT) in the presence or absence of a base such as but not limited to N-methyl morpholine, diisopropylethylamine in solvents such as but not limited to THF, N,N-dimethylacetamide, N,N-dimethylformamide, pyridine and chloroform. Typical reactions can be carried out between 0-65° C. or may be carried out in a microwave reactor to facilitate the coupling.

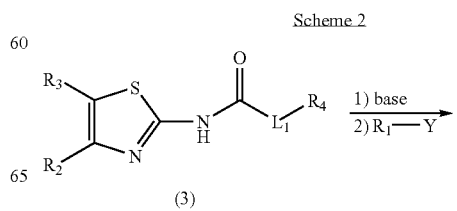

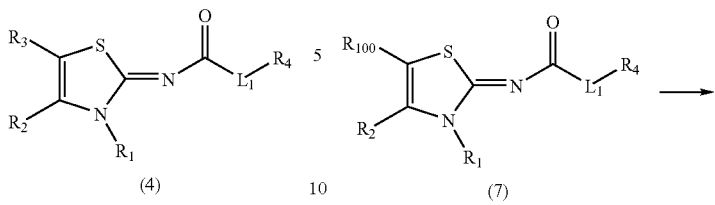

As shown in Scheme 2, compounds of formula (3) may be converted into compounds of formula (4) which are representative compounds of the present invention. Typical conditions include, but are not limited to, the treatment of compounds of formula (3) with sodium hydride in DMF at 0° C., followed by the addition of reagents such as $R_1$—Y, wherein $R_1$ is as defined in formula (I) and Y is chloro, bromo, iodo, mesyl or triflate. Alternatively, other bases such as potassium hydroxide or potassium tert-butoxide in a mixture of THF and DMF, followed by treatment with $R_1$—Y will also provide compounds of formula (4).

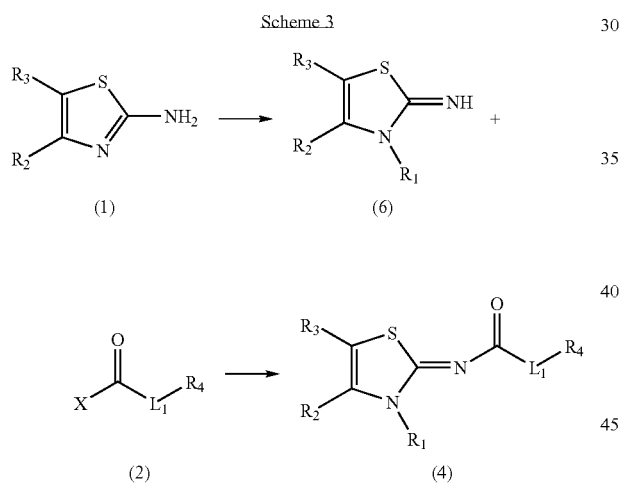

Alternatively, compounds of formula (4) may also be prepared according to the methods outlined in Scheme 3. Compounds of formula (1) when treated with sodium hydride in DMF at 0° C., followed by the addition of reagents such as $R_1$—Y, wherein $R_1$ is as defined in formula (I) and Y is chloro, bromo, iodo, tosyl, mesyl or triflate will provide compounds of formula (6). Alternatively, compounds of formula (1) may be heated neat or in the presence of a minimal amount of solvent to facilitate mixing with compounds of formula $R_1$—Y to obtain compounds of formula (6). Compounds of formula (6) may be isolated as a salt or a free base. The treatment of compounds of formula (6) with compounds of formula (2), wherein X is chloro or —OH, under coupling conditions as outlined in Scheme 1 will generate compounds of formula (4), which are representative compounds of the present invention.

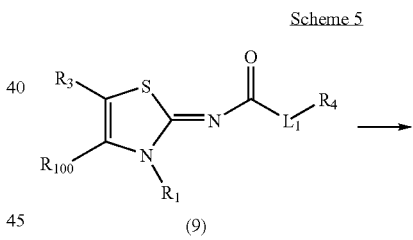

As outlined in Scheme 4, compounds of formula (7), wherein $R_{100}$ is halide or triflate and which can be prepared according to the methods outlined in Schemes 1-3, when treated with a boronic acid of formula $R_3B(OH)_2$, wherein $R_3$ is aryl, arylalkenyl, cycloalkyl, heterocycle or heteroaryl, a palladium catalyst such as dichlorobis(triphenyl)phosphine) palladium (II) and sodium carbonate in a mixture of solvents which include but are not limited to various mixtures of DME, ethanol and water under heated conditions will provide compounds of formula (4) which contain alkenyl, aryl, arylalkenyl, cycloalkyl, heterocycle or heteroaryl substituents in the $R_3$ position.

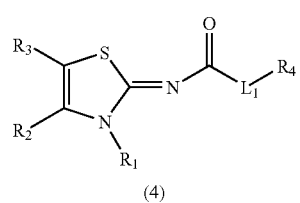

As outlined in Scheme 5, compounds of formula (9) wherein $R_{100}$ is halide or triflate and which can be prepared according to the methods outlined in Schemes 1-3, when treated with a boronic acid of formula $R_2B(OH)_2$, wherein $R_2$ is aryl, arylalkenyl, cycloalkyl, heterocycle or heteroaryl and a palladium catalyst according to the methods outlined is Scheme 4 will provide compounds of formula (4) which contain the aryl, arylalkenyl, cycloalkyl, heterocycle or heteroaryl in the $R_2$ position.

21

Scheme 6

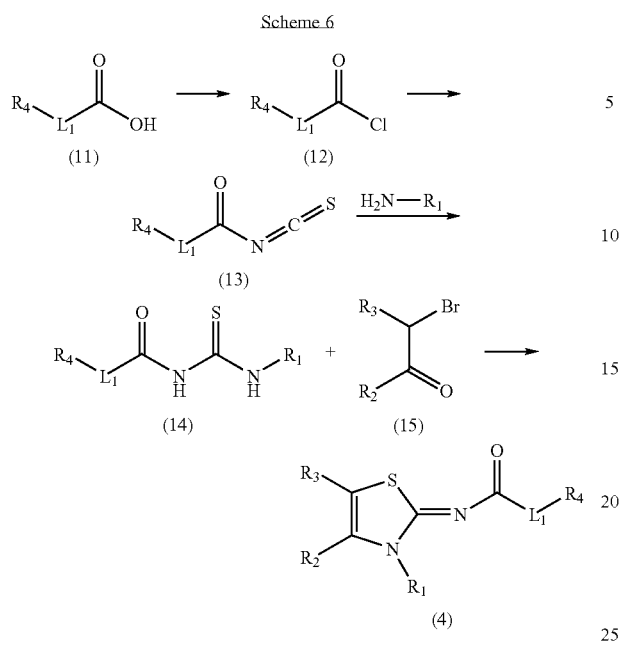

Scheme 6 describes another alternative method of preparation of compounds of formula (4). Compounds of formula (11) when treated with oxalyl chloride in dichloromethane containing a catalytic amount of DMF will provide the acid chloride of formula (12). The acid chloride of formula (12) when treated with potassium thiocyanate in acetone will provide compounds of formula (13). Compounds of formula (13) when treated with an amine of formula $R_1$—$NH_2$ in solvents such as but not limited to THF will provide compounds of formula (14). Compounds of formula (14) when treated with substituted alpha-bromo-ketones of formula (15) in ethanol or mixtures of ethanol and toluene under heated conditions will provide compounds of formula (4).

Scheme 7

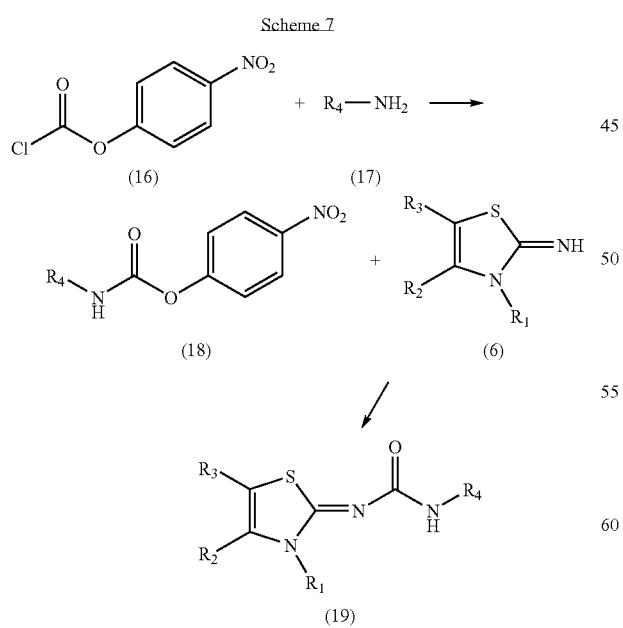

Compounds of formula (I) containing a $L_1$ group that is —NH—, may be prepared as outlined in Scheme 7. Compounds of formula (16) when treated with an amine of formula (17), wherein $R_4$ is defined in formula (I), will provide compounds of formula (18). Compounds of formula (18) when treated with compounds of formula (6) will provide compounds of formula (19) which are representative of compounds of formula (I).

Scheme 8

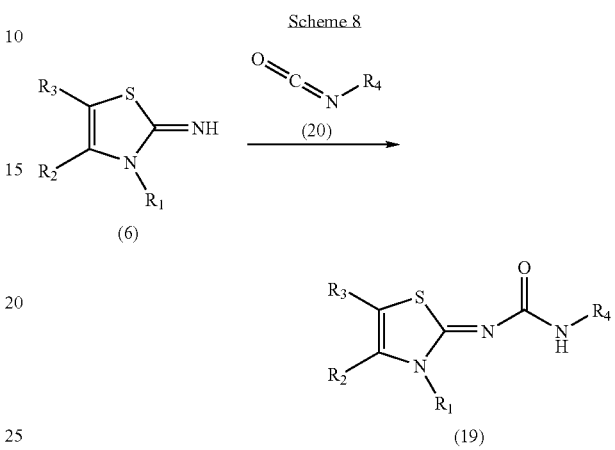

Alternatively, compounds of formula (6) when treated with an isocyanate of formula (20) wherein $R_4$ is defined in formula (I), will provide compounds of formula (19).

Scheme 9

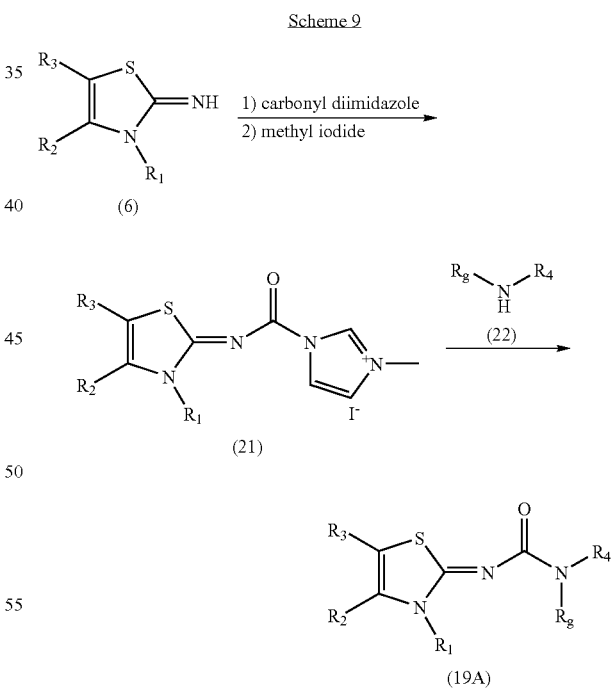

Similarly, compounds of formula (6) when treated with carbonyl diimidazole, followed by treatment with methyl iodide, will provide the imidazolide compounds of formula (21). Compounds of formula (21) when treated with an amine of formula (22), wherein $R_4$ and $R_g$ are defined in formula (I), will provide compounds of formula (19A) which are representative of compounds of formula (I).

Scheme 10

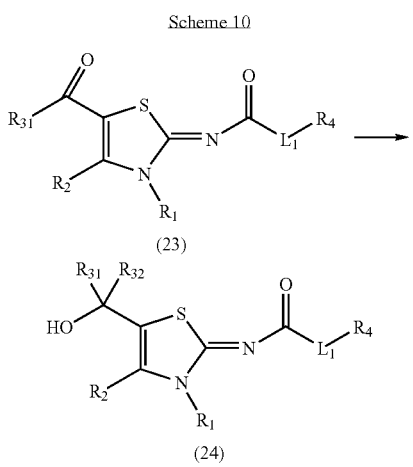

As shown in Scheme 10, compounds of formula (23) wherein $R_{31}$ is defined herein, when treated at low temperatures with an organolithium reagent such as but not limited to $R_{32}Li$ or a Grignard reagent such as but not limited to $R_{32}MgBr$ can be converted to compounds of formula (24). The reaction is typically conducted in a solvent such as but not limited to diethyl ether.

Scheme 11

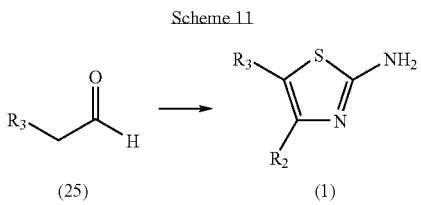

As shown in Scheme 11, compounds of formula (25) wherein $R_3$ is as defined in formula (I), when treated with pyrrolidine and p-toluenesulfonic acid monohydrate in a solvent such as but not limited to cyclohexane at reflux followed by treatment with sulfur and cyanamide in a solvent such as methanol, will provide compounds of formula (1) wherein $R_2$ is hydrogen.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

EXAMPLES

The compounds and processes of the present invention will be better understood by reference to the following Examples, which are intended as an illustration of and not a limitation upon the scope of the invention.

Example 1

N-[(2Z)-3-(2-methoxyethyl)-1,3-thiazol-2(3H)-ylidene]-2,2,3,3-tetramethylcyclopropanecarboxamide

Example 1A 2,2,3,3-tetramethylcyclopropanecarbonyl chloride

To a solution of 2,2,3,3-tetramethylcyclopropanecarboxylic acid (0.50 g, 3.5 mmol) in 18 mL of methylene chloride at 0° C. was added oxalyl chloride (0.61 mL, 7.0 mmol) and a catalytic amount of dimethylformamide (2 drops). The solution was stirred at ambient temperature for 1 hour, and then concentrated under reduced pressure to provide 0.56 g of the title compound.

Example 1B 2,2,3,3-tetramethyl-N-1,3-thiazol-2-ylcyclopropanecarboxamide

To a solution of 2-aminothiazole (0.39 g, 3.9 mmol) in 10 mL of methylene chloride at 0° C. was added a solution of the product from Example 1A in 8 mL of chloroform, followed by triethylamine (1.0 mL, 7.7 mmol). The mixture was stirred for 7 hours at 35° C., cooled to ambient temperature and diluted with water. The phases were separated and the aqueous phase was extracted with methylene chloride. The combined organic extracts were washed twice with water and then brine, dried over magnesium sulfate, filtered, and concentrated under reduced pressure. Purification by column chromatography (SiO$_2$, 30-60% ethyl acetate/hexanes gradient) afforded 0.11 g (14%) of the title compound. $^1$H NMR (CDCl$_3$, 300 MHz) δ ppm 1.18 (s, 1H), 1.25 (s, 6H), 1.35 (s, 6H), 6.92 (d, J=3.4 Hz, 1H), 7.39 (d, J=3.4 Hz, 1H), 10.7 (s, 1H); MS (DCI/NH$_3$) m/z 225 (M+H)$^+$. Anal. Calculated for C$_{11}$H$_{16}$N$_2$OS: C, 58.90; H, 7.19; N, 12.49. Found: C, 59.03; H, 7.34; N, 12.34.

Example 1C

N-[(2Z)-3-(2-methoxyethyl)-1,3-thiazol-2(3H)-ylidene]-2,2,3,3-tetramethylcyclopropanecarboxamide To a solution of Example 1B (0.16 g, 0.71 mmol) in 3.5 mL of 4:1 tetrahydrofuran:dimethylformamide at 0° C. was added potassium hydroxide (90 mg, 1.7 mmol). After stirring for 1 hour at room temperature, 2-bromoethyl methyl ether (73 μL, 7.1 mmol) was added and the solution was heated to 65° C. for 14 hours. The solution was allowed to cool to ambient temperature and then diluted with ethyl acetate and washed twice with water and then brine. The organic extract was dried over magnesium sulfate, filtered, and concentrated under reduced pressure. Purification by column chromatography (SiO$_2$, 30-50% ethyl acetate/hexanes gradient) afforded 22 mg (11%) of the title compound. $^1$H NMR (CDCl$_3$, 300 MHz) δ 1.25 (s, 12H), 1.75 (s, 1H), 3.32 (s, 3H), 3.74 (t, J=5.6 Hz, 2H), 4.44 (t, J=5.4 Hz, 2H), 6.95 (d, J=3.4 Hz, 1H), 7.48 (t, J=3.7 Hz, 1H); MS (DCI/NH$_3$) m/z 283 (M+H)$^+$. Anal. Calculated for C$_{14}$H$_{22}$N$_2$O$_2$S: C, 59.54; H, 7.85; N, 9.92. Found: C, 59.76; H, 7.97; N, 9.91.

Example 2

5-chloro-2-methoxy-N-[(2Z)-3-(2-methoxyethyl)-1,3-thiazol-2(3H)-ylidene]benzamide Example 2A 3-(2-methoxyethyl)-1,3-thiazol-2(3H)-imine hydrobromide A mixture of 2-aminothiazole (15 g, 0.15 mol) and 2-bromoethyl methyl ether (17 mL, 0.18 mol) were heated at 85° C. for 16 hours. After cooling to ambient temperature the resulting solid was triturated twice with isopropyl alcohol to afford 26 g (72%) of the title compound. $^1$H NMR (DMSO-d$_6$, 300 MHz) δ ppm 3.27 (s, 3H), 3.63 (t, J=5.1 Hz, 2H), 4.23 (t, J=4.9 Hz, 2H), 7.02 (d, J=4.7 Hz, 1H), 7.38 (d, J=4.4 Hz, 1H), 9.52 (s, 1H); MS (DCI/NH$_3$) m/z 159 (M+H)$^+$.

Example 2B

5-Chloro-2-methoxy-N-[(2Z)-3-(2-methoxyethyl)-1,3-thiazol-2(3H)-ylidene]benzamide To a solution of the product from Example 2A (0.77 g, 3.2 mmol) and 5-chloro-2-methoxybenzoic acid (0.50 g, 2.7 mmol) in 14 mL of THF at 0° C. was added O-(7-azabenzotriazol-1-yl)-N,N,N',N',-tetramethyluronium hexafluorophosphate (HATU, 1.24 g, 3.2 mmol) and N,N-diisopropylethylamine (1.1 mL, 6.2 mmol). The mixture was heated to 65° C. for 2.5 hours, cooled to ambient temperature and then diluted with ethyl acetate. The mixture was washed twice with water, then saturated aqueous sodium bicarbonate, and brine. The organic extract was dried over magnesium sulfate, and concentrated under reduced pressure. Purification by column chromatography (SiO$_2$, 20-35% ethyl acetate/hexanes gradient) afforded 0.38 g (43%) of the title compound. $^1$H NMR (CDCl$_3$, 300 MHz) δ ppm 3.35 (s, 3H), 3.72-3.81 (m, 2H), 3.91 (s, 3H), 4.41-4.48 (m, 2H), 6.65 (d, J=4.7 Hz, 1H), 6.92 (d, J=8.8 Hz, 1H), 7.16 (d, J=4.7 Hz, 1H), 7.34 (dd, J=8.8, 3.1 Hz, 1H), 7.99 (d, J=2.7 Hz, 1H); MS (DCI/NH$_3$) m/z 349 (M+H)$^+$. Anal. Calculated for C$_{18}$H$_{24}$N$_2$O$_3$S: C, 62.04; H, 6.94; N, 8.04. Found: C, 62.24; H, 7.08; N, 8.04.

Example 3

N-[(2Z)-3-(2-methoxyethyl)-1,3-thiazol-2(3H)-ylidene]cycloheptanecarboxamide

Cycloheptanecarboxylic acid (29 mg, 0.20 mmol), 3 equiv of polymer bound dicyclohexylcarbodiimide (PS-DCC), 1-hydroxybenzotriazole hydrate (HOBT, 22 mg, 0.16 mmol), N,N-diisopropylethylamine (62 mg, 0.50 mmol), and the product of Example 2A (39 mg, 0.16 mmol) were combined in dimethylacetamide (DMA, 2.8 mL) and heated in a microwave to 100° C. for 420 seconds. The mixture was filtered through Si-Carbonate (6 mL-1 g cartridge from Silicycle Chemical Division) and then concentrated to dryness. The residue was dissolved in 1:1 DMSO/MeOH and purified by reverse phase HPLC to afford the title compound. $^1$H NMR (500 MHz, DMSO-d$_6$) δ ppm 1.39-1.72 (m, 11H) 1.83-1.95 (m, 2H) 2.46-2.52 (m, 1H) 3.23-3.26 (m, 3H) 3.67 (t, 2H) 4.29 (t, 2H) 6.76-6.97 (d, 1H) 7.30-7.43 (d, 1H); MS (ESI) m/z 283 (M+H)$^+$.

Example 4

N-[(2Z)-3-(3-methoxypropyl)-1,3-thiazol-2(3H)-ylidene]-2,2,3,3-tetramethylcyclopropanecarboxamide Example 4A 3-(3-methoxypropyl)-1,3-thiazol-2(3H)-imine hydrobromide A mixture of 2-aminothiazole (1.0 g, 10 mmol) and 1-bromo-3-methoxypropane (1.8 g, 12 mmol) were heated at 85° C. for 16 hours. The solid was cooled to ambient temperature, triturated with ethanol, and then collected by filtration to provide 1.2 g (48%) of the title compound. MS (DCI/NH$_3$) m/z 173 (M+H)$^+$.

Example 4B

N-[(2Z)-3-(3-methoxypropyl)-1,3-thiazol-2(3H)-ylidene]-2,2,3,3-tetramethylcyclopropanecarboxamide The product of Example 4A (0.60 g, 2.4 mmol) and 2,2,3,3-tetramethylcyclopropanecarboxylic acid (0.34 g, 2.4 mmol) were processed using the method described in Example 2B. Purification by column chromatography (SiO$_2$, 20-40% ethyl acetate/hexanes gradient) afforded 0.33 g (47%) of the title compound. $^1$H NMR (CDCl$_3$, 300 MHz) δ ppm 1.21 (s, 6H), 1.34 (s, 6H), 1.56 (d, J=5.4 Hz, 1H), 2.00-2.13 (m, 2H), 3.31-3.39 (m, 5H), 4.23 (t, J=6.8 Hz, 2H), 6.50 (d, J=4.7 Hz, 1H), 6.88 (d, J=4.7 Hz, 1H); MS (DCI/NH$_3$) m/z 297 (M+H)$^+$. Anal. Calculated for C$_{15}$H$_{24}$N$_2$O$_2$S: C, 60.78; H, 8.27; N, 9.45. Found: C, 60.78; H, 8.27; N, 9.34.

Example 5

N-[(2Z)-3-(2-methoxyethyl)-4-methyl-1,3-thiazol-2 (3H)-ylidene]-2,2,3,3-tetramethylcyclopropanecarboxamide Example 5A 3-(2-methoxyethyl)-4-methyl-1,3-thiazol-2(3H)-imine hydrobromide A mixture of 4-methylthiazol-2-ylamine (0.75 g, 6.5 mmol) and 2-bromoethyl methyl ether (730 μL, 7.8 mmol) was heated at 85° C. for 15 hours. The mixture was cooled to ambient temperature and the resulting solid was triturated with isopropanol. Recrystallization from hot ethanol afforded 0.56 g (34%) of the title compound. $^1$H NMR (DMSO-d$_6$, 300 MHz) δ ppm 2.25 (d, J=1.4 Hz, 3H) 3.25 (s, 3H) 3.57 (t, J=5.1 Hz, 2H) 4.15 (t, J=5.1 Hz, 2H) 6.68 (d, J=1.4 Hz, 1H) 9.40 (s, 1H); MS (DCI/NH$_3$) m/z 173 (M+H)$^+$.

Example 5B

N-[(2Z)-3-(2-methoxyethyl)-4-methyl-1,3-thiazol-2 (3H)-ylidene]-2,2,3,3-tetramethylcyclopropanecarboxamide The product of Example 5A (0.30 g, 1.2 mmol) and 2,2,3,3-tetramethylcyclopropanecarboxylic acid (0.19 g, 1.3 mmol) were processed using the method described in Example 2B. Purification by column chromatography (SiO$_2$, 20-40% ethyl acetate/hexanes gradient) afforded 0.14 g (41%) of the title compound. $^1$H NMR (CDCl$_3$, 300 MHz) δ ppm 1.21 (s, 6H), 1.34 (s, 6H), 1.59 (s, 1H), 2.30 (s, 3H), 3.30 (s, 3H), 3.70 (t, J=50.9 Hz, 2H), 4.25 (t, J=5.26 Hz, 2H), 6.09 (s, 1H); MS (DCI/NH$_3$) m/z 297 (M+H)$^+$. Anal. Calculated for C$_{15}$H$_{24}$N$_2$O$_2$S: C, 60.78; H, 8.16; N, 9.45. Found; C, 60.79; H, 7.82; N, 9.36.

Example 6 ethyl ((2Z)-3-(2-methoxyethyl)-2-{[(2,2,3,3-tetramethylcyclopropyl)carbonyl]imino}-2,3-dihydro-1,3-thiazol-4-yl)acetate Example 6A ethyl [2-imino-3-(2-methoxyethyl)-2,3-dihydro-1,3-thiazol-4-yl]acetate hydrobromide A mixture of (2-aminothiazol-4-yl)acetic acid ethyl ester (18.6 g, 100 mmol) and 2-bromoethyl methyl ether (15.3 g, 110 mmol) were processed using the method described in Example 2A to afford 14.1 g (83%) of the title compound. $^1$H NMR (300 MHz, DMSO-d$_6$) δ ppm 1.14-1.28 (m, 3H) 3.24 (s, 3H) 3.54 (t, J=5 Hz, 2H) 3.91 (s, 2H) 4.04-4.25 (m, 4H) 6.92 (s, 1H) 9.50 (s, 1H); MS (DCI/NH$_3$) m/z 231 (M+H)$^+$.

Example 6B ethyl ((2Z)-3-(2-methoxyethyl)-2-{[(2,2,3,3-tetramethylcyclopropyl)carbonyl]imino}-2,3-dihydro-1,3-thiazol-4-yl)acetate The product of Example 6A (2.3 g, 10 mmol) and 2,2,3,3-tetramethylcyclopropane carboxylic acid (1.6 g, 11 mmol) were processed as described using the method described in Example 2B to afford 2.1 g (54%) of the title compound. $^1$H NMR (300 MHz, DMSO-d$_6$) δ ppm 1.06-1.33 (m, 15H) 1.48 (s, 1H) 3.22 (s, 3H) 3.59 (t, J=5 Hz, 2H) 3.91 (s, 2H) 4.12 (t, J=7 Hz, 2H) 4.14-4.24 (m, 2H) 6.69 (s, 1H); MS (DCI/NH$_3$) m/z 369 (M+H)$^+$ Anal. Calculated for C$_{18}$H$_{28}$N$_2$O$_4$SC, 68.67; H, 7.66; N, 7.62. Found: C, 68.67; H, 7.66; N, 7.60.

Example 7 ethyl (2Z)-3-(2-methoxyethyl)-2-{[(2,2,3,3-tetramethylcyclopropyl)carbonyl]imino}-2,3-dihydro-1,3-thiazole-4-carboxylate Example 7A ethyl 2-imino-3-(2-methoxyethyl)-2,3-dihydro-1,3-thiazole-4-carboxylate hydrobromide A mixture of 2-aminothiazole-4-carboxylic acid ethyl ester (17.2 g, 100 mmol) and 2-bromoethyl methyl ether (15.3 g, 110 mmol) were processed using the method described in Example 2A to afford 17.1 g (83%) of the title compound. $^1$H NMR (300 MHz, DMSO-d$_6$) δ ppm 1.30 (t, J=7 Hz, 3H) 3.22 (s, 3H) 3.60 (t, J=5 Hz, 2H) 4.32 (t, J=7 Hz, 2H) 4.35-4.61 (m, 2H) 7.84 (s, 1H) 9.76 (s, 1H); MS (DCI/NH$_3$) m/z 231 (M+H)$^+$.

Example 7B ethyl (2Z)-3-(2-methoxyethyl)-2-{[(2,2,3,3-tetramethylcyclopropyl)carbonyl]imino}-2,3-dihydro-1,3-thiazole-4-carboxylate The product of Example 7A (2.3 g, 10 mmol) and 2,2,3,3-tetramethylcyclopropane carboxylic acid (1.6 g, 11 mmol) were processed using the method described in Example 2B to afford 1.9 g (53%) of the title compound. $^1$H NMR (300 MHz, DMSO-d$_6$) δ ppm 1.11-1.36 (m, 12H) 1.53 (s, 1H) 3.21 (s, 3H) 3.31 (s, 3H) 3.53-3.62 (m, 2H) 4.30 (q, J=7 Hz, 2H) 4.62-4.75 (m, 2H) 7.77 (s, 1H); MS (DCI/NH$_3$) m/z 355 (M+H); Anal. Calculated for C$_{17}$H$_{26}$N$_2$O$_4$S: C, 57.61; H, 7.39; N, 7.86. Found: C, 57.86; H, 7.67; N, 7.85.

Example 8

N-[(2Z)-4-(hydroxymethyl)-3-(2-methoxyethyl)-1,3-thiazol-2(3H)-ylidene]-2,2,3,3-tetramethylcyclopropanecarboxamide To a solution of the product of Example 7B (0.355 g, 1.00 mmol) in 100 mL of THF at 0° C. was added lithium borohydride (10 mL of a 2.0 M solution in THF) and the resulting solution was allowed to warm to ambient temperature and stirred overnight. The mixture was quenched with water and then diluted with saturated aqueous Na$_2$CO$_3$ and extracted twice with ethyl acetate. The combined organic extracts were dried over anhydrous $Na_2SO_4$, filtered, and concentrated. Purification by column chromatography ($SiO_2$, 0-50% ethyl acetate/hexanes gradient) afforded 0.278 g (89%) of the title compound. $^1$H NMR (300 MHz, DMSO-$d_6$) δ ppm 1.20 (d, 12H) 1.47 (s, 1H) 3.24 (s, 3H) 3.64 (t, J=6 Hz, 2H) 4.30 (t J=6 Hz, 2H) 4.50 (d, J=5 Hz, 2H) 5.75 (s, 1H) 6.68 (s, 1H); MS (DCI/NH3) m/z 313 (M+H)$^+$; Anal. Calculated for $C_{15}H_{24}N_2O_3S.0.2H_2O$: C, 57.01; H, 7.78; N, 8.86. Found: C, 56.90; H, 7.61; N, 8.86.

Example 9

2-ethoxy-N-[(2Z)-3-(2-methoxyethyl)-4-(trifluoromethyl)-1,3-thiazol-2(3H)-ylidene]benzamide Example 9A 2-ethoxy-N-(4-trifluoromethyl-thiazol-2-yl)-benzamide A solution of 2-ethoxybenzoic acid (0.75 g, 4.5 mmol) in 23 mL of methylene chloride at 0° C. was treated with oxalyl chloride (0.44 mL, 4.9 mmol) followed by 2 drops of dimethylformamide. The solution was stirred at ambient temperature for 1 hour and then concentrated under reduced pressure to provide 0.83 g of 2-ethoxybenzoyl chloride. To a solution of 4-trifluoromethylthiazol-2-ylamine (0.50 g, 3.0 mmol) in 10 mL THF at 0° C. was added a solution of the fleshly prepared acid chloride in 5 mL of THF and 2 mL of methylene chloride, followed by triethylamine (1.0 mL, 6.6 mmol). The reaction mixture was warmed to 65° C. and stirred 8 hours. The mixture was diluted with ethyl acetate and washed twice with water, then brine. The organic extract was dried over magnesium sulfate, filtered, and concentrated under reduced pressure. Purification by column chromatography ($SiO_2$, 30-50% ethyl acetate/hexanes gradient) afforded 0.47 g (50%) of the title compound. $^1$H NMR (CDCl$_3$, 300 MHz) δ ppm 1.66 (t, J=6.95 Hz, 3H), 4.38 (q, J=6.89 Hz, 2H), 7.03-7.10 (m, 2H), 7.17 (d, J=7.80 Hz, 1H), 7.42 (s, 1H), 8.29 (dd, J=7.97, 1.86 Hz, 1H) MS (DCI/NH$_3$) m/z 317 (M+H)$^+$.

Example 9B 2-ethoxy-N-[(2Z)-3-(2-methoxyethyl)-4-(trifluoromethyl)-1,3-thiazol-2(3H)-ylidene]benzamide The product of Example 9A (0.47 g, 1.5 mmol) and 1-bromo-2-methoxy-ethane (0.16 ml, 1.6 mmol) were processed using the method described in Example 1B. Purification by column chromatography ($SiO_2$, 30-40% ethyl acetate/hexanes gradient) afforded 0.06 g (11%) of the title compound. $^1$H NNR (DMSO-$d_6$, 300 MHz) δ ppm 1.24 (t, J=6.95 Hz, 3H), 3.02 (s, 3H), 3.36-3.63 (m, 2H), 3.86-4.02 (m, 1H), 4.13 (q, J=7.12 Hz, 2H), 4.21-4.33 (m, 1H), 7.08 (t, J=7.46 Hz, 1H), 7.17 (d, J=8.14 Hz, 1H), 7.40 (dd, J=7.46, 1.70 Hz, 1H), 7.46-7.56 (m, 1H), 8.09 (s, 1H); MS (DCI/NH$_3$) m/z 375 (M+H)$^+$. Anal. Calculated for $C_{16}H_{17}F_3N_2O_3S.0.2H_2O$: C, 50.84; H, 4.64; N, 7.41. Found: C, 50.62; H, 4.35; N, 7.61.

Example 10

N-[(2Z)-3-(2-methoxyethyl)-5-methyl-1,3-thiazol-2 (3H)-ylidene]-2,2,3,3-tetramethylcyclopropanecarboxamide Example 10A 3-(2-Methoxyethyl)-5-methyl-3H-thiazol-2-ylideneamine hydrobromide A mixture of 5-methyl-thiazol-2-ylamine (1.0 g, 8.8 mmol) and 2-bromoethyl methyl ether (1.0 mL, 11 mmol) were heated at 85° C. for 16 hours. The mixture was cooled to ambient temperature, triturated with ethanol and the solid was collected by filtration to afford 0.90 g (40%) of the title compound. $^1$H NMR (CDCl$_3$, 300 MHz) δ ppm 2.25 (d, J=1.4 Hz, 3H), 3.36 (s, 3H), 3.72-3.81 (m, 2H), 4.36-4.43 (m, 2H), 6.61 (d, J=1.7 Hz, 1H), 9.54 (s, 1H); MS (DCI/NH$_3$) m/z 173 (M+H)$^+$.

Example 10B

N-[(2Z)-3-(2-methoxyethyl)-5-methyl-1,3-thiazol-2 (3H)-ylidene]-2,2,3,3-tetramethylcyclopropanecarboxamide The product of Example 10A (0.40 g, 1.6 mmol) and 2,2, 3,3-tetramethylcyclopropanecarboxylic acid (0.25 g, 1.8 mmol) were processed using the method described in Example 2B. Purification by column chromatography ($SiO_2$, 20-40% ethyl acetate/exanes gradient) afforded 0.30 g (63%) of the title compound. $^1$H NMR (CDCl$_3$, 300 MHz) δ ppm 1.21 (s, 6H), 1.33 (s, 6H), 1.52 (s, 1H), 2.22 (s, 3H), 3.35 (s, 3H), 3.68 (t, J=5.09 Hz, 2H), 4.24 (t, J=4.92 Hz, 2H), 6.67 (s, 1H); MS (DCI/NH$_3$) m/z 297 (M+H)$^+$. Anal. Calculated for $C_{15}H_{24}N_2O_2S$: C, 60.78; H, 8.16; N, 9.45. Found: C, 60.69; H, 8.31; N, 9.19.

Example 11

2-ethoxy-N-[(2Z)-3-(2-methoxyethyl)-5-methyl-1,3-thiazol-2(3H)-ylidene]benzamide To the product of Example 10A (0.55 g, 2.2 mmol) and 2-ethoxybenzoyl chloride (0.33 g, 1.8 mmol) in 10 mL of THF at 0° C. was added triethylamine (0.55 mL, 4.0 mmol). The solution was stirred at 65° C. for 4 hours then allowed to cool to ambient temperature and diluted with ethyl acetate. The solution was washed twice with water and then brine. The combined aqueous washings were extracted with ethyl acetate. The combined organic extracts were dried over magnesium sulfate, filtered, and concentrated under reduced pressure. Purification by column chromatography ($SiO_2$, 20-30% ethyl acetate/hexanes gradient) afforded 0.28 g (42%) of the title compound. $^1$H NMR (DMSO-$d_6$, 300 MHz) δ ppm 1.31 (t, J=7.0 Hz, 3H), 2.26 (d, J=1.4 Hz, 3H), 3.25 (s, 3H), 3.69 (t, J=5.3 Hz, 2H), 4.05 (q, J=7.1 Hz, 2H), 4.30 (t, J=5.3 Hz, 2H), 6.95 (t, J=7.5 Hz, 1H), 7.04 (d, J=7.8 Hz, 1H), 7.20 (d, J=1.4 Hz, 1H), 7.32-7.41 (m, 1H), 7.68 (dd, J=7.6, 1.9 Hz, 1H); MS (DCI/NH$_3$) m/z 321 (M+H)$^+$. Anal. Calculated for $C_{16}H_{20}N_2O_3S.0.2H_2O$: C, 59.31; H, 6.35; N, 8.65. Found: C, 59.18; H, 6.02; N, 8.29.

Example 12

3-fluoro-N-[(2Z)-3-(2-methoxyethyl)-4,5-dimethyl-1,3-thiazol-2(3H)-ylidene]-2-methylbenzamide

Example 12A 3-(2-Methoxyethyl)-4,5-dimethyl-3H-thiazol-2-ylideneamine hydrobromide A mixture of 4,5-dimethylthiazol-2-ylamine (9.0 g, 70 mmol) and 2-bromoethyl methyl ether (7.9 mL, 84 mmol) were heated at 85° C. for 12 hours. The mixture was cooled to ambient temperature and then triturated with isopropanol. The solid was collected by filtration and dried under vacuum to provide 10 g (56%) of the title compound. $^1$H NMR (DMSO-$d_6$, 300 MHz) δ ppm 2.17 (s, 3H), 2.19 (s, 3H), 3.25 (s, 3H) 3.56 (t, J=5.1 Hz, 2H) 4.16 (t, J=5.1 Hz, 2H) 9.41 (s, 1H); MS (DCI/NH$_3$) m/z 129 (M+H)$^+$.

Example 12B 3-fluoro-N-[(2Z)-3-(2-methoxyethyl)-4,5-dimethyl-1,3-thiazol-2(3H)-ylidene]-2-methylbenzamide The product of Example 12A (39 mg, 0.15 mmol) and 3-fluoro-2-methylbenzoic acid (31 mg, 0.22 mmol) were processed using the method described in Example 3 to afford the title compound. $^1$H NMR (500 MHz, DMSO-$d_6$) δ ppm 2.21-2.24 (m, 3H), 2.26-2.28 (m, 3H), 2.44-2.47 (m, 3H), 3.24 (s, 3H), 3.66-3.71 (m, 2H), 4.35 (t, 2H), 7.21-7.31 (m, 2H), 7.76 (d, 1H); MS (ESI) m/z 324 (M+H)$^+$.

Example 13

5-fluoro-N-[(2Z)-3-(2-methoxyethyl)-4,5-dimethyl-1,3-thiazol-2(3H)-ylidene]-2-methylbenzamide

Example 13A

5-Fluoro-2-methyl-benzoyl chloride

A solution of 5-fluoro-2-methylbenzoic acid (380 mg, 2.47 mmol) in thionyl chloride (5 mL) was heated to reflux for 3 hours. The solution was cooled to ambient temperature and the volatile components were removed under reduced pressure. The residue was dissolved in fresh toluene (10 mL) and concentrated under reduced pressure twice and then placed under high vacuum to afford the title compound (420 mg).

Example 13B 5-fluoro-N-[(2Z)-3-(2-methoxyethyl)-4,5-dimethyl-1,3-thiazol-2(3H)-ylidene]-2-methylbenzamide To a suspension of the product of Example 12A (549 mg, 2.05 mmol) and triethylamine (0.859 mL, 6.16 mmol) in THF (6 mL) were added a solution of the product from Example 13A in THF (2 mL). The mixture was heated at reflux for 14 hours, then cooled to ambient temperature and diluted with water and CH$_2$Cl$_2$. The phases were separated and the organic extract was washed with water and brine, dried (Na$_2$SO$_4$) and concentrated. The residue was dissolved in warm EtOAc (10 mL) and allowed to stand at room temperature for 14 hours. The crystals were isolated by filtration (EtOAc wash) to afford the title compound (450 mg, 68%). MS (ESI) m/z 324 (M+H)$^+$.

Example 14

3-methoxy-N-[(2Z)-3-(2-methoxyethyl)-4,5-dimethyl-1,3-thiazol-2(3H)-ylidene]-4-methylbenzamide The product of Example 12A (39 mg, 0.15 mmol) and 3-methoxy-4-methylbenzoic acid (37 mg, 0.22 mmol) were processed using the method described in Example 3 to afford the title compound. $^1$H NMR (500 MHz, DMSO-$d_6$) δ ppm 2.21 (d, 6H), 2.26 (s, 3H), 3.26 (s, 3H), 3.74 (t, 2H), 3.85 (s, 3H), 4.40 (t, 2H), 7.22 (d, 1H), 7.68-7.72 (m, 2H); MS (ESI) m/z 335 (M+H)$^+$.

Example 15

2-ethoxy-N-[(2Z)-3-(2-methoxyethyl)-4,5-dimethyl-1,3-thiazol-2(3H)-ylidene]benzamide The product of Example 12A (0.35 g, 1.3 mmol) and 2-ethoxybenzoic acid (0.43 g, 2.6 mmol) were processed using the methods described in Example 13. Purification by column chromatography (SiO$_2$, 30-50% ethyl acetate/hexanes gradient) afforded 0.078 g (18%) of the title compound. $^1$H NMR (CDCl$_3$, 300 MHz) δ ppm 1.46 (t, J=7.0 Hz, 3H), 2.18-2.31 (m, 6H), 3.30 (s, 3H), 3.78 (t, J=5.3 Hz, 2H), 4.17 (d, J=7.1 Hz, 2H), 4.37 (s, 2H), 6.89-7.04 (m, 2H), 7.36 (t, J=7.6 Hz, 1H), 7.96 (dd, J=7.8, 1.7 Hz, 1H); MS (DCI/NH$_3$) m/z 335 (M+H)$^+$. Anal. Calculated for C$_{17}$H$_{22}$N$_2$O$_3$S.0.1H$_2$O: C, 60.73; H, 6.65; N, 8.33. Found: C, 60.37; H, 6.42; N, 8.31.

Example 16

N-[(2Z)-3-(2-methoxyethyl)-4,5-dimethyl-1,3-thiazol-2(3H)-ylidene]-1-naphthamide The product of Example 12A (39 mg, 0.15 mmol) and 1-naphthoic acid (39 mg, 0.22 mmol) were processed using the method described in Example 3 to afford the title compound. $^1$H NMR (500 MHz, DMSO-$d_6$) δ ppm 2.25 (s, 3H), 2.28 (s, 3H), 3.26 (s, 3H), 3.72-3.77 (m, 2H), 4.37-4.43 (m, 2H), 7.52-7.60 (m, 3H), 7.95-7.99 (m, 1H), 8.02-8.06 (m, 1H), 8.28-8.31 (m, 1H), 9.03-9.07 (m, 1H); MS (ESI) m/z 341 (M+H)$^+$.

Example 17

N-[(2Z)-3-(2-methoxyethyl)-4,5-dimethyl-1,3-thiazol-2(3H)-ylidene]-2-naphthamide The product of Example 12A (39 mg, 0.15 mmol) and 2-napthoic acid (39 mg, 0.22 mmol) were processed using the method described in Example 3 to afford the title compound. $^1$H NMR (500 MHz, DMSO-$d_6$) δ ppm 2.24 (s, 3H) 2.29 (s, 3H) 3.28 (s, 3H) 3.80 (t, 2H) 4.49 (t, 2H) 7.55-7.62 (m, 2H) 7.95-7.99 (m, 2H) 8.08 (d, 1H) 8.26-8.29 (m, 1H) 8.76 (s, 1H); MS (ESI) m/z 341 (M+H)$^+$.

Example 18

5-chloro-2-methoxy-N-[(2Z)-3-(2-methoxyethyl)-4,5-dimethyl-1,3-thiazol-2(3H)-ylidene]benzamide The product of Example 12A (39 mg, 0.15 mmol) and 5-chloro-2-methoxybenzoic acid (41 mg, 0.22 mmol) were processed using the methods described in Example 13 to afford the title compound. MS (ESI) m/z 355 (M+H)+.

Example 19

1-hydroxy-N-[(2Z)-3-(2-methoxyethyl)-4,5-dimethyl-1,3-thiazol-2(3H)-ylidene]-2-naphthamide The product of Example 12A (39 mg, 0.15 mmol) and 1-hydroxy-2-naphthoic acid (41 mg, 0.22 mmol) were processed using the methods described in Example 13 to afford the title compound. $^1$H NMR (500 MHz, DMSO-$d_6$) δ ppm 2.27 (s, 3H), 2.31 (s, 3H), 3.28 (s, 3H), 3.80 (t, 2H), 4.44 (t, 2H) 7.36 (d, 1H), 7.53 (t, 1H), 7.61 (t, 1H), 7.86 (d, 1H), 8.06 (d, 1H), 8.28 (d, 1H), 14.38 (s, 1H); MS (ESI) m/z 357 (M+H)+.

Example 20

4-fluoro-N-[(2Z)-3-(2-methoxyethyl)-4,5-dimethyl-1,3-thiazol-2(3H)-ylidene]-1-naphthamide The product of Example 12A (39 mg, 0.15 mmol) and 4-fluoro-1-naphthoic acid (42 mg, 0.22 mmol) were processed using the method described in Example 3 to afford the title compound. $^1$H NMR (500 MHz, DMSO-$d_6$) δ ppm 2.25 (s, 3H) 2.28 (s, 3H) 3.26 (s, 3H) 3.74 (t, 2H) 4.41 (t, 2H) 7.38-7.44 (m, 1H) 7.65-7.72 (m, 2H) 8.12 (d, 1H) 8.37-8.41 (m, 1H) 9.23 (d, 1H) MS (ESI) m/z 359 (M+H)+.

Example 21

2-methoxy-N-[(2Z)-3-(2-methoxyethyl)-4,5-dimethyl-1,3-thiazol-2(3H)-ylidene]-4-(methylthio)benzamide The product of Example 12A (39 mg, 0.15 mmol) and 2-methoxy-4-methylsulfanylbenzoic acid (44 mg, 0.22 mmol) were processed using the method described in Example 3 to afford the title compound. $^1$H NMR (500 MHz, DMSO-$d_6$) δ ppm 2.20 (s, 3H) 2.23 (s, 3H) 2.53 (s, 3H) 3.24 (s, 3H) 3.68 (t, 2H) 3.81 (s, 3H) 4.29 (t, 2H) 6.83-6.87 (m, 1H) 6.87-6.90 (m, 1H) 7.75 (d, 1H) MS (ESI) m/z 367 (M+H)+.

Example 22

2-chloro-N-[(2Z)-3-(2-methoxyethyl)-4,5-dimethyl-1,3-thiazol-2(3H)-ylidene]-5-(methylthio)benzamide The product of Example 12A (39 mg, 0.15 mmol) and 2-chloro-5-methylsulfanylbenzoic acid (44 mg, 0.22 mmol) were processed using the method described in Example 3 to afford the title compound. $^1$H NMR (500 MHz, DMSO-$d_6$) δ ppm 2.23 (s, 3H) 2.27 (s, 3H) 3.24 (s, 3H) 3.29 (s, 3H) 3.69 (t, 2H) 4.33 (t, 2H) 7.30-7.33 (m, 1H) 7.39-7.42 (m, 1H) 7.67 (d, 1H) MS (ESI) m/z 371 (M+H)+.

Example 23

N-[(2Z)-3-(2-methoxyethyl)-4,5-dimethyl-1,3-thiazol-2(3H)-ylidene]-4-(trifluoromethyl)nicotinamide The product of Example 12A (0.30 g, 1.1 mmol) and 4-trifluoromethylnicotinic acid (0.43 g, 2.2 mmol) were processed as in the methods of Example 13. Purification by column chromatography (SiO$_2$, 0-20% methanol/methylene chloride gradient) afforded 0.23 g (28%) of the title compound. $^1$H NMR (CDCl$_3$, 300 MHz) δ ppm 2.26 (s, 3H), 2.29 (s, 3H), 3.30 (s, 3H), 3.72 (t, J=5.1 Hz, 2H), 4.33 (t, J=5.1 Hz, 2H), 7.59 (d, J=5.1 Hz, 1H), 8.79 (d, J=5.1 Hz, 1H), 9.23 (s, 1H); MS (DCI/NH$_3$) m/z 360 (M+H)+. Anal. Calculated for C$_{15}$H$_{16}$F$_3$N$_3$O$_2$S: C, 50.13; H, 4.49; N, 11.69. Found: C, 50.12; H, 4.33; N, 11.75.

Example 24

2-hydroxy-N-[(2Z)-3-(2-methoxyethyl)-4,5-dimethyl-1,3-thiazol-2(3H)-ylidene]benzamide The product of Example 12A (1.7 g, 9.4 mmol) and 2-hydroxybenzoic acid (1.6 g, 11 mmol) were processed using the method described in Example 2B. Purification by column chromatography (SiO$_2$, 20-40% ethyl acetate/hexanes gradient) afforded 0.91 g (32%) of the title compound. $^1$H NMR (CDCl$_3$, 300 MHz) δ ppm 2.26 (d, J=1.0 Hz, 3H), 2.29 (d, J=0.7 Hz, 3H), 3.31 (s, 3H), 3.78-3.86 (m, 2H), 4.34 (t, J=5.1 Hz, 2H), 6.89 (dt, J=7.9, 7.0, 1.0 Hz, 1H), 6.95 (dd, J=8.1, 1.0 Hz, 1H), 7.37 (dt, J=7.7, 1.9 Hz, 1H), 8.15 (dd, J=8.0, 1.9 Hz, 1H); MS (DCI/NH$_3$) m/z 307 (M+H)+. Anal. Calculated for C$_{15}$H$_{18}$N$_2$O$_3$S: C, 58.80; H, 5.92; N, 9.14. Found: C, 58.60; H, 5.86; N, 9.01.

Example 25

2-(2-methoxyethoxy)-N-[(2Z)-3-(2-methoxyethyl)-4,5-dimethyl-1,3-thiazol-2(3H)-ylidene]benzamide

Example 25A

Methyl-2-(2-Methoxy-ethoxy)-benzoate

To a solution of triphenylphosphine (0.36 g, 1.40 mmol) in 10 mL of THF at 0° C. was added diisopropyl azodicarboxylate (275 µL, 1.40 mmol). The mixture was stirred for 0.5 hours and then methyl-2-hydroxybenzoate (400 mg, 1.3 mmol) and 2-methoxyethanol (110 µL, 1.40 mmol) were added. The mixture was allowed to warm to ambient temperature and stirred for 16 hours. The mixture was concentrated under reduced pressure and the residue was used without purification. MS (DCI/NH$_3$) m/z 211 (M+H)+.

Example 25B

2-(2-Methoxy-ethoxy)-benzoic acid

A mixture of the product of Example 25A (0.27 g, 1.3 mmol) in 40% aqueous potassium hydroxide was stirred for 6 hours. The mixture was then diluted with water, made slightly acidic by the addition of 2 N aqueous HCl, and then extracted three times with ethyl acetate. The combined organic extracts were dried over magnesium sulfate, filtered, and concentrated under reduced pressure to afford 0.25 g of the title compound.

Example 25C

2-(2-Methoxy-ethoxy)-N-[3-(2-methoxyethyl)-4,5-dimethyl-3H-thiazol-2-ylidene]-benzamide The product of Example 25B (0.25 g, 1.3 mmol) and the product of Example 12A (0.28 g, 1.5 mmol) were processed using the methods described in Example 13. Purification by column chromatography (SiO$_2$, 30-60% ethyl acetate/hexanes gradient) afforded 35 mg, (7%) of the title compound.

MS (DCI/NH$_3$) m/z 365 (M+H)$^+$. Anal. Calculated for C$_{18}$H$_{24}$N$_2$O$_4$S.0.5H$_2$O: C, 57.89; H, 6.75; N, 7.50. Found: C, 57.77; H, 6.59; N, 7.44.

Example 26

5-chloro-2-ethoxy-N-[(2Z)-3-(2-methoxyethyl)-4,5-dimethyl-1,3-thiazol-2(3H)-ylidene]benzamide The product of Example 12A (97 mg, 0.52 mmol) and 5-chloro-2-ethoxybenzoic acid (95 mg, 0.47 mmol) were processed using the methods described in Example 13 to afford the title compound. $^1$H NMR (CDCl$_3$, 400 MHz) δ ppm 1.45 (t, J=6.9 Hz, 3H), 2.24 (s, 3H), 2.28 (s, 3H), 3.31 (s, 3H), 3.78 (t, J=4.8 Hz, 2H), 4.15 (q, J=7.1 Hz, 2H), 4.45 (s, 2H), 6.90 (d, J=8.6 Hz, 1H), 7.30 (dd, J=8.9, 2.8 Hz, 1H), 7.89 (d, J=2.8 Hz, 1H); MS (DCI/NH$_3$) m/z 369 (M+H)$^+$. Anal. Calculated for C$_{17}$H$_{21}$ClN$_2$O$_3$S: C, 55.35; H, 5.74; N, 7.59. Found: C, 55.13; H, 5.59; N, 7.54.

Example 27

2-ethoxy-N-[(2Z)-3-(2-methoxyethyl)-4,5-dimethyl-1,3-thiazol-2(3H)-ylidene]nicotinamide The product of Example 12A (0.40 g, 2.2 mmol) and 2-ethoxynicotinic acid (0.40 g, 2.4 mmol) were processed using the method described in Example 2B. Purification by column chromatography (SiO$_2$, 0-30% methanol/methylene chloride gradient) afforded 0.34 g (45%) of the title compound. $^1$H NMR (CDCl$_3$, 300 MHz) δ ppm 1.45 (t, J=7.1 Hz, 3H), 2.23 (s, 3H), 2.26 (s, 3H), 3.31 (s, 3H), 3.78 (t, J=5.3 Hz, 2H), 4.37 (d, J=4.7 Hz, 2H), 4.52 (q, J=7.0 Hz, 2H), 6.91 (dd, J=7.5, 4.7 Hz, 1H), 8.21 (dd, J=4.7, 2.0 Hz, 1H), 8.32 (dd, J=7.5, 2.0 Hz, 1H); MS (DCI/NH$_3$) m/z 336 (M+H)$^+$. Anal. Calculated for C$_{16}$H$_{21}$N$_3$O$_3$S.0.2H$_2$O: C, 56.68; H, 6.36; N, 12.39. Found: C, 56.65; H, 6.32; N, 12.38.

Example 28

2-chloro-N-[(2Z)-3-(2-methoxyethyl)-4,5-dimethyl-1,3-thiazol-2(3H)-ylidene]nicotinamide A mixture of 2-chloronicotinic acid (0.42 g, 2.7 mmol) and 1,1'-carbonyldiimidazole (0.43 g, 2.7 mmol) in 3 mL of ethyl acetate was stirred at ambient temperature for 4 hours. The mixture was treated with water (3 mL) and the product of Example 12A (0.45 g, 2.4 mmol) and then heated at 65° C. for 13 hours. The mixture was cooled to ambient temperature, diluted with ethyl acetate and the layers separated. The organic phase was washed with twice with water and then brine, dried over magnesium sulfate, filtered and concentrated under reduced pressure. The residue was recrystallized from methylene chloride and afforded 0.14 g (18%) of the title compound. $^1$H NMR (CDCl$_3$, 300 MHz) δ ppm 2.26 (s, 3H), 2.28 (s, 3H), 3.30 (s, 3H), 3.76 (t, J=5.1 Hz, 2H), 4.36 (t, J=5.1 Hz, 2H), 7.28-7.32 (m, 1H), 8.28 (dd, J=7.5, 2.0 Hz, 1H), 8.42 (dd, J=4.7, 2.0 Hz, 1H); MS (DCI/NH$_3$) m/z 326 (M+H)$^+$. Anal. Calculated for C$_{14}$H$_{16}$ClN$_3$O$_2$S: C, 51.61; H, 4.95; N, 12.90. Found: C, 51.57; H, 4.76; N, 12.74.

Example 29

N-[(2Z)-3-(2-methoxyethyl)-4,5-dimethyl-1,3-thiazol-2(3H)-ylidene]-2-(trifluoromethoxy)benzamide A mixture of 2-trifluoromethoxybenzoyl chloride (0.59 g, 2.6 mmol) and the product of Example 12A were processed using the method described in Example 11 to afford the title compound. $^1$H NMR (CDCl$_3$, 300 MHz) δ ppm 2.24 (s, 3H), 2.28 (s, 3H), 3.29 (s, 3H), 3.76 (t, J=4.9 Hz, 2H), 4.45 (t, J=4.7 Hz, 2H), 7.27-7.39 (m, 2H), 7.46 (td, J=7.7, 1.9 Hz, 1H), 8.06 (dd, J=7.6, 1.9 Hz, 1H); Anal. Calculated for C$_{16}$H$_{17}$F$_3$N$_2$O$_3$S: C, 51.33; H, 4.58; N, 7.48. Found: C, 51.29; H, 4.40; N, 7.37.

Example 30

5-bromo-2-ethoxy-N-[(2Z)-3-(2-methoxyethyl)-4,5-dimethyl-1,3-thiazol-2(3H)-ylidene]benzamide The product of Example 12A (0.20 g, 1.1 mmol) and 5-bromo-2-ethoxybenzoyl chloride (0.28 g, 1.1 mmol) were processed using the method described in Example 11. Purification by column chromatography (SiO$_2$, 30-60% ethyl acetate/hexanes gradient) afforded 149 mg (38%) of the title compound. $^1$H NMR (CDCl$_3$, 300 MHz) δ ppm 1.46 (t, J=7.0 Hz, 3H), 2.25 (s, 3H), 2.29 (s, 3H), 3.31 (s, 3H), 3.79 (t, J=4.6 Hz, 2H), 4.09-4.23 (m, 2H), 4.44-4.61 (m, 2H), 6.85 (d, J=8.8 Hz, 1H), 7.42-7.48 (m, 1H), 8.02 (d, J=2.7 Hz, 1H); MS (DCI/NH$_3$) m/z 415 (M+H)$^+$. Anal. Calculated for C$_{17}$H$_{21}$BrN$_2$O$_3$S: C, 49.40; H, 5.12; N, 6.78. Found: C, 49.68; H, 5.03; N, 6.71.

Example 31

N-[(2Z)-3-(2-methoxyethyl)-4,5-dimethyl-1,3-thiazol-2(3H)-ylidene]-2-(trifluoromethyl)benzamide The product of Example 12A (0.50 g, 2.7 mmol) and 2-trifluoromethylbenzoyl chloride (0.62 g, 3.0 mmol) were processed using the method described in Example 11. Purification by column chromatography (SiO$_2$, 20-40% ethyl acetate/hexanes gradient) afforded 0.43 g (44%) of the title compound. $^1$H NMR (CDCl$_3$, 300 MHz) δ ppm 2.26 (s, 3H), 2.28 (s, 3H), 3.29 (s, 3H), 3.72 (t, J=4.7 Hz, 2H), 4.41 (t, J=4.6 Hz, 2H), 7.45-7.62 (m, 2H), 7.71 (d, J=7.1 Hz, 1H), 7.86 (d, J=7.1 Hz, 1H); MS (DCI/NH$_3$) m/z 359 (M+H)$^+$. Anal. Calculated for C$_{16}$H$_{17}$F$_3$N$_2$O$_2$S: C, 53.62; H, 4.78; N, 7.82. Found: C, 53.58; H, 4.51; N, 7.70.

Example 32

2-iodo-N-[(2Z)-3-(2-methoxyethyl)-4,5-dimethyl-1,3-thiazol-2(3H)-ylidene]benzamide The product of Example 12A (0.25 g, 1.3 mmol) and 2-iodobenzoyl chloride (0.37 g, 1.4 mmol) were processed using the method described in Example 11. Purification by preparative HPLC on a Waters Symmetry C8 column (40 mm×100 mm, 7 μm particle size) using a gradient of 20% to 95% acetonitrile: 0.1% aqueous TFA over 12 minutes (15 minutes run time) at a flow rate of 70 mL/min afforded 0.12 g (23%) of the title compound. $^1$H NMR (CDCl$_3$, 300 MHz) δ ppm 2.30 (s, 3H), 2.31 (s, 3H), 3.29 (s, 3H), 3.72 (t, J=4.7 Hz, 2H), 4.41 (t, J=4.6 Hz, 2H), 7.45-7.62 (m, 2H), 7.71 (d, J=7.1 Hz, 1H), 7.86 (d, J=7.1 Hz, 1H); MS (DCI/NH$_3$) m/z 417 (M+H)$^+$.

Example 33

2-fluoro-N-[(8Z)-3-(2-methoxyethyl)-4,5-dimethyl-1,3-thiazol-2(3H)-ylidene]-5-(trifluoromethyl)benzamide The product of Example 12A (0.25 g, 1.3 mmol) and 2-fluoro-5-trifluoromethylbenzoyl chloride (0.32 g, 1.4 mmol) were processed using the method described in Example 11. Purification by preparative HPLC on a Waters Symmetry C8 column (40 mm×100 mm, 7 μm particle size) using a gradient of 20% to 95% acetonitrile: 0.1% aqueous TFA over 12 minutes (15 minutes run time) at a flow rate of 70 mL/min afforded 70 mg (14%) of the title compound. $^1$H NMR (CDCl$_3$, 300 MHz) δ ppm 2.29 (s, 3H), 231 (s, 3H), 3.33 (s, 3H), 3.73-3.89 (m, 2H), 4.44-4.57 (m, 2H), 7.18-7.24 (m, 1H), 7.68 (d, J=9.2 Hz, 1H), 8.38 (d, J=6.8 Hz, 1H); MS (DCI/NH$_3$) m/z 377 (M+H)$^+$. Anal. Calculated for C$_{16}$H$_{16}$F$_4$N$_2$O$_2$S.0.1H$_2$O: C, 51.06; H, 4.28; N, 7.44 Found: C, 50.54; H, 4.05; N, 7.27.

Example 34

2-bromo-5-methoxy-N-[(2Z)-3-(2-methoxyethyl)-4,5-dimethyl-1,3-thiazol-2(3H)-ylidene]benzamide The product of Example 12A (0.20 g, 1.1 mmol) and 2-bromo-5-methoxybenzoic acid (0.25 g, 1.1 mmol) were processed using the methods described in Example 13. Purification by preparative HPLC on a Waters Symmetry C8 column (40 mm×100 mm, 7 μm particle size) using a gradient of 20% to 95% acetonitrile: 0.1% aqueous TFA over 12 minutes (15 minutes Tun time) at a flow rate of 70 mL/min afforded 0.13 g (29%) of the title compound. $^1$H NMR (CDCl$_3$, 300 MHz) δ ppm 2.27 (s, 3H) 2.29 (s, 3H), 3.30 (s, 3H), 3.80 (t, J=4.7 Hz, 2H), 3.83 (s, 3H), 4.50-4.59 (m, 2H), 6.82 (dd, J=8.8, 3.1 Hz, 1H), 7.44 (d, J=3.1 Hz, 1H), 7.50 (d, J=8.8 Hz, 1H); MS (DCI/NH$_3$) m/z 401 (M+H)$^+$. Anal. Calculated for C$_{16}$H$_{19}$BrN$_2$O$_3$S: C, 48.13; H, 4.80; N, 7.02. Found: C, 47.88; H, 4.55; N, 6.89.

Example 35

5-fluoro-N-[(2Z)-3-(2-methoxyethyl)-4,5-dimethyl-1,3-thiazol-2(3H)-ylidene]-2-(trifluoromethyl)benzamide The product of Example 12A (0.20 g, 1.1 mmol) and 5-fluoro-2-trifluoromethylbenzoyl chloride (0.18 mL, 1.2 mmol) were processed using the method described in Example 11. Purification by preparative HPLC on a Waters Symmetry C8 column (40 mm×100 mm, 7 μm particle size) using a gradient of 20% to 95% acetonitrile: 0.1% aqueous TFA over 12 minutes (15 minutes run time) at a flow rate of 70 mL/min afforded 43 mg (11%) of the title compound. $^1$H NMR (CDCl$_3$, 300 MHz) δ ppm 2.27 (s, 3H), 2.29 (s, 3H), 3.30 (s, 3H), 3.65-3.76 (m, 2H), 4.37-4.48 (m, 2H), 7.13-7.20 (m, 1H), 7.56 (d, J=7.5 Hz, 1H), 7.71 (dd, J=9.2, 5.4 Hz, 1H); MS (DCI/NH$_3$) m/z 377 (M+H)$^+$. Anal. Calculated for C$_{16}$H$_{16}$F$_4$N$_2$O$_2$S.0.3H$_2$O: C, 50.34; H, 4.38; N, 7.34. Found: C, 49.95; H, 4.02; N, 7.09.

Example 36

N-[(2Z)-3-(2-methoxyethyl)-4,5-dimethyl-1,3-thiazol-2(3H)-ylidene]-2,5-bis(trifluoromethyl)benzamide The product of Example 12A (0.20 g, 1.1 mmol) and 2,5-bis-trifluoromethylbenzoyl chloride (0.33 g, 1.2 mmol) were processed using the method described in Example 11. Purification by preparative HPLC on a Waters Symmetry C8 column (40 mm×100 mm, 7 μm particle size) using a gradient of 20% to 95% acetonitrile: 0.1% aqueous TFA over 12 minutes (15 minutes run time) at a flow rate of 70 mL/min afforded 0.14 g (31%) of the title compound. $^1$H NMR (CDCl$_3$, 300 MHz) δ ppm 2.27 (s, 3H), 2.29 (s, 3H), 3.30 (s, 3H) 3.71 (t, J=4.9 Hz, 2H) 4.36 (t, J=5.1 Hz, 2) 7.72-7.77 (m, 1H) 7.82-7.87 (m, 1H) 8.15 (s, 1H); MS (DCI/NH$_3$) m/z 427 (M+H)$^+$. Anal. Calculated for C$_{17}$H$_{16}$F$_6$N$_2$O$_2$S: C, 47.89; H, 3.78; N, 6.57. Found: C, 47.49; H, 3.42; N, 6.38.

Example 37

2-fluoro-N-[(2Z)-3-(2-methoxyethyl)-4,5-dimethyl-1,3-thiazol-2(3H)-ylidene]-6-(trifluoromethyl)benzamide The product of Example 12A (0.20 g, 1.1 mmol) and 2-fluoro-6-trifluoromethylbenzoyl chloride (0.17 mL, 1.2 mmol) were processed using the method described in Example 11. Purification by preparative HPLC on a Waters Symmetry C8 column (40 mm×100 mm, 7 μm particle size) using a gradient of 20% to 95% acetonitrile: 0.1% aqueous TFA over 12 minutes (15 minutes run time) at a flow rate of 70 mL/min afforded 0.13 g (32%) of the title compound. $^1$H NMR (CDCl$_3$, 300 MHz) δ ppm 2.27 (s, 3H), 2.28 (s, 3H), 3.27 (s, 3H), 3.69 (t, J=4.9 Hz, 2H), 4.37 (t, J=4.6 Hz, 2H), 7.28-7.33 (m, 1H), 7.38-7.50 (m, 2H) MS (DCI/NH$_3$) m/z 377 (M+H)$^+$. Anal. Calculated for C$_{16}$H$_{16}$F$_4$N$_2$O$_2$S: C, 51.06; H, 4.28; N, 7.44. Found: C, 50.98; H, 4.07; N, 7.36.

Example 38

2-chloro-6-fluoro-N-[(2Z)-3-(2-methoxyethyl)-4,5-dimethyl-1,3-thiazol-2(3H)-ylidene]benzamide The product of Example 12A (0.20 g, 1.1 mmol) and 2-chloro-6-fluorobenzoyl chloride (0.23 g, 1.2 mmol) were processed using the method described in Example 11. Purification by preparative HPLC on a Waters Symmetry C8 column (40 mm×100 mm, 7 μm particle size) using a gradient of 20% to 95% acetonitrile: 0.1% aqueous TFA over 12 minutes (15 minutes run time) at a flow rate of 70 mL/min afforded 66 mg (18%) of the title compound. $^1$H NMR (CDCl$_3$, 300 MHz) δ ppm 2.26 (s, 3H), 2.27 (s, 3H), 3.28 (s, 3H), 3.73 (t, J=4.9 Hz, 2H), 4.35 (t, J=4.7 Hz, 2H), 6.97-7.05 (m, 1H), 7.19-7.24 (m, 2H); MS (DCI/NH$_3$) m/z 343 (M+H)$^+$. Anal. Calculated for C$_{15}$H$_{16}$ClFN$_2$O$_2$S.0.2C$_2$HF$_3$O$_2$: C, 50.59; H, 4.47; N, 7.66. Found: C, 50.70; H, 4.34; N, 7.55.

Example 39

3-fluoro-N-[(2Z)-3-(2-methoxyethyl)-4,5-dimethyl-1,3-thiazol-2(3H)-ylidene]-2-(trifluoromethyl)benzamide The product of Example 12A (0.335 g, 1.9 mmol) and 3-fluoro-2-trifluoromethylbenzoyl chloride (0.47 g, 2.1 mmol) were processed using the method described in Example 11. Purification by preparative HPLC on a Waters Symmetry C8 column (40 mm×100 mm, 7 μm particle size) using a gradient of 20% to 95% acetonitrile: 0.1% aqueous TFA over 12 minutes (15 minutes run time) at a flow rate of 70 mL/min afforded 0.14 g (20%) of the title compound. $^1$H NMR (CDCl$_3$, 300 MHz) δ ppm 2.25 (d, J=0.7 Hz, 3H), 2.27 (s, 3H), 3.28 (s, 3H), 3.68 (t, J=5.1 Hz, 2H), 4.31 (t, J=5.1 Hz, 2H), 7.18 (dd, J=11.0, 8.3 Hz, 1H), 7.38-7.42 (m, 1H), 7.52 (td, J=8.0, 5.1 Hz, 1H); MS (DCI/NH$_3$) m/z 377 (M+H)$^+$. Anal. Calculated for C$_{16}$H$_{16}$F$_4$N$_2$O$_2$S: C, 51.06; H, 4.28; N, 7.44. Found: C, 51.15; H, 3.96; N, 7.38.

Example 40

2-chloro-5-fluoro-N-[(2Z)-3-(2-methoxyethyl)-4,5-dimethyl-1,3-thiazol-2(3H)-ylidene]benzamide The product of Example 12A (0.20 g, 1.1 mmol) and 2-chloro-5-fluorobenzoyl chloride (0.23 g, 1.2 mmol) were processed using the method described in Example 11. Purification by preparative HPLC on a Waters Symmetry C8 column (40 mm×100 mm, 7 μm particle size) using a gradient of 20% to 95% acetonitrile: 0.1% aqueous TFA over 12 minutes (15 minutes run time) at a flow rate of 70 mL/min afforded 17 mg (4%) of the title compound. $^1$H NMR (DMSO-$d_6$, 500 MHz) δ ppm 2.23 (s, 3H), 226 (s, 3H), 3.22 (s, 3H), 3.68 (t, J=5.3 Hz, 2H), 433 (t, J=5.3 Hz, 2H), 7.30 (td, J=8.4, 3.1 Hz, 1H), 7.52 (dd, J=8.9, 5.2 Hz, 1H), 7.64 (dd, J=9.1, 3.3 Hz, 1H); MS (DCI/NH3) m/z 343 (M+H)$^+$. Anal. Calculated for $C_{15}H_{16}ClFN_2O_2S.0.1C_2HF_3O_2$: C, 51.54; H, 4.58; N, 7.91. Found: C, 51.68; H, 4.35; N, 7.95.

Example 41

N-[(2Z)-3-(2-methoxyethyl)-4,5-dimethyl-1,3-thiazol-2(3H)-ylidene]-2,2,3,3-tetramethylcyclopropanecarboxamide The product of Example 12A (1.5 g, 8.0 mmol) and 2,2,3,3-tetramethylcyclopropanecarboxylic acid (0.77 g, 5.4 mmol) were processed using the methods described in Example 13. Recrystallization from ethyl acetate afforded 0.99 g (60%) of the title compound. $^1$H NMR (DMSO-$d_6$, 300 MHz) δ ppm 1.16 (s, 6H), 1.23 (s, 6H), 1.44 (s, 1H), 2.13 (s, 3H), 2.19 (s, 3H), 3.24 (s, 3H), 3.61 (t, J=5.4 Hz, 2H), 4.21 (t, J=5.4 Hz, 2H); MS (DCI/NH$_3$) m/z 311 (M+H)$^+$. Anal. Calculated for $C_{16}H_{26}N_2O_2S$: C, 61.92; H, 8.44; N, 9.02. Found: C, 61.89; H, 8.38; N, 8.81.

Example 42

N-[(2Z)-3-(2-methoxyethyl)-4,5-dimethyl-1,3-thiazol-2(3H)-ylidene]-2-methylpentanamide The product of Example 12A (39 mg, 0.15 mmol) and 2-methylvaleric acid (26 mg, 0.22 mmol) were processed using the method described in Example 3 to afford the title compound. $^1$H NMR (DMSO-$d_6$, 300 MHz) δ ppm 0.85 (t, 3H) 1.09 (d, 3H) 1.20-1.28 (m, 2H) 1.32-1.40 (m, 1H) 1.59-1.67 (m, 1H) 2.19 (s, 3H) 2.22 (s, 3H) 2.52-2.57 (m, 1H) 3.24 (s, 3H) 3.63 (t, 2H) 4.26-4.33 (m, 2H) MS (EST) m/z 285 (M+H)$^+$.

Example 43

N-[(2Z)-3-(2-methoxyethyl)-4,5-dimethyl-1,3-thiazol-2(3H)-ylidene]-2,2-dimethylbutanamide The product of Example 12A (39 mg, 0.15 mmol) and 2,2-dimethylbutyric acid (26 mg, 0.22 mmol) were processed using the method described in Example 3 to afford the title compound. $^1$H NMR (DMSO-$d_6$, 300 MHz) δ ppm 0.72 (t, 3H) 1.11 (s, 6H) 1.53-1.59 (m, 2H) 2.15 (s, 3H) 2.19 (s, 3H) 3.24 (s, 3H) 3.63 (t, 2H) 4.22 (t, 2H) MS (ESI) m/z 285 (M+H)$^+$.

Example 44

2-ethyl-N-[(2Z)-3-(2-methoxyethyl)-4,5-dimethyl-1,3-thiazol-2(3H)-ylidene]butanamide The product of Example 12A (39 mg, 0.15 mmol) and 2-ethylbutyric acid (26 mg, 0.22 mmol) were processed using the method described in Example 3 to afford the title compound. $^1$H NMR (DMSO-$d_6$, 300 MHz) δ ppm 0.80 (t, 6H) 1.48 (s, 2H) 1.56-1.65 (m, 2H) 2.19 (s, 3H) 2.23 (s, 3H) 2.27-2.33 (m, 1H) 3.23 (s, 3H) 3.63 (t, 2H) 4.24-4.33 (m, 2H) MS (ESI) m/z 285 (M+H)$^+$.

Example 45

N-[(2Z)-3-(2-methoxyethyl)-4,5-dimethyl-1,3-thiazol-2(3H)-ylidene]cyclohexanecarboxamide The product of Example 12A (39 mg, 0.15 mmol) and cyclohexanecarboxylic acid (28 mg, 0.22 mmol) were processed using the method described in Example 3 to afford the title compound. $^1$H NMR (DMSO-$d_6$, 300 MHz) δ ppm 1.23-1.32 (m, 2H) 1.34-1.43 (m, 2H) 1.58-1.65 (m, 1H) 1.67-1.74 (m, 2H) 1.83-1.89 (m, 2H) 2.19 (s, 3H) 2.23 (s, 3H) 2.35-2.42 (m, 1H) 3.24 (s, 3H) 3.64 (t, 2H) 4.31 (t, 3H) MS (ESI) m/z 297 (M+H)$^+$.

Example 46

N-[(2Z)-3-(2-methoxyethyl)-4,5-dimethyl-1,3-thiazol-2(3H)-ylidene]-1-methylcyclohexanecarboxamide The product of Example 12A (0.30 g, 1.1 mmol) and 1-methylcyclohexane-carboxylic acid (0.32 g, 2.2 mmol) were processed using the methods described in Example 13. Purification by column chromatography (SiO$_2$, 30-50% ethyl acetate/hexanes gradient) afforded 80 mg (23%) of the title compound. $^1$H NMR (CDCl$_3$, 300 MHz) δ ppm 1.16 (s, 3H), 1.19-1.58 (m, 10H), 2.18 (s, 3H), 2.20 (s, 3H), 3.30 (s, 3H), 3.69 (t, J=5.3 Hz, 2H), 4.19-4.31 (m, 2H); MS (DCI/NH$_3$) m/z 311 (M+H)$^+$. Anal. Calculated for $C_{16}H_{26}N_2O_2S$: C, 61.90; H, 8.44; N, 9.02. Found: C, 61.86; H, 8.80; N, 9.02.

Example 47 cis-N-[(2Z)-3-(2-Methoxyethyl)-4,5-dimethyl-1,3-thiazol-2(3-ylidene]-2-methylcyclohexanecarboxamide The product of Example 12A (0.30 g, 1.1 mmol) and (cis)-2-methyl-cyclohexanecarboxylic acid (0.32 g, 2.2 mmol) were processed using the methods described in Example 13. Purification by column chromatography (SiO$_2$, 30-50% ethyl acetate/hexanes gradient) afforded 0.24 g (68%) of the title compound. $^1$H NMR (CDCl$_3$, 300 MHz) δ ppm 0.85 (d, J=7.1 Hz, 3H), 1.36-1.84 (m, 8H), 2.17 (s, 3H), 2.20 (s, 3H), 2.31-2.42 (m, 1H), 2.53-2.65 (m, 1H), 3.29 (s, 3H), 3.69 (t, J=4.2 Hz, 2H), 4.17-4.29 (m, 2H); MS (DCI/NH$_3$) m/z 311 (M+H)$^+$. Anal. Calculated for $C_{16}H_{26}N_2O_2S$: C, 61.90; H, 8.44; N, 9.02. Found: C, 62.15; H, 8.70; N, 8.73.

Example 48

N-[(2Z)-3-(2-methoxyethyl)-4,5-dimethyl-1,3-thiazol-2(3H)-ylidene]-4-methylcyclohexanecarboxamide The product of Example 12A (39 mg, 0.15 mmol) and 4-methylcyclohexanecarboxylic acid (31 mg, 0.22 mmol)

were processed using the methods described in Example 13 to afford the title compound. $^1$H NMR (DMSO-d$_6$, 300 MHz) δ ppm 0.84-0.89 (m, 3H) 1.15-1.23 (m, 2H) 1.47-1.56 (m, 4H) 1.95-2.03 (m, 2H) 2.19 (s, 3H) 2.23 (s, 3H) 3.24 (s, 3H) 3.60-3.67 (m, 2H) 4.26-4.36 (m, 4H) MS (ESI) m/z 311 (M+H)$^+$.

Example 49

N-[(2Z)-3-(2-methoxyethyl)-4,5-dimethyl-1,3-thiazol-2(3H)-ylidene]cycloheptanecarboxamide The product of Example 12A (39 mg, 0.15 mmol) and cycloheptanecarboxylic acid (31 mg, 0.22 mmol) were processed using the methods described in Example 13 to afford the title compound. $^1$H NMR (DMSO-d$_6$, 300 MHz) δ ppm 1.45-1.52 (m, 4H) 1.54-1.56 (m, 2H) 1.60-1.70 (m, 4H) 1.85-1.92 (m, 2H) 2.19 (s, 3H) 2.23 (s, 3H) 2.55-2.61 (m, 1H) 3.24 (s, 3H) 3.61-3.66 (m, 2H) 4.27-4.34 (m, 2H) MS (ESI) m/z 311 (M+H)$^+$.

Example 50

(1S)—N-[(2Z)-3-(2-methoxyethyl)-4,5-dimethyl-1,3-thiazol-2(3H)-ylidene]spiro[2.5]octane-1-carboxamide The product of Example 12A and (1S)-spiro[2.5]octane-1-carboxylic acid (Bennani, Y. L., et al. US 20042043961) were processed using the methods described in Example 13 to provide the title compound. MS (DCI/NH$_3$) m/z 323 (M+H)$^+$.

Example 51

(2R)—N-[(2Z)-3-(2-methoxyethyl)-4,5-dimethyl-1,3-thiazol-2(3H)-ylidene]-2-propylhex-4-ynamide The product of Example 12A (0.30 g, 1.1 mmol) and (2R)-propyl-hex-4-ynoic acid (0.35 g, 2.2 mmol) were processed using the methods described in Example 13. Purification by column chromatography (SiO$_2$, 20-30% ethyl acetate/hexanes gradient) afforded 0.30 g (82%) of the title compound. $^1$H NMR (CDCl$_3$, 300 MHz) δ ppm 0.90 (t, J=7.5 Hz, 3H), 1.27-1.39 (m, 2H), 1.62-1.72 (m, 2H), 1.75 (t, J=2.4 Hz, 3H), 2.19 (s, 3H), 2.22 (s, 3H), 2.31-2.74 (m, 3H), 3.29 (s, 3H), 3.65-3.75 (m, 2H), 4.16-4.33 (m, 2H); MS (DCI/NH$_3$) m/z 323 (M+H)$^+$. Anal. Calculated for C$_{17}$H$_{26}$N$_2$O$_2$S: C, 63.32; H, 8.13; N, 8.69. Found: C, 63.12; H, 8.35; N, 8.51.

Example 52

(1S,3R,5S)—N-[(2Z)-3-(2-methoxyethyl)-4,5-dimethyl-1,3-thiazol-2(3H)-ylidene]-3,5-dimethylcyclohexanecarboxamide The product of Example 12A (0.30 g, 1.1 mmol) and (1S,3R,5S)-dimethylcyclohexanecarboxylic acid (0.35 g, 2.2 mmol) were processed using the methods described in Example 13. Purification by column chromatography (SiO$_2$, 20-40% ethyl acetate/hexanes gradient) afforded 0.12 g (33%) of the title compound. $^1$H NMR (CDCl$_3$, 300 MHz) δ ppm 0.91 (s, 3H), 0.92-0.94 (m, 3H), 1.01-1.13 (m, 2H), 1.61-1.69 (m, 3H), 1.90-2.00 (m, 3H), 2.19 (s, 3H), 2.21-2.25 (m, 3H), 2.26-2.30 (m, 1H), 3.30 (s, 3H), 3.71 (t, J=5.3 Hz, 2H), 4.19-4.44 (m, 2H); MS (DCI/NH$_3$) m/z 325 (M+H)$^+$. Anal. Calculated for C$_{17}$H$_{28}$N$_2$O$_2$S: C, 62.93; H, 8.70; N, 8.63. Found: C, 63.29; H, 8.91; N, 8.71.

Example 53

(9R,1R,8S)—N-[(2Z)-3-(2-methoxyethyl)-4,5-dimethyl-1,3-thiazol-2(3H)-ylidene]bicyclo[6.1.0]nonane-9-carboxamide (exo)-Bicyclo[6.1.0]nonane-9-carboxylic acid (0.38 g, 2.2 mmol, Bennani, Y. L., et al., US2004077617) and the product of Example 12A (0.30 g, 1.1 mmol) were processed using the methods described in Example 13. Purification by column chromatography (SiO$_2$, 20-35% ethyl acetate/hexanes gradient) afforded 0.27 g (72%) of the title compound. $^1$H NMR (CDCl$_3$, 300 MHz) δ ppm 1.03-1.20 (m, 1H), 1.29-1.51 (m, 6H), 1.52-1.77 (m, 6H), 2.07 (dd, J=14.1, 2.9 Hz, 2H), 2.17 (s, 3H), 2.20 (s, 3H), 3.31 (s, 3H), 3.70 (t, J=4.9 Hz, 2H), 4.20-4.30 (m, 2H); MS (DCI/NH$_3$) m/z 337 (M+H)$^+$. Anal. Calculated for C$_{18}$H$_{28}$N$_2$O$_2$S: C, 64.25; H, 8.39; N, 8.32. Found: C, 64.06; H, 8.54; N, 8.22.

Example 54

(9S,1R,8S)—N-[(2Z)-3-(2-methoxyethyl)-4,5-dimethyl-1,3-thiazol-2(3H)-ylidene]bicyclo[6.1.0]nonane-9-carboxamide (exo)-Bicyclo[6.1.0]nonane-9-carboxylic acid (0.38 g, 2.2 mmol, Bennani, Y. L., et al., US2004077617) and the product of Example 12A (0.30 g, 1.1 mmol) were processed using the methods described in Example 13. Purification by column chromatography (SiO$_2$, 20-30% ethyl acetate/hexanes gradient) afforded 70 mg (19%) of the title compound. $^1$H NMR (CDCl$_3$, 300 MHz) δ ppm 1.17-1.29 (m, 2H), 1.34-1.49 (m, 6H), 1.57-1.76 (m, 6H), 1.95-2.04 (m, 1H), 2.15 (s, 3H), 2.20 (s, 3H), 3.30 (s, 3H), 3.70 (t, J=5.3 Hz, 2H), 4.24 (t, J=5.3 Hz, 2H); MS (DCI/NH$_3$) m/z 337 (M+H)$^+$. Anal. Calculated for C$_{18}$H$_{28}$N$_2$O$_2$S: C, 64.25; H, 8.39; N, 8.32. Found: C, 64.33; H, 8.52; N, 8.23.

Example 55

(1R,6R,7R)—N-[(2Z)-3-(2-methoxyethyl)-4,5-dimethyl-1,3-thiazol-2(3H)-ylidene]-1-methylbicyclo[4.1.0]heptane-7-carboxamide The product of Example 12A (0.30 g, 1.1 mmol) and 1-methylbicyclo[4.1.0]heptane-7-carboxylic acid (0.35 g, 2.2 mmol, Bennani, Y. L., et al., US2004077617) were processed using the methods described in Example 13. Purification by column chromatography (SiO$_2$, 20-35% ethyl acetate/hexanes gradient) afforded 40 mg (11%) of the title compound. $^1$H NMR (CDCl$_3$, 300 MHz) δ ppm 1.15-1.42 (m, 7H), 1.58-1.72 (m, 3H), 1.77 (d, J=5.4 Hz, 1H), 1.84-2.04 (m, 2H), 2.15 (s, 3H), 2.19 (s, 3H), 3.28-3.33 (m, 3H), 3.69 (t, J=5.3 Hz, 2H), 4.12-4.39 (m, 2H); MS (DCI/NH$_3$) m/z 323 (M+H)$^+$. Anal. Calculated for C$_{17}$H$_{26}$N$_2$O$_2$S: C, 63.32; H, 8.13; N, 8.69. Found: C, 63.35; H, 8.3; N, 8.56.

Example 57

2,2,3,3-Tetramethylcyclopropanecarboxylic acid [4,5-dimethyl-3-(2-phenoxy-ethyl)-3H-thiazol-2-ylidene]-amide

Example 57A

4,5-Dimethyl-3-(2-phenoxy-ethyl)-3H-thiazol-2-ylideneamine hydrobromide

A mixture of 4,5-dimethylthiazol-2-ylamine (1.0 g, 7.8 mmol) and (2-bromo-ethoxy)benzene (1.9 g, 9.4 mmol) were heated neat to 85° C. for 19 hours. The mixture was cooled to ambient temperature and the residue was crystallized from isopropanol. The solid was collected by filtration and dried under vacuum to afford 1.3 g (50%) of the title compound. MS (DCI/NH$_3$) m/z 249 (M+H)$^+$.

Example 57B

2,2,3,3-Tetramethylcyclopropanecarboxylic acid [4,5-dimethyl-3-(2-phenoxy-ethyl)-3H-thiazol-2-ylidene]-amide The product of Example 57A (0.40 g, 1.2 mmol) and 2,2,3,3-tetramethylcyclopropanecarboxylic acid (0.19 g, 1.3 mmol) were processed using the methods described in Example 13. Purification by column chromatography (SiO$_2$, 20-40% ethyl acetate/hexanes gradient) afforded 0.14 g (34%) of the title compound. $^1$H NMR (CDCl$_3$, 500 MHz) δ ppm 1.22 (s, 6H), 1.32-1.35 (m, 6H), 1.56 (s, 1H), 2.15 (s, 3H), 2.27 (s, 3H), 4.32 (t, J=5.5 Hz, 2H), 4.44 (t, J=5.3 Hz, 2H), 6.90 (d, J=8.1 Hz, 2H), 6.95 (t, J=7.3 Hz, 1H), 7.25-7.29 (m, 2H); MS (DCI/NH$_3$) m/z 373 (M+H)$^+$. Anal. Calculated for C$_{21}$H$_{28}$N$_2$O$_2$S: C, 67.71; H, 7.58; N, 7.52. Found: C, 67.31; H, 7.70; N, 7.30.

Example 58

N-[(2Z)-3-(2-methoxyethyl)-4,5-dimethyl-1,3-thiazol-2(3H)-ylidene]-2,2-dimethyltetrahydro-2H-pyran-4-carboxamide A mixture of the product of Example 12A (150 mg, 0.56 mmol), 2,2-dimethyl-tetrahydro-pyran-4-carboxylic acid (127 mg, 0.56 mmol), N-(3-dimethylaminopropyl)-N-ethyl-carbodiimide hydrochloride (133 mg, 0.70 mmol), 1-hydroxybenzotriazole (94.5 mg, 0.70 mmol) and triethylamine (312 µL, 2.24 mmol) in 5 mL of THF were stirred overnight at room temperature. The reaction mixture was diluted with ethyl acetate and washed with 1 M aqueous NaHCO$_3$ and brine. The organic extract was dried (Na$_2$SO$_4$), filtered and concentrated. Purification of the residue by chromatography afforded the title compound: $^1$H NMR (400 MHz, DMSO-d$_6$) δ 1.13 (s, 3H) 1.16 (s, 3H) 1.33-1.53 (m, 2H) 1.67-1.77 (m, 2H) 2.16 (s, 3H) 2.20 (s, 3H) 2.59-2.72 (m, 1H) 3.24 (s, 3H) 3.53-3.61 (m, 2H) 3.63 (t, J=5.1 Hz, 2H) 4.24 (t, J=5.4 Hz, 2H); MS (ESI+) m/z 327 (M+H)$^+$.

Example 59

2,2,3,3-tetrafluoro-N-[(2Z)-3-(2-methoxyethyl)-4,5-dimethyl-1,3-thiazol-2(3H)-ylidene]-1-methylcyclobutanecarboxamide The product of 12A (0.30 g, 1.6 mmol) and 2,2,3,3-tetrafluoro-1-methyl-cyclobutanecarborboxylic acid (0.37 g, 1.8 mmol) were processed using the methods described in Example 13. Purification by column chromatography (SiO$_2$, 30-45% ethyl acetate/hexanes gradient) afforded 0.15 g (27%) of the title compound. $^1$H NMR (CDCl$_3$, 300 MHz) δ ppm 1.59 (s, 3H), 2.23 (s, 3H), 2.25 (s, 3H), 2.29-2.43 (m, 1H), 3.29 (s, 3H), 3.31-3.46 (m, 1H), 3.70 (t, J=5.1 Hz, 2H), 4.26-4.48 (m, 2H); MS (DCI/NH$_3$) m/z 355 (M+H)$^+$. Anal. Calculated for C$_{14}$H$_{18}$F$_4$N$_2$O$_2$S: C, 47.45; H, 5.12; N, 7.91. Found: C, 47.41; H, 5.04; N, 7.81.

Example 60

1-hydroxy-N-[(2Z)-3-(2-methoxyethyl)-4,5-dimethyl-1,3-thiazol-2(3H)-ylidene]cyclohexanecarboxamide Commercially available 1-hydroxy-cyclohexanecarboxylic acid and the product of Example 12A were processed using the method described in Example 58 to afford the title compound. $^1$H NMR (300 MHz, DMSO-d$_6$) δ ppm 1.09-1.32 (m, 1H), 1.36-1.68 (m, 7H), 1.72-1.88 (m, 2H), 2.18 (s, 3H), 2.22 (s, 3H), 3.23 (s, 3H), 3.64 (t, J=5.3 Hz, 2H), 4.29 (t, J=5.4 Hz, 2H), 4.34 (s, 1H); MS (ESI$^+$) m/z 335 (M+Na)$^+$; Anal. Calculated for C$_{15}$H$_{24}$N$_2$O$_3$S: C, 57.66; H, 7.74; N, 8.97. Found: C, 57.76; H, 7.80; N, 8.88.

Example 61

1-({[(2Z)-4,5-dimethyl-1,3-thiazol-2(3H)-ylidene]amino}carbonyl)cyclohexyl propionate Propionyloxy-cyclohexanecarboxylic acid (Hartmann, Willy et al., Synthesis (1989), 4, 272-4) and the product from Example 12A were processed using the method described in Example 58 to afford the title compound. $^1$H NMR (300 MHz, DMSO-d$_6$) δ ppm 1.03 (t, J=7.5 Hz, 3H), 1.15-1.34 (m, 1H) 1.36-1.66 (m, 5H), 1.75 (td, J=13.1, 4.1 Hz, 2H), 2.01-2.13 (m, 2H), 2.16 (s, 3H), 2.20 (s, 3H), 2.32 (q, J=7.5 Hz, 2H), 3.22 (s, 3H), 3.58 (t, J=5.4 Hz, 2H), 4.19 (t, J=5.4 Hz, 2H); MS (ESI$^+$) m/z 369 (M+H)$^+$; Anal. Calculated for C$_{18}$H$_{28}$N$_2$O$_4$S: C, 58.67; H, 7.66; N, 7.60. Found: C, 58.46; H, 7.64; N, 7.75.

Example 62

N-[(2Z)-3-(2-methoxyethyl)-1,3-benzothiazol-2(3H)-ylidene]-2,2,3,3-tetramethylcyclopropanecarboxamide

Example 62A

2,2,3,3-Tetramethylcyclopropanecarboxylic acid benzothiazol-2-ylamide

A mixture of 2,2,3,3-tetramethylcyclopropanecarboxylic acid (0.50 g, 3.5 mmol) and benzothiazol-2-ylamine (0.58 g, 3.9 mmol) were processed as in Example 9A. Purification by column chromatography (SiO$_2$, 20-40% ethyl acetate/hexanes gradient) afforded 0.26 g (27%) of the title compound. $^1$H NMR (CDCl$_3$, 300 MHz) δ ppm 1.22-1.27 (m, 6H), 1.36 (s, 6H), 1.67 (s, 1H), 2.07-2.18 (m, 2H), 3.34 (s, 3H), 3.41 (t, J=5.8 Hz, 2H), 4.39-4.53 (m, 2H), 7.20-7.26 (m, 1H), 7.37-7.42 (m, 2H), 7.60 (d, J=7.5 Hz, 1H); MS (DCI/NH$_3$) m/z 275 (M+H)$^+$.

Example 62B

2,2,3,3-Tetramethylcyclopropanecarboxylic acid [3-(2-methoxyethyl)-3H-benzothiazol-2-ylidene]-amide The product of Example 62A (0.12 g, 0.43 mmol), 2-bromoethyl methyl ether (0.44 mL, 4.7 mmol) and potassium hydroxide (56 mg, 1.0 mmol) were processed using the method described in Example 1B. Purification by column chromatography (SiO$_2$, 20-50% ethyl acetate/hexanes gradient) afforded 12 nmg (8%) of the title compound. $^1$H NMR (CDC$_3$, 300 MHz) δ ppm 1.25 (s, 6H), 1.36 (s, 6H), 1.66 (s, 1H), 3.34 (s, 3H), 3.79 (t, J=5.6 Hz, 2H), 4.53 (t, J=5.6 Hz, 2H), 7.21-7.25 (m, 1H), 7.37-7.42 (m, 2H), 7.58 (d, J=7.8 Hz, 1H); MS (DCI/NH$_3$) m/z 371 (M+H)$^+$. Anal. Calculated for C$_{18}$H$_{24}$N$_2$O$_2$S: C, 65.03; H, 7.28; N, 8.43. Found. C, 64.94; H, 7.10; N, 8.40.

Example 63

N-[(2Z)-3-(3-methoxypropyl)-1,3-benzothiazol-2(3H)-ylidene]-2,2,3,3-tetramethylcyclopropanecarboxamide

Example 63A

3-(3-Methoxy-propyl)-3H-benzothiazol-2-ylidene-amine hydrobromide

Benzothiazol-2-ylamine (1.0 g, 6.6 mmol) and 1-bromo-3-methoxy-propane (1.2 g, 7.9 mmol) were processed using the method described in Example 12A. Recrystallization from ethyl acetate provided 1.7 g (89%) of the title compound. $^1$H NMR (DMSO-d$_6$, 300 MHz) δ ppm 1.90-2.02 (m, 2H), 3.18 (s, 3H), 3.39 (t, J=5.9 Hz, 2H), 4.31 (t, J=7.1 Hz, 2H), 7.37-7.48 (m, 1H), 7.53-7.69 (m, 2H), 8.00 (dd, J=8.0, 0.8 Hz, 1H), 10.08 (s, 1H); MS (DCI/NH$_3$) m/z 233 (M+H)$^+$.

Example 63B

2,2,3,3-Tetramethylcyclopropanecarboxylic acid [3-(3-methoxy-propyl)-3H-benzothiazol-2-ylidene)-amide The product of Example 63A (0.40 g, 1.3 mmol) and 2,2,3,3-Tetramethylcyclopropanecarboxylic acid (0.19 g, 1.3 mmol) were processed using the methods described in Example 13. Purification by column chromatography (SiO$_2$, 20-30% ethyl acetate/hexanes gradient) afforded 0.32 g (70%) of the title compound. $^1$H NMR (CDCl$_3$, 300 MHz) δ ppm 1.26 (s, 6H), 1.36 (s, 6H), 1.64 (br s, 1H), 1.71 (s, 1H), 3.87 (s, 3H), 7.27-7.32 (m, 2H), 7.40-7.47 (m, 1H), 7.62 (d, J=7.5 Hz, 1H); MS (DCI/NH$_3$) m/z 289 (M+H)$^+$. Anal. Calculated for C$_{16}$H$_{20}$N$_2$O$_2$S: C, 65.86; H, 7.56; N, 8.08. Found: C, 65.54; H, 7.65; N, 7.81.

Example 64

N-[(2Z)-3-(2-methoxyethyl)-1,3-benzothiazol-2(3H)-ylidene]-3-phenylpropanamide

Example 64A

3-(2-Methoxyethyl)-3H-benzothiazol-2-ylideneamine hydrobromide

Benzothiazol-2-ylamine (10.0 g, 66.6 mmol) and 2-bromoethyl methyl ether (9.39 mL, 99.9 mmol) were combined and heated at 85° C. for 6 hours. The dark solid was triturated with EtOH then filtered and dried under vacuum to afford the title compound (15.8 g, 82%). $^1$H NMR (DMSO-d$_6$, 300 MHz) δ ppm 3.23 (s, 3H), 3.69 (t, J=5.1 Hz, 2H), 4.51 (t, J=5.1 Hz, 2H), 7.42 (dt, J=1.0, 8.0 Hz, 1H), 7.56 (m, 1H), 7.72 (d, J=8.0 Hz, 1H), 8.00 (dd, J=1.1, 8.0 Hz, 1H), 10.16 (br s, 2H); MS (DCI/NH$_3$) m/z 209 (M+H)$^+$.

Example 64B

N-[3-(2-Methoxyethyl)-3H-benzothiazol-2-ylidene]-3-phenylpropionamide

The product of Example 64A (39 mg, 0.14 mmol) and hydrocinnamic acid (26 mg, 0.17 mmol) were processed using the method described in Example 3 to afford the title compound. $^1$H NMR (500 MHz, DMSO-d$_6$) δ ppm 2.77-2.85 (m, 2H) 2.92-3.05 (m 2H) 3.19-3.25 (m, 3H) 3.76 (t, 2H) 4.52 (t, 2H) 7.08-7.19 (m, 1H) 7.22-7.37 (m, 5H) 7.41-7.53 (m, 1H) 7.59-7.74 (m, 1H) 7.75-8.03 (m, 1H); MS(ESI) m/z 341 (M+H)$^+$.

Example 65

(2S)—N-[(2Z)-3-(2-methoxyethyl)-1,3-benzothiazol-2(3H)-ylidene]-2-phenylbutanamide The product of Example 64A (39 mg, 0.14 mmol) and (S)-(+)-2-phenylbutyric acid (26 mg, 0.17 mmol) were processed using the method described in Example 3 to afford the title compound. $^1$H NMR (500 MHz, DMSO-d$_6$) δ ppm 0.89 (t, 3H) 1.69-1.89 (m, 1H) 2.04-2.23 (m, 1H) 3.11-3.20 (m, 3H) 3.57-3.76 (m, 3H) 4.54 (t, 2H) 7.17-7.23 (m, 1H) 7.27-7.41 (m, 5H) 7.43-7.53 (m, 1H) 7.61-7.71 (m, 1H) 7.74-7.88 (m, 1H); MS(ESI) m/z 355 (M+H)$^+$.

Example 66

N-[(2Z)-3-(2-methoxyethyl)-1,3-benzothiazol-2(3H)-ylidene]-4-thien-2-ylbutanamide The product of Example 64A (39 mg, 0.14 mmol) and 4-(2-thienyl)butyric acid (29 mg, 0.17 mmol) were processed using the method described in Example 3 to afford the title compound. $^1$H NMR (500 MHz, DMSO-d$_6$) δ ppm 1.86-2.08 (m, 2H) 2.55 (t, 2H) 2.87 (t, 2H) 3.17-3.24 (m, 3H) 3.72 (t, 2H) 4.54 (t, 2H) 6.83-6.89 (m, 1H) 6.90-7.01 (m, 1H) 7.22-7.37 (m, 2H) 7.42-7.55 (m, 1H) 7.64-7.72 (m, 1H) 7.75-7.88 (m, 1H); MS(ESI) m/z 361 (M+H)$^+$.

Example 67

N$^2$-acetyl-N$^1$-[3-(2-methoxyethyl)-1,3-benzothiazol-2(3H)-ylidene]-L-leucinamide The product of Example 64A (39 mg, 0.14 mmol) and N-acetyl-L-leucine (29 mg, 0.17 mmol) were processed using the method described in Example 3 to afford the title compound. $^1$H NMR (500 MHz, DMSO-d$_6$) δ ppm 0.78-1.07 (m, 6H) 1.43-1.57 (m, 1H) 1.57-1.75 (m, 2H) 1.81-1.92 (m, 3H) 3.22-3.26 (m, 3H) 3.72 (t, 2H) 4.44-4.55 (m, 1H) 4.55-4.67 (m, 2H) 7.24-7.40 (m, 1H) 7.43-7.54 (m, 1H) 7.62-7.73 (m, 1H) 7.79-7.92 (m, 1H) 7.95-8.07 (m, 1H); MS(ESI) m/z 364 (M+H)$^+$.

Example 68

3-(2-chlorophenyl)-N-[(2Z)-3-(2-methoxyethyl)-1,3-benzothiazol-2(3H)-ylidene]propanamide The product of Example 64A (39 mg, 0.14 mmol) and 3-(2-chlorophenyl)propionic acid (31 mg, 0.17 mmol) were processed using the method described in Example 3 to afford the title compound. $^1$H NMR (500 MHz, DMSO-d$_6$) δ ppm 2.82 (t, 2H) 3.08 (t, 2H) 3.18-3.25 (m, 3H) 3.79 (t, 2H) 4.54 (t, 2H) 7.17-7.29 (m, 2H) 7.30-7.44 (m, 3H) 7.45-7.54 (m, 1H) 7.59-7.75 (m, 1H) 7.76-7.93 (m, 1H).

Example 69

N-[(2Z)-3-(2-methoxyethyl)-1,3-benzothiazol-2(3H)-ylidene]-3-methyl-2-phenylpentanamide The product of Example 64A (39 mg, 0.14 mmol) and 3-methyl-2-phenylvaleric acid (33 mg, 0.17 mmol) were processed using the method described in Example 3 to afford the title compound. $^1$H NMR (500 MHz, DMSO-d$_6$) δ ppm 0.59-0.68 (m, 2H) 0.72-0.82 (m, 2H) 0.84-0.98 (m, 3H) 1.08-1.27 (m, 1H) 2.21-2.39 (m, 1H) 3.11-3.24 (m, 3H) 3.38-3.50 (m, 1H) 3.65-3.82 (m, 2H) 4.57 (t, 2H) 7.16-7.23 (m, 1H) 7.25-7.36 (m, 3H) 7.37-7.54 (m, 3H) 7.60-7.73 (m, 1H) 7.75-7.88 (m, 1H); MS(ESI) m/z 383 (M+H)$^+$.

Example 70

4-ethyl-N-[(2Z)-3-(2-methoxyethyl)-1,3-benzothiazol-2(3H)-ylidene]benzamide

The product of Example 64A (39 mg, 0.14 mmol) and 4-ethylbenzoic acid (26 mg, 0.17 mmol) were processed using the method described in Example 3 to afford the title compound. $^1$H NMR (500 MHz, DMSO-d$_6$) δ ppm 1.22 (t, 3H) 2.66-2.72 (m, 2H) 3.25-3.26 (m, 3H) 3.85 (t, 2H) 4.75 (t, 2H) 7.31-7.42 (m, 3H) 7.47-7.60 (m, 1H) 7.68-7.79 (m, 1H) 7.85-7.94 (m, 1H) 8.12-8.23 (m, 2H); MS (ESI) m/z 341 (M+H)$^+$.

Example 71

3-fluoro-N-[(2Z)-3-(2-methoxyethyl)-1,3-benzothiazol-2(3H)-ylidene]-2-methylbenzamide The product of Example 64A (39 mg, 0.14 mmol) and 3-fluoro-2-methylbenzoic acid (26 mg, 0.17 mmol) were processed using the method described in Example 3 to afford the title compound. $^1$H NMR (500 MHz, DMSO-d$_6$) δ ppm 2.51-2.53 (m, 3H) 3.22-3.25 (m, 3H) 3.80 (t, 2H) 4.69 (t, 2H) 7.26-7.43 (m, 3H) 7.50-7.61 (m, 1H) 7.70-7.79 (m, 1H) 7.86-7.99 (m, 2H); MS (ESI) m/z 345 (M+H)$^+$.

Example 72

5-fluoro-N-[(2Z)-3-(2-methoxyethyl)-1,3-benzothiazol-2(3H)-ylidene]-2-methylbenzamide The product of Example 64A (39 mg, 0.14 mmol) and 5-fluoro-2-methylbenzoic acid (26 mg, 0.17 mmol) were processed using the method described in Example 3 to afford the title compound. $^1$H NMR (500 MHz, DMSO-d$_6$) δ ppm 2.51-2.53 (m, 3H) 3.22-3.25 (m, 3H) 3.80 (t, 2H) 4.69 (t, 2H) 7.26-7.43 (m, 3H) 7.50-7.61 (m, 1H) 7.70-7.79 (m, 1H) 7.86-7.99 (m, 2H); MS (ESI) m/z 345 (M+H)$^+$.

Example 73

3-fluoro-N-[(2Z)-3-(2-methoxyethyl)-1,3-benzothiazol-2(3H)-ylidene]-4-methylbenzamide The product of Example 64A (39 mg, 0.14 mmol) and 5-fluoro-4-methylbenzoic acid (26 mg, 0.17 mmol) were processed using the method described in Example 3 to afford the title compound. $^1$H NMR (500 MHz, DMSO-d$_6$) δ ppm 2.31-234 (m, 3H) 3.23-3.26 (m, 3H) 3.83 (t, 2H) 4.77 (t, 2H) 7.33-7.40 (m, 1H) 7.41-7.49 (m, 1H) 7.49-7.59 (m, 1H) 7.69-7.78 (m, 1H) 7.86-7.95 (m, 2H) 7.97-8.02 (m, 1H); MS (ESI) m/z 345 (M+H)$^+$.

Example 74

2,3-difluoro-N-[(2Z)-3-(2-methoxyethyl)-1,3-benzothiazol-2(3H)-ylidene]benzamide The product of Example 64A (39 mg, 0.14 mmol) and 2,3-difluorobenzoic acid (27 mg, 0.17 mmol) were processed using the method described in Example 3 to afford the title compound. $^1$H NMR (500 MHz, DMSO-d$_6$) δ ppm 3.20-3.26 (m, 3H) 3.82 (t, 2H) 4.72 (t, 2H) 7.28-7.36 (m, 1H) 7.37-7.43 (m, 1H) 7.51-7.59 (m, 1H) 7.59-7.67 (m, 1H) 7.73-7.81 (m, 1H) 7.90-8.00 (m, 2H); MS (ESI) m/z 349 (M+H)$^+$.

Example 75

2,5-difluoro-N-[(2Z)-3-(2-methoxyethyl)-1,3-benzothiazol-2(3H)-ylidene]benzamide The product of Example 64A (39 mg, 0.14 mmol) and 2,5-difluorobenzoic acid (27 mg, 0.17 mmol) were processed using the method described in Example 3 to afford the title compound. $^1$H NMR (500 MHz, DMSO-d$_6$) δ ppm 3.23 (s, 3H) 3.82 (t, 2H) 4.72 (t, 2H) 7.38 (s, 2H) 7.46 (s, 1H) 7.54 (s, 1H) 7.77 (s, 1H) 7.89 (s, 1H) 7.92-7.98 (m, 1H); MS (ESI) m/z 349 (M+H)$^+$.

Example 76

2-acetyl-N-[(2Z)-3-(2-methoxyethyl)-1,3-benzothiazol-2(3H)-ylidene]benzamide

The product of Example 64A (39 mg, 0.14 mmol) and 2-acetylbenzoic acid (28 mg, 0.17 mmol) were processed using the method described in Example 3 to afford the title compound. $^1$H NMR (500 MHz, DMSO-d$_6$) δ ppm 2.44-2.48 (m, 3H) 3.21-3.25 (m, 3H) 3.77 (t, 2H) 4.67 (t, 2H) 7.30-7.44 (m, 2H) 7.51-7.66 (m, 3H) 7.70-7.82 (m, 1H) 7.89-8.00 (m, 1H) 8.11-8.25 (m, 1H); MS (ESI) m/z 355 (M+H)$^+$.

Example 77

3-methoxy-N-[(2Z)-3-(2-methoxyethyl)-1,3-benzothiazol-2(3H)-ylidene]-4-methylbenzamide The product of Example 64A (39 mg, 0.14 mmol) and 3-methoxy-4-methylbenzoic acid (28 mg, 0.17 mmol) were processed using the method described in Example 3 to afford the title compound. $^1$H NMR (500 MHz, DMSO-d$_6$) δ ppm 2.21-2.26 (m, 3H) 3.25-3.28 (m, 3H) 3.85 (t, 2H) 3.88-3.90 (m, 3H) 4.76 (t, 2H) 7.26-7.31 (m, 1H) 7.32-7.39 (m, 1H)

7.47-7.57 (m, 1H) 7.71-7.78 (m, 2H) 7.79-7.84 (m, 1H) 7.88-7.93 (m, 1H); MS (ESI) m/z 357 (M+H)+.

Example 78

2-ethoxy-N-[(2Z)-3-(2-methoxyethyl)-1,3-benzothiazol-2(3H)-ylidene]benzamide

The product of Example 64A (39 mg, 0.14 mmol) and 2-ethoxybenzoic acid (28 mg, 0.17 mmol) were processed using the method described in Example 3 to afford the title compound. $^1$H NMR (500 MHz, DMSO-$d_6$) δ ppm 2.21-2.26 (m, 3H) 3.25-3.28 (m, 3H) 3.85 (t, 2H) 3.88-3.90 (m, 3H) 4.76 (t, 2H) 7.26-7.31 (m, 1H) 7.32-7.39 (m, 1H) 7.47-7.57 (m, 1H) 7.71-7.78 (m, 2H) 7.79-7.84 (m, 1H) 7.88-7.93 (m, 1H); MS (ESI) m/z 357 (M+H)+.

Example 79

N-[(2Z)-3-(2-methoxyethyl)-1,3-benzothiazol-2(3H)-ylidene]-4-(methylthio)benzamide The product of Example 64A (39 mg, 0.14 mmol) and 4-methylsulfanylbenzoic acid (29 mg, 0.17 mmol) were processed using the method described in Example 3 to afford the title compound. $^1$H NMR (500 MHz, DMSO-$d_6$) δ ppm 2.53-2.58 (m, 3H) 3.22-3.27 (m, 3H) 3.84 (t, 2H) 4.73 (t, 2H) 7.31-7.44 (m, 3H) 7.47-7.61 (m, 1H) 7.67-7.79 (m, 1H) 7.82-8.02 (m, 1H) 8.08-8.22 (m, 2H); MS (ESI) m/z 359 (M+H)+.

Example 80

N-[(2Z)-3-(2-methoxyethyl)-1,3-benzothiazol-2(3H)-ylidene]-1-naphthamide

The product of Example 64A (39 mg, 0.14 mmol) and 1-naphthoic acid (29 mg, 0.17 mmol) were processed using the method described in Example 3 to afford the title compound. $^1$H NMR (500 MHz, DMSO-$d_6$) δ ppm 3.23-3.27 (m, 3H) 3.90 (t, 2H) 4.71 (t, 2H) 7.32-7.42 (m, 1H) 7.45-7.68 (m, 4H) 7.71-7.79 (m, 1H) 7.83-8.22 (m, 3H) 8.40-8.56 (m, 1H) 9.05-9.17 (m, 1H); MS (ESI) m/z 363 (M+H)+.

Example 81

N-[(2Z)-3-(2-methoxyethyl)-1,3-benzothiazol-2(3H)-ylidene]-2-naphthamide

The product of Example 64A (39 mg, 0.14 mmol) and 2-naphthoic acid (29 mg, 0.17 mmol) were processed using the method described in Example 3 to afford the title compound. $^1$H NMR (500 MHz, DMSO-$d_6$) δ ppm 3.28-3.29 (m, 3H) 3.91 (t, 2H) 4.78 (t, 2H) 7.25-7.44 (m, 1H) 7.50-7.58 (m, 1H) 7.58-7.67 (m, 2H) 7.71-7.82 (m, 1H) 7.88-7.97 (m, 1H) 7.99-8.07 (m, 2H) 8.08-8.21 (m, 1H) 8.26-8.40 (m, 1H) 8.72-8.93 (m, 1H); MS (ESI) m/z 363 (M+H)+.

Example 82

5-chloro-2-hydroxy-N-[(2Z)-3-(2-methoxyethyl)-1,3-benzothiazol-2(3H)-ylidene]benzamide The product of Example 64A (39 mg, 0.14 mmol) and 5-chloro-2-hydroxybenzoic acid (29 mg, 0.17 mmol) were processed using the method described in Example 3 to afford the title compound. $^1$H NMR (500 MHz, DMSO-$d_6$) δ ppm 3.22-3.25 (m, 3H) 3.85 (t, 2H) 4.73 (t, 2H) 6.94-7.08 (m, 2H) 7.36-7.53 (m, 2H) 7.57-7.67 (m, 1H) 7.79-7.92 (m, 1H) 7.96-8.09 (m, 2H); MS (ESI) m/z 363 (M+H)+.

Example 83

5-chloro-2-methoxy-N-[(2Z)-3-(2-methoxyethyl)-1,3-benzothiazol-2(3H)-ylidene]benzamide The product of Example 64A (39 mg, 0.14 mmol) and 5-chloro-2-methoxybenzoic acid (32 mg, 0.17 mmol) were processed using the method described in Example 3 to afford the title compound. $^1$H NMR (500 MHz, DMSO-$d_6$) δ ppm 3.22-3.26 (m, 3H) 3.80 (t, 2H) 3.83-3.88 (m, 3H) 4.62 (t, 2H) 7.13-7.23 (m, 1H) 7.32-7.43 (m 1H) 7.46-7.59 (m, 2H) 7.69-7.77 (m, 1H) 7.79-7.88 (m, 1H) 7.88-7.98 (m, 1H); MS (ESI) m/z 377 (M+H)+.

Example 84

1-hydroxy-N-[(2Z)-3-(2-methoxyethyl)-1,3-benzothiazol-2(3H)-ylidene]-2-naphthamide The product of Example 64A (39 mg, 0.14 mmol) and 1-hydroxy-2-naphthoic acid (32 mg, 0.17 mmol) were processed using the method described in Example 3 to afford the title compound. $^1$H NMR (500 MHz, DMSO-$d_6$) δ ppm 3.25-3.28 (m, 3H) 3.89 (t, 2H) 4.75 (t, 2H) 7.35-7.47 (m, 2H) 7.53-7.63 (m, 2H) 7.63-7.70 (m, 1H) 7.79-7.93 (m, 2H) 7.96-8.06 (m, 1H) 8.04-8.19 (m, 1H) 8.23-8.40 (m, 1H); MS (ESI) m/z 379 (M+H)+.

Example 85

4-fluoro-N-[(2Z)-3-(2-methoxyethyl)-1,3-benzothiazol-2(3H)-ylidene]-1-naphthamide The product of Example 64A (39 mg, 0.14 mmol) and 4-fluoro-1-naphthoic acid (32 mg, 0.17 mmol) were processed using the method described in Example 3 to afford the title compound. $^1$H NMR (500 MHz, DMSO-$d_6$) δ ppm 3.22-3.26 (m, 3H) 3.83 (t, 2H) 4.67 (t, 2H) 7.35-7.59 (m, 3H) 7.65-7.82 (m, 3H) 7.83-8.03 (m, 1H) 8.09-8.28 (m, 1H) 8.46-8.71 (m, 1H) 9.08-9.38 (m, 1H); MS (ESI) m/z 381 (M+H)+.

Example 86

2-methoxy-N-[(2Z)-3-(2-methoxyethyl)-1,3-benzothiazol-2(3H)-ylidene]-4-(methylthio)benzamide The product of Example 64A (39 mg, 0.14 mmol) and 2-methoxy-4-methylsulfanylbenzoic acid (34 mg, 0.17 mmol) were processed using the method described in Example 3 to afford the title compound. $^1$H NMR (500 MHz, DMSO-$d_6$) δ ppm 2.53-2.61 (m, 3H) 3.21-3.25 (m, 3H) 3.79 (t, 2H) 3.82-3.89 (m, 3H) 4.58 (t, 2H) 6.73-7.05 (m, 2H) 7.25-7.38 (m, 1H) 7.47-7.61 (m, 1H) 7.60-7.78 (m, 1H) 7.80-7.91 (m, 1H) 7.89-8.09 (m, 1H); MS (ESI) m/z 389 (M+H)+.

Example 87

2-chloro-N-[(2Z)-3-(2-methoxyethyl)-1,3-benzothiazol-2(3H)-ylidene]-5-(methylthio)benzamide The product of Example 64A (39 mg, 0.14 mmol) and 2-chloro-5-methylsulfanylbenzoic acid (34 mg, 0.17 mmol) were processed using the method described in Example 3 to afford the title compound. $^1$H NMR (500 MHz, DMSO-$d_6$) δ ppm 2.52-2.56 (m, 3H) 3.20-3.26 (m, 3H) 3.82 (t, 2H) 4.68 (t, 2H) 7.33-7.43 (m, 2H) 7.44-7.51 (m, 1H) 7.51-7.58 (m, 1H) 7.71-7.86 (m, 2H) 7.91-8.00 (m, 1H); MS (ESI) m/z 393 (M+H)+.

Example 88

2-fluoro-N-[(2Z)-3-(2-methoxyethyl)-1,3-benzothiazol-2(3H)-ylidene]-5-(trifluoromethyl)benzamide The product of Example 64A (39 mg, 0.14 mmol) and 2-fluoro-5-trifluoromethylbenzoic acid (34 mg, 0.17 mmol) were processed using the method described in Example 3 to afford the title compound. $^1$H NMR (500 MHz, DMSO-$d_6$) δ ppm 3.23-3.26 (m, 3H) 3.84 (t, 2H) 4.67 (t, 2H) 7.30-7.47 (m, 1H) 7.52-7.64 (m, 2H) 7.72-7.89 (m, 1H) 7.91-8.07 (m, 2H) 8.34-8.58 (m, 1H); MS (ESI) m/z 399 (M+H)+.

Example 89

2-benzyl-N-[(2Z)-3-(2-methoxyethyl)-1,3-benzothiazol-2(3H)-ylidene]benzamide

The product of Example 64A (39 mg, 0.14 mmol) and α-phenyl-o-toluic acid (36 mg, 0.17 mmol) were processed using the method described in Example 3 to afford the title compound. $^1$H NMR (500 MHz, DMSO-$d_6$) δ ppm 3.18-3.20 (m, 3H) 3.72 (t, 2H) 4.48-4.52 (m, 2H) 4.63 (t, 2H) 7.07-7.30 (m, 6H) 7.30-7.41 (m, 2H) 7.40-7.47 (m, 1H) 7.49-7.57 (m, 1H) 7.67-7.79 (m, 1H) 7.85-7.96 (m, 1H) 8.02-8.12 (m, 1H); MS (ESI) m/z 403 (M+H)+.

Example 90

2-chloro-N-[(2Z)-3-(2-methoxyethyl)-1,3-benzothiazol-2(3H)-ylidene]-5-(trifluoromethyl)benzamide The product of Example 64A (39 mg, 0.14 mmol) and 2-chloro-5-trifluoromethylbenzoic acid (38 mg, 0.17 mmol) were processed using the method described in Example 3 to afford the title compound. $^1$H NMR (500 MHz, DMSO-$d_6$) δ ppm 3.20-3.25 (s, 3H) 3.80 (t, 2H) 4.70 (t, 2H) 7.35-7.45 (m, 1H) 7.50-7.65 (m, 1H) 7.76-7.83 (m, 2H) 7.84-7.91 (m, 1H) 7.94-8.03 (m, 1H) 8.22-8.32 (m, 1H); MS (ESI) m/z 415 (M+H)+.

Example 91

N-[(2Z)-3-(2-methoxyethyl)-1,3-benzothiazol-2(3H)-ylidene]-2-(2-phenylethyl)benzamide The product of Example 64A (39 mg, 0.14 mmol) and 2-phenethylbenzoic acid (38 mg, 0.17 mmol) were processed using the method described in Example 3 to afford the title compound. $^1$H NMR (500 MHz, DMSO-$d_6$) δ ppm 2.78-2.95 (m, 2H) 3.16-3.22 (m, 3H) 3.32-3.37 (m, 2H) 3.76 (t, 2H) 4.65 (t, 2H) 6.99-7.46 (m, 9H) 7.49-7.57 (m, 1H) 7.67-7.80 (m, 1H) 7.82-7.97 (m, 1H) 7.97-8.15 (m, 1H); MS (ESI) m/z 417 (M+H)+.

Example 92

2-bromo-5-methoxy-N-[(2Z)-3-(2-methoxyethyl)-1,3-benzothiazol-2(3H)-ylidene]benzamide The product of Example 64A (39 mg, 0.14 mmol) and 2-bromo-5-methoxybenzoic acid (39 mg, 0.17 mmol) were processed using the method described in Example 3 to afford the title compound. $^1$H NMR (500 MHz, DMSO-$d_6$) δ ppm 3.20-3.26 (m, 3H) 3.72-3.87 (m, 5H) 4.67 (t, 2H) 6.91-7.08 (m, 1H) 7.30-7.43 (m, 1H) 7.45-7.51 (m, 1H) 7.51-7.65 (m, 2H) 7.70-7.83 (m, 1H) 7.86-7.98 (m, 1H); MS (ESI) m/z 423 (M+H)+.

Example 93

2-iodo-N-[(2Z)-3-(2-methoxyethyl)-1,3-benzothiazol-2(3H)-ylidene]benzamide

The product of Example 64A (39 mg, 0.14 mmol) and 2-iodobenzoic acid (42 mg, 0.17 mmol) were processed using the method described in Example 3 to afford the title compound. $^1$H NMR (500 MHz, DMSO-$d_6$) δ ppm 3.20-3.24 (m, 3H) 3.81 (t, 2H) 4.69 (t, 2H) 7.15-7.25 (m, 1H) 7.34-7.41 (m, 1H) 7.47-7.62 (m, 2H) 7.70-7.81 (m, 1H) 7.87-7.97 (m, 2H) 7.97-8.03 (m, 1H); MS (ESI) m/z 439 (M+H)+.

Example 94

3-iodo-N-[(2Z)-3-(2-methoxyethyl)-1,3-benzothiazol-2(3H)-ylidene]benzamide

The product of Example 64A (39 mg, 0.14 mmol) and 3-iodobenzoic acid (42 mg, 0.17 mmol) were processed using the method described in Example 3 to afford the title compound. $^1$H NMR (500 MHz, DMSO-$d_6$) δ ppm 3.26-3.27 (m, 3H) 3.79 (t, 2H) 4.76 (t, 2H) 7.26-7.43 (m, 2H) 7.48-7.61 (m, 1H) 7.69-7.81 (m, 1H) 7.89-8.00 (m, 2H) 8.18-8.31 (m, 1H) 8.49-8.59 (m, 1H); MS (ESI) m/z 439 (M+H)+.

Example 95

4-iodo-N-[(2Z)-3-(2-methoxyethyl)-1,3-benzothiazol-2(3H)-ylidene]benzamide

The product of Example 64A (39 mg, 0.14 mmol) and 4-iodobenzoic acid (42 mg, 0.17 mmol) were processed using the method described in Example 3 to afford the title compound. $^1$H NMR (500 MHz, DMSO-$d_6$) δ ppm 3.23-3.25 (m, 3H) 3.80 (t, 2H) 4.75 (t, 2H) 7.29-7.45 (m, 1H) 7.47-7.62 (m, 1H) 7.70-7.80 (m, 1H) 7.85-7.96 (m, 3H) 7.98-8.05 (m, 2H); MS (ESI) m/z 439 (M+H)+.

Example 96

N-[(2Z)-3-(2-methoxyethyl)-1,3-benzothiazol-2(3H)-ylidene]-3-methylbutanamide

The product of Example 64A (39 mg, 0.14 mmol) and isovaleric acid (17 mg, 0.17 mmol) were processed using the method described in Example 3 to afford the title compound. $^1$H NMR (500 MHz, DMSO-$d_6$) δ ppm 0.93 (d, 6H) 2.10-2.23 (m, 1H) 2.37 (d, 2H) 3.21-3.25 (m 3H) 3.74 (t, 2H) 4.57 (t, 2H) 7.31 (m, 1H) 7.48 (m, 1H) 7.66 (m, 1H) 7.83 (m, 1H); MS (ESI) m/z 393 (M+H)+.

Example 97

N-[(2Z)-3-(2-methoxyethyl)-1,3-benzothiazol-2(3H)-ylidene]-2-methylpentanamide

The product of Example 64A (39 mg, 0.14 mmol) and 2-methylvaleric acid (20 mg, 0.17 mmol) were processed using the method described in Example 3 to afford the title compound. ¹H NMR (500 MHz, DMSO-d₆) δ ppm 0.88 (t, 3H) 1.14 (d, 3H) 1.21-1.34 (m, 2H) 1.35-1.47 (m, 1H) 1.63-1.76 (m, 1H) 2.53-2.62 (m, 1H) 3.22-3.26 (m, 3H) 3.75 (t, 2H) 4.58 (t, 2H) 7.31 (m, 1H) 7.49 (m, 1H) 7.66 (m, 1H) 7.83 (m, 1H); MS (ESI) m/z 307 (M+H)⁺.

Example 98

N-[(2Z)-3-(2-methoxyethyl)-1,3-benzothiazol-2(3H)-ylidene]-3-methylpentanamide

The product of Example 64A (39 mg, 0.14 mmol) and 3-methylvaleric acid (20 mg, 0.17 mmol) were processed using the method described in Example 3 to afford the title compound. ¹H NMR (500 MHz, DMSO-d₆) δ ppm 0.82-0.96 (m, 6H) 1.14-1.27 (m, 1H) 1.31-1.44 (m, 1H) 1.87-2.05 (m, 1H) 2.25-2.34 (m, 1H) 2.43-2.49 (m, 1H) 3.21-3.26 (m, 3H) 3.74 (t, 2H) 4.56 (t, 2H) 7.31 (m, 1H) 7.48 (m, 1H) 7.66 (m, 1H) 7.84 (m, 1H); MS (ESI) m/z 307 (M+H)⁺.

Example 99

N-[(2Z)-3-(2-methoxyethyl)-1,3-benzothiazol-2(3H)-ylidene]-4-methylpentanamide

The product of Example 64A (39 mg, 0.14 mmol) and 4-methylvaleric acid (20 mg, 0.17 mmol) were processed using the method described in Example 3 to afford the title compound. ¹H NMR (500 MHz, DMSO-d₆) δ ppm 0.90 (d, 6H) 1.49-1.61 (m, 3H) 2.45-2.50 (m, 2H) 3.21-3.26 (m, 3H) 3.74 (t, 2H) 4.58 (t, 2H) 7.32 (m, 1H) 7.48 (m, 1H) 7.66 (m, 1H) 7.84 (m, 1H); MS (ESI) m/z 307 (M+H)⁺.

Example 100

N-[(2Z)-3-(2-methoxyethyl)-1,3-benzothiazol-2(3H)-ylidene]-2,2-dimethylbutanamide The product of Example 64A (39 mg, 0.14 mmol) and 2,2-dimethylbutyric acid (20 mg, 0.17 mmol) were processed using the method described in Example 3 to afford the title compound. ¹H NMR (500 MHz, DMSO-d₆) δ ppm 0.76 (t, 3H) 1.11-1.23 (m, 6H) 1.62 (t, 2H) 3.18-3.27 (m, 3H) 3.75 (t, 2H) 4.58 (t, 2H) 7.26 (m, 1H) 7.46 (m, 1H) 7.66 (m, 1H) 7.84 (m, 1H); MS (ESI) m/z 307 (M+H)⁺.

Example 101

N-[(2Z)-3-(2-methoxyethyl)-1,3-benzothiazol-2(3H)-ylidene]-3,3-dimethylbutanamide The product of Example 64A (0.64 g, 2.2 mmol) and 3,3-dimethyl-butyric acid (0.26 mL, 2.0 mmol) were processed using the method described in Example 3. Purification by column chromatography (SiO₂, 20-30% ethyl acetate/hexanes gradient) afforded 0.44 g (71%) of the title compound. ¹H NMR (DMSO-d₆, 300 MHz) δ ppm 1.03 (s, 9H), 2.36-2.43 (s, 2H), 3.22 (s, 3H), 3.73 (t, J=5.4 Hz, 2H), 4.56 (t, J=5.4 Hz, 2H), 7.32 (m, 1H), 7.49 (td, J=7.8, 1.0 Hz, 1H), 7.67 (d, J=8.5 Hz, 1H), 7.84 (dd, J=8.0, 1.2 Hz, 1H); MS (DCI/NH₃) m/z 331 (M+H)⁺. Anal. Calculated for C₁₆H₂₂N₂O₂S: C, 62.71; H, 7.24; N, 9.14. Found: C, 62.79; H, 7.41; N, 9.06.

Example 102

2-ethyl-N-[(2Z)-3-(2-methoxyethyl)-1,3-benzothiazol-2(3H)-ylidene]butanamide

The product of Example 64A (39 mg, 0.14 mmol) and 2-ethylbutyric acid (20 mg, 0.17 mmol) were processed using the method described in Example 3 to afford the title compound. ¹H NMR (500 MHz, DMSO-d₆) δ ppm 0.84 (t, 6H) 1.47-1.59 (m, 2H) 1.60-1.72 (m, 2H) 2.27-2.39 (m, 1H) 3.21-3.26 (m, 3H) 3.75 (t, 2H) 4.58 (t, 2H) 7.32 (m, 1H) 7.48 (m, 1H) 7.65 (m, 1H) 7.82 (m, 1H); MS (ESI) m/z 307 (M+H)⁺.

Example 103

N-[(2Z)-3-(2-methoxyethyl)-1,3-benzothiazol-2(3H)-ylidene]cyclopentanecarboxamide The product of Example 64A (39 mg, 0.14 mmol) and cyclopentanecarboxylic acid (19 mg, 0.17 mmol) were processed using the method described in Example 3 to afford the title compound. ¹H NMR (500 MHz, DMSO-d₆) δ ppm 1.50-1.62 (m, 2H) 1.62-1.72 (m, 2H) 1.76-1.95 (m, 4H) 2.85-2.98 (m, 1H) 3.22-3.26 (m, 3H) 3.74 (t, 2H) 4.56 (m, 2H) 7.31 (m, 1H) 7.48 (m, 1H) 7.66 (m, 1H) 7.83 (d, 1H); MS (ESI) m/z 305 (M+H)⁺.

Example 104

2-cyclopentyl-N-[(2Z)-3-(2-methoxyethyl)-1,3-benzothiazol-2(3H)-ylidene]acetamide The product of Example 64A (39 mg, 0.14 mmol) and cyclopentylacetic acid (22 mg, 0.17 mmol) were processed using the method described in Example 3 to afford the title compound. ¹H NMR (500 MHz, DMSO-d₆) δ ppm 1.09-1.25 (m, 2H) 1.44-1.56 (m, 2H) 1.55-1.65 (m, 2H) 1.70-1.84 (m, 2H) 2.20-2.38 (m, 1H) 2.46-2.49 (m, 1H) 3.21-3.24 (m, 3H) 3.24-3.29 (m, 1H) 3.74 (t, 2H) 4.56 (t, 2H) 7.32 (m, 1H) 7.49 (m, 1H) 7.65 (m, 1H) 7.83 (m, 1H); MS (ESI) m/z 319 (M+H)⁺.

Example 105

N-[(2Z)-3-(2-methoxyethyl)-1,3-benzothiazol-2(3H)-ylidene]cyclohexanecarboxamide The product of Example 64A (39 mg, 0.14 mmol) and cyclohexanecarboxylic acid (22 mg, 0.17 mmol) were processed using the method described in Example 3 to afford the title compound. ¹H NMR (500 MHz, DMSO-d₆) δ ppm 1.13-1.36 (m, 3H) 1.37-1.52 (m, 2H) 1.58-1.67 (m, 1H) 1.66-1.80 (m, 2H) 1.84-2.00 (m, 2H) 2.32-2.46 (m, 1H) 3.22-3.25 (m, 3H) 3.75 (t, 2H) 4.56 (t, 2H) 7.30 (m, 1H) 7.48 (m, 1H) 7.65 (m, 1H) 7.83 (m, 1H); MS (ESI) m/z 319 (M+H)⁺.

Example 106

N-[(2Z)-3-(2-methoxyethyl)-1,3-benzothiazol-2(3H)-ylidene]-1-methylcyclohexanecarboxamide The product of Example 64A (39 mg, 0.14 mmol) and 1-methylcyclohexane-carboxylic acid (24 mg, 0.17 mmol) were processed using the method described in Example 3 to afford the title compound. ¹H NMR (500 MHz, DMSO-d₆) δ ppm 1.10-1.16 (m, 3H) 1.21-1.39 (m, 5H) 1.40-1.48 (m, 1H) 1.48-1.58 (m, 2H) 2.06-2.21 (m, 2H) 3.21-3.25 (m, 3H) 3.76 (t, 2H) 4.58 (t, 2H) 7.30 (m, 1H) 7.47 (m, 1H) 7.65 (m, 1H) 7.82 (m, 1H); MS (ESI) m/z 333 (M+H)⁺.

Example 107 cis-N-[(2Z)-3-(2-methoxyethyl)-1,3-benzothiazol-2(3H)-ylidene]-2-methylcyclohexanecarboxamide The product of Example 64A (39 mg, 0.14 mmol) and (cis)-2-methylcyclohexanecarboxylic acid (24 mg, 0.17 mmol) were processed using the method described in Example 3 to afford the title compound. $^1$H NMR (500 MHz, DMSO-d$_6$) δ ppm 0.79 (d, 3H) 1.14-1.87 (m, 8H) 2.24-2.39 (m, 1H) 2.56-2.65 (m, 1H) 3.19-3.23 (m, 3H) 3.72 (t, 2H) 4.54 (t, 2H) 7.22-7.37 (m, 1H) 7.42-7.50 (m, 1H) 7.58-7.67 (m, 1H) 7.75-7.88 (m, 1H); MS (ESI) m/z 333 (M+H)$^+$.

Example 108

N-[(2Z)-3-(2-methoxyethyl)-1,3-benzothiazol-2 (3H)-ylidene]-4-methylcyclohexanecarboxamide The product of Example 64A (39 mg, 0.14 mmol) and 4-methylcyclohexanecarboxylic acid (24 mg, 0.17 mmol) were processed using the method described in Example 3 to afford the title compound. $^1$H NMR (500 MHz, DMSO-d$_6$) δ ppm 0.78-0.91 (m, 3H) 0.94-1.26 (m, 2H) 1.38-1.63 (m, 4H) 1.69-2.01 (m, 1H) 2.04-2.40 (m, 2H) 2.53-2.65 (m, 1H) 3.19-3.26 (m, 3H) 3.76 (t, 2H) 4.56 (t, 2H) 7.23-7.37 (m, 1H) 7.40-7.56 (m, 1H) 7.59-7.70 (m, 1H) 776-7.86 (m, 1H); MS (ESI) m/z 333 (M+H)$^+$.

Example 109

2-cyclohexyl-N-[(2Z)-3-(2-methoxyethyl)-1,3-benzothiazol-2(3H)-ylidene]acetamide The product of Example 64A (39 mg, 0.14 mmol) and cyclohexylacetic acid (24 mg, 0.17 mmol) were processed using the method described in Example 3 to afford the title compound. $^1$H NMR (500 MHz, DMSO-d$_6$) δ ppm 0.86-1.05 (m, 2H) 1.06-1.35 (m, 3H) 1.54-1.75 (m, 5H) 1.77-1.92 (m, 1H) 2.36 (d, 2H) 3.19-3.25 (m, 3H) 3.75 (t, 2H) 4.54 (t 2H) 7.25-7.36 (m, 1H) 7.43-7.56 (m, 1H) 7.60-7.69 (m, 1H) 7.77-7.88 (m, 1H); MS (ESI) m/z 333 (M+H)$^+$.

Example 110

N-[(2Z)-3-(2-methoxyethyl)-1,3-benzothiazol-2 (3H)-ylidene]cycloheptanecarboxamide The product of Example 64A (39 mg, 0.14 mmol) and cycloheptylacetic acid (24 mg, 0.17 mmol) were processed using the method described in Example 3 to afford the title compound. $^1$H NMR (500 MHz, DMSO-d$_6$) δ ppm 1.42-1.62 (m, 6H) 1.63-1.82 (m, 4H) 1.85-2.05 (m, 2H) 2.54-2.72 (m, 1H) 3.18-3.26 (m, 3H) 3.72 (t, 2H) 4.55 (t, 2H) 7.23-7.40 (m, 1H) 7.42-7.55 (m, 1H) 7.60-7.72 (m, 1H) 7.75-7.88 (m, 1H); MS (ESI) m/z 333 (M+H)$^+$.

Example 111

N-[(2Z)-3-(2-methoxyethyl)-1,3-benzothiazol-2 (3H)-ylidene]-5-methylthiophene-2-carboxamide The product of Example 64A (39 mg, 0.14 mmol) and 5-methylthiophene-2-carboxylic acid (28 mg, 0.20 mmol) were processed using the method described in Example 3 to afford the title compound. $^1$H NMR (500 MHz, DMSO-d$_6$) δ ppm 2.51 (s, 3H) 3.26 (s, 3H) 3.82 (t, 2H) 4.66 (t, 2H) 6.91-6.93 (m, 1H) 7.35 (t, 1H) 7.51 (t, 1H) 7.68-7.72 (m, 2H) 7.89 (d, 1H); MS (ESI) m/z 332 (M+H)$^+$.

Example 112

N-[(2E)-6-fluoro-3-(2-methoxyethyl)-1,3-benzothiazol-2(3H)-ylidene]-2,2,3,3-tetramethylcyclopropanecarboxamide Example 112A N-(6-fluoro-1,3-benzothiazol-2-yl)-2,2,3,3-tetramethylcyclopropanecarboxamide A mixture of 6-fluoro-benzothiazol-2-ylamine (1 equiv), N-(3-dimethylaminopropyl)-N-ethylcarbodiimide hydrochloride (1 equiv), 1-hydroxybenzotniazole, triethylamine (1.1 equiv), and 2,2,3,3-tetramethylcyclopropanecarboxylic acid (0.8 equiv) in 3:1 THF/Et$_3$N (1 M) and were stirred overnight at room temperature. The mixture was diluted with EtOAc, washed with 1 M aqueous NaHCO$_3$, dried (Na$_2$SO$_4$), filtered, and concentrated. Puried by silica gel chromatography afforded the title compound. MS (ESI$^+$) m/z 293 (M+H)$^+$.

Example 112B 2,2,3,3-Tetramethylcyclopropanecarboxylic acid [6-fluoro-3-(2-methoxyethyl-3H-benzothiazol-2-ylidene]-amide To a solution of the product of Example 112A (1 equiv) in 1:1 DMF/THF (0.1 M) was added sodium hydride (60% dispersion in mineral oil, 1.2 equiv) and 2-bromoethyl methyl ether (1.2 equiv). The mixture was stirred at 65° C. overnight then cooled to ambient temperature and diluted with EtOAc. The mixture was washed with 1 M saturated aqueous NaHCO$_3$, dried (Na$_2$SO$_4$), filtered and concentrated. Purified by silica gel chromatography afforded the title compound. $^1$H NMR (300 MHz, DMSO-d$_6$) δ ppm 1.20 (s, 6H), 1.27 (s, 6H), 1.60 (s, 1H), 3.23 (s, 3H), 3.72 (t, J=5.4 Hz, 2H), 4.54 (t, J=5.4 Hz, 2H), 7.33 (td, J=9.0, 2.7 Hz, 1H), 7.65 (dd, J=8.8, 4.4 Hz, 1H), 7.75 (dd, J=8.1, 2.7 Hz, 1H); MS (ESI$^+$) m/z 351 (M+H)$^+$.

Example 113

2-cyclopentyl-N-[(2Z)-6-fluoro-3-(2-methoxyethyl)-1,3-benzothiazol-2(3H)-ylidene]acetamide Example 113A 6-Fluoro-3-(2-methoxyethyl)-3H-benzothiazol-2-ylideneamine hydrobromide Commercially available 6-fluoro-benzothiazol-2-ylamine and 2-bromoethyl methyl ether were processed as described for example 12A to afford the title compound. MS (ESI$^+$) m/z 227 (M+H)$^+$.

Example 113B 2-cyclopentyl-N-[(2Z)-6-fluoro-3-(2-methoxyethyl)-1,3-benzothiazol-2(3H)-ylidene]acetamide The product from Example 113A and cyclopentylacetyl chloride were processed as described for example 11 to afford the title compound. $^1$H NMR (400 MHz, DMSO-d$_6$) δ ppm 4.54 (d, J=5.76 Hz, 2H) 7.65 (t, J=8.14 Hz, 1H) 7.75 (dd, J=8.81, 2.71 Hz, 1H) 7.83 (dd, J=7.97, 1.53 Hz, 2H) 7.97 (dd, J=8.14, 1.36 Hz, 1H) 8.41 (d, J=3.05 Hz, 1H); MS (ESI$^+$) m/z

Example 114

N-[(2Z)-6-fluoro-3-(2-methoxyethyl)-1,3-benzothiazol-2(3H)-ylidene]-2-tetrahydro-2H-pyran-4-ylacetamide

Example 114A (Tetrahydro-pyran-4-yl)-acetyl chloride

Commercially available (tetrahydro-pyran-4-yl)-acetic acid and oxalyl chloride were processed as described for example 9A to afford the title compound. MS (DCI/NH$_3$) m/z 159 (M+H)$^+$.

Example 114B

N-[6-Fluoro-3-(2-methoxyethyl)-3H-benzothiazol-2-ylidene]-2-(tetrahydro-pyran-4-yl)-acetamide The product from Example 113A and the product from Example 114A were processed as described for Example 11 to afford the title compound. $^1$H NMR (300 MHz, DMSO-d$_6$) δ ppm 1.13-1.35 (m, 2H), 1.52-1.66 (m, 2H), 2.05 (d, 1H), 2.43 (d, J=7.1 Hz, 2H), 3.22 (s, 3H), 3.72 (t, J=5.3 Hz, 2H), 3.78-3.88 (m, 4H), 4.56 (t, J=5.3 Hz, 2H), 7.36 (td, J=9.0, 2.7 Hz, 1H), 7.70 (dd, J=9.0, 4.2 Hz, 1H), 7.81 (dd, J=8.5, 2.7 Hz, 1H); MS (ESI$^+$) m/z 353 (M+H)$^+$; Anal. Calculated for C$_{17}$H$_{21}$FN$_2$O$_3$S: C, 57.94; H, 6.01; N, 7.95. Found: C, 58.03; H, 5.97; N, 7.87.

Example 115

5-fluoro-N-[(2Z)-6-fluoro-3-(2-methoxyethyl)-1,3-benzothiazol-2(3H)-ylidene]-2-methoxybenzamide The product from Example 113A and 5-fluoro-2-methoxybenzoic acid were processed using the methods described in Example 13 to afford the title compound. $^1$H NMR (300 MHz, DMSO-d$_6$) δ ppm 3.23 (s, 3H), 3.72-3.87 (m, 5H), 4.65 (t, J=5.4 Hz, 2H), 7.15 (dd, J=9.3, 4.2 Hz, 1H), 7.37 (dd, 2H), 7.64 (dd, J=9.2, 3.4 Hz, 1H), 7.77 (dd, J=9.2, 4.4 Hz, 1H), 7.88 (dd, J=8.1, 2.7 Hz, 1H); MS (ESI$^+$) m/z 379 (M+H)$^+$; Anal. Calculated for C$_{18}$H$_{16}$F$_2$N$_2$O$_3$S: C, 57.13; H, 4.26; N, 7.40. Found: C, 57.05; H, 4.08; N, 7.35.

Example 116

5-chloro-N-[(2Z)-6-fluoro-3-(2-methoxyethyl)-1,3-benzothiazol-2(3H)-ylidene]-2-methoxybenzamide The product from Example 113A and 5-chloro-2-methoxybenzoic acid were processed using the methods described in Example 13 to afford the title compound. $^1$H NMR (300 MHz, DMSO-d$_6$) δ ppm 3.24 (s, 3H), 3.79 (t, J=5.3 Hz, 2H), 3.83 (s, 3H), 4.65 (t, J=5.3 Hz, 2H), 7.17 (d, J=9.2 Hz, 1H), 7.41 (td, J=9.1, 2.5 Hz, 1H), 7.52 (dd, J=8.8, 2.7 Hz, 1H), 7.78 (dd, J=9.0, 4.2 Hz, 1H), 7.83 (d, J=2.7 Hz, 1H), 7.89 (dd, J=8.5, 2.7 Hz, 1H); MS (ESI$^+$) m/z 395 (M+H)$^+$; Anal. Calculated for C$_{18}$H$_{16}$ClFN$_2$O$_3$S: C, 54.75; H, 4.08; N, 7.09. Found: C, 54.29; H, 3.94; N, 6.99.

Example 117

N-[(2Z)-3-(2-methoxyethyl)-4-methyl-5-morpholin-4-yl-1,3-thiazol-2(3H)-ylidene]-2,2,3,3-tetramethylcyclopropanecarboxamide

Example 117A 2,2,3,3-Tetramethylcyclopropanecarboxylic acid (4-methyl-5-morpholin-4-yl-thiazol-2-yl)-amide A mixture of 4-methyl-5-morpholin-4-yl-thiazol-2-ylamine (prepared using the method described in Christopher et al., Bioorganic and Medicinal Chemistry Letters 2004, 14(22), 5521-5525), N-(3-dimethylaminopropyl)-N-ethylcarbodiimide hydrochloride, 1-hydroxybenzotriazole, triethylamine, and 2,2,3,3-tetramethylcyclopropanecarboxylic acid were processed using the method described in Example 58 to afford the title compound. MS (ESI$^+$) m/z 324 (M+H)$^+$.

Example 117B 2,2,3,3-Tetramethylcyclopropanecarboxylic acid [3-(2-methoxyethyl)-4-methyl-5-morpholin-4-yl-3H-thiazol-2-ylidene]-amide The product from Example 117A was processed using the method described in Example 112B to afford the title compound. $^1$H NMR (300 MHz, DMSO-d$_6$) δ ppm 1.16 (s, 6H), 1.23 (s, 6H), 1.44 (s, 1H), 2.22 (s, 3H), 2.70-2.79 (m, 4H), 3.24 (s, 3H), 3.62 (t, J=5.3 Hz, 2H), 3.66-3.72 (m, 4H), 4.21 (t, J=5.4 Hz, 2H); MS (ESI$^+$) m/z 382 (M+H)$^+$.

Example 118

N-[(2Z)-5-chloro-3-(2-methoxyethyl)-4-methyl-1,3-thiazol-2(3H)-ylidene]-2,2,3,3-tetramethylcyclopropanecarboxamide

Example 118A 2,2,3,3-Tetramethylcyclopropanecarboxylic acid (5-chloro-4-methyl-thiazol-2-yl)-amide A mixture of 2-amino-5-chloro-2-methyl-thiazole (Matsuo, Masaaki; Ogino, Takashi; Igari, Norihiro; Seno, Hachiro; Shimomura, Kyoichi, EP 412404) (150 mg, 0.81 mmol), 2,2,3,3-tetramethylcyclopropanecarbonyl chloride (143 mg, 0.89 mmol), 4-dimethylaminopyridine (50.0 mg, 0.41 mmol) and triethylamine (226 μL, 1.62 mmol) in 15 mL of THF heated at reflux for 48 hours. The mixture was cooled to ambient temperature, diluted with EtOAc and washed with brine. The layers were separated and the aqueous phase was extracted with EtOAc (2×). The combined organic extracts were dried (Na$_2$SO$_4$), filtered, and concentrated. Purification by silica gel chromatography afforded the title compound: MS (LC/MS) m/z 273 (M+H)$^+$.

Example 118B 2,2,3,3-Tetramethylcyclopropanecarboxylic acid (5-chloro-3-(2-methoxy-ethy)-4-methyl-3H-thiazol-2-ylidene]-amide A mixture of the product of Example 118A (150 mg, 0.55 mmol), NaH (60% dispersion in mineral oil, 29.0 mg, 0.71 mmol) and 2-bromoethyl methyl ether (57 μl, 0.61 mmol) in 20 mL of 2:1 THF/DMF was processed according to the method desribed in Example 112B to provide the title compound: $^1$H NMR (300 MHz, DMSO-$d_6$) δ 1.18 (s, 6H) 1.23 (s, 6H) 1.50 (s, 1H) 2.29 (s, 3H) 3.25 (s, 3H) 3.63 (t, J=5.3 Hz, 2H) 4.27 (t, J=5.3 Hz, 2H); MS (DCI/NH$_3$) m/z 331 (M+H)$^+$.

Example 119

N-[(2Z)-3-(2-methoxyethyl)-5-methyl-4-phenyl-1,3-thiazol-2(3H)-ylidene]-2,2,3,3-tetramethylcyclopropanecarboxamide Example 119A 3-(2-methoxyethyl)-5-methyl-4-phenyl-3H-thiazol-2-ylideneamine hydrobromide A mixture of 5-methyl-4-phenyl-thiazol-2-ylamine (300 mg, 1.58 mmol) and 2-bromoethyl methyl ether (300 μL, 3.20 mmol) was processed using the method described in Example 12A to provide the title compound.

Example 119B 2,2,3,3-Tetramethylcyclopropanecarboxylic acid [3-(2-methoxy-ethy)-5-methyl-4-phenyl-3H-thiazol-2-ylidene]-amide A mixture of the product of Example 119A (290 mg, 1.16 mmol), 2,2,3,3-tetramethylcyclopropanecarboxylic acid (182 mg, 1.28 mmol), HATU (661 mg, 1.74 mmol) and triethylamine (0.97 mL, 6.96 mmol) in 15 mL of DMF was processed according to the method of Example 2B to provide the title compound: $^1$H NMR (400 MHz, DMSO-$d_6$) δ 1.17 (s, 6H) 1.26 (s, 6H) 1.49 (s, 1H) 2.01 (s, 3H) 3.02 (s, 3H) 3.43 (t, J=6.0 Hz, 2H) 4.06 (t, J=5.8 Hz, 2H) 7.39-7.43 (m, 2H) 7.50-7.57 (m, 3H); MS (DCI/NH$_3$) m/z 373 (M+H)$^+$.

Example 120

N-[(2Z)-4-(4-chlorophenyl)-3-(2-methoxyethyl)-5-methyl-1,3-thiazol-2(3H)-ylidene]-2,2,3,3-tetramethylcyclopropanecarboxamide Example 120A 4-(4-chlorophenyl)-3-(2-methoxyethyl)-5-methyl-3H-thiazol-2-ylideneamine hydrobromide A mixture of 4-(4-chlorophenyl)-5-methyl-thiazol-2-ylamine (420 mg, 1.87 mmol) and 2-bromoethyl methyl ether (600 μL, 6.40 mmol) was processed according to the method of Example 12A to provide the title compound: MS (DCI/NH$_3$) m/z 283 (M+H)$^+$.

Example 120B 2,2,3,3-Tetramethylcyclopropanecarboxylic acid [4-(4-chlorophenyl)-3-(2-methoxy-ethy)-5-methyl-3H-thiazol-2-ylidene]-amide A mixture of the product of Example 120A (156 mg, 0.55 mmol), 2,2,3,3-tetramethylcyclopropanecarboxylic acid (94 mg, 0.66 mmol), HATU (479 mg, 0.83 mmol) and triethylamine (0.46 mL, 3.30 mmol) in 10 mL of DMF was processed according to the method of Example 2B to provide the title compound: $^1$H NMR (500 MHz, DMSO-$d_6$) δ 1.17 (s, 6H) 1.25 (s, 6H) 1.49 (s, 1H) 2.00 (s, 3H) 3.04 (s, 3H) 3.44 (t, J=5.8 Hz, 2H) 4.04 (t, J=5.8 Hz, 2H) 7.45 (d, J=8.2 Hz, 2H) 7.60 (d, J=8.5 Hz, 2H); MS (DCI/NH$_3$) m/z 407 (M+H)$^+$.

Example 121

N-[(2Z)-3-(2-methoxyethyl)-4,5,6,7-tetrahydro-1,3-benzothiazol-2(3H)-ylidene]-2,2,3,3-tetramethylcyclopropanecarboxamide Example 121A 3-(2-methoxy-ethy)-4,5,7-tetrahydro-3H-benzothiazol-2-ylideneamine hydrobromide A mixture of 4,5,6,7-tetrahydro-benzothiazol-2-ylamine (300 mg, 1.94 mmol) and 2-bromoethyl methyl ether (600 μL, 6.40 mmol) was processed according to the method of Example 12A to provide the title compound as crude product: MS (LC/MS) m/z 213 (M+H)$^+$.

Example 121B 2,2,3,3-Tetramethylcyclopropanecarboxylic acid [3-(2-methoxy-ethy)-4,5,6,7-tetrahydro-3H-benzothiazol-2-ylidene]-amide A mixture of the product of Example 121A (156 mg, 0.55 mmol), 2,2,3,3-tetramethylcyclopropanecarboxylic acid (94 mg, 0.66 mmol), HATU (479 mg, 0.83 mmol) and triethylamine (0.46 mL, 3.30 mmol) in 10 mL of DMF was processed according to the method of Example 2B to provide the title compound: $^1$H NMR (500 MHz, DMSO-$d_6$) δ 1.16 (s, 6H) 1.23 (s, 6H) 1.45 (s, 1H) 1.69-1.82 (m, 4H) 2.43-2.48 (m, 2H) 2.54-2.59 (m, 2H) 3.24 (s, 3H) 3.60 (t, J=5.3 Hz, 2H) 4.16 (t, J=5.3 Hz, 2H); MS (DCI/NH$_3$) m/z 337 (M+H)$^+$.

Example 122

N-[(2Z)-3-(2-methoxyethyl)-3,4,5,6-tetrahydro-2H-cyclopenta[d][1,3]thiazol-2-ylidene]-2,2,3,3-tetramethylcyclopropanecarboxamide Example 122A 2,2,3,3-Tetramethylcyclopropanecarboxylic acid (5,6-dihydro-4H-cyclopentathiazol-2-yl)-amide A mixture of 5,6-dihydro-4H-cyclopentathiazole-2-ylamine (177 mg, 1.26 mmol), 2,2,3,3-tetramethylcyclopropanecarboxylic acid (244 mg, 1.52 mmol), 4-dimethylaminopyridine (50.0 mg, 0.41 mmol) and triethylamine (351 μL, 2.52 mmol) in 20 mL of THF was processed according to the method of Example 118A to provide the title compound: MS (DCI/NH$_3$) m/z 265 (M+H)$^+$.

Example 122B 2,2,3,3-Tetramethylcyclopropanecarboxylic acid [3-(2-methoxy-ethy)-(3,4,5,6-tetrahydro-cyclopentathiazol-2-ylidene)-amide A mixture of the product of Example 122A (254 mg, 0.95 mmol), NaH (60% dispersion in mineral oil, 50.0 mg, 1.22 mmol) and 2-bromoethyl methyl ether (100 μL, 1.07 mmol) in 30 mL of THF/DMF (2/1) was processed according to the method of Example 112B to provide the title compound: $^1$H NMR (500 MHz, DMSO-$d_6$) δ 1.16 (s, 6H) 1.23 (s, 6H) 1.45 (s, 1H) 2.31-2.38 (m, 2H) 2.72 (t, J=7.0 Hz, 2H) 2.78 (t, J=7.2 Hz, 2H) 3.24 (s, 3H) 3.61 (t, J=5.3 Hz, 2H) 4.15 (t, J=5.2 Hz, 2H); MS (DCI/NH$_3$) m/z 323 (M+H)$^+$.

Example 123

N-[(7Z)-8-(2-methoxyethyl)-5,8-dihydro[1,3]thiazolo[4,5-e][2,1,3]benzoxadiazol-7(4H)-ylidene]-2,2,3,3-tetramethylcyclopropanecarboxamide

Example 123A 4,5-dihydro[1,3]thiazolo[4,5-e][2,1,3]benzoxadiazol-7-amine hydrobromide To a solution of commercially available 5-bromo-6,7-dihydro-5H-benzo[1,2,5]oxadiazol-4-one (1.1 g, 5.1 mmol) in absolute ethanol (60 mL) was added thiourea. The reaction mixture was stirred at 60° C. for overnight and then concentrated. The residue was triturated in hexanes to afford 1.3 g (90%) of the title compound MS (ESI$^+$) m/z 195 (M+H)$^+$.

Example 123B

N-4,5-dihydro[1,3]thiazolo[4,5-e][2,1,3]benzoxadiazol-7-yl-2,2,3,3-tetramethylcyclopropanecarboxamide Example 123A and 2,2,3,3-tetramethylcyclopropanecarbonyl chloride were processed as described for example 118A to afford the title compound. MS (ESI$^+$) m/z 319 (M+H)$^+$.

Example 123C

N-[(7Z)-8-(2-methoxyethyl)-5,8-dihydro[1,3]thiazolo[4,5-e][2,1,3]benzoxadiazol-7(4H)-ylidene]-2,2,3,3-tetramethylcyclopropanecarboxamide The product of Example 123B (1 equiv), potassium tert-butoxide (1.1 equiv) and 2-bromoethyl methyl ether (1 equiv) were combined in DME (0.1 M) and heated in a SmithSynthesizer™ microwave at 250° C. for 15 minutes. The mixture was diluted with EtOAc and washed with 1 M aqueous NaHCO$_3$. The phases were separated and the aqueous phase was extracted with EtOAc (3×). The combined organic extracts were dried over Na$_2$SO$_4$, filtered, and concentrated. Purification by silica gel chromatography afforded the title compound and the product of Example 124. $^1$H NMR (400 MHz, DMSO-$d_6$) δ ppm 1.20 (s, 6H), 1.26 (s, 6H), 1.57 (s, 1H), 3.10 (t, J=7.5 Hz, 2H), 3.23 (s, 3H), 3.26 (t, J=7.4 Hz, 2H), 3.71 (t, J=5.8 Hz, 2H), 4.67 (t, J=5.8 Hz, 2H); MS (ESI$^+$) m/z 377 (M+H)$^+$.

Example 124

N-[(7Z)-8-(2-methoxyethyl)[1,3]thiazolo[4,5-e][2,1,3]benzoxadiazol-7(8H)-ylidene]-2,2,3,3-tetramethyl-cyclopropanecarboxamide The title compound was obtained as byproduct during the synthesis of example 123C. $^1$H NMR (400 MHz, DMSO-$d_6$) δ ppm 1.23 (s, 6H), 1.29 (s, 6H), 1.67 (s, 1H), 3.24 (s, 3H), 3.85 (t, J=5.7 Hz, 2H), 4.96 (t, J=5.5 Hz, 2H), 7.94 (d, J=9.2 Hz, 1H), 8.06 (d, J=9.5 Hz, 1H); MS (ESI$^+$) m/z 374 (M+H)$^+$.

Example 125

2-Ethoxy-N-[(2Z)-3-(2-methoxyethyl)-4,6-dihydro-furo[3,4-d]thiazol-2(3H)-ylidene]-benzamide

Example 125A

4-Bromo-dihydrofuran-3-one

The title compound was prepared according to the procedure using the method described in Baker, Tracy J, Wiemer, David F, *J. Org. Chem.*, 1998, 63(8), 2613-2618 and was used immediately using the method described in Example 125B.

Example 125B

3α-Ethoxy-3α,4,6,6α-tetrahydrofuro[3,4-d]thiazol-2-ylamine

The product of Example 125A and thiourea were processed using the method described in Example 123A to afford the title compound. MS (ESI$^+$) m/z 189 (M+H)$^+$.

Example 125C

3α-Ethoxy-3-(2-methoxy-ethyl)-tetrahydro-furo[3,4-d]thiazol-2-ylideneamine

The product from Example 125B and 1-bromo-2-methoxyethane were processed using the method described in Example 12A to afford the title compound. MS (ESI$^+$) m/z 247 (M+H)$^+$.

Example 125D

2-Ethoxy-N-[3α-ethoxy-3-(2-methoxy-ethyl)-tetrahydro-furo[3,4-d]thiazol-2-ylidene]-benzamide The product from Example 125B and 2-ethoxybenzoyl chloride were processed as described for example 118A to afford the title compound. MS (ESI$^+$) m/z 395 (M+H)$^+$.

Example 125E

2-Ethoxy-N-[3-(2-methoxyethyl)-4,6-dihydro-3H-furo[3,4-d]thiazol-2-ylidene]-benzamide To a solution of the product from Example 125D (15 mg, 0.04 mmol) in toluene (10 mL) was added p-toluenesulfonic acid monohydrate (2 mg). The mixture was refluxed for 3 hours and then cooled to room temperature, diluted with ethyl acetate, washed with 1 M NaHCO$_3$, dried (Na$_2$SO$_4$), filtered and concentrated. Purification by preparative HPLC on a waters Symmetry C8 column (40 mm×100 mm, 7 μm particle size) using a gradient of 10% to 100% acetonitrile: ammonium acetate (10 mM) over 15 min at a flow rate of 70 mL/min afforded the title compound. $^1$H NMR (300 MHz, DMSO-$d_6$) δ ppm 1.33 (t, J=7.0 Hz, 3H), 3.24 (S, 3H), 3.65 (t, J=4.9 Hz, 2H), 4.07 (q, J=6.8 Hz, 2H), 4.25 (t, J=5.1 Hz, 2H), 4.96 (s, 4H), 6.92-7.01 (m, 1H), 7.07 (d, J=8.1 Hz, 1H), 7.36-7.44 (m, 1H), 7.74 (dd, J=7.5, 1.7 Hz, 1H); MS (ESI$^+$) m/z 349 (M+H)$^+$.

Example 126

3-chloro-2-fluoro-N-[(2Z)-3-(2-methoxyethyl)-4,5-dimethyl-1,3-thiazol-2(3H)-ylidene]-6-(trifluoromethyl)benzamide

Example 126A 3-(2-Methoxy-ethyl)-4,5-dimethyl-3H-thiazol-2-ylideneamine

The product of Example 12A was purified via flash column chromatography (SiO$_2$, 9:1:0.1 CH$_2$Cl$_2$:CH$_3$OH:NH$_4$OH) to provide the title compound. $^1$H NMR (300 MHz, CDCl$_3$) δ ppm 2.18 (s, 6H) 3.32 (s, 3H) 3.78 (t, J=5.10 Hz, 2H) 4.39 (t, J=4.70 Hz, 2H) 9.45 (s, 2H); MS (DCI/NH$_3$) m/z 187 (M+H)$^+$,

Example 126B

3-Chloro-2-fluoro-N-[3-(2-methoxy-ethyl)-4,5-dimethyl-3H-thiazol-2-ylidene]-6-trifluoromethyl-benzamide To a suspension of the product of Example 126A (0.20 g, 1.1 mmol) in 35 mL THF was added Et$_3$N (0.37 mL, 2.7 mmol). This mixture was cooled to 0° C. and 3-chloro-2-fluoro-6-trifluoromethyl benzoyl chloride (Alfa Aesar, 0.35 g, 1.3 mmol) in 5 mL THF was added dropwise via syringe. The mixture was allowed to stir at ambient temperature for 1 hour, then was warmed to reflux and was allowed to stir for 8 hours. The mixture was then cooled to ambient temperature and filtered. The filtrate was concentrated under reduced pressure and purified via flash column chromatography (SiO$_2$, 7:3 hexanes:EtOAc) to provide the title compound (0.20 g, 0.50 mmol, 46% yield). $^1$H NMR (300 MHz, CDCl$_3$) δ ppm 2.27 (s, 3H), 2.28 (s, 3H), 3.27 (s, 3H), 3.68 (t, J=4.7 Hz, 2H), 4.28-4.37 (m, 2H), 7.37-7.43 (m, 1H), 7.44-7.52 (m, 1H); MS (DCI/NH$_3$) m/z 411 (M+H)$^+$; Anal. calculated for C$_{16}$H$_{15}$ClF$_4$N$_2$O$_2$S: C, 46.78; H, 3.68; N, 6.82. Found: C, 46.83; H, 3.30; N, 6.65.

Example 127

5-chloro-N-[(2Z)-3-(2-methoxyethyl)-4,5-dimethyl-1,3-thiazol-2(3H)-ylidene]-2-(trifluoromethyl)benzamide To the product of Example 126A (0.20 g, 1.1 mmol) in 35 mL THF at 0° C. was added Et$_3$N (0.37 mL, 2.7 mmol) followed by 5-chloro-2-trifluoromethyl-benzoyl chloride (Matrix, 0.26 g, 1.3 mmol) in 5 mL THF dropwise via syringe. This mixture was stirred at ambient temperature for 1 hour then was warmed to reflux and allowed to stir for 8 hours. The mixture was then cooled to ambient temperature and filtered. The filtrate was concentrated under reduced pressure and the residue was purified via flash column chromatography (SiO$_2$, 4:1 hexanes:EtOAc) to provide the title compound (0.23 g, 0.57 mmol, 53% yield). $^1$H NMR (300 MHz, CDCl$_3$) δ ppm 2.26 (s, 3H), 2.28 (s, 3H), 3.30 (s, 3H), 3.71 (t, J=4.9 Hz, 2H), 4.36 (t, J=4.9 Hz, 2H), 7.45 (ddd, J=8.5, 2.0, 0.7 Hz, 1H), 7.64 (d, J=8.5 Hz, 1H), 7.84 (d, J=2.0 Hz, 1H); MS (DCI/NH$_3$) m/z 393 (M+H)$^+$; Anal. calculated for C$_{16}$H$_{16}$ClF$_3$N$_2$O$_2$S: C, 48.92; H, 4.11; N, 7.13. Found: C, 48.66; H, 3.81; N, 7.01.

Example 128

2,3-dichloro-N-[(2Z)-3-(2-methoxyethyl)-4,5-dimethyl-1,3-thiazol-2(3H)-ylidene]benzamide To the product of Example 126A (0.20 g, 1.1 mmol) in 35 mL THF was added Et$_3$N (0.37 mL, 2.7 mmol). This mixture was cooled to 0° C. and 2,3-dichlorobenzoyl chloride (Lancaster, 0.27 g, 1.3 mmol) in 5 mL THF was added dropwise via syringe. This mixture stirred at ambient temperature for 1 hour then was warmed to reflux and was allowed to stir for 3 hours. The mixture was cooled to ambient temperature and was quenched with 5 mL saturated, aqueous NH$_4$Cl and diluted with 10 mL EtOAc. The layers were separated and the aqueous layer was extracted 2×5 mL EtOAc and 2×5 mL CH$_2$Cl$_2$. The combined organics were washed 1×5 mL saturated, aqueous NaCl then were dried over anhydrous Na$_2$SO$_4$, filtered, concentrated under reduced pressure and purified via flash column chromatography (SiO$_2$, 10% CH$_3$OH:EtOAc). The material was still impure so it was purified again via flash column chromatography (SiO$_2$, 1:1 hexanes:EtOAc) to provide the title compound (0.105 g, 0.29 mmol, 27% yield). $^1$H NMR (300 MHz, CDCl$_3$) δ ppm 2.26 (s, 3H), 2.28 (s, 3H), 3.30 (s, 3H), 3.76 (t, J=4.6 Hz, 2H), 4.40 (t, J=4.2 Hz, 2H), 7.23 (t, J=7.7 Hz, 1H), 7.49 (dd, J=8.0, 1.5 Hz, 1H), 7.72 (dd, J=7.6, 1.5 Hz, 1H); MS (DCI/NH$_3$) m/z 359 (M+H)$^+$; Anal. calculated for C$_{15}$H$_{16}$Cl$_2$N$_2$O$_2$S: C, 50.15; H, 4.49; N, 7.80. Found; C, 50.17; H, 4.26; N, 7.69

Example 129

N-[(2Z)-3-(2-methoxyethyl)-4,5-dimethyl-1,3-thiazol-2(3H)-ylidene]-2,2-dimethyl-2,3-dihydro-1-benzofuran-7-carboxamide To a solution of the product of Example 126A (0.20 g, 1.1 mmol) and Et$_3$N (0.45 mL, 3.2 mmol) in 30 mL THF was added 2,2-dimethyl-2,3-dihydro-1-benzofuran-7-carbonyl chloride (Acros, 0.34 g, 1.6 mmol). This mixture was warmed to reflux and allowed to stir for 2 hours. The mixture was then cooled to ambient temperature and concentrated under reduced pressure. The residue was diluted with 10 mL EtOAc and washed with 5 mL saturated, aqueous NH$_4$Cl. The layers were separated and the aqueous layer was extracted 2×5 mL EtOAc. The combined organics were dried over anhydrous Na$_2$SO$_4$, filtered, concentrated under reduced pressure and purified via flash column chromatography (SiO$_2$, 4:1 hexanes:EtOAc) to provide the title compound (0.21 mmol, 0.57 mmol, 53% yield). $^1$H NMR (300 MHz, CDCl$_3$) δ ppm 1.55 (s, 6H), 2.22 (s, 3H), 2.27 (s, 3H), 3.02 (s, 2H), 3.31 (s, 3H), 3.77-3.89 (m, 2H), 4.33-4.50 (m, 2H), 6.85 (t, J=7.5 Hz, 1H), 7.22 (d, J=7.5 Hz, 1H), 8.00 (d, J=8.1 Hz, 1H); MS (DCI/NH$_3$) m/z 361 (M+H)$^+$; Anal. calculated for C$_{19}$H$_{24}$N$_2$O$_3$S: C, 63.31; H, 6.71; N, 7.77. Found: C, 63.19; H, 6.50; N, 7.66.

Example 130

2,2-difluoro-N-[(2Z)-3-(2-methoxyethyl)-4,5-dimethyl-1,3-thiazol-2(3H-ylidene]-1,3-benzodioxole-4-carboxamide To the product of Example 126A (0.20 g, 1.1 mmol) in 30 mL THF was added Et$_3$N (0.37 mL, 2.7 mmol) followed by 2,2-difluoro-1,3-benzodioxole-4-carbonyl chloride (Lancaster, 0.29 g, 1.3 mmol). This mixture was stirred at ambient temperature for 17 hours then was warmed to reflux and allowed to stir for an additional 4 hours. The mixture was then cooled to ambient temperature and additional 2,2-difluoro-1,3-benzodioxole-4-carbonyl chloride (73 mg, 0.33 mmol) and Et$_3$N (0.37 mL, 2.7 mmol) were added. This mixture was warmed to reflux at which temperature it stirred for 2 hours. The mixture was then cooled to ambient temperature, diluted with 10 ml EtOAc and washed with 5 mL saturated, aqueous NH$_4$Cl. The layers were separated and the aqueous layer was extracted 2×5 mL EtOAc. The combined organics were dried over anhydrous Na$_2$SO$_4$, filtered, concentrated under reduced pressure and purified via flash column chromatography (SiO$_2$, 50% hexanes:EtOAc) to afford the title compound (0.22 g, 0.59 mmol, 55% yield). $^1$H NMR (300 MHz, CDCl$_3$) δ ppm 2.26 (s, 3H) 2.28 (s, 3H), 3.32 (s, 3H), 3.83 (t, J=5.1 Hz, 2H), 4.44 (t, J=5.1 Hz, 2H), 7.12 (d, J=4.4 Hz, 1H), 7.14 (s, 1H), 7.89 (dd, J=6.6, 2.9 Hz, 1H); MS (DCI/NH$_3$) m/z 371 (M+H)$^+$; Anal. calculated for C$_{16}$H$_{16}$F$_2$O$_4$S: C, 51.89; H, 4.35; N, 7.56. Found: C, 52.27; H, 4.24; N, 7.53.

Example 131

5-bromo-N-[(2Z)-3-(2-methoxyethyl)-4,5-dimethyl-1,3-thiazol-2(3H)-ylidene]-2,3-dihydro-1-benzofuran-7-carboxamide The product of Example 126A (0.20 g, 1.1 mmol), Et$_3$N (0.45 mL, 3.2 mmol) and 5-bromo-2,3-dihydrobenzo[b]-furan-7-carbonyl chloride (Maybridge, 0.42 g, 1.6 mmol) in 35 mL THF were processed as in Example 126B. The resulting crude material was purified via flash column chromatography (SiO$_2$, 7:3 hexanes:EtOAc) to afford the title compound (0.16 g, 0.39 mmol, 36% yield). $^1$H NMR (300 MHz, CDCl$_3$) δ ppm 2.24 (s, 3H), 2.28 (s, 3H), 3.23 (t, J=8.5 Hz, 2H), 3.33 (s, 3H), 3.78-3.87 (m, 2H), 4.45-4.56 (m, 2H), 4.70-4.81 (m, 2H), 7.35-7.39 (m, 1H), 8.09 (d, J=20 Hz, 1H); MS (DCI/NH$_3$) m/z 411, 413 (M+H)$^+$; Anal. calculated for C$_{17}$H$_{19}$BrN$_2$O$_3$S.0.3H$_2$O: C, 49.00; H, 4.74; N, 6.72. Found: C, 48.91; H, 4.36; N, 6.57.

Example 132

2-bromo-N-[(2Z)-3-(2-methoxyethyl)-4,5-dimethyl-1,3-thiazol-2(3H)-ylidene]benzamide To a solution of the product of Example 126A (0.20 g, 1.1 mmol) and Et$_3$N (0.3 mL, 2.2 mmol) in 25 mL THF was added 2-bromobenzoyl chloride (Aldrich, 0.18 mL, 1.4 mmol). This mixture stirred at ambient temperature for 20 hours then was concentrated under reduced pressure and the residue was diluted with 10 mL EtOAc and washed with 5 mL NH$_4$Cl. The layers were separated and the aqueous layer was extracted (2×5 mL EtOAc). The combined organic layers were dried over anhydrous Na$_2$SO$_4$, filtered, concentrated under reduced pressure and purified via recrystallization with 50% hexanes/EtOAc to afford 0.18 g of the title compound (0.49 mmol, 46% yield). $^1$H NMR (300 MHz, CDCl$_3$) δ ppm 2.26 (s, 3H), 2.28 (s, 3H), 3.30 (s, 3H), 3.78 (t, J=5.1 Hz, 2H), 4.42 (t, J=5.1 Hz, 2H), 7.22 (dt, J=7.8, 1.7 Hz, 1H), 7.34 (dt, J=7.5, 1.4 Hz, 1H), 7.63 (dd, J=8.0, 1.2 Hz, 1H), 7.90 (dd, J=7.6, 1.9 Hz, 1H); MS (DCI/NH$_3$) m/z 369, 371 (M+H)$^+$; Anal. calculated for C$_{15}$H$_{17}$BrN$_2$O$_2$S: C, 48.79; H, 4.64; N, 7.59. Found: C, 48.84; H, 4.49; N, 7.40.

Example 133

2,6-dichloro-N-[(2Z)-3-(2-methoxyethyl)-4,5-dimethyl-1,3-thiazol-2(3H)-ylidene]benzamide The product of Example 126A (0.20 g, 1.1 mmol), Et$_3$N (0.3 mL, 2.2 mmol) and 2,6-dichlorobenzoyl chloride (Aldrich, 0.2 mL, 1.4 mmol) in 25 mL THF were processed as in Example 132 to afford the title compound (0.12 g, 0.32 mmol, 30% yield). $^1$H NMR (300 MHz, CDCl$_3$) δ ppm 2.28 (s, 6H), 3.27 (s, 3H), 3.74 (t, J=4.6 Hz, 2H), 4.34-4.44 (m, 2H), 7.19 (dd, J=8.8, 6.8 Hz, 1H), 7.28-7.34 (m, 2H); MS (DCI/NH$_3$) m/z 359 (M+H)$^+$.

Example 134

N-[(2Z)-3-(2-methoxyethyl)-4,5-dimethyl-1,3-thiazol-2(3H)-ylidene]quinoline-4-carboxamide

Example 134A

Quinoline-4-carbonyl chloride

A solution of 4-quinolinecarboxylic acid (Aldrich, 0.25 g, 1.4 mmol) in 5 mL of thionyl chloride was warmed to reflux and allowed to stir for 1 hour. The mixture was then cooled to ambient temperature and concentrated under reduced pressure. This material was dissolved in 10 mL toluene and concentrated under reduced pressure (3×) to afford the title compound.

Example 134B

N-[(2Z)-3-(2-methoxyethyl)-4,5-dimethyl-1,3-thiazol-2(3H)-ylidene]quinoline-4-carboxamide To a suspension of the product of Example 126A (0.20 g, 1.1 mmol) in 25 mL THF was added Et$_3$N (0.3 mL, 2.2 mmol) followed by the freshly prepared quinoline-4-carbonyl chloride. This mixture was warmed to reflux and allowed to stir for 18 hours. The material was then concentrated under reduced pressure and 10 mL EtOAc, 5 mL H$_2$O and 5 mL NH$_4$OH were added. The layers were separated and the aqueous layer was extracted 2×5 mL EtOAc. The combined organic layers were dried over anhydrous Na$_2$SO$_4$, filtered, concentrated under reduced pressure and purified via flash column chromatography (SiO$_2$, 5% CH$_3$OH in EtOAc) to afford the title compound (0.12 g, 0.35 mmol, 33% yield). $^1$H NMR (300 MHz, CD$_3$OD) δ ppm 2.32 (d, J=0.7 Hz, 3H), 2.35 (d, J=0.7 Hz, 3H), 3.31 (s, 3H), 3.78 (t, J=5.3 Hz, 2H), 4.48 (t, J=5.1 Hz, 2H), 7.65 (ddd, J=8.5, 7.0, 1.2 Hz, 1H), 7.80 (ddd, J=8.4, 6.9, 1.4 Hz, 1H), 8.00 (d, J=4.4 Hz, 1H), 8.06-8.11 (m, 1H), 8.84 (ddd, J=8.5, 1.4, 0.7 Hz, 1H), 8.93 (d, J=4.4 Hz, 1H); MS (DCI/NH$_3$) m/z 342 (M+H)$^+$; Anal. calculated for C$_{18}$H$_{19}$N$_3$O$_2$S: C, 63.32; H, 5.61; N, 12.31. Found: C, 63.23; H, 5.46; N, 12.10.

Example 135

N-[(2Z)-3-(2-methoxyethyl)-4,5-dimethyl-1,3-thiazol-2(3H)-ylidene]quinoline-5-carboxamide The quinoline-5-carboxylic acid (Lancaster, 0.25 g, 1.4 mmol) was converted to quinoline-5-carbonyl chloride using 5 mL SOCl$_2$ using the method described in Example 134A. The product of Example 126A (0.20 g, 1.1 mmol), Et$_3$N (0.3 mL, 2.2 mmol) and quinoline-5-carbonyl chloride in 30 mL THF were processed as in Example 134B to afford the title compound (0.18 g, 0.53 mmol, 49% yield). $^1$H NMR (300 MHz, CD$_3$OD) δ ppm 2.30 (d, J=0.7 Hz, 3H), 2.34 (s, 3H), 3.31 (s, 3H), 3.80 (t, J=5.1 Hz, 2H), 4.49 (t, J=5.3 Hz, 2H), 7.60 (dd, J=8.6, 4.2 Hz, 1H), 7.83 (dd, J=8.5, 7.1 Hz, 1H), 8.15 (dt, J=8.5, 1.0 Hz, 1H), 8.40 (dd, J=7.3, 1.2 Hz, 1H), 8.87 (dd, J=4.1, 1.7 Hz, 1H), 9.55 (ddd, J=8.8, 1.7, 0.7 Hz, 1H);

MS (DCI/NH$_3$) m/z 342 (M+H)$^+$; Anal. calculated for C$_{18}$H$_{19}$N$_3$O$_2$S: C, 63.32; H, 5.61; N, 12.31. Found: C, 63.44; H, 5.05; N, 12.10.

Example 136

N-[(2Z)-3-(2-methoxyethyl)-4,5-dimethyl-1,3-thiazol-2(3H)-ylidene]isoquinoline-5-carboxamide The isoquinoline-5-carboxylic acid (Lancaster, 0.25 g, 1.4 mmol) was converted to the corresponding acid chloride with 5 mL of thionyl chloride using the method described in Example 134A. The product of Example 126A (0.20 g, 1.1 mmol), Et$_3$N (0.3 mL, 2.2 mmol) and the acid chloride in 30 mL THF were processed as in Example 134B to afford the title compound (98 mg, 0.29 mmol, 27% yield). $^1$H NMR (300 MHz, CD$_3$OD) δ ppm 2.31 (s, 3H), 2.35 (s, 3H), 3.31 (s, 3H), 3.81 (t, J=5.3 Hz, 2H), 4.50 (t, J=5.3 Hz, 2H), 7.76 (dd, J=7.5, 7.5 Hz, 1H), 8.23 (d, J=8.1 Hz, 1H), 8.48 (d, J=6.4 Hz, 1H), 8.61 (dd, J=7.1, 1.4 Hz, 1H), 9.03 (d, J=6.1 Hz, 1H), 9.27 (d, J=1.0 Hz, 1H); MS (DCI/NH$_3$) m/z 342 (M+H)$^+$; Anal. calculated for C$_{18}$H$_{19}$N$_3$O$_2$S: C, 63.32; H, 5.61; N, 12.31. Found: C, 62.97; H, 5.54; N, 12.07.

Example 137

N-[(2Z)-3-(2-methoxyethyl)-4,5-dimethyl-1,3-thiazol-2(3H)-ylidene]-2,3-dihydro-1-benzofuran-7-carboxamide The 2,3-dihydrobenzofuran-7-carboxylic acid (TCI-US, 0.25 g, 1.4 mmol) was converted to 2,3-dihydrobenzofuran-7-carbonyl chloride with 5 mL of thionyl chloride using the method described in Example 134A. The product of Example 126A (0.20 g, 1.1 mmol), Et$_3$N (0.3 mL, 2.2 mmol) and the fleshly prepared 2,3-dihydrobenzofuran-7-carbonyl chloride in 30 mL THF were processed as in Example 134B. Purification of the crude material via recrystallization with 50% hexanes:EtOAc gave the title compound (0.12 g, 0.36 mmol, 34% yield). $^1$H NMR (300 MHz, CD$_3$OD) δ ppm 2.25 (s, 3H), 2.30 (s, 3H), 3.22 (t, J=8.8 Hz, 2H), 3.31 (s, 3H), 3.81 (t, J=5.3 Hz, 2H), 4.44 (t, J=5.3 Hz, 2H), 4.64 (t, J=8.8 Hz, 2H), 6.86 (t, J=7.5 Hz, 1H), 7.32 (dd, J=7.3, 1.2 Hz, 1H), 7.93 (dd, J=8.0, 0.8 Hz, 1H); MS (DCI/NH$_3$) m/z 333 (M+H)$^+$; Anal. calculated for C$_{17}$H$_{20}$N$_2$O$_3$S.0.1H$_2$O: C, 61.09; H, 6.09; N, 8.38. Found. C, 60.99; H, 5.91; N, 8.25.

Example 138

2-chloro-N-[(2Z)-3-(2-methoxyethyl)-4,5-dimethyl-1,3-thiazol-2(3H)-ylidene]quinoline-4-carboxamide The 2-chloroquinoline-4-carboxylic acid (TCI-JP, 0.29 g, 1.4 mmol) was converted to 2-chloroquinoline-4-carbonyl chloride with 5 mL of thionyl chloride using the method described in Example 134A. The product of Example 126A (0.20 g, 1.1 mmol), Et$_3$N (0.3 mL, 2.2 mmol) and 2-chloroquinoline-4-carbonyl chloride in 30 mL THF were processed as in Example 134B to afford the title compound (0.14 g, 0.37 mmol, 35% yield), $^1$H NMR (300 MHz, CD$_3$OD) δ ppm 2.33 (s, 3H), 2.35 (s, 3H), 3.31 (s, 3H), 3.78 (t, J=5.3 Hz, 2H), 4.49 (t, J=5.3 Hz, 2H), 7.66 (ddd, J=8.5, 7.1, 1.4 Hz, 1H), 7.81 (ddd, J=8.5, 7.1, 1.4 Hz, 1H), 7.94 (s, 1H), 7.99 (dt, J=8.5, 0.7 Hz, 1H), 8.83 (dd, J=8.6, 1.2 Hz, 1H); MS (DCI/NH$_3$) m/z 376 (M+H)$^+$; Anal. calculated for C$_{18}$H$_{18}$ClN$_3$O$_2$S: C, 57.52; H, 4.83; N, 11.18. Found: C, 57.44; H, 4.59; N, 10.97.

Example 139

N-[(2Z)-3-(2-methoxyethyl-4,5-dimethyl-1,3-thiazol-2(3H)-ylidene]-1,2-dihydroacenaphthylene-5-carboxamide The acenaphthene-5-carboxylic acid (Aldrich, 0.29 g, 1.4 mmol) in 5 mL of thionyl chloride was converted to acenaphthene-5-carbonyl chloride using the method described in Example 134A. The product of Example 126A (0.20 g, 1.1 mmol), Et$_3$N (0.3 mL, 2.2 mmol) and acenaphthene-5-carbonyl chloride in 30 mL THF were processed as in Example 134B to afford the title compound (87 mg, 0.24 mmol, 22% yield). $^1$H NMR (300 MHz, CD$_3$OD) δ ppm 2.28 (d, J=0.7 Hz, 3H), 2.33 (d, J=0.7 Hz, 3H), 3.33 (s, 3H), 3.42 (s, 4H), 3.84 (t, J=5.3 Hz, 2H), 4.51 (t, J=5.3 Hz, 2H), 7.30-7.36 (m, 2H), 7.52 (dd, J=8.6, 7.0 Hz, 1H), 8.43 (d, J=7.5 Hz, 1H), 8.81 (d, J=8.8 Hz, 1H); MS (DCI/NH$_3$) m/z 367 (M+H)$^+$; Anal. calculated for C$_{21}$H$_{22}$N$_2$O$_2$S: C, 68.82; H, 6.05; N, 7.64. Found: C, 68.63; H, 5.72; N, 7.40.

Example 140

2,3-dichloro-N-[(2Z)-3-(2-methoxyethyl)-5-methyl-1,3-thiazol-2(3H)-ylidene]benzamide Example 140A 3-(2-Methoxy-ethyl)-5-methyl-3H-thiazol-2-ylidene-amine The product of Example 10A (17.6 g, 70 mmol) was treated with ~50 mL 20% aqueous K$_2$CO$_3$ then the mixture was extracted with EtOAc (3×25 mL). The combined organics were dried over anhydrous Na$_2$SO$_4$, filtered and concentrated under reduced pressure to afford the title compound (5.9 g, 34 mmol, 49% yield). $^1$H NMR (300 MHz, CDCl$_3$) δ ppm 2.03 (d, J=1.70 Hz, 3H) 3.36 (s, 3H) 3.62 (t, J=5.10 Hz, 2H) 3.83 (t, J=4.80 Hz, 2H) 6.15-6.21 (m, 1H); MS (DCI/NH$_3$) m/z 173 (M+H)$^+$.

Example 140B 2,3-dichloro-N-[(2Z)-3-(2-methoxyethyl)-5-methyl-1,3-thiazol-2(3H)-ylidene]benzamide To the product of Example 140A (0.20 g, 1.2 mmol) in 15 mL THF was added Et$_3$N (0.48 mL, 3.5 mmol) followed by a solution of 2,3-dichlorobenzoyl chloride (Lancaster, 0.31 g, 1.5 mmol) in 5 mL THF. This mixture stirred at ambient temperature for 1 hour then was concentrated under reduced pressure, quenched with 5 mL saturated, aqueous NH$_4$Cl and extracted with EtOAc (3×5 mL). The combined organic extracts were dried over anhydrous Na$_2$SO$_4$, filtered and concentrated under reduced pressure. The resulting solids were recrystallized from 50% hexanes/EtOAc to afford the title compound (0.27 g, 0.78 mmol, 68% yield) $^1$H NMR (300 MHz, CDCl$_3$) δ ppm 2.32 (d, J=1.4 Hz, 3H), 3.34 (s, 3H), 3.71 (t, J=5.1 Hz, 2H), 4.34 (t, J=4.8 Hz, 2H), 6.82-6.86 (m, 1H), 7.22 (t, J=7.8 Hz, 1H), 7.49 (dd, J=8.1, 1.7 Hz, 1H), 7.73 (dd, J=7.5, 1.7 Hz, 1H); MS (DCI/NH$_3$) m/z 345 (M+H)$^+$; Anal. calculated for C$_{14}$H$_{14}$Cl$_2$N$_2$O$_2$S: C, 48.70; H, 4.09; N, 8.11. Found: C, 48.39; H, 3.70; N, 7.94.

Example 141

5-chloro-N-[(2Z)-3-(2-methoxyethyl)-5-methyl-1,3-thiazol-2(3H)-ylidene]-2-(trifluoromethyl)benzamide The product of Example 140A (0.20 g, 1.2 mmol), Et$_3$N (0.48 mL, 3.5 mmol) and 5-chloro-2-(trifluoromethyl)benzoyl chloride (Matrix, 0.31 g, 1.5 mmol) in 20 mL THF were processed using the method described in Example 140B to afford the title compound (0.16 g, 0.42 mmol, 36% yield). $^1$H NMR (300 MHz, CDCl$_3$) δ ppm 2.33 (d, J=0.7 Hz, 3H), 3.34 (s, 3H), 3.69 (t, J=5.1 Hz, 2H), 4.34 (t, J=4.6 Hz, 2H), 6.85 (s, 1H), 7.42-7.48 (m, 1H), 7.64 (d, J=8.5 Hz, 1H), 7.85 (d, J=2.0 Hz, 1H); MS (DCI/NH$_3$) m/z 379 (M+H)$^+$; Anal. calculated for C$_{15}$H$_{14}$ClF$_3$N$_2$O$_2$S: C, 47.56; H, 3.73; N, 7.40. Found: C, 47.31; H, 3.30; N, 7.33.

Example 142

2-chloro-N-[(2Z)-3-(2-methoxyethyl)-4,5-dimethyl-1,3-thiazol-2(3H)-ylidene]benzamide The product of Example 126A (0.20 g, 1.1 mmol), Et$_3$N (0.45 mL, 3.2 mmol) and 2-chlorobenzoyl chloride (Aldrich, 0.26 g, 1.4 mmol) in 15 mL THF were processed as in Example 132 to afford the title compound (0.13 g, 0.40 mmol, 37% yield). $^1$H NMR (300 MHz, CD$_3$OD) δ ppm 2.28 (s, 3H), 2.32 (s, 3H), 3.31 (s, 3H), 3.76 (t, J=5.3 Hz, 2H), 4.42 (t, J=5.1 Hz, 2H), 7.30-7.46 (m, 3H), 7.77-7.83 (m, 1H); MS (DCI/NH$_3$) m/z 325 (M+H)$^+$; Anal. calculated for C$_{15}$H$_{17}$ClN$_2$O$_2$S: C, 55.46; H, 5.28; N, 8.62. Found: C, 55.59; H, 4.81; N, 8.47.

Example 143

N-[(2Z)-5-tert-butyl-3-(2-methoxyethyl)-4-methyl-1,3-thiazol-2(3H)-ylidene]-2-ethoxybenzamide

Example 143A 5-tert-Butyl-3-(2-methoxyethyl)-4-methyl-1,3-thiazol-2(3H)-ylideneamine A mixture of 5-tert-butyl-4-methylthiazole-2-ylamine (1.5 g, 8.8 mmol) and 2-bromoethyl methyl ether (0.91 mL, 9.7 mmol) was warmed to 85° C. and allowed to stir for 24 hours. The crude material was dissolved in ~5 mL of a 1:1 mixture of CH$_2$Cl$_2$ and CH$_3$OH and a small amount of silica gel was added. This mixture was concentrated to dryness and the residue was purified via flash column chromatography (SiO$_2$, 9:1:01: CH$_2$Cl$_2$:CH$_3$OH:NH$_4$OH) to afford the title compound (1.0 g, 4.4 mmol, 50% yield). $^1$H NMR (300 MHz, CD$_3$OD) δ ppm 1.41 (s, 9H) 2.38 (s, 3H) 3.35 (s, 3H) 3.66 (t, J=4.70 Hz, 2H) 4.16 (t, J=4.70 Hz, 2H); MS (DCI/NH$_3$) m/z 229 (M+H)$^+$.

Example 143B

N-[(2Z)-5-tert-butyl-3-(2-methoxyethyl)-4-methyl-1,3-thiazol-2(3H)-ylidene]-2-ethoxybenzamide A mixture of the product of Example 143A (0.15 g, 0.66 mmol), Et$_3$N (0.28 mL, 2.0 mmol) and 2-ethoxybenzoyl chloride (Aldrich, 0.16 g, 0.86 mmol) in 15 mL THF were processed using the method described in Example 129 to afford the title compound (0.12 g, 0.33 mmol, 50% yield). $^1$H NMR (300 MHz, CD$_3$OD) δ ppm 1.41 (t, J=7.1 Hz, 3H), 1.45 (s, 9H), 247 (s, 3H), 3.31 (s, 3H), 3.77 (t, J=5.3 Hz, 2H), 4.11 (q, J=6.8 Hz, 2H), 4.43 (t, J=5.3 Hz, 2H), 6.95 (dt, J=7.5, 1.0 Hz, 1H), 7.04 (d, J=8.1 Hz, 1H), 7.37 (ddd, J=8.7, 6.9, 1.7 Hz, 1H), 7.78 (dd, J=7.6, 1.9 Hz, 1H); MS (DCI/H$_3$) m/z 377 (M+H)$^+$; Anal. calculated for C$_{20}$H$_{28}$N$_2$O$_3$S: C, 63.80; H, 7.50; N, 7.44. Found: C, 64.19; H, 7.44; N, 7.19.

Example 144

N-[(2Z)-5-tert-butyl-3-(2-methoxyethyl)-4-methyl-1,3-thiazol-2(3H)-ylidene]-2,3-dichlorobenzamide A mixture of the product of Example 143A (0.15 g, 0.66 mmol), Et$_3$N (0.28 mL, 2.0 mmol) and 2,3-dichlorobenzoyl chloride (Lancaster, 0.18 g, 0.86 mmol) in 15 mL THF were processed using the method described in Example 129 to afford the title compound (0.11 g, 0.27 mmol, 42% yield). $^1$H NMR (300 MHz, CDCl$_3$) δ ppm 1.43 (s, 9H), 2.43 (s, 3H), 3.30 (s, 3H), 3.74 (t, J=5.3 Hz, 2H), 4.36 (t, J=5.3 Hz, 2H), 7.22 (dd, J=8.0, 8.0 Hz, 1H), 7.48 (dd, J=8.1, 1.7 Hz, 1H), 7.72 (dd, J=7.6, 1.5 Hz, 1H); MS (DCI/NH$_3$) m/z 401 (M+H)$^+$; Anal. calculated for C$_{18}$H$_{22}$Cl$_2$N$_2$O$_2$S: C, 53.87; H, 5.53; N, 6.98. Found: C, 53.86; H, 5.37; N, 6.76.

Example 145

N-[(2Z)-5-tert-butyl-3-(2-methoxyethyl)-4-methyl-1,3-thiazol-2(3H)-ylidene]-5-chloro-2-(trifluoromethyl)benzamide A mixture of the product of Example 143A (0.15 g, 0.66 mmol), Et$_3$N (0.28 mL, 2.0 mmol) and 5-chloro-2-trifluoromethylbenzoyl chloride (Matrix, 0.17 g, 0.86 mmol) in 15 mL THF were processed using the method described in Example 129 to afford the title compound (0.16 g, 0.37 mmol, 56% yield). $^1$H NMR (300 MHz, CD$_3$OD) δ ppm 1.46 (s, 9H), 2.49 (s, 3H), 3.31 (s, 3H), 3.70 (t, J=5.3 Hz, 2H), 4.41 (t, J=5.3 Hz, 2H), 7.56-7.62 (m, 1H), 7.71-7.76 (m, 2H); MS (DCI/NH$_3$) m/z 435 (M+H)$^+$; Anal. calculated for C$_{19}$H$_{22}$ClF$_3$N$_2$O$_2$S: C, 52.47; H, 5.10; N, 6.44. Found; C, 52.52; H, 4.94; N, 6.05.

Example 146

N-[(2Z)-3-(2-methoxyethyl)-5-methyl-1,3-thiazol-2(3H)-ylidene]-1-naphthamide

The product of Example 140A (0.20 g, 1.2 mmol), Et$_3$N (0.48 mL, 3.5 mmol) and 1-naphthoyl chloride (Aldrich, 0.22 g, 1.5 mmol) in 15 mL THF were processed using the method described in Example 140B to afford the title compound (0.23 g, 0.69 mmol, 60% yield). $^1$H NMR (300 MHz, CD$_3$OD) δ ppm 2.36 (d, J=1.0 Hz, 3H), 3.35 (s, 3H), 3.78 (t, J=5.4 Hz, 2H), 4.45 (t, J=5.1 Hz, 2H), 7.10-7.15 (m, 1H), 7.46-7.58 (m, 3H), 7.88-7.94 (m, 1H), 7.97 (d, J=8.1 Hz, 1H), 8.17 (dd, J=7.3, 1.2 Hz, 1H), 8.83-8.90 (m, 1H); MS (DCI/NH$_3$) m/z 327 (M+H)$^+$; Anal. calculated for C$_{18}$H$_{18}$N$_2$O$_2$S: C, 66.23; H, 5.56; N, 8.58. Found: C, 66.10; H, 5.64; N, 8.51.

Example 147

N-[(2Z)-5-tert-butyl-3-(2-methoxyethyl)-4-methyl-1,3-thiazol-2(3H)-ylidene]-5-chloro-2-methoxybenzamide The 5-chloro-2-methoxybenzoic acid (Aldrich, 0.21 g, 1.1 mmol) was converted to 5-chloro-2-methoxybenzoyl chloride with 5 mL of thionyl chloride using the method described in Example 134A. A mixture of the product of Example 143A (0.20 g, 0.88 mmol), Et₃N (0.48 mL, 3.4 mmol) and 5-chloro-2-methoxybenzoyl chloride in 15 mL THF were processed using the method described in Example 129 to afford the title compound (0.13 g, 0.32 mmol, 37% yield). ¹H NMR (300 MHz, CDCl₃) δ ppm 1.41 (s, 9H), 2.42 (s, 3H), 3.32 (s, 3H), 3.77 (t, J=5.3 Hz, 2H), 3.90 (s, 3H), 4.36 (t, J=5.1 Hz, 2H), 6.90 (d, J=8.8 Hz, 1H), 7.31 (dd, J=8.8, 3.1 Hz, 1H), 7.94 (d, J=2.7 Hz, 1H); MS (DCI/NH₃) m/z 397 (M+H)⁺; Anal. calculated for C₁₉H₂₅ClN₂O₃S: C, 57.49; H, 6.35; N, 7.06. Found: C, 57.51; H, 6.30; N, 6.85.

Example 148

N-[(2Z)-3-(2-methoxyethyl)-5-methyl-1,3-thiazol-2(3H)-ylidene]-2-methylbenzamide The product of Example 140A (0.20 g, 1.2 mmol), Et₃N (0.48 mL, 3.5 mmol) and o-toloyl chloride (Aldrich, 0.23 g, 1.2 mmol) in 15 mL THF were processed using the method described in Example 140B to afford the title compound (0.26 g, 0.90 mmol, 78% yield). ¹H NMR (300 MHz, CDCl₃) δ ppm 2.30 (s, 3H), 2.70 (s, 3H), 3.35 (s, 3H), 3.74 (t, J=5.1 Hz, 2H), 4.36 (t, J=4.8 Hz, 2H), 6.77-6.81 (m, 1H), 7.23 (t, J=7.3 Hz, 2H), 7.28-7.35 (m, 1H), 8.08-8.13 (m, 1H); MS (DCI/NH₃) m/z 291 (M+H)⁺; Anal. calculated for C₁₅H₁₈N₂O₂S: C, 62.04; H, 6.25; N, 9.65. Found: C, 62.40; H, 6.11; N, 9.70.

Example 149

2,3-dichloro-N-[(2Z)-5-methyl-3-(tetrahydrofuran-2-ylmethyl)-1,3-thiazol-2(3H)-ylidene]benzamide

Example 149A

5-Methyl-3-(tetrahydro-furan-2-ylmethyl)-3H-thiazol-2-ylideneamine

A mixture of 2-amino-5-methylthiazole (1.0 g, 8.7 mmol) and 2-(bromomethyl)tetrahydrofuran (Maybridge, 1.1 mL, 10 mmol) was warmed to 85° C. and allowed to stir for 24 hours. The mixture was then cooled to ambient temperature and purified via column chromatography (SiO₂, 9:1:0.1 CH₂Cl₂:CH₃OH:NH₄OH) to afford the title compound (1.5 g, 7.5 mmol, 86% yield). ¹H NMR (300 MHz, CD₃OD) δ ppm 1.55-1.70 (m, 1H) 1.89-2.01 (m, 2H) 2.07-2.20 (m, 1H) 2.28 (d, J=1.36 Hz, 3H) 3.72-3.82 (m, 1H) 3.86-4.00 (m, 2H) 4.08-4.24 (m, 2H) 6.98-7.04 (m, 1H); MS (DCI/NH₃) m/z 199 (M+H)⁺.

Example 149B 2,3-dichloro-N-[(2Z)-5-methyl-3-(tetrahydrofuran-2-ylmethyl)-1,3-thiazol-2(3H)-ylidene]benzamide To a solution of the product of Example 149A (0.17 g, 0.86 mmol) in 10 mL THF and 1 mL DMF was added Et₃N (0.36 mL, 2.6 mmol) followed by 2,3-dichlorobenzoyl chloride (Lancaster, 0.27 g, 1.3 mmol). This mixture was warmed to 50° C. and allowed to stir for 2 hours. The mixture was cooled to ambient temperature, diluted with 10 mL EtOAc, and quenched with 10 mL NH₄Cl. The layers were separated and the aqueous layer was extracted 2×5 mL EtOAc. The combined organics were dried over anhydrous Na₂SO₄, filtered, concentrated under reduced pressure and purified via column chromatography (SiO₂, 20% hexanes/EtOAc) to afford the title compound (0.24 g, 0.64 mmol, 75% yield). ¹H NMR (300 MHz, CDCl₃) δ ppm 1.58-1.68 (m, 1H), 1.78-1.94 (m, 2H), 2.00-2.13 (m, 1H), 2.32 (s, 3H), 3.72-3.91 (m, 2H), 4.06-4.15 (m, 1H), 4.24 (ddd, J=14.0, 7.0, 2.7 Hz, 1H), 4.47 (dd, J=13.6, 2.7 Hz, 1H), 6.91-6.95 (m, 1H), 7.22 (t, J=8.0 Hz, 1H), 7.49 (dd, J=8.1, 1.7 Hz, 1H), 7.72 (dd, J=7.5, 1.7 Hz, 1H); MS (DCI/NH₃) m/z 371 (M+H)⁺; Anal. calculated for C₁₆H₁₆Cl₂N₂O₂S: C, 51.76; H, 4.34; N, 7.55. Found: C, 51.66; H, 4.17; N, 7.46.

Example 150

N-[(2Z)-3-(2-methoxyethyl)-4,5-dimethyl-1,3-thiazol-2(3H)-ylidene]-2-methylbenzamide The product of Example 126A (0.20 g, 1.1 mmol), Et₃N (0.45 mL, 3.2 mmol) and o-toloyl chloride (Aldrich, 0.22 g, 1.4 mmol) in 15 mL THF were processed using the method described in Example 129 to afford the title compound (0.15 g, 0.49 mmol, 46% yield). ¹H NMR (300 MHz, CDCl₃) δ ppm 2.23 (d, J=0.7 Hz, 3H), 2.26 (s, 3H), 2.70 (s, 3H), 3.31 (s, 3H), 3.77 (t, J=5.3 Hz, 2H), 4.35 (t, J=5.3 Hz, 2H), 7.23 (t, J=7.5 Hz, 2H), 7.27-7.35 (m, 1H), 8.08-8.14 (m, 1H); MS (DCI/NH₃) m/z 305 (M+H)⁺; Anal. calculated for C₁₆H₂₀N₂O₂S: C, 63.13; H, 6.62; N, 9.20. Found: C, 63.43; H, 6.53; N, 9.14.

Example 151

N-[(2Z)-3-(2-methoxyethyl)-4,5-dimethyl-1,3-thiazol-2(3H)-ylidene]benzamide

The product of Example 126A (0.20 g, 1.1 mmol), Et₃N (0.45 mL, 3.2 mmol) and benzoyl chloride (Aldrich, 0.16 mL, 1.4 mmol) in 15 mL THF were processed using the method described in Example 129 to afford the title compound (0.11 g, 0.38 mmol, 35% yield). ¹H NMR (300 MHz, CDCl₃) δ ppm 2.24 (s, 3H), 2.27 (d, J=0.7 Hz, 3H), 3.32 (s, 3H), 3.82 (t, J=5.3 Hz, 2H), 4.41 (t, J=5.3 Hz, 2H), 7.38-7.51 (m, 3H), 8.27-8.34 (m, 2H); MS (DCI/NH₃) m/z291 (M+H)⁺; Anal. calculated for C₁₅H₁₈N₂O₂S: C, 62.04; H, 6.25; N, 9.65. Found: C, 62.02; H, 6.05; N, 9.56.

Example 152

2-chloro-4-fluoro-N-[(2Z)-3-(2-methoxyethyl)-4,5-dimethyl-1,3-thiazol-2(3H)-ylidene]benzamide The product of Example 126A (0.20 g, 1.1 mmol), Et₃N (0.37 mL, 2.7 mmol) and 2-chloro-4-fluorobenzene-1-carbonyl chloride (Acros, 0.25 g, 1.3 mmol) in 15 mL THF were processed using the method described in Example 132 to afford the title compound (0.19 g, 0.56 mmol, 52% yield). ¹H NMR (300 MHz, CDCl₃) δ ppm 2.24 (s, 3H), 2.27 (s, 3H), 3.30 (s, 3H), 3.76 (t, J=5.1 Hz, 2H), 4.35 (t, J=5.1 Hz, 2H), 7.00 (ddd, J=8.5, 7.8, 2.4 Hz, 1H), 7.15 (dd, J=8.8, 2.4 Hz, 1H), 8.04 (dd, J=8.8, 6.4 Hz, 1H); MS (DCI/NH₃) m/z 343 (M+H)⁺; Anal. calculated for C₁₅H₁₆ClFN₂O₂S: C, 52.55; H, 4.70; N, 8.17. Found: C, 52.60; H, 4.38; N, 8.06.

Example 153

2-chloro-4-fluoro-N-[(2Z)-3(2-methoxyethyl)-5-methyl-1,3-thiazol-2(3H)-ylidene]benzamide The product of Example 140A (0.17 g, 1.0 mmol), Et₃N (0.35 mL, 2.5 mmol) and 2-chloro-4-fluorobenzene-1-carbonyl chloride (Acros, 0.23 g, 1.2 mmol) in 15 mL THF were processed using the method described in Example 140B to afford the title compound (0.15 g, 0.46 mmol, 46% yield). $^1$H NMR (300 MHz, CDCl$_3$) δ ppm 2.32 (d, J=1.4 Hz, 3H), 3.35 (s, 3H), 3.73 (t, J=5.4 Hz, 2H), 4.36 (t, J=4.7 Hz, 2H), 6.80-6.84 (m, 1H), 7.00 (ddd, J=8.6, 7.8, 2.5 Hz, 1H), 7.16 (dd, J=8.6, 2.5 Hz, 1H), 8.04 (dd, J=8.8, 6.4 Hz, 1H); MS (DCI/NH$_3$) m/z 329 (M+H)$^+$; Anal. calculated for C$_{14}$H$_{14}$ClFN$_2$O$_2$S: C, 51.15; H, 4.29; N, 8.52. Found: C, 51.11; H, 3.90; N, 8.43.

Example 154

2,5-dichloro-N-[(2Z)-3-(2-methoxyethyl)-4,5-dimethyl-1,3-thiazol-2(3H)-ylidene]benzamide The 2,5-dichlorobenzoic acid (Aldrich, 0.28 g, 1.4 mmol) was converted to 2,5-dichlorobenzoyl chloride with 5 mL of thionyl chloride using the method described in Example 134A. The product of Example 126A (0.20 g, 1.1 mmol), Et$_3$N (0.45 mL, 3.2 mmol) and 2,5-dichlorobenzoyl chloride in 15 mL THF were processed using the method described in Example 132 to afford the title compound (0.10 g, 0.28 mmol, 26% yield). $^1$H NMR (300 MHz, CDCl$_3$) δ ppm 2.25 (d, J=1.0 Hz, 3H), 2.28 (d, J=1.0 Hz, 3H), 3.31 (s, 3H), 3.76 (t, J=5.3 Hz, 2H) 4.36 (t, J=5.3 Hz, 2H), 7.28 (d, J=2.4 Hz, 1H), 7.32-7.36 (m, 1H), 7.94 (d, J=2.4 Hz, 1H); MS (DCI/NH$_3$) m/z 359 (M+H)$^+$; Anal. calculated for C$_{15}$H$_{16}$Cl$_2$N$_2$O$_2$S: C, 50.15; H, 4.49; N, 7.80. Found: C, 50.22; H, 4.15; N, 7.63.

Example 155

2,5-dichloro-N-[(2Z)-3-(2-methoxyethyl)-5-methyl-1,3-thiazol-2(3H)-ylidene]benzamide The 2,5-dichlorobenzoic acid (Aldrich, 0.28 g, 1.4 mmol) was converted to 2,5-dichlorobenzoyl chloride with 5 mL of thionyl chloride using the method described in Example 134A. The product of Example 140A (0.20 g, 1.1 mmol), Et$_3$N (0.45 mL, 3.2 mmol) and 2,5-dichlorobenzoyl chloride in 15 mL THF were processed using the method described in Example 129 to afford the title compound (0.24 g, 0.70 mmol, 65% yield). $^1$H NMR (300 MHz, CDCl$_3$) δ ppm 2.32 (d, J=1.4 Hz, 3H), 3.35 (s, 3H), 3.73 (t, J=5.1 Hz, 2H), 4.37 (t, J=4.7 Hz, 2H), 6.83-6.86 (m, 1H), 7.28 (dd, J=8.5, 2.4 Hz, 1H), 7.35 (d, J=8.5 Hz, 1H), 7.94 (d, J=2.7 Hz, 1H); MS (DCI/NH$_3$) m/z 345 (M+H)$^+$; Anal. calculated for C$_{14}$H$_{14}$Cl$_2$N$_2$O$_2$S: C, 48.70; H, 4.09; N, 8.11. Found: C, 48.60; H, 3.78; N, 8.02.

Example 156

5-chloro-2-methoxy-N-[(2Z)-3-(2-methoxyethyl)-5-methyl-1,3-thiazol-2(3H-ylidene]benzamide The 5-chloro-2-methoxybenzoic acid (Aldrich, 0.28 g, 1.5 mmol) was converted to 5-chloro-2-methoxybenzoyl chloride with 5 mL of thionyl chloride using the method described in Example 134A. The product of Example 140A (0.19 g, 1.1 mmol), Et$_3$N (0.45 mL, 3.2 mmol) and 5-chloro-2-methoxybenzoyl chloride in 15 mL THF were processed using the method described in Example 129 to afford the title compound (0.25 g, 0.72 mmol, 67% yield). $^1$H NMR (300 MHz, CDCl$_3$) δ ppm 2.30 (d, J=1.0 Hz, 3H), 3.36 (s, 3H), 3.74 (t, J=5.1 Hz, 2H), 3.90 (s, 3H), 4.36 (t, J=4.7 Hz, 2H), 6.82 (s, 1H), 6.90 (d, J=8.8 Hz, 1H), 7.33 (dd, J=8.8, 2.7 Hz, 1H), 7.96 (d, J=2.7 Hz, 1H); MS (DCI/NH$_3$) m/z 341 (M+H)$^+$; Anal. calculated for C$_{15}$H$_{17}$ClN$_2$O$_3$S: C, 52.86; H, 5.03; N, 8.22. Found: C, 52.84; H, 4.72; N, 8.13.

Example 157

2,3-dichloro-N-[(2Z)-5-methyl-3-(tetrahydro-2H-pyran-2-ylmethyl)-1,3-thiazol-2(3H)-ylidene]benzamide Example 157A 5-Methyl-3-(tetrahydro-pyran-2-ylmethyl)-3H-thiazol-2-ylideneamine A mixture of 2-amino-5-methylthiazole (1.2 g, 10.5 mmol) and 2-(bromomethyl)tetrahydro-2H-pyran (Aldrich, 1.5 mL, 11.6 mmol) was warmed to 85° C. and allowed to stir for 18 hours. The mixture was cooled to ambient temperature and purified by flash column chromatography (SiO$_2$, first 10% CH$_3$OH:EtOAc then 9:1:0.1 CH$_2$Cl$_2$:CH$_3$OH:NH$_4$OH) to afford the title compound (1.1 g, 5.2 mmol, 49% yield). $^1$H NMR (300 MHz, CDCl$_3$) δ ppm 1.12-1.32 (m, 1H) 1.44-1.63 (m, 2H) 1.79-1.95 (m, 2H) 2.06 (d, J 12.89 Hz, 1H) 2.25 (d, J=1.36 Hz, 3H) 3.33-3.45 (m, 1H) 3.65-3.78 (m 1H) 3.86-4.01 (m, 2H) 4.44 (dd, J=14.92, 2.03 Hz, 1H) 6.56-6.65 (m, 1H) 9.48 (s, 1H); MS (DCI/NH$_3$) m/z 213 (M+H)$^+$.

Example 157B 2,3-dichloro-N-[(2Z)-5-methyl-3-(tetrahydro-2H-pyran-2-ylmethyl)-1,3-thiazol-2(3H)-ylidene]benzamide The product of Example 157A (0.15 g, 0.71 mmol), Et$_3$N (0.30 mL, 2.1 mmol) and 2,3-dichlorobenzoyl chloride (Lancaster, 0.19 g, 0.92 mmol) in 15 mL THF were processed as in Example 129 to afford the title compound (0.14 g, 0.36 mmol, 51% yield). $^1$H NMR (300 MHz, CDCl$_3$) δ ppm 1.16-1.33 (m, 1H), 1.46-1.56 (m, 3H), 1.64-1.73 (m, 1H), 1.80-1.92 (m, 1H), 2.32 (d, J=1.4 Hz, 3H), 3.30-3.43 (m, 1H), 3.69 (qt, J=11.5, 8.8, 2.0 Hz, 1H), 3.91-4.01 (m, 2H), 4.41 (dd, J=13.9, 2.7 Hz, 1H), 6.86 (d, J=1.4 Hz, 1H), 7.23 (t, J=7.8 Hz, 1H), 7.49 (dd, J=8.0, 1.5 Hz, 1H), 7.74 (dd, J=7.6, 1.5 Hz, 1H); MS (DCI/NH$_3$) m/z 385 (M+H)$^+$; Anal. calculated for C$_{17}$H$_{18}$Cl$_2$N$_2$O$_2$S: C, 52.99; H, 4.71; N, 7.27. Found: C, 53.15; H, 4.72; N, 7.14.

Example 158

2-ethoxy-N-[(2Z)-5-methyl-3-(tetrahydro-2H-pyran-2-ylmethyl)-1,3-thiazol-2(3H)-ylidene]benzamide The product of Example 157A (0.15 g, 0.71 mmol), Et$_3$N (0.30 mL, 2.1 mmol) and 2-ethoxybenzoyl chloride (Aldrich, 0.18 g, 0.92 mmol) in 15 mL THF were processed as in Example 129 to afford the title compound (0.14 g, 0.39 mmol, 55% yield). $^1$H NMR (300 MHz, CDCl$_3$) δ ppm 1.20-1.32 (m, 1H), 1.46 (t, J=7.0 Hz, 3H), 1.50-1.54 (m, 3H), 1.63-1.79 (m, 1H), 1.80-1.90 (m, 1H), 2.29 (s, 3H), 3.32-3.43 (m, 1H), 3.64-3.76 (m, 1H), 3.92-4.00 (m, 2H), 4.16 (q, J=6.8 Hz, 2H), 4.37-4.47 (m, 1H), 6.76-6.84 (m, 1H), 6.93-7.00 (m, 2H), 7.35 (t, J=8.1 Hz, 1H), 7.96 (dd, J=8.0, 1.9 Hz, 1H); MS (DCI/NH$_3$) m/z 361 (M+H)$^+$; Anal. calculated for C$_{19}$H$_{24}$N$_2$O$_3$S: C, 63.61; H, 6.71; N, 7.77. Found: C, 63.56; H, 6.73; N, 7.26.

Example 159

5-chloro-2-methoxy-N-[(2Z)-5-methyl-3-(tetrahydrofuran-2-ylmethyl)-1,3-thiazol-2(3H)-ylidene]benzamide The 5-chloro-2-methoxybenzoic acid (Aldrich, 0.66 g, 3.5 mmol) was converted to 5-chloro-2-methoxybenzoyl chloride with 5 mL of thionyl chloride using the method described in Example 134A. The product of Example 149A (0.35 g, 0.18 mmol), Et$_3$N (0.74 mL, 53 mmol) and 5-chloro-2-methoxybenzoyl chloride in 20 mL THF were processed using the method described in Example 149B to afford the title compound (0.25 g, 0.68 mmol, 20% yield). $^1$H NMR (300 MHz, CD$_3$OD) δ ppm 1.67-1.78 (m, 1H), 1.84-1.96 (m, 2H), 2.00-2.13 (m, 1H), 2.34 (d, J=1.4 Hz, 3H), 3.71-3.81 (m, 1H), 3.85 (s, 3H), 3.86-3.93 (m, 1H), 4.20-4.42 (m, 3H), 7.07 (d, J=9.2 Hz, 1H), 7.12-7.16 (m, 1H), 7.39 (dd, J=8.8, 2.7 Hz, 1H), 7.81 (d, J=2.7 Hz, 1H); MS (DCI/NH$_3$) m/z 367 (M+H)$^+$; Anal. calculated for C$_{17}$H$_{19}$ClN$_2$O$_3$S.0.2H$_2$O: C, 55.12; H, 5.28; N, 7.56. Found: C, 54.90; H, 4.95; N, 7.55.

Example 160

5-chloro-2-methoxy-N-[(2Z)-5-methyl-3-(tetrahydro-2H-pyran-2-ylmethyl)-1,3-thiazol-2(3H)-ylidene]benzamide The 5-chloro-2-methoxybenzoic acid (Aldrich, 0.17 g, 0.92 mmol) was converted to 5-chloro-2-methoxybenzoyl chloride with 5 mL of thionyl chloride using the method described in Example 134A. A mixture of the product of Example 157A (0.15 g, 0.71 mmol), Et$_3$N (0.30 mL, 2.1 mmol) and 5-chloro-2-methoxybenzoyl chloride in 15 mL THF were processed using the method described in Example 129 to afford the title compound (0.11 g, 0.29 mmol, 41% yield). $^1$H NMR (300 MHz, CDCl$_3$) δ ppm 1.20-1.36 (m, 1H), 1.48-1.61 (m, 3H), 1.66-1.76 (m, 1H), 1.83-1.92 (m, 1H), 2.30 (d, J=1.0 Hz, 3H), 3.33-3.44 (m, 1H), 3.67-3.77 (m, 1H), 3.90 (s, 3H), 3.93-4.05 (m, 2H), 4.40 (dd, J=13.9, 2.4 Hz, 1H), 6.83 (s, 1H), 6.90 (d, J=8.8 Hz, 1H), 7.32 (dd, J=8.8, 2.7 Hz, 1H), 7.97 (d, J=2.7 Hz, 1H); MS (DCI/NH$_3$) m/z 381 (M+H)$^+$; Anal. calculated for C$_{18}$H$_{21}$ClN$_2$O$_3$S.0.15H$_2$O: C, 56.36; H, 5.60; N, 7.30. Found. C, 56.70; H, 5.41; N, 6.91.

Example 161

2-ethoxy-N-[(2Z)-5-methyl-3-(tetrahydrofuran-2-ylmethyl)-1,3-thiazol-2(3H)-ylidene]benzamide The product of Example 149A (0.20 g, 1.0 mmol), Et$_3$N (0.42 mL, 3.0 mmol) and the 2-ethoxybenzoyl chloride (Aldrich, 0.23 mL, 1.5 mmol) in 15 mL THF were processed using the method described in Example 149B to afford the title compound (0.18 g, 0.52 mmol, 52% yield). $^1$H NMR (300 MHz, CD$_3$OD) δ ppm 1.40 (t, J=7.0 Hz, 3H), 1.64-1.75 (m, 1H), 1.83-1.94 (m, 2H), 2.00-2.12 (m, 1H), 2.33 (d, J=1.4 Hz, 3H), 3.70-3.80 (m, 1H), 3.83-3.93 (m, 1H), 4.11 (q, J=7.1 Hz, 2H), 4.18-4.27 (m, 1H), 4.28-4.42 (m, 2H), 6.96 (dt, J=7.5, 1.0 Hz, 1H), 7.04 (d, J=8.1 Hz, 1H) 7.09-7.13 (m, 1H), 7.38 (ddd, J=8.4, 7.4, 1.9 Hz, 1H), 7.77 (dd, J=7.6, 1.9 Hz, 1H); MS (DCI/NH$_3$) m/z 347 (M+H)$^+$; Anal. calculated for C$_{18}$H$_{22}$N$_2$O$_3$S.0.1H$_2$O: C, 62.40; H, 6.40; N, 8.09. Found: C, 63.49; H, 5.90; N, 7.84.

Example 162

5-chloro-2-methoxy-N-[(2Z)-5-methyl-3-(tetrahydrofuran-3-ylmethyl)-1,3-thiazol-2(3H)-ylidene]benzamide

Example 162A

Toluene-4-sulfonic acid tetrahydro-furan-3-ylmethyl ester

To a solution of tetrahydro-3-furanmethanol (Aldrich, 1.0 mL, 10.4 mmol) in 5 mL CH$_2$Cl$_2$ and 5 mL pyridine was added para-toluenesulfonyl chloride (3.0 g, 15.6 mmol) portion-wise over 15 minutes. This mixture stirred at ambient temperature for 3 hours then 5 mL H$_2$O was added. The layers were separated and the aqueous layer was extracted 2×5 mL CH$_2$Cl$_2$. The combined organics were dried over Na$_2$SO$_4$, filtered, concentrated under reduced pressure and dried under vacuum (~1 mm Hg) to afford the title compound (2.62 g, 10.2 mmol, 98% yield). $^1$H NMR (300 Mhz, CDCl$_3$) δ ppm 1.49-1.63 (m, 1H) 1.94-2.08 (m, 1H) 2.46 (s, 3H) 2.52-2.68 (m, 1H) 3.49 (dd, J=9.16, 5.09 Hz, 1H) 3.64-3.84 (m, 3H) 3.88-4.03 (m, 2H) 7.36 (d, J=8.14 Hz, 2H) 7.76-7.82 (m, 2H); MS (DCI/NH$_3$) m/z 257 (M+H)$^+$.

Example 162B

5-Methyl-3-tetrahydro-furan-3-ylmethyl)-3H-thiazol-2-ylideneamine

A mixture of the product of Example 162A (1.62 g, 6.3 mmol), 2-amino-5-methylthiazole (0.72 g, 6.3 mmol) and LiBr (55 mg, 0.63 mmol) in 2 mL DMF was warmed to 85° C. and allowed to stir for 16 hours. The mixture was then allowed to cool to ambient temperature, diluted with 10 mL CH$_2$Cl$_2$ and washed with 1×5 mL 10% aqueous Na$_2$CO$_3$ solution. The layers were separated and the aqueous layer was extracted 2×5 mL CH$_2$Cl$_2$. The combined organics were dried over anhydrous Na$_2$SO$_4$, filtered, concentrated under reduced pressure and purified by column chromatography (SiO$_2$, 9:1: 0.1 CH$_2$Cl$_2$:CH$_3$OH:NH$_4$OH) to afford the title compound (0.31 g, 1.6 mmol, 25% yield). $^1$H NMR (300 MHz, CD$_3$OD) δ ppmn 1.61-1.74 (m, 1H) 1.96-2.04 (m, 1H) 2.05 (d, J=1.36 Hz, 3H) 2.69-2.84 (m, 1H) 3.53 (dd, J=8.82, 5.76 Hz, 1H) 3.63 (dd, J=7.63, 2.20 Hz, 2H) 3.69-3.81 (m, 2H) 3.89 (ddd, J=8.31, 5.42 Hz, 1H) 6.36-6.42 (m, 1H); MS (DCI/NH$_3$) m/z 199 (M+H)$^+$.

Example 162C 5-chloro-2-methoxy-N-[(2Z)-5-methyl-3-(tetrahydrofuran-3-ylmethyl)-1,3-thiazol-2(3H)-ylidene]benzamide The 5-chloro-2-methoxybenzoic acid (Aldrich, 0.40 g, 2.1 mmol) was converted to 5-chloro-2-methoxybenzoyl chloride with 5 mL of thionyl chloride using the method described in Example 134A. The product of Example 162B (0.21 g, 1.1 mmol), Et$_3$N (0.44 mL, 3.2 mmol) and 5-chloro-2-methoxybenzoyl chloride in 15 mL THF were processed using the method described in Example 149B to afford the title compound (0.28 g, 0.76 mmol, 72% yield). $^1$H NMR (300 MHz, CD$_3$OD) δ ppm 1.69-1.83 (m, 1H), 1.96-2.09 (m, 1H), 2.34 (d, J=1.4 Hz, 3H), 2.84-3.00 (m, 1H), 3.64 (dd, J=8.8, 5.1 Hz, 1H), 3.72-3.81 (m, 2H), 3.85 (s, 3H), 3.89-3.99 (m, 1H), 4.17-4.33 (m, 2H), 7.06 (d, J=8.8 Hz, 1H), 7.14-7.17 (m, 1H), 7.39 (dd, J=8.8, 2.7 Hz, 1H), 7.84 (d, J=2.7 Hz, 1H); MS (DCI/NH$_3$) m/z 367 (M+H)$^+$; Anal. calculated for C$_{17}$H$_{19}$ClN$_2$O$_3$S: C, 55.66; H, 5.22; N, 7.64. Found: C, 55.77; H, 4.85; N, 7.26.

Example 163

2-ethoxy-N-[(2Z)-5-methyl-3-(tetrahydrofuran-3-ylmethyl)-1,3-thiazol-2(3H)-ylidene]benzamide The product of Example 162B (0.17 g, 0.86 mmol), Et$_3$N (0.36 mL, 2.6 mmol) and the 2-ethoxybenzoyl chloride (Aldrich, 0.15 mL, 0.94 mmol) in 10 mL THF were processed using the method described in Example 149B to afford the title compound (0.26 g, 0.74 mmol, 86% yield). $^1$H NMR (300 MHz, CD$_3$OD) δ ppm 1.39 (t, J=7.0 Hz, 3H), 1.68-1.82 (m, 1H), 1.92-2.05 (m, 1H), 2.34 (d, J=1.4 Hz, 3H), 2.85-3.02 (m, 1H), 3.63 (dd, J=8.8, 5.4 Hz, 1H), 3.70-3.80 (m, 2H), 3.88-3.97 (m, 1H), 4.12 (q, J=6.9 Hz, 2H), 4.17-4.33 (m, 2H), 6.96 (dt, J=7.5, 1.0 Hz, 1H), 7.05 (d, J=7.8 Hz, 1H), 7.11-7.16 (m, 1H), 7.38 (ddd, J=8.6, 7.0, 1.7 Hz, 1H), 7.79 (dd, J=7.8, 1.7 Hz, 1H); MS (DCI/NH$_3$) m/z 347 (M+H)$^+$; Anal. calculated for C$_{18}$H$_{22}$N$_2$O$_3$S: C, 62.40; H, 6.40; N, 8.09. Found: C, 62.43; H, 6.29; N, 7.96.

Example 164

2-ethoxy-N-[(2Z)-3-[2-(2-methoxyethoxy)ethyl]-5-methyl-1,3-thiazol-2(3H)-ylidene]benzamide

Example 164A

3-[2-(2-Methoxyethoxy)ethyl]-5-methyl-1,3-thiazol-2(3H)-ylideneamine

A mixture of 2-amino-5-methylthiazole (1.5 g, 13.0 mmol) and 1-bromo-2-(2-methoxyethoxy)ethane (Aldrich, 2.0 mL, 14.5 mmol) was processed as in Example 157A to afford the title compound (2.2 g, 10.9 mmol, 78% yield). $^1$H NMR (300 MHz, CD$_3$OD) δ ppm 2.29 (d, J=1.36 Hz, 3H) 3.34 (s, 3H) 3.49-3.54 (m, 2H) 3.60-3.66 (m, 2H) 3.80 (t, J=5.10 Hz, 2H) 4.13 (t, J=4.80 Hz, 2H) 6.99-7.04 (m, 1H), MS (DCI/NH$_3$) m/z 217 (M+H)$^+$.

Example 164B 2-ethoxy-N-[(2Z)-3-[2-(2-methoxyethoxy)ethyl]-5-methyl-1,3-thiazol-2(3H)-ylidene]benzamide The product of Example 164A (0.22 g, 1.0 mmol), Et$_3$N (0.23 mL, 2.0 mmol) and 2-ethoxybenzoyl chloride (Aldrich, 0.25 g, 1.3 mmol) in 15 mL THF were processed as in Example 129 to afford the title compound (0.15 g, 0.40 mmol, 40% yield). $^1$H NMR (300 MHz, CD$_3$OD) δ ppm 1.40 (t, J=7.0 Hz, 3H), 2.33 (d, J=1.4 Hz, 3H), 3.31 (s, 3H), 3.46-3.51 (m, 2H), 3.58-3.63 (m, 2H), 3.85 (t, J=5.3 Hz, 2H), 4.11 (q, J=6.8 Hz, 2H), 4.40 (t, J=5.3 Hz, 2H), 6.96 (dt, J=7.5, 1.0 Hz, 1H), 7.04 (d, J=8.5 Hz, 1H), 7.11-7.15 (m, 1H), 7.38 (ddd, J=8.4, 7.4, 1.9 Hz, 1H), 7.79 (dd, J=7.6, 1.9 Hz, 1H); MS (DCI/NH$_3$) m/z 365 (M+H)$^+$; Anal. calculated for C$_{18}$H$_{24}$N$_2$O$_4$S: C, 59.88; H, 6.86; N, 7.51. Found: C, 60.05; H, 6.81; N, 7.60.

Example 166

2,3-dichloro-N-[(2Z)-3-[2-(2-methoxyethoxy)ethyl]-5-methyl-1,3-thiazol-2(3H)-ylidene]benzamide The product of Example 164A (0.22 g, 1.0 mmol), Et$_3$N (0.23 mL, 2.0 mmol) and 2,3-dichlorobenzoyl chloride (Lancaster, 0.27 g, 1.3 mmol) in 15 mL THF were processed as in Example 129 to afford the title compound (95 mg, 0.24 mmol, 24% yield). $^1$H NMR (300 MHz, CD$_3$OD) δ ppm 2.36 (d, J=1.4 Hz, 3H), 3.31 (s, 3H), 3.46-3.50 (m, 2H), 3.57-3.62 (m, 2H), 3.83 (t, J=5.4 Hz, 2H), 4.40 (t, J=5.1 Hz, 2H), 7.18-7.21 (m, 1H), 7.33 (t, J=7.8 Hz, 1H), 7.58 (dd, J=8.0, 1.5 Hz, 1H), 7.64 (dd, J=7.6, 1.5 Hz, 1H); MS (DCI/NH$_3$) m/z 389 (M+H)$^+$; Anal. calculated for C$_{16}$H$_{18}$Cl$_2$N$_2$O$_3$S: C, 49.36; H, 4.66; N, 7.20. Found: C, 48.98; H, 4.60; N, 6.99

Example 167

5-chloro-2-methoxy-N-[(2Z)-3-[2-(2-methoxyethoxy)ethyl]-5-methyl-1,3-thiazol-2(3H)-ylidene]benzamide The 5-chloro-2-methoxybenzoic acid (Aldrich, 0.24 g, 1.3 mmol) was converted to the 5-chloro-2-methoxybenzoyl chloride with 5 mL of thionyl chloride using the method described in Example 134A. The product of Example 164A (0.22 g, 1.0 mmol), Et$_3$N (0.42 mL, 3.0 mmol) and 5-chloro-2-methoxybenzoyl chloride in 15 mL THF were processed using the method described in Example 129 to afford the title compound (0.21 g, 0.55 mmol, 55% yield). $^1$H NMR (300 MHz, CD$_3$OD) δ ppm 2.34 (d, J=1.4 Hz, 3H), 3.31 (s, 3H), 3.47-3.52 (m, 2H), 3.59-3.64 (m, 2H), 3.86 (s, 3H), 3.88 (t, J=5.4 Hz, 2H), 4.41 (t, J=4.8 Hz, 2H), 7.07 (d, J=8.8 Hz, 1H), 7.14-7.17 (m, 1H), 7.39 (dd, J=9.0, 2.9 Hz, 1H), 7.83 (d, J=2.7 Hz, 1H); MS (DCI/NH$_3$) m/z 385 (M+H)$^+$; Anal. calculated for C$_{17}$H$_{21}$ClN$_2$O$_4$S: C, 53.05; H, 5.50; N, 7.28. Found: C, 52.93; H, 5.61; N, 7.26.

Example 168

2-methoxy-N-[(2Z)-5-methyl-3-(tetrahydrofuran-2-ylmethyl)-1,3-thiazol-2(3H)-ylidene]benzamide The product of Example 149A (0.15 g, 0.76 mmol), Et$_3$N (0.32 mL, 2.3 mmol) and the o-anisoyl chloride (Aldrich, 0.15 mL, 1.1 mmol) in 10 mL THF were processed using the method described in Example 149B to afford the title compound (88 mg, 0.26 mmol, 35% yield). $^1$H NMR (300 MHz, CD$_3$OD) δ ppm 1.66-1.76 (m, 1H) 1.84-1.95 (m, 2H), 2.02-2.12 (m, 1H), 2.33 (d, J=1.4 Hz, 3H), 3.71-3.79 (m, 1H), 3.85 (s, 3H), 3.84-3.92 (m, 1H), 4.22-4.28 (m, 1H), 4.29-4.41 (m, 1H), 6.98 (dt, J=7.6, 1.0 Hz, 1H), 7.07 (dd, J=8.5, 1.0 Hz, 1H), 7.10-7.12 (m, 1H), 7.42 (ddd, J=9.2, 7.5, 2.0 Hz, 1H), 7.85 (dd, J=7.8, 1.7 Hz, 1H); MS (DCI/NH$_3$) m/z 333 (M+H)$^+$; Anal. calculated for C$_{17}$H$_{20}$N$_2$O$_3$S: C, 61.42; H, 6.06; N, 8.43. Found: C, 61.35; H, 6.10; N, 8.28.

Example 169

1-(1,1-Dimethylpropyl)-3-[(2Z)-3-(2-methoxyethyl)-4,5-dimethyl-1,3-thiazol-2(3H)-ylidene]urea hydrochloride

Example 169A 1-(1,1-Dimethylpropyl)-3-[(2Z)-3-(2-methoxyethyl)-4,5-dimethyl-1,3-thiazol-2(3H)-ylidene]urea To a solution of 1,1-dimethylpropylamine (174 mg, 2.0 mmole) in 19 mL of THF and 1 mL of N,N-diisopropylethyl amine was added 4-nitrophenyl chloroformate (403 mg, 2.0 mmole). The solution was irradiated in a sealed tube placed in a single node microwave at 70° C. for 300 sec (maximum power 300 W) with stirring. The resulting solution was cooled to room temperature and 3-(2-methoxyethyl)-4,5-dimethyl-3H-thiazol-2-ylideneamine hydrobromide (587 mg, 2.2 mmole) from Example 12A was added. The sealed tube was irradiated at 120° C. for 1800 sec with stirring. The mixture was cooled and the volatile components were removed under reduced pressure. The residue was partitioned between water and ethyl acetate. The phases were separated and organic extract was dried over anhydrous $Na_2SO_4$, filtered, and concentrated. Purification by column chromatography ($SiO_2$, 0-70% ethyl acetate/hexanes gradient) afforded the title compound. $^1$H NMR (300 MHz, DMSO-$d_6$) δ ppm 0.76 (t, J=7 Hz, 3H) 1.20 (s, 6H) 1.66 (d, J=7 Hz, 2H) 2.06 (s, 3H) 2.11 (s, 3H) 3.30 (s, 3H) 3.55 (t, J=5 Hz, 2H) 4.06 (t, J=5 Hz, 2H) 6.13 (s, 1H)), MS (DCI/$NH_3$) m/z 300 (M+H)$^+$.

Example 169B 1-(1,1-Dimethylpropyl)-3-[(2Z)-3-(2-methoxyethyl)-4,5-dimethyl-1,3-thiazol-2(3H)-ylidene]urea hydrochloride To a solution of the product from Example 169A in MeOH was added a solution of HCl in $Et_2O$. The title compound was isolated by filtration. $^1$H NMR (300 MHz, DMSO-$d_6$) δ ppm 0.84 (t, J=7 Hz, 3H) 1.26 (s, 6H) 1.65 (q, J=7 Hz, 2H) 2.24 (s, 6H) 3.24 (s, 3H) 3.64 (t, J=5 Hz, 2H) 4.45 (s, 2H), MS (DCI/$NH_3$) m/z 300 (M+H)$^+$. Anal. Calculated for $C_{14}H_{25}ClN_3O_2S$: C, 50.06; H, 7.80; N, 12.51. Found: C, 50.11; H, 7.87; N, 12.35.

Example 170

1-(1,1-Dimethyl-propyl)-3-[(2Z)-3-(2-methoxyethyl)-1,3-benzothiazol-2(3H)-ylidene]urea To a solution of 1,1-dimethyl-propylamine (0.60 mL, 5.2 mmol) and triethylamine (0.40 mL, 2.9 mmol) in 12 mL of a 1:1 mixture of THF:DMF at 0° C. was added p-nitrophenylchloroformate (0.58 g, 2.9 mmol). After 30 minutes, the product of Example 64A (0.75 g, 2.6 mmol) and another aliquot of triethylamine (0.40 mL, 2.9 mmol) were added and the solution stirred at ambient temperature for 9 hours. The mixture was diluted with ethyl acetate then washed twice with water and brine. The organic extract was dried over magnesium sulfate, filtered, and concentrated under reduced pressure. Purification by column chromatography ($SiO_2$, 20-40% ethyl acetate/hexanes gradient) afforded 0.06 g (8%) of the title compound. $^1$H NMR (CDCl$_3$, 300 MHz) δ ppm 0.91 (t, J=7.46 Hz, 3H), 1.39 (s, 6H), 1.78 (q, J=7.46 Hz, 2H), 3.28 (s, 3H), 3.86 (t, J=4.92 Hz, 2H), 4.82 (t, J=4.58 Hz, 2H), 7.46 (t, J=7.63 Hz, 1H), 7.58 (t, J=7.63 Hz, 1H), 7.64-7.70 (m, 1H), 7.75 (d, J=7.80 Hz, 1H), 9.06 (s, 1H), MS (DCI/$NH_3$) m/z 322 (M+H)$^+$.

Example 171

1-[(2Z)-3-(2-Methoxyethyl)-4,5-dimethyl-1,3-thiazol-2(3H)-ylidene]-3-(3,3,5,5-tetramethylcyclohexyl)urea The product of Example 12A and 3,3,5,5-tetramethylcyclohexylamine were processed using the method described in Example 169A to afford the title compound. $^1$H NMR (300 MHz, DMSO-$d_6$) δ ppm 0.90 (s, 6H) 1.02 (s, 6H) 1.17-1.27 (m, 1H) 1.61 (d, J=12 Hz, 2H) 2.18-2.27 (m, 6H) 3.24 (s, 3H) 3.62 (t, J=5 Hz, 2H) 3.76-3.87 (m, J=5 Hz, 2H) 3.98 (s, 2H) 4.40 (s, 2H), MS (DCI/$NH_3$) m/z 366 (M+H)$^+$. Anal. Calculated for $C_{19}H_{14}ClN_3O_2S.0.7CH_4O$: C, 55.49; H, 8.7; N, 9.85. Found C, 55.81; H, 8.37; N, 9.52.

Example 172

1-[(2Z)-3-(2-Methoxyethyl)-4,5-dimethyl-1,3-thiazol-2(3H)-ylidene]-3-(1-methyl-3-phenylpropyl)urea The product of Example 12A and 1-methyl-3-phenylpropylamine were processed using the method described in Example 169A to afford the title compound. $^1$H NMR (300 MHz, DMSO-$d_6$) δ ppm 1.13 (d, J=6 Hz, 3H) 1.60-1.82 (m, 2H) 2.18 (s, 3H) 2.20 (s, 3H) 2.55-2.68 (m, 2H) 3.25 (s, 3H) 3.53-3.80 (m, 3H) 4.31 (s, 2H) 7.08-7.35 (m, 5H), MS (DCI/$NH_3$) m/z 362 (M+H)$^+$.

Example 173 ethyl N-({[(2Z)-3-(2-methoxyethyl)-4,5-dimethyl-1,3-thiazol-2(3H)-ylidene]amino}carbonyl)-L-leucinate The product of Example 12A and (2S)-ethyl-2-amino-4-methylpentanoate were processed using the method described in Example 169A to afford the title compound. $^1$H NMR (300 MHz, DMSO-$d_6$) δ ppm 0.87 (dd, J=9, 6 Hz, 6H) 1.37-1.50 (m, 1H) 1.51-1.65 (m, 2H) 1.84 (s, 3H) 2.17 (s, 3H) 2.21 (s, 3H) 3.22-3.23 (m, 3H) 3.62 (t, J=5 Hz, 2H) 4.18-4.33 (m, 2H) 4.37-4.48 (m, 1H) 7.88 (d, J=9 Hz, 1H)), MS (DCI/$NH_3$) m/z 342 (M+H)$^+$. Anal. Calculated for $C_{16}H_{27}N_3O_3S$: C, 56.26; H, 7.97; N, 12.31. Found C, 56.20; H, 8.04; N, 12.31.

Example 174

1-(1,1-Dimethylpropy)-3-[(2Z)-5-methyl-3-(tetrahydropyran-2-ylmethyl)-1,3-thiazol-2(3H)-ylidene]urea The product of Example 157A and 2,2-dimethylpropylamine were processed using the method described in Example 169A to afford the title compound. $^1$H NMR (300 MHz, DMSO-$d_6$) δ ppm 0.76 (t, 3H) 1.12-1.17 (m, 1H) 1.20 (s, 6H) 1.38-1.49 (m, J=3 Hz, 3H) 1.50-1.59 (m, 1H) 1.66 (q, J=7 Hz, 2H) 1.75-1.82 (m, 1H) 2.12 (s, 3H) 3.22-3.30 (m, 1H) 3.54-3.65 (m, 1H) 3.80-3.93 (m, 3H) 6.19 (s, 1H) 6.79 (s, 1H), MS (DCI/$NH_3$) m/z 326 (M+H)$^+$. Anal. Calculated for $C_{16}H_2 7N_3O_2S$: C, 59.04; H, 8.36; N, 12.91. Found C, 59.06; H, 8.36; N, 12.91.

Example 175

1-(1,2-Dimethyl-propyl)-3-[(2Z)-5-methyl-3-(tetrahydropyran-2-ylmethyl)-1,3-thiazol-2(3H)-ylidene]urea hydrochloride The product of Example 157A and 1,2-dimethylpropylamine were processed according to the method described in Example 169A to afford the title compound. $^1$H NMR (300 MHz, DMSO-$d_6$) δ ppm 0.81 (dd, J=7, 3 Hz, 1H) 0.84-0.96 (m, 6H) 1.06 (d, J=7 Hz, 3H) 1.20 (t, 1H) 1.34-1.54 (m, 3H) 1.60-1.76 (m, 1H) 1.69-1.95 (m, 2H) 2.28 (s, 3H) 3.22-3.37 (m, 1H) 3.84 (d, J=11 Hz, 2H) 4.10-4.30 (m, 1H) 4.31-4.47 (m, 1H) 7.23-7.41 (m, 1H) 7.83-8.06 (m, 1H),), MS (DCI/$NH_3$) m/z 326 (M+H)$^+$. Anal. Calculated for $C_{16}H_{28}ClN_3O_2S$: C, 53.10; H, 7.80; N, 11.16. Found C, 52.73; H, 7.96; N, 10.82.

Example 176

1-Cyclohexyl-3-[(2Z)-4,5-dimethyl-3-(tetrahydropyran-2-ylmethyl)-1,3-thiazol-2(3H)-ylidene]urea

Example 176A 4,5-Dimethyl-3-(tetrahydropyran-2-ylmethyl)-1,3-thiazol-2(3H)-ylideneamine hydrobromide A mixture of 2-amino-4,5-dimethylthiazole and 2-(bromomethyl)tetrahydro-2H-pyran were processed using the method described in Example 12A to afford the title compound. $^1$H NMR (300 MHz, DMSO-$d_6$) δ ppm 1.13-1.31 (m, 1H) 1.36-1.52 (m, 3H) 1.64-1.85 (m, 2H) 2.18 (d, J=4 Hz, 6H) 3.19-3.33 (m, 1H) 3.49-3.63 (m, 1H) 3.77-3.89 (m, 1H) 3.94-4.02 (m, 2H) 9.34 (s, 2H),), MS (DCI/NH$_3$) m/z 227 (M+H)$^+$.

Example 176B

1-Cyclohexyl-3-[(2Z)-4,5-dimethyl-3-(tetrahydropyran-2-ylmethyl)-1,3-thiazol-2(3H)-ylidene]urea The product of Example 176A and cyclohexylamine were processed using the method described in Example 169A to afford the title compound. $^1$H NMR (300 MHz, DMSO-$d_6$) δ ppm 1.05-1.29 (m, 6H) 1.37-1.49 (m, 3H) 1.51-1.63 (m, 2H) 1.76 (m, 5H) 2.06 (s, 3H) 2.11 (s, 3H) 3.19-3.30 (m, 1H) 3.56-3.68 (m, 1H) 3.70-3.88 (m, 3H) 3.99 (dd, J=14, 3 Hz, 1H) 6.59 (d, J=8 Hz, 1H),), MS (DCI/NH$_3$) m/z 352 (M+H)$^+$. Anal. Calculated for $C_{18}H_{29}N_3O_2S \cdot 0.1H_2O$: C, 61.19; H, 8.33; N, 11.89. Found C, 61.03; H, 8.45; N, 11.69.

Example 177

1-(4-Methylcyclohexyl)-3-[(2Z)-5-methyl-3-(tetrahydropyran-2-ylmethyl)-1,3-thiazol-2(3H)-ylidene]urea The product of Example 157A and 4-methylcyclohexylamine were processed using the method described in Example 169A to afford the title compound. $^1$H NMR (300 MHz, DMSO-$d_6$) δ ppm 0.88 (dd, J=12, 7 Hz, 3H) 0.96 (d, J=3 Hz, 1H) 1.09-1.31 (m, 3H) 1.31-1.70 (m, 9H) 1.69-1.85 (m, 2H) 2.12 (s, 3H) 3.21-3.29 (m, 1H) 3.55-3.64 (m, J=3 Hz, 2H) 3.79-3.95 (m, 3H) 6.62 (t, J=8 Hz, 1H) 6.77-6.81 (m, J=1 Hz, 1H), MS (DCI/NH$_3$) m/z 352 (M+H)$^+$.

Example 178

1-(1,1-Dimethylpropyl)-3-[(2Z)-3-(tetrahydropyran-2-ylmethyl)-1,3-thiazol-2(3H)-ylidene]urea

Example 178A 3-(tetrahydropyran-2-ylmethyl)-1,3-thiazol-2(3H)-ylideneamine hydrobromide A mixture of 2-aminothiazole and 2-(bromomethyl)tetrahydro-2H-pyran were processed using the method described in Example 12A to afford the title compound. MS (DCI/NH$_3$) m/z 199 (M+H)$^+$.

Example 178B 1-(1,1-Dimethylpropyl)-3-[(2Z)-3-(tetrahydropyran-2-ylmethyl)-1,3-thiazol-2(3H)-ylidene]urea The product of Example 178A and 1,1-dimethylpropylamine were processed using the method described in Example 169A to afford the title compound. $^1$H NMR (300 MHz, DMSO-$d_6$) δ ppm 0.77 (t, J=7 Hz, 3H) 1.14-1.19 (m, 1H) 1.21 (s, 6H) 1.39-1.49 (m, 3H) 1.50-1.59 (m, 1H) 1.61-1.72 (m, 2H) 1.79 (s, 1H) 3.19-3.28 (m, 1H) 3.56-3.68 (m, 1H) 3.78-3.89 (m, 1H) 3.92-4.02 (m, 2H) 6.23 (s, 1H) 6.55 (d, J=5 Hz, 1H) 7.08 (d, J=5 Hz, 1H), MS (DCI/NH$_3$) m/z 312 (M+H)$^+$. Anal. Calculated for $C_{15}H_{25}N_3O_2S$: C, 57.85; H, 8.09; N, 13.49. Found C, 58.01; H, 8.23; N, 13.30.

Example 179

N-[(2Z)-4,5-dimethyl-3-(tetrahydro-2H-pyran-2-ylmethyl)-1,3-thiazol-2(3H)-ylidene]-N'-[(1S)-1,2,2-trimethylpropyl]urea The product of Example 176A and (1S)-1,2,2-trimethylpropylamine were processed using the method described in Example 169A to afford the title compound. $^1$H NMR (300 MHz, DMSO-$d_6$) δ ppm 0.84 (s, 9H) 0.98 (d, J=7 Hz, 3H) 1.12-1.28 (m, 1H) 1.40-1.49 (m, 3H) 1.47-1.64 (m, J=13 Hz, 1H) 1.73-1.84 (m, 1H) 2.12 (s, 3H) 3.23-3.30 (m, 1H) 3.50-3.68 (m, 2H) 3.80-4.03 (m, 3H) 6.46 (dd, J=9, 3 Hz, 1H) 6.80 (dd, J=5, 2 Hz, 1H), MS (DCI/NH$_3$) m/z 354 (M+H)$^+$. Anal. Calculated for $C_{18}H_{31}N_3O_2SC$, 61.15; H, 8.84; N, 11.69. Found C, 60.80; H, 8.88; N, 11.69.

Example 180

1-(2,2-Dimethylpropyl)-3-[(2Z)-4,5-dimethyl-3-(tetrahydropyran-2-ylmethyl)-1,3-thiazol-2(3H)-ylidene]urea The product of Example 176A and 2,2-dimethylpropylamine were processed using the method described in Example 169A to afford the title compound. $^1$H NMR (300 MHz, DMSO-$d_6$) δ ppm 0.84 (s, 9H) 1.16-1.28 (m, 1H) 1.45 (s, 3H) 1.56-1.68 (m, 1H) 1.76-1.87 (m, 1H) 2.06 (s, 3H) 2.11 (s, 3H) 2.77-2.87 (m, 1H) 2.90-3.02 (m, 1H) 3.15-3.28 (m, 1H) 3.60-3.70 (m, 1H) 3.72-3.86 (m, 2H) 3.94-4.11 (m, 1H) 6.58-6.78 (m, 1H),), MS (DCI/NH$_3$) m/z 339 (M+H)$^+$. Anal. Calculated for $C_{17}H_{29}N_3O_2S$: C, 60.14; H, 8.61; N, 12.38. Found C, 60.22; H, 8.71; N, 12.35.

Example 181

N-[(2Z)-3-(tetrahydro-2H-pyran-2-ylmethyl)-1,3-thiazol-2(3H)-ylidene]-N'-[(1S)-1,2,2-trimethylpropyl]urea The product of Example 178A and (1S)-1,2,2-trimethylpropylamine were processed using the method described in Example 169A to afford the title compound. $^1$H NMR (300 MHz, DMSO-$d_6$) δ ppm 0.84 (s, 9H) 0.99 (d, J=7 Hz, 3H) 1.14-1.26 (m, J=11 Hz, 1H) 1.36-1.49 (m, 3H) 1.52-1.59 (m, 1H) 1.74-1.82 (m, 1H) 3.20-3.28 (m, 1H) 3.52-3.70 (m, 2H) 3.78-4.08 (m, 3H) 6.46-6.60 (m, 2H) 7.10 (t, J=5 Hz, 1H), MS (DCI/NH$_3$) m/z 326 (M+H)$^+$. Anal. Calculated for $C_{16}H_{27}N_3O_2S$: C, 59.04; H, 8.36; N, 12.91. Found C, 59.08; H, 8.28; N, 12.80.

Example 182

N-[(2Z)-5-methyl-3-(tetrahydro-2H-pyran-2-ylmethyl)-1,3-thiazol-2(3H)-ylidene]-N'-[(1S)-1,2,2-trimethylpropyl]urea The product of Example 157A and (1S)-1,2,2-trimethylpropylamine were processed using the method described in Example 169A to afford the title compound ¹H NMR (300 MHz, DMSO-d$_6$) δ ppm 0.84 (s, 9H) 0.98 (d, J=7 Hz, 3H) 1.11-1.30 (m, 1H) 1.45 (s, 3H) 1.51 (d, 2H) 2.12 (s, 4H) 3.21-3.30 (m, 1H) 3.48-3.70 (m, 2H) 3.78-4.05 (m, 3H) 6.46 (dd, J=9, 3 Hz, 1H) 6.80 (dd, J=5, 2 Hz, 1H), MS (DCI/NH$_3$) m/z 339 (M+H)⁺. Anal. Calculated for C$_{17}$H$_{29}$N$_3$O$_2$S, 60.14; H, 8.61; N, 12.38. Found C, 60.10; H, 8.81; N, 12.02.

Example 183

1-(4-Methylcyclohexyl)-3-[(2Z)-4,5-dimethyl-3-(tetrahydropyran-2-ylmethyl)-1,3-thiazol-2(3H)-ylidene]urea The product of Example 176A and 4-methylcyclohexylamine were processed using the method described in Example 169A to afford the title compound. ¹H NMR (300 MHz, DMSO-d$_6$) δ ppm 0.82-1.02 (m, 4H) 1.15-1.29 (m, 3H) 1.38-1.51 (m, 4H) 1.52-1.70 (m, 4H) 1.78 (s, 3H) 2.06 (s, 3H) 2.11 (s, 3H) 3.19-3.28 (m, 1H) 3.61 (s, 1H) 3.69-3.86 (m, 3H) 3.98 (dd, J=14, 3 Hz, 1H) 6.57 (d, J=8 Hz, 1H), MS (DCI/NH$_3$) m/z 366 (M+H)⁺. Anal. Calculated for C$_{18}$H$_{23}$N$_3$O$_2$S: C, 62.45; H, 8.55; N, 11.50. Found C, 62.77; H, 8.86; N, 1150.

Example 184

1-(2,2-Dimethylpropyl)-3-[(2Z)-5-methyl-3-(tetrahydropyran-2-ylmethyl)-1,3-thiazol-2(3H)-ylidene]urea The product of Example 157A and 2,2-dimethylpropylamine were processed using the method described in Example 169A to afford the title compound. ¹H NMR (300 MHz, DMSO-d$_6$) δ ppm 0.81 (s, 9H) 1.09-1.26 (m, 1H) 1.34-1.59 (m, 4H) 1.69-1.87 (m, 1H) 2.12 (d, J=1 Hz, 3H) 2.80-2.98 (m, 2H) 3.08-3.27 (m, 1H) 3.52-3.67 (m, 1H) 3.80-4.06 (m, 3H) 6.68-6.76 (m, 1H) 6.78-6.90 (m, 1H), MS (DCI/NH$_3$) m/z 326 (M+H)⁺. Anal. Calculated for C$_{16}$H$_{27}$N$_3$O$_2$S: C, 59.04; H, 8.36; N, 12.91. Found C, 58.89; H, 8.56; N, 12.71.

Example 185

1-tert-Butyl-3-[(2Z)-4,5-dimethyl-3-(tetrahydropyran-2-ylmethyl)-1,3-thiazol-2(3H)-ylidene]urea The product of Example 176A and tert-butylamine were processed using the method described in Example 169A to afford the title compound. ¹H NMR (300 MHz, DMSO-d$_6$) δ ppm 1.13-1.22 (m, 1H) 1.27 (s, 9H) 1.44 (d, J=4 Hz, 3H) 1.60 (d, J=12 Hz, 1H) 1.77 (s, 1H) 2.06 (s, 3H) 2.11 (s, 3H) 3.16-3.28 (m, 1H) 3.55-3.68 (m, 1H) 3.68-3.87 (m, 2H) 4.00 (dd, J=14, 3 Hz, 1H) 6.90 (d, J=9 Hz, 1H), MS (DCI/NH$_3$) m/z 326 (M+H)⁺. Anal. Calculated for C$_{16}$H$_{27}$N$_3$O$_2$S.0.3H$_2$O: C, 58.02; H, 8.41; N, 12.70. Found C, 58.44; H, 8.12; N, 12.41.

Example 186

1-(1,1-Dimethylpropyl)-3-[(2Z)-4,5-dimethyl-3-(tetrahydrofuran-2-ylmethyl)-1,3-thiazol-2(3H)ylidene]urea Example 186A 4,5-Dimethyl-3-(tetrahydrofuran-2-ylmethyl)-1,3-thiazol-2(3H)-ylideneamine hydrobromide A mixture of 2-amino-4,5-dimethylthiazole and 2-(bromomethyl)tetrahydrofuran were processed using the method described in Example 12A to afford the title compound. ¹H NMR (300 MHz, DMSO-d$_6$) δ ppm 1.43-1.64 (m, 1H) 1.73-2.00 (m, 3H) 2.17 (s, 3H) 2.19 (s, 3H) 3.53-3.68 (m, 1H) 3.71-3.85 (m, 1H) 3.91-4.17 (m, 3H) 9.34 (s, 1H),), MS (DCI/NH$_3$) m/z 212 (M+H)⁺.

Example 186B 1-(1,1-Dimethylpropyl)-3-[(2Z)-4,5-dimethyl-3-(tetrahydrofuran-2-ylmethyl)-1,3-thiazol-2(3H)-ylidene]urea The product of Example 186A and 1,1-dimethylpropylamine were processed using the method described in Example 169A to afford the title compound. ¹H NMR (300 MHz, DMSO-d$_6$) δ ppm 0.84 (t, J=7 Hz, 3H) 1.22-1.31 (m, 6H) 1.53-1.72 (m, 3H) 1.75-1.86 (m, 1H) 1.91-2.05 (m, 1H) 2.08-2.20 (m, 1H) 2.24 (s, 6H) 3.55-3.71 (m, 1H) 3.76-3.88 (m, 1H) 4.09-4.20 (m, 1H) 4.30 (s, 1H) 4.40-4.54 (m, 1H) 6.94 (d, J=9 Hz, 1H), MS (DCI/NH$_3$) m/z 326 (M+H)⁺.

Example 187

1-(2,2-Dimethylpropyl)-3-[(2Z)-4,5-dimethyl-3-(tetrahydrofuran-2-ylmethyl)-1,3-thiazol-2(3H)-ylidene]urea The product of Example 186A and 2,2-dimethylpropylamine were processed using the method described in Example 169A to afford the title compound. ¹H NMR (300 MHz, DMSO-d$_6$) δ ppm 0.86 (s, 9H) 1.54-1.65 (m, 1H) 1.77-1.97 (m, 3H) 2.07 (s, 3H) 2.10-2.14 (m, 3H) 2.78-2.97 (m, 2H) 3.54-3.65 (m, 1H) 3.71-3.85 (m, 2H) 3.98-4.11 (m, 1H) 4.14-4.31 (m, 1H) 6.66 (t, J=7 Hz, 1H), MS (DCI/NH$_3$) m/z 326 (M+H)⁺. Anal. Calculated for C$_{16}$H$_{27}$N$_3$O$_2$S: C, 59.04; H, 8.36; N, 12.91. Found C, 58.91; H, 8.64; N, 12.77.

Example 188

1-[(2Z)-4,5-Dimethyl-3-(tetrahydropyran-2-ylmethyl)-1,3-thiazol-2(3H)-ylidene]-3-(3,3,5,5-tetramethylcyclohexyl)urea The product of Example 176A and 3,3,5,5-tetramethylcyclohexylamine were processed using the method described in Example 169A to afford the title compound. ¹H NMR (300 MHz, DMSO-d$_6$) δ ppm 0.88 (s, 6H) 0.91-1.01 (m, 2H) 1.01-1.05 (m, 6H) 1.20 (d, J=14 Hz, 2H) 1.37-1.62 (m, 7H) 1.77 (d, J=4 Hz, 1H) 2.04-2.09 (m, 3H) 2.09-2.15 (m, 3H) 3.09-3.28 (m, 1H) 3.55-3.87 (m, 4H) 3.98 (dd, J=14, 3 Hz, 1H) 6.56 (d, J=8 Hz, 1H), MS (DCI/NH$_3$) m/z 408 (M+H)⁺. Anal. Calculated for C$_{22}$H$_{37}$N$_3$O$_2$S.0.4H$_2$O: C, 63.7; H, 89.18; N, 10.13. Found C, 63.49; H, 8.93; N, 10.12.

Example 189

N-[(2Z)-4,5-dimethyl-3-(tetrahydrofuran-2-ylmethyl)-1,3-thiazol-2(3H)-ylidene]-N'-[(1S)-1,2,2-trimethylpropyl]urea The product of Example 186A and (1S)-1,2,2-trimethylpropylamine were processed using the method described in Example 169A to afford the title compound. ¹H NMR (300 MHz, DMSO-d$_6$) δ ppm 0.83 (s, 9H) 0.98 (dd, J=7, 2 Hz, 3H) 1.53-1.64 (m, 1H) 1.76-1.99 (m, 3H) 2.06 (s, 3H) 2.11 (s, 3H) 3.53-3.65 (m, 2H) 3.73-3.84 (m, 2H) 4.05-4.14 (m, 1H) 4.17-4.22 (m, 1H) 6.34-6.42 (m, 1H), MS (DCI/NH$_3$) m/z 339

(M+H)+. Anal. Calculated for C$_{17}$H$_{29}$N$_3$O$_2$S: C, 60.14; H, 8.61; N, 12.38. Found C, 60.06; H, 8.95; N, 12.29.

Example 190

N-[(2Z)-4,5-dimethyl-3-(tetrahydro-2H-pyran-2-ylmethyl)-1,3-thiazol-2(3H)-ylidene]-N'-[(1R)-1,2,2-trimethylpropyl]urea The product of Example 176A and (1R)-1,2,2-trimethyl-propylamine were processed using the method described in Example 169A to afford the title compound. $^1$H NMR (300 MHz, DMSO-d$_6$) δ ppm 0.84 (s, 9H) 0.99 (dd, J=7, 5 Hz, 3H) 1.13-1.30 (m, 1H) 1.38-1.50 (m, 3H) 1.54-1.68 (m, J=11 Hz, 1H) 1.74-1.85 (m, 1H) 2.06 (s, 3H) 2.11 (s, 3H) 3.19-3.27 (m, 1H) 353-3.66 (m, 1H) 3.71-3.88 (m, 3H) 3.95-4.12 (m, 1H) 6.37 (d, J=9 Hz, 1H), MS (DCI/NH$_3$) m/z 354 (M+H)+. Anal. Calculated for C$_{18}$H$_{31}$N$_3$O$_2$S: C, 61.15; H, 9.04; N, 11.89. Found C, 61.36; H, 9.08; N, 11.80.

Example 191

1-tert-Butyl-3-[(2Z)-5-methyl-3-(tetrahydropyran-2-ylmethyl)-1,3-thiazol-2(3H)-ylidene]urea The product of Example 157A and tert-butyl amine were processed using the method described in Example 169A to afford the title compound. $^1$H NMR (300 MHz, DMSO-d$_6$) δ ppm 1.11-1.22 (m, 1H) 1.27 (s, 9H) 1.42-1.47 (m, J=1 Hz, 3H) 1.47-1.60 (m, 1H) 1.78 (d, J=5 Hz, 1H) 2.12 (s, 3H) 3.17-3.26 (m, 1H) 3.55-3.66 (m, J=6 Hz, 1H) 3.80-3.95 (m, 3H) 6.34 (s, 1H) 6.79 (s, 1H), MS (DCI/NH$_3$) m/z 326 (M+H)+. Anal. Calculated for C$_{16}$H$_{27}$N$_3$O$_2$S.0.3H$_2$O: C, 58.08; H, 8.41; N, 12.70. Found C, 58.44; H, 8.12; N, 12.41.

Example 192

1-(2,3-Dichlorophenyl)-3-[(2Z)-4,5-dimethyl-3-(tetrahydrofuran-2-ylmethyl)-1,3-thiazol-2(3H)-ylidene]urea The product of Example 186A and 2,3-dichlorophenylamine were processed using the method described in Example 169A to afford the title compound. $^1$H NMR (300 MHz, DMSO-d$_6$) δ ppm 1.50-1.67 (m, 1H) 1.75-2.06 (m, 3H) 2.15 (s, 3H) 2.18 (s, 3H) 3.57-3.69 (m, 1H) 3.72-3.83 (m, 1H) 3.83-3.96 (m, 1H) 4.10-4.30 (m, 2H) 7.30 (s, 1H) 7.32 (d, J=1 Hz, 1H) 7.97-8.03 (m, 1H) 8.22 (s, 1H), MS (DCI/NH$_3$) m/z 400, 401 (M+H)+. Anal. Calculated for C$_{13}$H$_{23}$Cl$_3$N$_3$O$_2$S.0.3 MeOH: C, 54.15; H, 8.23; N, 14.20. Found C, 54.47; H, 7.91; N, 13.99.

Example 193

1-(2,2-Dimethylpropyl)-3-[(2Z)-3-(2-methoxyethyl)-4-methyl-1,3-thiazol-2(3H)-ylidene]urea The product of Example 5A and 2,2-dimethylpropylamine were processed using the method described in Example 169A to afford the title compound. $^1$H NMR (300 MHz, DMSO-d$_6$) δ ppm 0.77 (t, J=7 Hz, 3H) 1.21 (s, 6H) 1.66 (q, J=7 Hz, 2H) 2.21 (s, 3H) 3.23 (s, 3H) 3.57 (t, J=5 Hz, 2H) 4.07 (t, J=5 Hz, 2H) 6.21 (s, 1H) 8.10 (d, J=9 Hz, 1H),), MS (DCI/NH$_3$) m/z 286 (M+H)+. Anal. Calculated for C$_{13}$H$_{23}$N$_3$O$_2$S.0.1MeOH: C, 54.70; H, 8.15; N, 14.26. Found C, 54.47; H, 7.91; N, 13.99.

Example 194

N-[(2Z)-4,5-dimethyl-3-(tetrahydrofuran-2-ylmethyl)-1,3-thiazol-2(3H)-ylidene]-N'-[(1R)-1,2,2-trimethylpropyl]urea The product of Example 186A and (1R)-1,2,2-trimethyl-propylamine were processed using the method described in Example 169A to afford the title compound. $^1$H NMR (300 MHz, DMSO-d$_6$) δ ppm 0.84 (s, 9H) 0.98 (dd, J=7, 2 Hz, 3H) 1.49-1.66 (m, 1H) 1.74-1.99 (m, 3H) 2.06 (s, 3H) 2.11 (s, 3H) 3.52-3.67 (m, 2H) 3.72-3.88 (m, 2H) 4.10 (dt, J=14, 4 Hz, 1H) 4.16-4.27 (m, 1H) 6.37 (dd, J=10, 4 Hz, 1H), m/z 339 (M+H)+. Anal. Calculated for C$_{17}$H$_{29}$N$_3$O$_2$S: C, 60.14; H, 8.61; N, 12.38. Found C, 60.18; H, 8.88; N, 12.33.

Example 195

N-[(1S)-1,2-dimethylpropyl]-N'-[(2Z)-4,5-dimethyl-3-(tetrahydrofuran-2-ylmethyl)-1,3-thiazol-2(3H)-ylidene]urea The product of Example 186A and (1S)-1,2,2-trimethyl-propylamine were processed using the method described in Example 169A to afford the title compound. $^1$H NMR (300 MHz, DMSO-d$_6$) δ ppm 0.83 (s, 9H) 0.98 (dd, J=7, 2 Hz, 3H) 1.52-1.66 (m, 1H) 1.75-1.97 (m, 3H) 2.06 (s, 3H) 2.11 (s, 3H) 3.51-3.66 (m, 2H) 3.72-3.86 (m, 2H) 4.10 (dt, J=14, 4 Hz, 1H) 4.19 (s, 1H) 6.37 (dd, J=10, 4 Hz, 1H), m/z 339 (M+H)+. Anal. Calculated for C$_{17}$H$_{29}$N$_3$O$_2$S: C, 60.14; H, 8.61; N, 12.38. Found C, 60.06; H, 8.95; N, 12.29.

Example 196

1-(1-Cyclopropylethyl)-3-[(2Z)-4,5-dimethyl-3-(tetrahydrofuran-2-ylmethyl)-1,3-thiazol-2(3H)-ylidene]urea The product of Example 12A and 1-cyclopropylethylamine were processed using the method described in Example 169A to afford the title compound. $^1$H NMR (300 MHz, DMSO-d$_6$) δ ppm 0.05-0.15 (m, 1H) 0.18-0.55 (m, 3H) 0.78-0.92 (m, 1H) 1.11 (dd, J=7, 2 Hz, 3H) 1.51-1.64 (m, 1H) 1.75-1.99 (m, 3H) 2.07 (s, 3H) 2.12 (s, 3H) 3.06-3.22 (m, 1H) 3.61 (dd, 1H) 3.73-3.85 (m, 2H) 4.02-4.14 (m, 1H) 4.15-4.25 (m, 1H) 6.57-6.70 (m, 1H); m/z 324 (M+H)+. Anal. Calculated for C$_{16}$H$_{25}$N$_3$O$_2$S: C, 59.41; H, 7.79; N, 12.99. Found C, 59.13; H, 7.78; N, 12.88.

Example 197

1-[(2Z)-5-(2,4-Difluorophenyl)-3-(2-methoxyethyl)-1,3-thiazol-2(3H)-ylidene]-3-(1,1-dimethylpropyl)urea Example 197A N-[5-chloro-3-(2-methoxyethyl)-1,3-thiazol-2(3H)-ylidene]acetamide A flask was charged with 2-acetamido-5-chlorothiazole (Lancaster, 19.3 g, 110 mmol) in 200 mL of 2:1 THF/DMF. To the solution was added sodium hydride (60% dispersion in mineral oil, 5.44 g, 142 mmol). The mixture was stirred at room temperature for 15 min and then 2-bromoethyl methyl ether (18.3 g, 131 mmol) was added. The reaction mixture was warmed to 85° C. and stirred overnight. After cooling to room temperature, the mixture was diluted with ethyl acetate and washed with water. The organic extract was dried (MgSO$_4$), filtered, and concentrated. The residue was purified by flash chromatography on SiO$_2$ using a gradient of 0% to 100% ethyl acetate: hexane to provide 10.3 g (42%) of the title compound as the more polar regioisomer: $^1$H NMR (300 MHz, CDCl$_3$) δ 2.28 (s, 3H) 3.35 (s, 3H) 3.65-3.71 (m, 2H) 4.28-4.36 (m, 2H) 7.00 (s, 1H); MS (ESI$^+$) m/z 235 (M+H)$^+$.

Example 197B

N-[5-(2,4-difluorophenyl)-3-(2-methoxyethyl)-1,3-thiazol-2(3H)-ylidene]acetamide A flask was charged with the product from Example 197A (10.2 g, 42.6 mmol), 2,6-difluorophenylboronic acid (8.08 g, 51.1 mmol), Na$_2$CO$_3$ (64.0 mL of a 2 M aqueous solution, 128 mmol) and PdCl$_2$(PPh$_3$)$_2$ (1.5 g, 2.13 mmol) in 100 mL of DME/H$_2$O/ethanol (7:3:2). The mixture was warmed to 85° C. and stirred overnight. After cooling to room temperature, the mixture was diluted with ethyl acetate and washed with water. The organic extract was dried (MgSO$_4$), filtered and concentrated. The residue was purified by flash chromatography on SiO$_2$ using a gradient of 0% to 100% ethyl acetate: hexane to provide 11.5 g (86%) of the title compound: $^1$H NMR (300 MHz, CDCl$_3$) δ 2.17 (s, 3H) 3.27 (s, 3H) 3.71 (t, J=5.3 Hz, 2H) 4.37 (t, J=5.4 Hz, 2H) 7.17-7.24 (m, 1H) 7.38-7.48 (m, 1H) 7.64-7.74 (m, 1H) 7.88 (s, 1H); MS (ESI$^+$) m/z 313 (M+H)$^+$.

Example 197C

N-5-(2,4-difluoro-phenyl)-3-(2-methoxyethyl)-1,3-thiazol-2(3H)-ylideneamine

To a solution of the product from Example 197B (11.5 g, 36.8 mmol) in 100 mL of THF was added 25 mL of 5 N aqueous HCl. The mixture was warmed to 40° C. and stirred overnight. After cooling to room temperature, the solvent was removed under reduced pressure and the residue diluted with ethyl acetate. The mixture was neutralized to pH 7 with saturated aqueous NaHCO$_3$ and then washed with water. The organic extract was dried (MgSO$_4$), filtered and concentrated. The residue was purified by flash chromatography on SiO$_2$ using a gradient of 0% to 100% ethyl acetate: hexane to provide 8.5 g (85%) of the title compound: $^1$H NMR (300 MHz, DMSO-d$_6$) δ 3.27 (s, 3H) 3.57 (t, J=5.3 Hz, 2H) 3.86 (t, J=5.4 Hz, 2H) 7.06-7.14 (m, Hz, 1H) 7.25 (s, 1H) 7.29 (dd, J=9.2, 2.7 Hz, 2H) 7.34 (dd, J=5.9, 3.2 Hz, 1H) 7.94 (s, 1H); MS (ESI$^+$) m/z 271 (M+H)$^+$.

Example 197D

1-[(2Z)-5-(2,4-Difluorophenyl)-3-(2-methoxyethyl)-1,3-thiazol-2-ylidene]-3-(1,1-dimethylpropyl)urea A mixture of the product of Example 197C and 1,1-dimethylpropylamine were processed using the method described in Example 169A to afford the title compound. $^1$H NMR (400 MHz, DMSO-d$_6$) δ ppm 0.78 (t, J=7.06 Hz, 3H) 1.24 (s, 6H) 1.68 (q, J=7.67 Hz, 2H) 3.27 (s, 3H) 3.66 (t, J=5.52 Hz, 2H) 4.20 (t, J=5.22 Hz, 2H) 6.49 (m, 1H) 7.16 (td, J=7.98, 1.84 Hz, 1H) 7.38 (m, 1H) 7.58 (m, 1H) 7.61 (s, 1H); MS (DCI/NH3) m/z 384 (M+H)$^+$.

Example 198

1-[(2Z)-5-(2,4-Difluorophenyl)-3-(2-methoxyethyl)-1,3-thiazol-2-ylidene]-3-(1-methylpropyl)urea A mixture of the product of Example 197C and sec-butylamine were processed using the method described in Example 169A to afford the title compound. $^1$H NMR (500 MHz, DMSO-d$_6$) δ ppm 0.84 (t, J=7.32 Hz, 3H) 1.05 (d, J=6.41 Hz, 3H) 1.42 (m, 2H) 3.27 (s, 3H) 3.59 (m, 1H) 3.66 (t, J=5.49 Hz, 2H) 4.21 (t, J=5.80 Hz, 2H) 6.93 (d, J=8.54 Hz, 1H) 7.18 (td, J=8.24, 2.44 Hz, 1H) 7.39 (m, 1H) 7.57 (td, J=8.85, 6.41 Hz, 1H) 7.62 (brs, 1H); MS (DCI/NH$_3$) m/z 370 (M+H)$^+$.

Example 199

1-Cyclopentyl-3-[(2Z)-5-(2,4-difluorophenyl)-3-(2-methoxyethyl)-1,3-thiazol-2(3H)-ylidene]urea A mixture of the product of Example 197C and cyclopentylamine were processed using the method described in Example 169A to afford the title compound. $^1$H NMR (500 MHz, DMSO-d$_6$) δ ppm 1.47 (m, 4H) 1.65 (m, 2H) 1.80 (m, 2H) 3.27 (s, 3H) 3.66 (t, J=5.49 Hz, 2H) 3.95 (m, 1H) 4.20 (t, J=5.19 Hz, 2H) 7.10 (d, J=7.63 Hz, 1H) 7.18 (td, J=8.24, 2.44 Hz, 1H) 7.39 (m, 1H) 7.57 (m, 1H) 7.63 (s, 1H); MS (DCI/NH$_3$) m/z 382 (M+H)$^+$.

Example 200

1-[(2Z)-5-(2,4-Difluorophenyl)-3-(2-methoxyethyl)-1,3-thiazol-2(3H)-ylidene]-3-(4-methylcyclohexyl)urea A mixture of the product of Example 197C and 4-methylcyclohexylamine were processed using the method described in Example 169A to afford the title compound. $^1$H NMR (400 MHz, DMSO-d$_6$) δ ppm 0.90 (m, 3H) 0.98 (m, 2H) 1.49 (m, 8H) 3.27 (s, 3H) 3.66 (m, 2H) 4.21 (m, 2H) 6.93 (t, J=8.90 Hz, 1H) 7.17 (td, J=7.06, 2.45 Hz, 1H) 7.38 (m, 1H) 7.56 (m, 1H) 7.62 (m, 1H); MS (DCI/NH$_3$) m/z 410 (M+H)$^+$.

Example 202

N-[(2Z)-5-tert-butyl-3-(2-methoxyethyl)-1,3-thiazol-2(3H)-ylidene]-2-ethoxybenzamide

Example 202A 5-tert-butylthiazol-2-amine

To a flask equipped with a Dean-Stark trap was added 3,3-dimethylbutanal (Aldrich, 5.0 g, 50 mmol), pyrrolidine (Aldrich, 4.4 mL, 52 mmol) and p-toluenesulfonic acid monohydrate (10 mg) in cyclohexane (70 mL). The mixture was heated to reflux for 3 hours, the water was removed and the organic phase was concentrated under reduced pressure. The residue was dissolved in methanol (20 mL) and cooled to 0° C. Sulfur (Aldrich, 1.6 g, 50 mmol) and a solution of cyanamide (Aldrich, 2.1 g, 50 mmol) in methanol (5 mL) were added. The reaction mixture was allowed to warm to ambient temperature, stirred for 12 hours, and was concentrated under reduced pressure. The residue was purified by column chromatography (SiO$_2$, 2% methanol in CH$_2$Cl$_2$) to afford the title compound. MS (ESI$^+$) m/z 157 (M+H)$^+$.

Example 202B 5-tert-butyl-3-(2-methoxyethyl)thiazol-2(3H)-imine hydrobromide A mixture of Example 202A and commercially available 2-bromoethyl methyl ether (Aldrich) were processed according to the method described in Example 12A to afford the title compound. MS (ESI$^+$) m/z 215 (M+H)$^+$.

Example 202C

N-[(2Z)-5-tert-butyl-3-(2-methoxyethyl)-1,3-thiazol-2(3H)-ylidene]-2-ethoxybenzamide Commercially available 2-ethoxybenzoic acid (Aldrich) and Example 202B were processed using the method described in Example 58 to afford the title compound. $^1$H NMR (300 MHz, dimethylsulfoxide-d$_6$) δ ppm 1.28-1.36 (m, 12H), 3.26 (s, 3H), 3.71 (t, J=5.4 Hz, 2H), 4.06 (q, J=6.9 Hz, 2H), 4.31 (t, J=5.4 Hz, 2H), 6.95 (td, J=7.4, 0.8 Hz, 1H), 7.05 (dd, J=8.5, 0.7 Hz, 1H), 7.21 (s, 1H), 7.32-7.42 (m, 1H), 7.67 (dd, J=7.6, 1.9 Hz, 1H)); MS (ESI$^+$) m/z 363 (M+H)$^+$.

Example 203

2-ethoxy-N-[(2Z)-5-methyl-3-(tetrahydro-2H-pyran-4-ylmethyl)-1,3-thiazol-2(3H)-ylidene]benzamide

Example 203A (tetrahydro-2H-pyran-4-yl)methyl 4-methylbenzenesulfonate

To a solution of tetrahydro-2H-pyran-4-ylmethanol (Combi-Blocks, 2.0 g, 17.2 mmol) in 10 mL of of CH$_2$Cl$_2$ and 10 mL of of pyridine was added p-toluenesulfonyl chloride (3.5 g, 18.1 mmol) in portions over 15 minutes. The mixture stirred at ambient temperature for 16 hours and was quenched with 10 mL of saturated, aqueous NaHCO$_3$. The layers were separated and the aqueous layer was extracted with three 10 mL portions of CH$_2$Cl$_2$. The combined organic extracts were dried over anhydrous Na$_2$SO$_4$, filtered and concentrated under reduced pressure to afford the title compound. $^1$H NMR (300 MHz, dimethylsulfoxide-d$_6$) δ ppm 1.05-1.25 (m, 2H), 1.40-1.53 (m, 2H), 1.73-1.94 (m, 1H), 2.43 (s, 3H), 3.14-3.28 (m, 2H), 3.71-3.84 (m, 2H), 3.88 (d, J=6.4 Hz, 2H), 7.48 (d, J=8.5 Hz, 2H), 7.79 (d, J=8.5 Hz, 2H); MS (DCI/NH$_3$) m/z 288 (M+NH$_4$)$^+$.

Example 203B 5-methyl-3-((tetrahydro-2H-pyran-4-yl)methyl)thiazol-2(3H)-imine A mixture of Example 203A (1.9 g, 7.0 mmol), 2-amino-5-methylthiazole (0.80 g, 7.0 mmol) and tetrabutylammonium iodide (1.3 g, 3.5 mmol) in 3 mL of N,N-dimethylformamide was warmed to 85° C. and was allowed to stir for 24 hours. The mixture was diluted with 10 mL of CH$_2$Cl$_2$, washed with 10% aqueous NaHCO$_3$, dried over anhydrous Na$_2$SO$_4$, filtered and concentrated under reduced pressure. Purification via column chromatography (SiO$_2$, 10% methanol in ethyl acetate then 9:1:0.1 CH$_2$Cl$_2$:methanol:NH$_4$OH) afforded the title compound. MS (DCI/NH$_3$) m/z 213 (M+H)$^+$.

Example 203C 2-ethoxy-N-[(2Z)-5-methyl-3-(tetrahydro-2H-pyran-4-ylmethyl)-1,3-thiazol-2(3H)-ylidene]benzamide To a solution of Example 203B (0.11 g, 0.52 mmol) in 10 mL of tetrahydrofuran and 1 mL of N,N-dimethylformamide at ambient temperature was added triethylamine (0.22 mL, 1.6 mmol) followed by 2-ethoxybenzoyl chloride (0.11 g, 0.57 mmol). This mixture was warmed to 50° C., stirred for 3 hours, was quenched with 10 mL of saturated aqueous NH$_4$Cl, and diluted with 10 mL of CH$_2$Cl$_2$. The layers were separated and the aqueous layer was extracted with three 5 mL portions of CH$_2$Cl$_2$. The combined organic extracts were dried over anhydrous Na$_2$SO$_4$, filtered and concentrated under reduced pressure. Purification via flash column chromatography (SiO$_2$, 50% hexanes in ethyl acetate) afforded the title compound. $^1$H NMR (300 MHz, CDCl$_3$) δ ppm 1.46 (t, J=7.0 Hz, 3H), 1.52-1.61 (m, 1H), 1.57 (s, 3H), 2.14-2.26 (m, 1H), 2.29 (d, J=1.4 Hz, 3H), 3.36 (dt, J=11.7, 2.4 Hz, 2H), 3.98 (ddd, J=11.4, 4.1, 1.5 Hz, 2H), 4.06 (d, J=7.5 Hz, 2H), 4.17 (q, J=6.8 Hz, 2H), 6.59-6.62 (m, 1H), 6.93-7.01 (m, 2H), 7.36 (ddd, J=8.3, 7.5, 1.9 Hz, 1H), 7.97 (dd, J=8.0, 1.9 Hz, 1H); MS (DCI/NH$_3$) m/z 361 (M+H)$^+$. Anal. Calculated for C$_{19}$H$_{24}$N$_2$O$_3$S: C, 63.31; H, 6.71; N, 7.77. Found: C, 63.27; H, 6.57; N, 7.48.

Example 204

2,4-dimethoxy-N-[(2Z)-5-methyl-3-(tetrahydrofuran-2-ylmethyl)-1,3-thiazol-2(3H)-ylidene]benzamide

Example 204A 5-methyl-3-((tetrahydrofuran-2-yl)methyl)thiazol-2(3H)-imine

A mixture of 2-amino-5-methylthiazole (1 g, 8.7 mmol) and 2-(bromomethyl)tetrahydrofuran (1.1 mL, 10 mmol) was warmed to 85° C. and was allowed to stir for 24 hours. The mixture was cooled to ambient temperature and purified via flash column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 199 (M+H)$^+$.

Example 204B 2,4-dimethoxybenzoyl chloride

A solution of 2,4-dimethoxybenzoic acid (0.25 g, 1.4 mmol) in 5 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to give the crude title compound which was used without additional purification or characterization.

Example 204C 2,4-dimethoxy-N-[(2Z)-5-methyl-3-(tetrahydrofuran-2-ylmethyl)-1,3-thiazol-2(3H)-ylidene]benzamide To a solution of Example 204A (0.18 g, 0.91 mmol) in 10 mL of tetrahydrofuran at ambient temperature was added triethylamine (0.38 mL, 2.7 mmol) followed by Example 204B (1.4 mmol) in 3 mL of tetrahydrofuran via cannula. This mixture was warmed to 50° C., stirred for 3 hours, then quenched with 10 mL of saturated aqueous NH$_4$Cl, and diluted with 10 mL of CH$_2$Cl$_2$. The layers were separated and the aqueous phase was extracted three 5 mL portions of CH$_2$Cl$_2$. The combined organic extracts were dried over anhydrous Na$_2$SO$_4$, filtered and concentrated under reduced pressure. Purification via column chromatography (SiO$_2$, 50% hexanes in ethyl acetate) afforded the title compound. $^1$H NMR (300 MHz, CD$_3$OD) δ ppm 1.65-1.79 (m, 1H), 1.84-1.96 (m, 2H), 1.99-2.15 (m, 1H), 2.31 (d, J=1.4 Hz, 3H), 3.71-3.81 (m, 1H), 3.84-3.93 (m, 1H), 3.85 (s, 3H), 3.86 (s, 3H), 4.19-4.42 (m, 3H), 6.51-6.62 (m, 2H), 7.05-7.10 (m, 1H), 8.03 (d, J=8.8 Hz, 1H); MS (DCI/NH$_3$) m/z 363 (M+H)$^+$. Anal. Calculated for C$_{18}$H$_{22}$N$_2$O$_4$S: C, 59.65; H, 6.12; N, 7.73. Found: C, 59.47; H, 6.01; N, 7.62.

Example 205

5-chloro-2-methoxy-N-[(2Z)-4-methyl-3-(tetrahydro-2H-pyran-2-ylmethyl)-1,3-thiazol-2(3H)-ylidene]benzamide Example 205A 4-methyl-3-((tetrahydro-2H-pyran-2-yl)methyl)thiazol-2(3H)-imine A mixture of 2-amino-4-methylthiazole (1.0 g, 8.8 mmol) and 2-(bromomethyl)tetrahydropyran (1.1 mL, 8.8 mmol) was warmed to 85° C. and was allowed to stir for 24 hours. The mixture was cooled to ambient temperature and the crude material was purified via column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 213 (M+H)$^+$.

Example 205

5-chloro-2-methoxybenzoyl chloride

A solution of 2-methoxy-5-chlorobenzoic acid (0.37 g, 2.0 mmol) in 10 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to afford the title compound. $^1$H NMR (300 MHz, dimethylsulfoxide-d$_6$) δ ppm 3.82 (s, 3H), 7.16 (d, J=8.8 Hz, 1H), 7.49-7.59 (m, 1H), 7.61 (d, J=2.7 Hz, 1H).

Example 205C 5-chloro-2-methoxy-N-[(2Z)-4-methyl-3-(tetrahydro-2H)-pyran-2-ylmethyl)-1,3-thiazol-2(3H)-ylidene]benzamide To a solution of Example 205A (0.21 g, 1.0 mmol) in 10 mL of tetrahydrofuran at ambient temperature was added triethylamine (0.41 mL, 3.0 mmol) followed by Example 205B (2.0 mmol) in 5 mL of tetrahydrofuran via cannula. This mixture was warmed to 50° C., stirred for 2 hours, then quenched with 10 mL of saturated aqueous NH$_4$Cl, and diluted with 10 mL of CH$_2$Cl$_2$. The layers were separated and the aqueous phase was extracted with three 5 mL portions of CH$_2$Cl$_2$. The combined organic extracts were dried over anhydrous Na$_2$SO$_4$, filtered and concentrated tinder reduced pressure. Purification via column chromatography (SiO$_2$, 50% hexanes in ethyl acetate) afforded the title compound. $^1$H NMR (300 MHz, CD$_3$OD) δ ppm 1.31-1.48 (m, 1H), 1.47-1.67 (m, 3H), 1.70-1.82 (m, 1H), 1.84-1.98 (m, 1H), 2.40 (d, J=1.0 Hz, 3H), 3.26-3.40 (m, 1H), 3.82-3.94 (m, 2H), 3.87 (s, 3H), 4.00-4.11 (m, 1H), 4.42 (dd, J=13.9, 2.7 Hz, 1H), 6.55 (d, J=1.0 Hz, 1H), 7.07 (d, J=8.8 Hz, 1H), 7.40 (dd, J=8.8, 2.7 Hz, 1H), 7.87 (d, J=2.7 Hz, 1H); MS (DCI/NH$_3$) m/z 381 (M+H)$^+$. Anal. Calculated for C$_{18}$H$_{21}$ClN$_2$O$_3$S: C, 56.76; H, 5.56; N, 7.35. Found: C, 56.58; H, 5.43; N, 7.19.

Example 206

5-chloro-2-methoxy-N-[(2Z)-5-methyl-3-(tetrahydro-2H-pyran-4-ylmethyl)-1,3-thiazol-2(3H)-ylidene]benzamide To Example 203B (0.11 g, 0.52 mmol) and triethylamine (0.22 mL, 1.6 mmol) in 10 mL of tetrahydrofuran and 1 mL of N,N-dimethylformamide was added Example 205B (0.68 mmol) in 2 mL of tetrahydrofuran. This mixture was warmed to 50° C., stirred for 2 hours, then quenched with 10 mL of saturated aqueous NH$_4$Cl, and diluted with 10 mL of CH$_2$Cl$_2$. The layers were separated and the aqueous phase was extracted with three 5 mL portions of CH$_2$Cl$_2$. The combined organic extracts were dried over anhydrous Na$_2$SO$_4$, filtered and concentrated under reduced pressure. Purification via flash column chromatography (SiO$_2$, 50% hexanes in ethyl acetate) resulted in the title compound. $^1$H NMR (300 MHz, CD$_3$OD) δ ppm 1.34-1.60 (m, 4H), 2.18-2.32 (m, 1H), 2.34 (d, J=1.4 Hz, 3H), 3.38 (dt, J=11.6, 2.5 Hz, 2H), 3.86 (s, 3H), 3.94 (ddd, J=11.6, 4.2, 1.9 Hz, 2H), 4.14 (d, J=7.5 Hz, 2H), 7.07 (d, J=8.8 Hz, 1H), 7.12 (q, J=1.4 Hz, 1H), 7.40 (dd, J=8.8, 2.7 Hz, 1H), 7.83 (d, J=2.7 Hz, 1H); MS (DCI/NH$_3$) m/z 381 (M+H)$^+$. Anal. Calculated for C$_{18}$H$_{21}$ClN$_2$O$_3$S: C, 56.76; H, 5.56; N, 7.35. Found: C, 56.48; H, 5.46; N, 7.23.

Example 207

5-chloro-2-methoxy-N-[(2Z)-3-tetrahydro-2H-pyran-2-ylmethyl)-1,3-thiazol-2(3H)-ylidene]benzamide Example 207A 3-((tetrahydro-2H-pyran-2-yl)methyl)thiazol-2(3H)-imine A mixture of 2-aminothiazole (1.0 g, 10 mmol) and 2-(bromomethyl)tetrahydro-2H-pyran (1.3 mL, 10 mmol) was warmed to 85° C. and was allowed to stir for 24 hours. The mixture was cooled to ambient temperature and the crude material was purified via column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 199 (M+H)$^+$.

Example 207B 5-chloro-2-methoxy-N-[(2Z)-3-(tetrahydro-2H-pyran-2-ylmethyl)-1,3-thiazol-2(3H)-ylidene]benzamide To a solution of Example 207A (0.19 g, 0.96 mmol) in 10 mL of tetrahydrofuran at ambient temperature was added triethylamine (0.40 mL, 2.9 mmol) followed by Example 205B (2.0 mmol) in 5 mL of tetrahydrofuran via cannula. This mixture was warmed to 50° C., stirred for 2 hours, then quenched with 10 mL of saturated aqueous $NH_4Cl$, and diluted with 10 mL of $CH_2Cl_2$. The layers were separated and the aqueous phase was extracted with three 5 mL portions of $CH_2Cl_2$. The combined organic extracts were dried over anhydrous $Na_2SO_4$, filtered and concentrated under reduced pressure. Purification via column chromatography ($SiO_2$, 50% hexanes in ethyl acetate) afforded the title compound. $^1H$ NMR (300 MHz, $CD_3OD$) δ ppm 1.20-1.41 (m, 1H, 1.46-1.63 (m, 3H), 1.67-1.77 (m, 1H), 1.82-1.96 (m, 1H), 3.35-3.45 (m, 1H), 3.75-3.85 (m, 1H), 3.86 (s, 3H), 3.89-4.00 (m, 1H), 4.19-4.27 (m, 1H), 4.38-4.46 (m, 1H), 6.91 (d, J=4.7 Hz, 1H), 7.08 (d, J=8.8 Hz, 1H), 7.38 (d, J=4.7 Hz, 1H), 7.41 (dd, J=8.8, 3.1 Hz, 1H), 7.85 (d, J=3.1 Hz, 1H); MS ($DCI/NH_3$) m/z 367 $(M+H)^+$. Anal. Calculated for $C_{17}H_{19}ClN_2O_3S$: C, 55.66; H, 5.22; N, 7.64. Found: C, 55.72; H, 5.08; N, 7.55.

Example 208

5-chloro-2-methoxy-N-[(2Z)-5-methyl-3-[(2R)-tetrahydrofuran-2-ylmethyl]-1,3-thiazol-2(3H)-ylidene] benzamide Example 208A (R)-(tetrahydrofuran-2-yl)methyl 4-methylbenzenesulfonate To a solution of (R)-tetrahydrofurfuryl alcohol (Lancaster, 1.0 g, 9.8 mmol) in 5 mL of $CH_2Cl_2$ and 5 mL of pyridine was added p-toluenesulfonyl chloride (2.8 g, 14.7 mmol) in portions over 15 minutes. The mixture was stirred at ambient temperature for 3 hours and was quenched with 10 mL of saturated, aqueous $NaHCO_3$. The layers were separated and the aqueous layer was extracted with three 5 mL portions of $CH_2Cl_2$. The combined organic extracts were dried over anhydrous $Na_2SO_4$, filtered and concentrated under reduced pressure to afford the title compound. MS ($DCI/NH_3$) m/z 257 $(M+H)^+$, 274 $(M+NH_4)^+$.

Example 208B (R)-5-methyl-3-((tetrahydrofuran-2-yl)methyl)thiazol-2(3H)-imine

A mixture of Example 208A (1.5 g, 5.9 mmol), 2-amino-5-methylthiazole (0.68 g, 5.9 mmol) and tetrabutylammonium iodide (1.1 g, 3.0 mmol) in 3 mL of N,N-dimethylformamide was warmed to 85° C. and was allowed to stir for 48 hours. The mixture was diluted with 10 mL of $CH_2Cl_2$ and the solution was quenched with 10 mL of saturated, aqueous $NaHCO_3$. The layers were separated and the aqueous layer was extracted twice with 10 mL portions of $CH_2Cl_2$. The combined organic extracts were dried over anhydrous $Na_2SO_4$, filtered and concentrated under reduced pressure. Purification via column chromatography ($SiO_2$, 10% methanol in ethyl acetate then 9:1:0.1 $CH_2Cl_2$:methanol:$NH_4OH$) afforded the title compound. MS ($DCI/NH_3$) m/z 199 $(M+H)^+$.

Example 208C 5-chloro-2-methoxybenzoyl chloride

A solution of 2-methoxy-5-chlorobenzoic acid (0.22 g, 1.2 mmol) in 10 mL of $SOCl_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to afford the title compound. $^1H$ NMR (300 MHz, dimethylsulfoxide-$d_6$) δ ppm 3.82 (s, 3H), 7.16 (d, J=8.8 Hz, 1H), 7.49-7.59 (m, 1H), 7.61 (d, J=2.7 Hz, 1H).

Example 208D 5-chloro-2-methoxy-N-[(2Z)-5-methyl-3-[(2R)-tetrahydrofuran-2-ylmethyl]-1,3-thiazol-2(3H)-ylidene] benzamide To a solution of Example 208B (0.23 g, 1.2 mmol) in 10 mL of tetrahydrofuran at ambient temperature was added triethylamine (0.49 mL, 3.5 mmol) followed by Example 208C (1.2 mmol) in 5 mL of tetrahydrofuran via cannula. This mixture was warmed to 50° C. and was allowed to stir for 3 hours and was quenched with 10 mL of $NH_4Cl$ and diluted with 10 mL of $CH_2Cl_2$. The layers were separated and the aqueous layer was extracted with three 5 mL portions of $CH_2Cl_2$. The combined organic extracts were dried over anhydrous $Na_2SO_1$, filtered and concentrated under reduced pressure. Purification via flash column chromatography ($SiO_2$, 1:1:1 hexanes:ethyl acetate:$CH_2Cl_2$) afforded the title compound. $^1H$ NMR (300 MHz, $CD_3OD$) δ ppm 1.64-1.79 (m, 1H), 1.84-1.96 (m, 2H), 2.00-2.14 (m, 1H), 2.34 (d, J=1.4 Hz, 3H), 3.69-3.81 (m, 1H), 3.84-3.93 (m, 1H), 3.85 (s, 3H), 4.20-4.43 (m, 3H), 7.07 (d, J=8.8 Hz, 1H), 7.14 (q, J=1.1 Hz, 1H), 7.39 (dd, J=9.0, 2.9 Hz, 1H), 7.81 (d, J=2.7 Hz, 1H); MS ($DCI/NH_3$) m/z 367 $(M+H)^+$. Anal. Calculated for $C_{17}H_{19}ClN_2O_3S$: C, 55.66; H, 5.22; N, 7.64. Found: C, 55.42; H, 5.08; N, 7.58.

Example 209

5-chloro-2-methoxy-N-[(2Z)-5-methyl-3-[(2S)-tetrahydrofuran-2-ylmethyl]-1,3-thiazol-2(3H)-ylidene] benzamide Example 209A (S)-(tetrahydrofuran-2-yl)methyl 4-methylbenzenesulfonate To a solution of (S)-tetrahydrofurfuryl alcohol (Codexis, 1.6 g, 15.2 mmol) in 5 mL of $CH_2Cl_2$ and 5 mL of pyridine was added p-toluenesulfonyl chloride (4.3 g, 22.8 mmol) in portions over 15 minutes. The mixture stirred at ambient temperature for 3 hours and was quenched with 10 mL of saturated, aqueous $NaHCO_3$. The layers were separated and the aqueous layer was extracted with three 5 mL portions of $CH_2Cl_2$. The combined organic extracts were dried over anhydrous $Na_2SO_4$, filtered and concentrated under reduced pressure to afford the title compound. MS ($DCI/NH_3$) m/z 257 $(M+H)^+$, 274 $(M+NH_4)^+$.

Example 209B (S)-5-methyl-3-((tetrahydrofuran-2-yl)methyl)thiazol-2(3H)-imine

A mixture of Example 209A (1.6 g, 6.1 mmol), 2-amino-5-methylthiazole (0.7 g, 6.1 mmol) and tetrabutylammonium iodide (2.3 g, 6.1 mmol) in 5 mL of N,N-dimethylformamide was warmed to 85° C. and was allowed to stir for 18 hours.

The mixture was diluted with 10 mL of CH$_2$Cl$_2$, washed with 10% aqueous NaHCO$_3$, dried over anhydrous Na$_2$SO$_4$, filtered and concentrated under reduced pressure. Purification via column chromatography (SiO$_2$, 10% methanol in ethyl acetate then 9:1:0.1 CH$_2$Cl$_2$:methanol:NH$_4$OH) afforded the title compound. MS (DCI/NH$_3$) m/z 199 (M+H)$^+$.

Example 209C 5-chloro-2-methoxy-N-[(2Z)-5-methyl-3-[(2S)-tetrahydrofuran-2-ylmethyl]-1,3-thiazol-2-(3H)-ylidene]benzamide Example 209B (0.32 g, 1.6 mmol), triethylamine (0.67 mL, 4.8 mmol) and Example 205B (1.9 mmol) in 20 mL of tetrahydrofuran were processed as in Example 208D to afford the title compound. $^1$H NMR (300 MHz, CD$_3$OD) δ ppm 1.64-1.79 (m, 1H), 1.84-1.96 (m, 2H), 2.00-2.13 (m, 1H), 2.34 (d, J=1.4 Hz, 3H), 3.71-3.81 (m, 1H), 3.84-3.93 (m, 1H), 3.85 (s, 3H), 4.20-4.43 (m, 3H), 7.07 (d, J=8.8 Hz, 1H), 7.14 (q, J=1.4 Hz, 1H) 7.39 (dd, J=9.0, 2.9 Hz, 1H), 7.81 (d, J=2.7 Hz, 1H); MS (DCI/NH$_3$) m/z 367 (M+H)$^+$. Anal. Calculated for C$_{17}$H$_{19}$ClN$_2$O$_3$S: C, 55.66; H, 5.22; N, 7.64. Found: C, 55.48; H, 4.96; N, 7.52.

Example 210

2,2,3,3-tetrafluoro-1-methyl-N-[(2Z)-5-methyl-3-(tetrahydrofuran-2-ylmethyl)-1,3-thiazol-2(3H)-ylidene]cyclobutanecarboxamide Example 204A (0.20 g, 1.0 mmol), triethylamine (0.42 mL, 3.0 mmol) and 2,2,3,3-tetrafluoro-1-(methyl)cyclobutanecarbonyl chloride (ABCR, 0.27 g, 1.3 mmol) in 15 mL of tetrahydrofuran were processed as in Example 208D to afford the title compound. $^1$H NMR (300 MHz, CD$_3$OD) δ ppm 1.53 (s, 3H), 1.62-1.73 (m, 1H), 1.81-1.93 (m, 2H), 1.95-2.10 (m, 1H), 2.27-2.44 (m, 1H), 2.32 (d, J=1.4 Hz, 3H), 3.33-3.43 (m, 1H), 3.69-3.79 (m, 1H), 3.80-3.90 (m, 1H), 4.20-4.36 (m, 3H), 7.11 (dd, J=1.4, 0.7 Hz, 1H); MS (DCI/NH$_3$) m/z 367 (M+H)$^+$. Anal. Calculated for C$_{15}$H$_{18}$F$_4$N$_2$O$_2$S: C, 49.17; H, 4.95; N, 7.65. Found: C, 49.27; H, 4.88; N, 7.58.

Example 211

5-chloro-2-methoxy-N-[(2Z)-5-methyl-3-(oxetan-2-ylmethyl)-1,3-thiazol-2(3H)-ylidene]benzamide Example 211A oxetan-2-ylmethyl 4-methylbenzenesulfonate To a solution of 2-hydroxymethyloxetane (TCI-US, 2.0 g, 23 mmol) in 10 mL of CH$_2$Cl$_2$ and 10 mL of pyridine was added p-toluenesulfonyl chloride (6.5 g, 34 mmol) in portions over 15 minutes. The mixture was stirred at ambient temperature for 3 hours and was quenched with 10 mL of saturated, aqueous NaHCO$_3$. The layers were separated and the aqueous layer was extracted with three 5 mL portions of CH$_2$Cl$_2$. The combined organic extracts were dried over anhydrous Na$_2$SO$_4$, filtered and concentrated under reduced pressure. Purification via column chromatography (SiO$_2$, 70% hexanes in ethyl acetate) afforded the title compound. MS (DCI/NH$_3$) m/z 243 (M+H)$^+$, 260 (M+NH$_4$)$^+$.

Example 211B 5-methyl-3-(oxetan-2-ylmethyl)thiazol-2(3H)-imine

A mixture of Example 211A (1.1 g, 4.6 mmol), 2-amino-5-methylthiazole (0.53 g, 4.6 mmol) and tetrabutylammonium iodide (0.85 g, 2.3 mmol) in 5 mL of N,N-dimethylformamide was warmed to 85° C. and was allowed to stir for 18 hours. The mixture was diluted with 10 mL of CH$_2$Cl$_2$, washed with 10% aqueous NaHCO$_3$, dried over anhydrous Na$_2$SO$_4$, filtered and concentrated under reduced pressure. Purification via column chromatography (SiO$_2$, 10% methanol in ethyl acetate then 9:1:0.1 CH$_2$Cl$_2$:methanol:NH$_4$OH) afforded the title compound. MS (DCI/NH$_3$) m/z 185 (M+H)$^+$.

Example 211C 5-chloro-2-methoxy-N-[(2Z)-5-methyl-3-(oxetan-2-ylmethyl)-1,3-thiazol-2(3H)-ylidene]benzamide Example 211B (0.26 g, 1.4 mmol), triethylamine (0.59 mL, 4.2 mmol) and Example 205B (1.7 mmol) in 15 mL of tetrahydrofuran were processed as in Example 208D to afford the title compound. $^1$H NMR (300 MHz, CD$_3$OD) δ ppm 2.35 (d, J=1.4 Hz, 3H), 2.43-2.59 (m, 1H), 2.70-2.85 (m, 1H), 3.85 (s, 3H), 4.37-4.51 (m, 2H), 4.57-4.71 (m, 2H), 5.15-5.25 (m, 1H), 7.06 (d, J=9.2 Hz, 1H), 7.18 (q, J=1.1 Hz, 1H), 7.39 (dd, J=8.8, 2.7 Hz, 1H), 7.79 (d, J=2.7 Hz, 1H); MS (DCI/NH$_3$) m/z 353 (M+H)$^+$. Anal. Calculated for C$_{16}$H$_{17}$ClN$_2$O$_3$S: C, 54.46; H, 4.86; N, 7.94. Found: C, 54.41; H, 4.88; N, 7.80.

Example 212

5-chloro-N-[(2Z)-3-(1,3-dioxolan-2-ylmethyl)-5-methyl-1,3-thiazol-2(3H)-ylidene]-2-methoxybenzamide Example 212A 3-((1,3-dioxolan-2-yl)methyl)-5-methylthiazol-2(3H)-imine A mixture of 2-amino-5-methylthiazole (1 g, 8.7 mmol) and 2-bromomethyl-1,3-dioxolane (0.98 mL, 9.6 mmol) was warmed to 85° C. and was allowed to stir for 18 hours. The mixture was cooled to ambient temperature and purified via column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 201 (M+H)$^+$.

Example 212B 5-chloro-N-[(2Z)-3-(1,3-dioxolan-2-ylmethyl)-5-methyl-1,3-thiazol-2(3H)-ylidene]-2-methoxybenzamide Example 212A (0.25 g, 1.3 mmol), triethylamine (0.52 mL, 3.8 mmol) and Example 205B (1.5 mmol) in 15 mL of tetrahydrofuran were processed as in Example 208D to afford the title compound. $^1$H NMR (300 MHz, CD$_3$OD) δ ppm 2.33 (d, J=1.4 Hz, 3H), 3.86 (s, 3H), 3.87-3.99 (m, 4H), 4.41 (d, J=4.1 Hz, 2H), 5.27 (t, J=4.1 Hz, 1H), 7.07 (d, J=8.8 Hz, 1H), 7.12 (q, J=1.4 Hz, 1H), 7.40 (dd, J=8.8, 2.7 Hz, 1H), 7.87 (d, J=27 Hz, 1H); MS (DCI/NH$_3$) m/z 369 (M+H)$^+$. Anal. Calculated for C$_{16}$H$_{17}$ClN$_2$O$_4$S: C, 52.10, H, 4.65; N, 7.60. Found: C, 52.15; H, 4.42; N, 7.44.

Example 213

5-chloro-N-[(2Z)-3-[2-(1,3-dioxolan-2-yl)ethyl]-5-methyl-1,3-thiazol-2(3H)-ylidene]-2-methoxybenzamide

Example 213A 3-(2-(1,3-dioxolan-2-yl)ethyl)-5-methylthiazol-2(3H)-imine

A mixture of 2-amino-5-methylthiazole (1.0 g, 8.7 mmol) and 2-(2-bromoethyl)-1,3-dioxolane (1.1 mL, 8.7 mmol) was warmed to 85° C. and was allowed to stir for 18 hours. The mixture was cooled to ambient temperature and purified via column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 215 (M+H)$^+$.

Example 213B 5-chloro-N-[(2Z)-3-[2-(1,3-dioxolan-2-yl)ethyl]-5-methyl-1,3-thiazol-2(3H)-ylidene]-2-methoxybenzamide Example 213A (0.25 g, 1.2 mmol), triethylamine (0.49 mL, 3.5 mmol) and Example 205B (1.3 mmol) in 10 mL of tetrahydrofuran were processed as in Example 208D to afford the title compound. $^1$H NMR (300 MHz, CD$_3$OD) δ ppm 2.18-2.25 (m, 2H), 233 (d, J=1.0 Hz, 3H), 3.82-3.87 (m, 2H), 3.86 (s, 3H), 3.93-4.01 (m, 2H), 4.36 (dd, J=7.1 Hz, 2H), 4.93 (t, J=4.4 Hz, 1H), 7.07 (d, J=8.8 Hz, 1H), 7.10 (q, J=1.4 Hz, 1H), 7.40 (dd, J=8.8, 2.7 Hz, 1H), 7.96 (d, J=3.1 Hz, 1H); MS (DCI/NH$_3$) m/z 383 (M+H)$^+$. Anal. Calculated for C$_{17}$H$_{19}$ClN$_2$O$_4$S: C, 53.33; H, 5.00; N, 7.32. Found: C, 53.02; H, 4.52; N, 7.22.

Example 214

N-[(2Z)-3-(1,3-dioxolan-2-ylmethyl)-5-methyl-1,3-thiazol-2(3H)-ylidene]-2-ethoxybenzamide Example 212A (0.20 g, 1.0 mmol), triethylamine (0.42 mL, 3.0 mmol) and 2-ethoxybenzoyl chloride (0.17 g, 1.1 mmol) in 10 mL of tetrahydrofuran were processed as in Example 208D to afford the title compound. $^1$H NMR (300 MHz, CD$_3$OD) δ ppm 1.41 (t, J=7.0 Hz, 3H), 2.33 (d, J=1.4 Hz, 3H), 3.82-4.01 (m, 4H), 4.12 (q, J=6.9 Hz, 2H), 4.40 (d, J=4.4 Hz, 2H), 5.27 (t, J=4.2 Hz, 1H), 6.96 (dt, J=7.5, 0.8 Hz, 1H), 7.05 (d, J=8.5 Hz, 1H), 7.09 (q, J=1.4 Hz, 1H), 7.39 (ddd, J=8.7, 6.9, 1.7 Hz, 1H), 7.83 (dd, J=7.6, 1.9 Hz, 1H); MS (DCI/NH$_3$) m/z 349 (M+H)$^+$. Anal. Calculated for C$_{17}$H$_{20}$N$_2$O$_4$S: C, 58.60; H, 5.79; N, 8.04. Found: C, 58.22; H, 5.32; N, 7.93.

Example 215

5-bromo-2-ethoxy-N-[(2Z)-5-methyl-3-[(2R)-tetrahydrofuran-2-ylmethyl]-1,3-thiazol-2(3H)-ylidene]benzamide

Example 215A 5-bromo-2-ethoxybenzoic acid

To a solution of 2-ethoxybenzoic acid (3.3 g, 20.0 mmol) in 75 mL of acetonitrile at 0° C. was added N-bromosuccinimide (3.7 g, 21 mmol) in 15 mL of acetonitrile. The reaction mixture was warmed to ambient temperature and the mixture was allowed to stir for 48 hours. The mixture was quenched with 20 mL of H$_2$O and the layers were separated. The aqueous layer was extracted with three 15 mL portions of CH$_2$Cl$_2$ and the combined organic extracts were dried over anhydrous Na$_2$SO$_4$, filtered and concentrated under reduced pressure. Purification via column chromatography (SiO$_2$, 10% hexanes in ethyl acetate) afforded the title compound. MS (DCI/NH$_3$) m/z 262, 264 (M+NH$_4$)$^+$.

Example 215B 5-bromo-2-ethoxybenzoyl chloride

A solution of Example 215A (0.21 g, 0.86 mmol) in 5 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to give the crude title compound which was used without additional purification or characterization.

Example 215C 5-bromo-2-ethoxy-N-[(2Z)-5-methyl-3-[(2R)-tetrahydrofuran-2-ylmethyl]-1,3-thiazol-2(3H)-ylidene]benzamide Example 208B (0.17 g, 0.86 mmol), triethylamine (0.36 mL, 2.6 mmol) and Example 215B (0.86 mmol) in 10 mL of tetrahydrofuran were processed as in Example 208D to afford the title compound. $^1$H NMR (300 MHz, CD$_3$OD) δ ppm 1.39 (t, J=7.0 Hz, 3H), 1.63-1.78 (m, 1H), 1.84-1.96 (m, 2H), 2.00-2.15 (m, 1H), 2.34 (d, J=1.4 Hz, 3H), 3.69-3.81 (m, 1H), 3.84-3.95 (m, 1H), 4.10 (q, J=70 Hz, 2H), 4.19-4.43 (m, 3H), 6.99 (d, J=8.8 Hz, 1H), 7.14 (q, J=1.2 Hz, 1H), 7.49 (dd, J=8.8, 2.7 Hz, 1H), 7.87 (d, J=2.7 Hz, 1H); MS (DCI/NH$_3$) m/z 425, 427 (M+H)$^+$. Anal. Calculated for C$_{18}$H$_{21}$BrN$_2$O$_3$S: C, 50.83; H, 4.98; N, 6.59. Found: C, 50.89; H, 4.87; N, 6.51.

Example 216

5-chloro-2-ethoxy-N-[(2Z)-5-methyl-3-[(2R)-tetrahydrofuran-2-ylmethyl]-1,3-thiazol-2(3H)-ylidene]benzamide

Example 216A 5-chloro-2-ethoxybenzoic acid

To a solution of 2-ethoxybenzoic acid (4.4 g, 26.6 mmol) in 80 mL of acetonitrile at 0° C. was added N-chlorosuccinimide (3.7 g, 28 mmol) in 20 mL of acetonitrile dropwise over 30 minutes. The reaction mixture was warmed to ambient temperature and the mixture was allowed to stir for 70 hours. The mixture was quenched with 20 mL of H$_2$O and the layers were separated. The aqueous layer was extracted with three 15 mL portions of CH$_2$Cl$_2$ and the combined organic extracts were dried over anhydrous Na$_2$SO$_4$, filtered and concentrated under reduced pressure. Purification via recrystallization with ether and hexanes afforded the title compound. MS (DCI/NH$_3$) m/z 201 (M+H)$^+$, 218 (M+NH$_4$)$^+$.

Example 216B

5-chloro-2-ethoxybenzoyl chloride

A solution of Example 216A (0.25 g, 1.0 mmol) in 5 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to give the crude title compound which was used without additional purification or characterization.

Example 216C

5-chloro-2-ethoxy-N-[(2Z)-5-methyl-3-[(2R)-tetrahydrofuran-2-ylmethyl]-1,3-thiazol-2(3H)-ylidene]benzamide Example 208B (0.20 g, 1.0 mmol), triethylamine (0.42 mL, 3.0 mmol) and Example 216B (1.0 mmol) in 10 mL of tetrahydrofuran were processed as in Example 208D to afford the title compound. $^1$H NMR (300 MHz, CD$_3$OD) δ ppm 1.39 (t, J=7.0 Hz, 3H), 1.62-1.77 (m, 1H), 1.83-1.97 (m, 2H) 1.99-2.14 (m, 1H), 2.34 (d, J=1.4 Hz, 3H), 3.70-3.80 (m, 1H), 3.84-3.93 (m, 1H) 4.10 (q, J=6.9 Hz, 2H), 4.20-4.44 (m, 3H), 7.04 (d, J=8.8 Hz, 1H), 7.14 (q, J=1.4 Hz, 1H), 7.35 (dd, J=8.8, 2.7 Hz, 1H), 7.73 (d, J=2.7 Hz, 1H); MS (DCI/NH$_3$) m/z 381 (M+H)$^+$. Anal. Calculated for C$_{18}$H$_{21}$ClN$_2$O$_3$S: C, 56.76; H, 5.56; N, 7.35. Found: C, 56.36; H, 5.28; N, 7.25.

Example 217

4-chloro-2-methoxy-N-[(2Z)-5-methyl-3-(tetrahydrofuran-2-ylmethyl)-1,3-thiazol-2(3H)-ylidene]benzamide

Example 217A

4-chloro-2-methoxybenzoyl chloride

A solution of the 4-chloro-2-methoxybenzoic acid (0.24 g, 1.3 mmol) in 7 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to give the crude title compound which was used without additional purification or characterization.

Example 217B

4-chloro-2-methoxy-N-[(2Z)-5-methyl-3-(tetrahydrofuran-2-ylmethyl)-1,3-thiazol-2(3H)-ylidene]benzamide Example 204A (0.20 g, 1.0 mmol), triethylamine (0.42 mL, 3.0 mmol) and Example 217A (1.3 mmol) in 15 mL of tetrahydrofuran and 1 mL of N,N-dimethylformamide were processed as in Example 208D to afford the title compound. $^1$H NMR (300 MHz, CDCl$_3$) δ ppm 1.61-1.74 (m, 1H), 1.77-1.98 (m, 2H), 1.99-2.14 (m, 1H), 2.30 (d, J=1.4 Hz, 3H), 3.72-3.82 (m, 1H), 3.82-3.90 (m, 1H), 3.91 (s, 3H), 4.11-4.20 (m, 1H) 4.27 (ddd, J=13.7, 6.8, 2.9 Hz, 1H), 4.41-4.51 (m, 1H), 6.87-6.91 (m, 1H), 6.93-6.99 (m, 2H), 7.97 (d, J=8.8 Hz, 1H); MS (DCI/NH$_3$) m/z 367 (M+H)$^+$. Anal. Calculated for C$_{17}$H$_{19}$ClN$_2$O$_3$S: C, 55.66; H, 5.22; N, 7.64. Found: C, 55.40; H, 5.31; N, 7.48.

Example 218

5-chloro-2-methoxy-N-[(2Z)-1-(2-methoxyethyl)-1,4,6,7-tetrahydro-2H-pyrano[4,3-d][1,3]thiazol-2-ylidene]benzamide

Example 218A

6,7-dihydro-4H-pyrano[4,3-d][1,3]thiazol-2-amine

To a solution of tetrahydro-4H-pyran-4-one (Aldrich) (7.22 g, 72.11 mmol) in cyclohexane (70 mL) were added pyrrolidine (6.26 mL, 7.57 mmol) and p-toluenesulfonic acid monohydrate (13.72 mg, 0.07 mmol). The reaction mixture was refluxed for 3 hours with a Dean-Stark trap, cooled and concentrated. The residue was dissolved in methanol (20 mL) and then sulfur (2.31 g, 72.11 mmol) was added followed by a solution of cyanamide (3.03 g, 72.11 mmol) in methanol (5 ml) at 0° C. The reaction mixture was stirred at room temperature overnight, filtered, concentrated and purified by column chromatography using an Analogix® Intelliflash280™ (SiO$_2$, 0-5% methanol in dichloromethane) to afford the title compound. MS (ESI$^+$) m/z 157 (M+H)$^+$.

Example 218B

1-(2-methoxyethyl)-6,7-dihydro-1H-pyrano[4,3-d]thiazol-2(4H)-imine hydrobromide A mixture of product of Example 218A (1.0 g, 6.4 mmol) and 2-bromoethyl methyl ether (3.0 mL, 32.0 mmol) was processed according to the method of Example 2A to afford the title compound: MS (LC/MS) m/z 213 (M+H)$^+$.

Example 218C

5-chloro-2-methoxy-N-[(2Z)-1-(2-methoxyethyl)-1,4,6,7-tetrahydro-2H-pyrano[4,3-d][1,3]thiazol-2-ylidene]benzamide To a solution of Example 218B (150.0 mg, 0.51 mmol) in tetrahydrofuran (10 mL) was added N-(3-dimethylaminopropyl)-N-ethylcarbodiimide hydrochloride (97.0 mg, 0.51 mmol), 1-hydroxybenzotriazole (69.0 mg, 0.51 mmol), triethylamine (178.0 µL, 1.28 mmol), and 5-chloro-2-methoxybenzoic acid (Aldrich) (95.0 mg, 0.51 mmol). The mixture was stirred overnight at 80° C., and then diluted with ethyl acetate, washed with 1 M aqueous NaHCO$_3$, dried (Na$_2$SO$_4$), filtered and concentrated. Purification by preparative HPLC on a Waters Symmetry C8 column (40 mm×100 mm, 7 µm particle size) using a gradient of 10% to 100% acetonitrile:ammonium acetate (10 mM) over 15 minutes at a flow rate of 70 mL/minutes afforded the title compound. $^1$H NMR (300 MHz, dimethylsulfoxide-d$_6$) δ 2.75 (t, J=5.4 Hz, 2H), 3.25 (s, 3H), 3.69 (t, J=5.3 Hz, 2H), 3.80 (s, 3H), 3.95 (t, J=5.4 Hz, 1H), 4.27 (t, J=5.3 Hz, 2H), 4.58 (s, 2H), 7.12 (d, J=8.8 Hz, 1H), 7.46 (dd, J=9.0, 2.9 Hz, 1H), 7.69 (d, J=2.7 Hz, 1H); MS (ESI$^+$) m/z 383 (M+H)$^+$. Anal. Calculated for C$_{17}$H$_{19}$ClN$_2$O$_4$S: C, 53.33; H, 5.00; N, 7.32. Found: C, 53.21; H, 4.80; N, 7.27.

Example 219

5-bromo-2-methoxy-N-[(2Z)-5-methyl-3-[(2R)-tetrahydrofuran-2-ylmethyl]-1,3-thiazol-2(3H)-ylidene]benzamide

Example 219A 5-bromo-2-methoxybenzoic acid

To a solution of 2-methoxybenzoic acid (6 g, 39.4 mmol) in 80 mL of acetonitrile was added N-bromosuccinimide (7.4 g, 41.4 mmol) in 20 mL of acetonitrile. The reaction mixture was warmed to ambient temperature and the mixture was allowed to stir for 16 hours. Additional N-bromosuccinimide (14.8 g, 82.8 mmol) was added and the reaction mixture stirred for an additional 48 hours. The mixture was quenched with 25 mL of $H_2O$ and the layers were separated. The aqueous layer was extracted with three 15 mL of portions of $CH_2Cl_2$ and the combined organic extracts were dried over anhydrous $Na_2SO_4$, filtered and concentrated under reduced pressure. Purification via column chromatography ($SiO_2$, 50% hexanes in ethyl acetate) afforded the title compound. MS (DCI/$NH_3$) m/z 248, 250 (M+$NH_4$)$^+$.

Example 219B 5-bromo-2-methoxybenzoyl chloride

A solution of Example 219A (0.28 g, 1.4 mmol) in 5 mL of $SOCl_2$ was warned to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to give the crude title compound which was used without additional purification or characterization.

Example 219C 5-bromo-2-methoxy-N-[(2Z)-5-methyl-3-[(2R)-tetrahydrofuran-2-ylmethyl]-1,3-thiazol-2(3H)-ylidene]benzamide Example 208B (0.25 g, 1.3 mmol), triethylamine (0.53 mL, 3.8 mmol) and Example 219B (1.4 mmol) in 15 mL of tetrahydrofuran were processed as in Example 208D to afford the title compound. $^1$H NMR (300 MHz, $CD_3OD$) δ ppm 1.65-1.80 (m, 1H), 1.85-1.96 (m, 2H) 2.01-2.14 (m, 1H), 2.34 (d, J=1.4 Hz, 3H) 3.71-3.80 (m, 1H), 3.85 (s, 3H), 3.85-3.93 (m, 1H), 4.21-4.41 (m, 3H), 7.02 (d, J=9.2 Hz, 1H), 7.14 (q, J=1.1 Hz, 1H), 7.53 (dd, J=8.8, 2.7 Hz, 1H), 7.95 (d, J=2.4 Hz, 1H); MS (DCI/$NH_3$) m/z 411, 413 (M+H)$^+$. Anal. Calculated for $C_{17}H_{19}BrN_2O_3S$: C, 49.64; H, 4.66; N, 6.81. Found: C, 49.48; H, 4.53; N, 6.72.

Example 220

5-chloro-2-methoxy-N-[(2Z)-5-methyl-3-(2-tetrahydro-2H-pyran-4-ylethyl)-1,3-thiazol-2(3H)-ylidene]benzamide

Example 220A 2-(tetrahydro-2H-pyran-4-yl)ethyl 4-methylbenzenesulfonate

To a solution of 2-(tetrahydropyran-4-yl)-ethanol (1.5 g, 11.5 mmol) in 10 mL of $CH_2Cl_2$ and 7 mL of pyridine was added p-toluenesulfonyl chloride (2.4 g, 12.7 mmol) portion wise over 15 minutes. The mixture stirred at ambient temperature for 3 hours and was quenched with 10 mL of saturated, aqueous $NaHCO_3$. The layers were separated and the aqueous layer was extracted with three 5 mL of portions of $CH_2Cl_2$. The combined organic extracts were dried over anhydrous $Na_2SO_4$, filtered and concentrated under reduced pressure. Purification via column chromatography ($SiO_2$, 70% hexanes in ethyl acetate) afforded the title compound. MS (DCI/$NH_3$) m/z 302 (M+$NH_4$)$^+$.

Example 220B 5-methyl-3-(2-(tetrahydro-2H-pyran-4-yl)ethyl)thiazol-2(3H)-imine A mixture of Example 220A (1.9 g, 6.7 mmol), 2-amino-5-methylthiazole (0.77 g, 6.7 mmol) and tetrabutylammonium iodide (1.1 g, 3.3 mmol) in 2 mL of N,N-dimethylformamide was warmed to 85° C. and was allowed to stir for 18 hours. The mixture was diluted with 10 mL of $CH_2Cl_2$, washed with 10 mL of 10% aqueous $NaHCO_3$, dried over anhydrous $Na_2SO_4$, filtered and concentrated under reduced pressure. Purification via column chromatography ($SiO_2$, 10% methanol in ethyl acetate then 9:1:0.1 $CH_2Cl_2$:methanol:$NH_4OH$) afforded the title compound. MS (DCI/$NH_3$) m/z 227 (M+H)$^+$.

Example 220C 5-chloro-2-methoxy-N-[(2Z)-5-methyl-3-(2-tetrahydro-2H-pyran-4-ylethyl)-1,3-thiazol-2(3H)-ylidene]benzamide Example 220B (0.20 g, 0.9 mmol), triethylamine (0.37 mL, 0.26 mmol) and Example 205B (0.9 mmol) in 10 mL of tetrahydrofuran were processed as in Example 208D to afford the title compound. $^1$H NMR (300 MHz, $CD_3OD$) δ ppm 1.26-1.44 (m, 2H), 1.47-1.65 (m, 1H), 1.71-1.89 (m, 4H), 2.34 (d, J=1.4 Hz, 3H), 3.32-3.41 (m, 2H), 3.86 (s, 3H), 3.86-3.94 (m, 2H), 4.26-4.35 (m, 2H), 7.07 (d, J=8.8 Hz, 1H), 7.14 (q, J=1.4 Hz, 1H), 7.40 (dd, J=9.0, 2.9 Hz, 1H), 7.89 (d, J=3.1 Hz, 1H); MS (DCI/$NH_3$) m/z 395 (M+H)$^+$. Anal. Calculated for $C_{19}H_{23}ClN_2O_3S$: C, 57.79; H, 5.87; N, 7.09. Found: C, 57.54; H, 5.67; N, 7.07.

Example 221

5-chloro-N-[(2Z)-5-ethyl-3-(tetrahydrofuran-2-ylmethyl)-1,3-thiazol-2(3H)-ylidene]-2-methoxybenzamide

Example 221A 5-ethyl-3-((tetrahydrofuran-2-yl)methyl)thiazol-2(3H)-imine

A mixture of 5-ethylthiazol-2-amine and 2-(bromomethyl)tetrahydrofuran were processed using the method described in Example 2A to afford the title compound. MS (ESI) m/z 213 (M+H)$^+$.

Example 221B 5-chloro-N-[(2Z)-5-ethyl-3-(tetrahydrofuran-2-ylmethyl)-1,3-thiazol-2(3H)-ylidene]-2-methoxybenzamide Example 221A and 5-chloro-2-methoxybenzoic acid were processed using the method described in Example 2B to afford the title compound. ¹H NMR (500 MHz, dimethylsulfoxide-d₆) δ ppm 1.21 (t, J=7.63 Hz, 3H) 1.59-1.68 (m, 1H) 1.77-1.85 (m, 2H) 1.89-1.97 (m, 1H) 2.67 (dd, J=15.56, 7.63 Hz, 2H) 3.65 (dd, J=14.95, 7.02 Hz, 1H) 3.75-3.82 (m, 1H) 3.78 (s, 3H) 4.13-4.24 (m, 2H) 4.24-4.30 (m, 1H) 7.10 (d, J=8.85 Hz, 1H) 7.26 (t, J=1.22 Hz, 1H) 7.44 (dd, J=8.85, 2.75 Hz, 1H) 7.64 (d, J=2.75 Hz, 1H); MS (ESI) m/z 381 (M+H)⁺.

Example 222

5-chloro-2-methoxy-N-[(2Z)-5-propyl-3-(tetrahydrofuran-2-ylmethyl)-1,3-thiazol-2(3H)-ylidene]benzamide Example 222A 5-propyl-3-((tetrahydrofuran-2-yl)methyl)thiazol-2(3H)-imine A mixture of 5-propylthiazol-2-amine and 2-(bromomethyl)tetrahydrofuran were processed using the method described in Example 2A to afford the title compound. MS (ESI) m/z 227 (M+H)⁺.

Example 222B 5-chloro-2-methoxy-N-[(2Z)-5-propyl-3-(tetrahydrofuran-2-ylmethyl)-1,3-thiazol-2(3H)-ylidene]benzamide Example 222A and 5-chloro-2-methoxybenzoic acid were processed using the method described in Example 2B to afford the title compound. ¹H NMR (500 MHz, dimethylsulfoxide-d₆) δ ppm 0.93 (t, J=7.32 Hz, 3H) 1.56-1.67 (m, 3H) 1.77-1.85 (m, 2H) 1.93 (dt, J=19.22, 7.02 Hz, 1H) 2.62 (t, J=7.02 Hz, 2H) 3.65 (dd, J=14.95, 6.71 Hz, 1H) 3.74-3.80 (m, 1H) 3.77-3.79 (m, 3H) 4.15-4.24 (m, 2H) 4.24-4.30 (m, 1H) 7.10 (d, J=8.85 Hz, 1H) 7.25-7.28 (m, 1H) 7.44 (dd, J=8.85, 2.75 Hz, 1H) 7.64 (d, J=2.75 Hz, 1H); MS (ESI) m/z 395 (M+H)⁺.

Example 223

5-chloro-N-[(2Z)-5-chloro-3-(tetrahydrofuran-2-ylmethyl)-1,3-thiazol-2(3H)-ylidene]-2-methoxybenzamide Example 223A 5-chloro-N-(5-chlorothiazol-2-yl)-2-methoxybenzamide A mixture of 5-chlorothiazol-2-amine hydrochloride (513 mg, 3 mmol, 5-chloro-2-methoxybenzoic acid (670 mg, 3.6 mmol, 1-ethyl-3-[3-(dimethylamino)propyl]-carbodiimide hydrochloride (1.15 g, 6 mmol), 1-hydroxybenzotriazole hydrate (810 mg, 6 mmol) and 4-(dimethylamino)pyridine (73 mg, 0.6 mmol) in pyridine was stirred at room temperature for 2 hours. The volatiles were removed under vacuum, and the resulting mixture was diluted with water and extracted with ethyl acetate. The organic extract was dried (Na₂SO₄), filtered and concentrated The residue was washed with a small amount of ethyl acetate, and filtered to afford the title compound. MS (ESI) m/z 303 (M+H)⁺.

Example 223B 5-chloro-N-[(2Z)-5-chloro-3-(tetrahydrofuran-2-ylmethyl)-1,3-thiazol-2(3H)-ylidene]-2-methoxybenzamide Example 223A (250 mg, 0.83 mmol) in tetrahydrofuran/N,N-dimethylformamide (1:2) (9 mL) was treated with NaH (60%) (40 mg, 1.0 mmol) for 10 minutes then 2-(bromomethyl)tetrahydrofuran (164 mg, 1.0 mmol was added. The mixture was heated at 150° C. for 2 hours. After cooling to ambient temperature, the mixture was diluted with water and extracted with ethyl acetate. The organic extract was dried (Na₂SO₄), filtered and concentrated. Purification by reverse phase HPLC afforded the title compound. ¹H NMR (400 MHz, dimethylsulfoxide-d₆) δ ppm 1.60-1.70 (m, 1H) 1.79-1.89 (m, 2H) 1.92-2.01 (m, 1H) 3.66 (dd, J=15.04, 7.06 Hz, 1H) 3.76-3.83 (m, 1H) 3.79-3.81 (m, 3H) 4.15-4.23 (m, 1H) 4.24-4.33 (m, 2H) 7.14 (d, J=8.90 Hz, 1H) 7.49 (dd, J=8.90, 2.76 Hz, 1H) 7.74 (d, J=3.07 Hz, 1H) 7.77 (s, 1H) MS (ESI) m/z 387 (M+H)⁺. 81887-154-2.

Example 224

4,5-dichloro-2-methoxy-N-[(2Z)-5-methyl-3-[(2R)-tetrahydrofuran-2-ylmethyl]-1,3-thiazol-2(3H)-ylidene]benzamide Example 224A 4,5-dichloro-2-methoxybenzoic acid To a solution of 4-chloro-2-methoxybenzoic acid (5 g, 26.8 mmol) in 200 mL of acetonitrile was added N-chlorosuccinimide (17.9 g, 134 mmol). The mixture was allowed to stir for 72 hours at ambient temperature and was quenched with 50 mL of H₂O. The layers were separated and the aqueous layer was extracted with three 25 mL portions of CH₂Cl₂. The combined organic extracts were dried over anhydrous Na₂SO₄, filtered and concentrated under reduced pressure. Purification via column chromatography (SiO₂, 25% hexanes in ethyl acetate) afforded the title compound. MS (DCI/NH₃) m/z 238 (M+NH₄)⁺.

Example 224B 4,5-dichloro-2-methoxybenzoyl chloride

A solution of Example 224A (0.18 g, 0.81 mmol) in 5 mL of SOCl₂ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to afford the title compound which was used without additional purification or characterization.

Example 224C 4,5-dichloro-2-methoxy-N-[(2Z)-5-methyl-3-[(2R)-tetrahydrofuran-2-ylmethyl]-1,3-thiazol-2(3H)-ylidene]benzamide Example 208B (0.16 g, 0.81 mmol), triethylamine (0.34 mL, 2.4 mmol) and Example 224B (0.81 mmol) in 10 mL of tetrahydrofuran were processed as in Example 208D to afford the title compound. $^1$H NMR (300 MHz, CD$_3$OD) δ ppm 1.64-1.79 (m, 1H), 1.83-1.96 (m, 2H) 2.03-2.15 (m, 1H) 2.34 (d, J=1.4 Hz, 3H), 3.70-3.80 (m, 1H), 3.83-3.93 (m, 1H), 3.87 (s, 3H), 4.20-4.44 (m, 3H), 7.15 (q, J=1.1 Hz, 1H), 7.26 (s, 1H), 7.99 (s, 1H); MS (DCI/NH$_3$) m/z 401 (M+H)$^+$. Anal. Calculated for C$_{17}$H$_{18}$Cl$_2$N$_2$O$_3$S: C, 50.88; H, 4.52; N, 6.98. Found: C, 50.63; H, 4.41; N, 6.83.

Example 225

5-chloro-2-methoxy-N-[(2Z)-5-methyl-3-(tetrahydro-2H-pyran-3-ylmethyl)-1,3-thiazol-2(3H)-ylidene]benzamide Example 225A (tetrahydro-2H-pyran-3-yl)methyl 4-methylbenzenesulfonate To a solution of (tetrahydropyran-3-yl)-methanol (Matrix, 1.67 g, 14.4 mmol) in 15 mL of CH$_2$Cl$_2$ and 15 mL of pyridine was added p-toluenesulfonyl chloride (2.9 g, 15.1 mmol) in portions over 10 minutes. The mixture stirred at ambient temperature for 18 hours and was quenched with 10 mL of saturated, aqueous NaHCO$_3$. The layers were separated and the aqueous phase was extracted three 5 mL of portions of CH$_2$Cl$_2$. The combined organic extracts were dried over anhydrous Na$_2$SO$_4$, filtered and concentrated under reduced pressure. Purification via column chromatography (SiO$_2$, 70% hexanes in ethyl acetate) afforded the title compound. MS (DCI/NH$_3$) m/z 288 (M+NH$_4$)$^+$.

Example 225B 5-methyl-3-((tetrahydro-2H-pyran-3-yl)methyl)thiazol-2(3H)-imine

A mixture of Example 225A (1.0 g, 3.7 mmol), 2-amino-5-methylthiazole (0.42 g, 3.7 mmol and tetrabutylammonium iodide (0.68 g, 1.85 mmol) in 1 mL of N,N-dimethylformamide was warmed to 85° C. and was allowed to stir for 16 hours. The mixture was diluted with 10 mL of CH$_2$Cl$_2$, washed with 10 mL of 10% aqueous NaHCO$_3$, dried over anhydrous Na$_2$SO$_4$, filtered and concentrated under reduced pressure. Purification via column chromatography (SiO$_2$, 10% methanol in ethyl acetate then 9:1:0.1 CH$_2$Cl$_2$:methanol:NH$_4$OH) afforded the title compound. MS (DCI/NH$_3$) m/z 213 (M+H)$^+$.

Example 225C 5-chloro-2-methoxy-N-[(2Z)-5-methyl-3-(tetrahydro-2H-pyran-3-ylmethyl)-1,3-thiazol-2(3H)-ylidene]benzamide Example 225B (0.19 g, 0.89 mmol), triethylamine (0.29 mL, 2.1 mmol) and Example 205B (0.63 mmol) in 10 mL of tetrahydrofuran were processed as in Example 208D to afford the title compound. $^1$H NMR (300 MHz, CD$_3$OD) δ ppm 1.33-1.49 (m, 1H), 1.50-1.67 (m, 1H), 1.69-1.86 (m, 2H), 2.20-2.32 (m, 1H), 2.34 (d, J=1.4 Hz, 3H), 3.32-3.38 (m, 1H), 3.50 (ddd, J=11.5, 9.5, 3.1 Hz, 1H), 3.72-3.82 (m, 2H), 3.86 (s, 3H), 4.17 (d, J=7.5 Hz, 2H), 7.07 (d, J=8.8 Hz, 1H), 7.11 (q, J=1.4 Hz, 1H), 7.40 (dd, J=8.8, 2.7 Hz, 1H), 7.85 (d, J=2.7 Hz, 1H); MS (DCI/NH$_3$) m/z 381 (M+H)$^+$. Anal. Calculated for C$_{18}$H$_{21}$ClN$_2$O$_3$S: C, 56.76; H, 5.56; N, 7.35. Found: C, 56.84; H, 5.32; N, 7.29.

Example 226

2-chloro-N-[(2Z)-4,5-dimethyl-3-(tetrahydrofuran-2-ylmethyl)-1,3-thiazol-2(3H)-ylidene]nicotinamide A mixture of Example 186A (0.15 g), 2-chloronicotinic acid (99 mg), 1-hydroxybenzotriazole hydrate (80 mg), 1-ethyl-3-[3-(dimethylamino)propyl]-carbodiimide hydrochloride (120 mg) and triethylamine (0.15 mL) in N,N-dimethylformamide was stirred overnight at room temperature, poured into water and extracted with ether (3×). The combined organic extracts were dried (Na$_2$SO$_4$), filtered and the solvent evaporated. The crude material was purified by gradient flash chromatography over silica gel eluting with ethyl acetate:hexane (1:4 to 1:1) to afford the title compound. $^1$H NMR (300 MHz, dimetlhylsulfoxide-d$_6$) δ ppm 1.65 (m, 1H), 1.85 (m, 2H), 2.0 (m, 1H), 2.25 (s, 3H), 2.28 (s, 3H), 3.62 (dd, 1H), 3.77 (dd, 1H), 4.08 (dd, 1H), 4.28 (m, 1H), 4.38 (dd, 1H), 7.50 (dd, 1H), 8.24 (dd, 1H), 8.45 (dd, 1H); MS (ESI+) m/z 352 (M+H)$^+$.

Example 227

5-chloro-N-[(2Z)-4,5-dimethyl-3-[(3-methyl-4,5-dihydroisoxazol-5-yl)methyl]-1,3-thiazol-2(3H)-ylidene]-2-methoxybenzamide Example 227A 3-allyl-4,5-dimethylthiazol-2(3H)-imine hydrobromide A mixture of 4,5-dimethyl-1,3-thiazol-2-amine (1 g) and allylbromide (0.95 g) in toluene (5 mL) was heated to 85° C. for 12 hours, cooled, diluted with ether, filtered and the solvent was evaporated to afford crude product that was taken on to the next step without further characterization.

Example 227B (Z)—N-(3-allyl-4,5-dimethylthiazol-2(3H)-ylidene)-5-chloro-2-methoxybenzamide A mixture of Example 227A (1.3 g), Example 205B (1.36 g) and triethylamine (1.0 g) in tetrahydrofuran (40 mL) was heated to 60° C. for 4 hours, cooled and solvent was evaporated. The crude material was triturated with ether, filtered and solvent evaporated. The crude was flash chromatographed over silica gel gradient eluting with ethyl acetate:hexane (2:3 to 3:2) to afford the title compound. $^1$H NMR (300 MHz, dimethylsulfoxide-d$_6$) δ ppm 2.22 (s, 3H), 2.23 (s, 3H), 3.78 (s, 3H), 4.85 (m, 2H), 4.96, (dq, J=17.3, 1.3 Hz, 1H), 5.19 (dq, J=10.5, 1.3 Hz, 1H), 5.92-6.05 (m, 1H), 7.10 (d, 1H), 7.44 (dd, 1H), 7.66 (d, 1H); MS (ESI+) m/z 337 (M+H)$^+$.

Example 227C 5-chloro-N-[(2Z)-4,5-dimethyl-3-[(3-methyl-4,5-dihydroisoxazol-5-yl)methyl]-1,3-thiazol-2(3H)-ylidene]-2-methoxybenzamide To a solution of acetaldoxime (56 mg, 1.48 mmol) in CHCl$_3$ (10 mL) under N$_2$ was added N-chlorosuccinimide (200 mg) and pyridine (10 μL). After 4.5 hours at room temperature, Example 227B (100 mg) was added, followed by triethylamine (0.15 g) and the reaction continued to stir at room temperature for 21 hours. The reaction mixture was washed with water and partitioned. The aqueous layer was extracted again with $CH_2Cl_2$ and the combined organic extracts were dried ($MgSO_4$), filtered and solvent evaporated. The crude was purified by flash chromatography over silica gel eluting with ethyl acetate:hexane (1:1) to afford the title compound. $^1$H NMR (300 MHz, dimethylsulfoxide-$d_6$) δ ppm 1.93 (s, 3H), 2.23 (s, 6H), 2.90 (dd, 1H), 3.14 (dd, 1H), 3.79 (s, 3H), 4.11 (dd, 1H), 4.27, (dd, 1H), 4.98 (m, 1H), 7.11 (d, 1H), 7.44 (dd, 1H), 7.67 (d, 1H); MS (ESI+) m/z 394 $(M+H)^+$.

Example 228

N-[(2Z)-4,5-dimethyl-3-(tetrahydrofuran-2-ylmethyl)-1,3-thiazol-2(3H)-ylidene]-4-(trifluoromethyl)nicotinamide Example 186A (0.15 g) and 4-(trifluoromethyl)nicotinic acid (0.12 g) were processed according to the method of Example 226. The crude was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes) to afford the title compound. $^1$H NMR (300 MHz, dimethylsulfoxide-$d_6$) δ ppm 1.63 (m, 1H), 1.85 (m, 2H), 1.96 (m, 1H), 2.25 (s, 3H), 2.29 (s, 3H), 3.62 (dd, 1H), 3.77 (dd, 1H), 4.07 (dd, 1H), 4.25 (m, 1H), 4.38 (dd, 1H), 7.80 (d, 1H), 8.89 (d, 1H), 9.12 (s, 1H); MS (ESI+) m/z 386 $(M+H)^+$.

Example 229

N-[(2Z)-4,5-dimethyl-3-(tetrahydrofuran-2-ylmethyl)-1,3-thiazol-2(3H)-ylidene]-2-ethoxynicotinamide Example 186A (0.15 g) and 2-ethoxynicotinic acid (0.1 g) were processed according to the method of Example 226. The crude was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow Tate of 40 mL/minutes) to afford the title compound. $^1$H NMR (300 MHz, dimethylsulfoxide-$d_6$) δ ppm 1.32 (t, 3H), 1.66 (m, 1H), 1.85 (m, 2H), 1.97 (m, 1H), 2.22 (s, 3H), 2.26 (s, 3H), 3.62 (dd, 1H), 3.78 (dd, 1H), 4.06 (dd, 1H), 4.3-4.42 (m, 3H), 7.02 (dd, 1H), 8.13 (dd, 1H), 8.22 (dd, 1H); MS (ESI+) m/z 362 $(M+H)^+$.

Example 230

N-[(2Z)-4,5-dimethyl-3-(tetrahydrofuran-2-ylmethyl)-1,3-thiazol-2(3H)-ylidene]-2,3,6-trifluoroisonicotinamide Example 186A (0.15 g) and 2,3,6-trifluoroisonicotinic acid (0.11 g) were processed according to the method of Example 226. The crude was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes) to afford the title compound. $^1$H NMR (300 MHz, dimethylsulfoxide-$d_6$) δ ppm 1.67 (m, 1H), 1.86 (m, 2H), 2.00 (m, 1H), 2.27 (s, 3H), 2.30 (s, 3H), 3.62 (dd, 1H), 3.78 (dd, 1H), 4.15 (dd, 1H), 4.28 (m, 1H), 4.43 (dd, 1H), 7.57 (t, 1H); MS (ESI+) m/z 372 $(M+H)^+$.

Example 231

6-chloro-N-[(2Z)-4,5-dimethyl-3-(tetrahydrofuran-2-ylmethyl)-1,3-thiazol-2(3H)-ylidene]-4-(trifluoromethyl)nicotinamide Example 186A (0.15 g) and 6-chloro-4-(trifluoromethyl)nicotinic acid (0.17 g) were processed according to the method of Example 226. The crude was purified by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes) to afford the title compound. $^1$H NMR (300 MHz, dimethylsulfoxide-$d_6$) δ ppm 1.62 (m, 1H), 1.85 (m, 2H), 1.96 (m, 1H), 2.25 (s, 3H), 2.29 (s, 3H), 3.62 (dd, 1H), 3.77 (dd, 1H), 4.08 (dd, 1H), 4.24 (m, 1H), 4.38 (dd, 1H), 7.99 (s, 1H), 9.00 (s, 1H); MS (ESI+) m/z 420 $(M+H)^+$.

Example 232

5-chloro-2-methoxy-N-[(2Z)-5-methyl-3-[(3-methyl-4,5-dihydroisoxazol-5-yl)methyl]-1,3-thiazol-2(3H)-ylidene]benzamide

Example 232A 3-allyl-5-methylthiazol-2(3H)-imine hydrobromide

A mixture of 2-amino-5-methylthiazole (2.5 g) and allylbromide (3.31 g) was processed according to the method of Example 227A to afford the title compound that was taken directly to the next step. MS (ESI+) m/z 155 $(M+H)^+$.

Example 232B (Z)—N-(3-ally-5-methylthiazol-2(3H)-ylidene)-5-chloro-2-methoxybenzamide A mixture of Example 232A (0.5 g) and 5-chloro-2-methoxybenzoylchloride (0.57 g) were processed according to the method of Example 227B to afford the title compound. $^1$H NMR (300 MHz, dimethylsulfoxide-$d_6$) δ ppm 2.28 (d, J=1.4 Hz, 3H), 3.78 (s, 3H), 4.77 (d, 2H), 5.13 (dq, J=16.9, 1.3 Hz, 1H), 5.24 (dq, J=10.5, 1.4 Hz, 2H), 5.94-6.07 (m, 1H), 7.11 (d, 1H), 7.23 (q, J=1.4 Hz, 1H), 7.43 (dd, 1H), 7.68 (d, 1H); MS (ESI+) m/z 323 $(M+H)^+$.

Example 232C 5-chloro-2-methoxy-N-[(2Z)-5-methyl-3-[(3-methyl-4,5-dihydroisoxazol-5-yl)methyl]-1,3-thiazol-2(3H)-ylidene]benzamide Example 232B was processed according to the method of Example 227C to afford the title compound. $^1$H NMR (300 MHz, dimethylsulfoxide-$d_6$) δ ppm 1.90 (s, 3H), 2.28 (s, 3H), 2.87 (dd, 1H), 3.11 (dd, 1H), 4.23 (d, 2H), 4.94 (m, 1H), 7.11 (d, 1H), 7.25 (s, 1H), 7.45 (dd, 1H), 7.67 (d, 1H); MS (ESI+) m/z 380 $(M+H)^+$.

Example 233

N-[(2Z)-4,5-dimethyl-3-(tetrahydrofuran-2-ylmethyl)-1,3-thiazol-2(3H)-ylidene]-2-(ethylamino)benzamide Example 186A (0.15 g) and 2-ethylaminobenzoic acid (Pellon *Syn. Lett.* 2005, 10, 1606) (0.1 g) were processed according to the method of Example 226. The crude was purified by flash chromatography over silica gel gradient eluting with ethyl acetate:hexane (1.9 to 1:3) to afford the title compound. $^1$H NMR (300 MHz, dimethylsulfoxide-$d_6$) δ ppm 1.25 (t, 3H), 1.70 (m, 1H), 1.87 (m, 2H), 2.01 (m, 1H), 2.20 (s, 3H), 2.26 (s, 3H), 3.20 (m, 2H), 3.62 (dd, 1H), 3.79 (dd, 1H), 4.12 (dd, 1H), 4.28 (m, 1H), 4.38 (dd, 1H), 6.55 (t, 1H), 6.67 (d, 1H), 7.27 (t, 1H), 8.22 (dd, 1H), 8.52 (t, 1H); MS (ESI+) m/z 360 (M+H)$^+$.

Example 234

N-[(2Z)-4,5-dimethyl-3-(tetrahydrofuran-2-ylmethyl)-1,3-thiazol-2(3H)-ylidene]-5-iodo-2-(methylamino)benzamide Example 186A (0.15 g) and 5-iodo-2-methylaminobenzoic acid (0.17 g) were processed according to the method of Example 226. The crude was purified by flash chromatography over silica gel gradient eluting with ethyl acetate:hexane (1:19 to 1:10) to afford the title compound. $^1$H NMR (300 MHz, dimethylsulfoxide-$d_6$) δ ppm 1.7-1.82 (m, 1H), 1.84-1.95 (m, 2H), 1.95-2.08 (m, 1H), 2.22 9s, 3H), 2.27 (s, 3H), 2.84 (d, 3H), 3.65 (dd, 1H), 3.82 (dd, 1H), 4.12 (dd, 1H), 4.28 (m, 1H), 4.36 (dd, 1H), 6.52 (d, 1H), 7.53 (dd, 1H), 8.46 (d, 1H), 8.52 (q, 1H); MS (ESI+) m/z 472 (M+H)$^+$.

Example 235

5-bromo-N-[(2Z)-5-tert-butyl-3-[(2R)-tetrahydrofuran-2-ylmethyl]-1,3-thiazol-2(3H)-ylidene]-2-methoxybenzamide To a mixture of 3,3-dimethylbutyraldehyde (Aldrich) (5 mL, 39.8 mmol) and Example 278A (641.0 mg, 4.0 mmol) was added a mixture of dimethylsulfoxide (560 μL, 8 mmol) and 12 N aqueous HCl (667 μL, 8 mmol). The reaction mixture was heated at 40° C. overnight. The mixture was concentrated and the residue was dried under vacuum for 2 hours. The residue (252 mg. 0.9 mmol) was dissolved in tetrahydrofuran (10 mL). To this solution was added 5-bromo-2-methoxy-benzoic acid (209.0 mg, 0.9 mmol), N-(3-dimethylaminopropyl)-N-ethylcarbodiimide hydrochloride (73 mg, 0.9 mmol), 1-hydroxybenzotriazole (122.0 mg, 0.9 mmol) and triethylamine (315.0 μL, 2.3 mmol). The mixture was stirred overnight at 80° C., and cooled to room temperature. The mixture was diluted with ethyl acetate, washed with 1 M aqueous NaHCO$_3$, dried (Na$_2$SO$_4$), filtered and concentrated. The residue was purified by flash chromatography using an Analogix® Intelliflash280™ (SiO$_2$, 0-75% ethyl acetate in hexanes) to afford the title compound. $^1$H NMR (300 MHz, dimethylsulfoxide-$d_6$) δ 1.32 (s, 9H), 1.58-1.71 (m, 1H), 1.75-1.86 (m, 2H), 1.87-2.00 (m, 1H), 3.64 (dd, J=15, 6.8 Hz, 1H), 3.78 (s, 3H), 3.79-3.83 (m, 1H), 4.19 (d, J=5.8 Hz, 2H), 4.23-4.35 (m, 1H), 7.05 (d, J=8.8 Hz, 1H), 7.25 (s, 1H), 7.56 (dd, J=8.8, 2.7 Hz, 1H), 7.76 (d, J=2.7 Hz, 1H); MS (ESI+) m/z 453 (M)$^+$, 455 (M+2)$^+$.

Example 236

5-chloro-2-(cyclopropyloxy)-N-[(2Z)-5-methyl-3-[(2R)-tetrahydrofuran-2-ylmethyl]-1,3-thiazol-2(3H)-ylidene]benzamide

Example 236A methyl 5-chloro-2-(2-chloroethoxy)benzoate

A mixture of methyl-5-chlorosalicylate (19.5 g, 105 mmol), 2-chloroethyl p-toluenesulfonate (19.3 mL, 107 mmol) and K$_2$CO$_3$ (28.9 g, 210 mmol) in 105 mL of N,N-dimethylformamide was warmed to 50° C. and allowed to stir for 18 hours. The mixture was cooled to ambient temperature, diluted with 25 mL of ethyl acetate and 25 mL of H$_2$O. The layers were separated and the organic layer was dried over anhydrous Na$_2$SO$_4$, filtered and concentrated under reduced pressure. Purification via column chromatography (SiO$_2$, 75% hexanes in ethyl acetate) afforded the title compound. MS (DCI/NH$_3$) m/z 249 (M+H)$^+$, 266 (M+NH$_4$)$^+$.

Example 236B 5-chloro-2-(vinyloxy)benzoic acid

To Example 236A (15 g, 60 mmol) in 100 mL of tetrahydrofuran at 0° C. was added potassium t-butoxide (8.9 g, 75.6 mmol) portion wise with the internal reaction temperature being maintained below 5° C. After the addition was complete, the mixture was allowed to warm to ambient temperature and was allowed to stir for 18 hours. The mixture was diluted with 25 mL of H$_2$O and 25 mL of ethyl acetate and the layers were separated. The aqueous layer was acidified with 1 N aqueous HCl to pH 7 and was extracted with three 15 mL portions of ethyl acetate. These organic extracts (excluding the original organic layer before acidification) were combined and dried over anhydrous Na$_2$SO$_4$, filtered and concentrated under reduced pressure to afford the title compound. MS (DCI/NH$_3$) m/z 216 (M+NH$_4$)$^+$.

Example 236C methyl 5-chloro-2-(vinyloxy)benzoate

To Example 236B (5.1 g, 26 mmol) in 30 mL of N,N-dimethylformamide was added K$_2$CO$_3$ (10.7 g, 78 mmol) followed by CH$_3$I (1.8 mL, 29 mmol). The mixture stirred at ambient temperature for 3 hours and was diluted with 20 mL of H$_2$O and 20 mL of ether. The layers were separated and the aqueous layer was extracted twice with 10 mL of ether. The combined organic extracts were dried over anhydrous Na$_2$SO$_4$, filtered and concentrated under reduced pressure. Purification via column chromatography (SiO$_2$, 75% hexanes in ethyl acetate) afforded the title compound. MS (DCI/NH$_3$) m/z 213 (M+H)$^+$, 230 (M+NH$_4$)$^+$.

Example 236D methyl 5-chloro-2-cyclopropoxybenzoate

To a solution of Example 236C (1.29 g, 6.1 mmol) in 15 mL of dichloroethane at −5° C. was added chloro-iodomethane (1.4 mL, 19.4 mmol). A solution of diethylzinc (1M solution in hexanes, 9.7 mL, 9.7 mmol) was added dropwise over 1 hour using a syringe pump. After the addition was complete, the mixture was allowed to warm to ambient temperature and was stirred for 45 minutes. The mixture was cooled to 0° C. and quenched with 5 mL of saturated, aqueous NH$_4$Cl and 1 mL of concentrated NH$_4$OH. This mixture was diluted with 10 mL of ethyl acetate and the layers were separated. The aqueous layer was extracted twice with 10 mL of ethyl acetate and the combined organic extracts were dried over anhydrous Na$_2$SO$_4$, filtered and concentrated under reduced pressure. Purification via column chromatography (SiO$_2$, 75% hexanes in ethyl acetate) afforded the title compound. MS (DCI/NH$_3$) m/z 227 (M+H)$^+$, 244 (M+NH$_4$)$^+$.

Example 236E 5-chloro-2-cyclopropoxybenzoic acid

To a solution of Example 236D (1.24 g, 5.5 mmol) in 10 mL of ethanol at ambient temperature was added 5 mL of 40% aqueous KOH. The mixture was stirred at ambient temperature for 2 hours and was partially concentrated to remove the ethanol The aqueous residue was extracted with three 10 mL of portions of CH$_2$Cl$_2$. The aqueous layer was acidified with 10% aqueous HCl to ~pH 1 and then extracted with three 10 mL of portions of CH$_2$Cl$_2$. The combined organic extracts (from both extractions) were dried over anhydrous Na$_2$SO$_4$, filtered and concentrated under reduced pressure to afford the title compound. MS (DCI/NH$_3$) m/z 213 (M+H)$^+$, 230 (M+NH$_4$)$^+$.

Example 236F 5-chloro-2-(cyclopropyloxy)-N-[(2Z)-5-methyl-3-[(2R)-tetrahydrofuran-2-ylmethyl]-1,3-thiazol-2(3H)-ylidene]benzamide A mixture of Example 236E (0.30 g, 1.4 mmol) and 1,1'-carbonyldiimidazole (0.27 g, 1.7 mmol) in 10 mL of ethyl acetate was stirred at ambient temperature for 4 hours. Example 208B (0.28 g, 1.4 mmol) in 2 mL of ethyl acetate and 2 mL of tetrahydrofuran was added and the mixture was warmed to reflux for 16 hours. The mixture was cooled to ambient temperature and was quenched with 10 mL of H$_2$O and 5 mL 5% aqueous HCl and was diluted with 10 mL of ethyl acetate. The layers were separated and the aqueous layer was extracted twice with 5 mL of ethyl acetate. The combined organic extracts were dried over anhydrous Na$_2$SO$_4$, filtered and concentrated under reduced pressure. Purification via column chromatography (SiO$_2$, 40% hexanes in ethyl acetate) afforded the title compound. $^1$H NMR (300 MHz, CD$_3$OD) δ ppm 0.76-0.82 (m, 2H), 1.63-1.77 (m, 1H), 1.84-1.96 (m, 2H), 2.01-2.14 (m, 1H), 2.33 (d, J=1.4 Hz, 3H), 3.69-3.93 (m, 4H), 4.18-4.43 (m, 4H), 7.13 (q, J=1.4 Hz, 1H), 7.38-7.41 (m, 2H), 7.74 (dd, J=2.0, 1.0 Hz, 1H); MS (DCI/NH$_3$) m/z 393 (M+H)$^+$. Anal. Calculated for C$_{19}$H$_{21}$ClN$_2$O$_3$S: C, 58.08; H, 5.39; N, 7.13. Found: C, 57.77; H, 5.45; N, 7.09.

Example 237

5-chloro-N-[(2Z)-3-(1,4-dioxan-2-ylmethyl)-5-methyl-1,3-thiazol-2(3H)-ylidene]-2-methoxybenzamide Example 237A 3-((1,4-dioxan-2-yl)methyl)-5-methylthiazol-2(3H)-imine A mixture of 2-amino-5-methylthiazole (0.77 g, 6.7 mmol) and 2-iodomethyl-1,4-dioxane (Synchem-OHG, 1.5 g, 6.7 mmol) was warmed to 85° C. and was allowed to stir for 18 hours. The mixture was cooled to ambient temperature and the crude material was purified via column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 215 (M+H)$^+$.

Example 237B 5-chloro-N-[(2Z)-3-(1,4-dioxan-2-ylmethyl)-5-methyl-1,3-thiazol-2(3H)-ylidene]-2-methoxybenzamide Example 237A (0.20 g, 0.93 mmol), triethylamine (0.39 mL, 2.8 mmol) and Example 205B (0.93 mmol) in 10 mL of tetrahydrofuran were processed as described in Example 208D to afford the title compound. $^1$H NMR (300 MHz, CD$_3$OD) δ ppm 2.33 (d, J=1.4 Hz, 3H), 3.34 (dd, J=11.5, 9.5 Hz, 1H), 3.50-3.71 (m, 3H), 3.82 (dt, J=10.5, 3.1 Hz, 2H), 3.86 (s, 3H) 3.99-4.09 (m, 1H), 4.19-4.36 (m, 2H), 7.08 (d, J=8.8 Hz, 1H), 7.09 (q, J=1.0 Hz, 1H), 7.40 (dd, J=9.0, 2.9 Hz, 1H), 7.81 (d, J=2.7 Hz, 1H); MS (DCI/NH$_3$) m/z 383 (M+H)$^+$. Anal. Calculated for C$_{17}$H$_{19}$ClN$_2$O$_4$S: C, 53.33; H, 5.00; N, 7.32. Found: C, 53.51; H, 4.93; N, 7.29.

Example 238

N-[(2Z)-5-acetyl-4-methyl-3-[(2R)-tetrahydrofuran-2-ylmethyl]-1,3-thiazol-2(3H)-ylidene]-5-chloro-2-methoxybenzamide Example 238A N-(5-acetyl-4-methylthiazol-2-yl)-5-chloro-2-methoxybenzamide To a solution of 5-acetyl-2-amino-4-methylthiazole (5.0 g, 32 mmol) in 50 mL of tetrahydrofuran was added triethylamine (13.4 mL, 96 mmol) followed by Example 205B (32 mmol) in 10 mL of tetrahydrofuran via cannula. The mixture was warmed to 50° C. and was allowed to stir for 18 hours. The mixture was cooled to ambient temperature quenched with 15 mL of NH$_4$Cl and diluted with 15 mL of ethyl acetate. The layers were separated and the aqueous layer was extracted with three 10 mL of portions of ethyl acetate. The combined organic extracts were dried over anhydrous Na$_2$SO$_4$, filtered and concentrated under reduced pressure. The residue was washed with ethyl acetate and the remaining solids were pure title compound. MS (DCI/NH$_3$) m/z 325 (M+H)$^+$.

Example 238B

N-[(2Z)-5-acetyl-4-methyl-3-[(2R)-tetrahydrofuran-2-ylmethyl]-1,3-thiazol-2(3H)-ylidene]-5-chloro-2-methoxybenzamide A mixture of Example 238A (1.1 g, 3.2 mmol), Example 208A (1.0 g, 3.9 mmol), tetrabutylammonium iodide (0.36 g, 0.98 mmol) and potassium t-butoxide (0.58 g, 4.9 mmol) in 12 mL of N,N-dimethylformamide was warmed to 65° C. and was allowed to stir for 16 hours. The mixture was cooled to ambient temperature quenched with 10 mL of NH$_4$Cl and diluted with 10 mL of ethyl acetate. The layers were separated and the aqueous layer was extracted twice with 10 mL of ethyl acetate. The combined organic extracts were dried over anhydrous Na$_2$SO$_4$, filtered and concentrated under reduced pressure. Purification via column chromatography (SiO$_2$, 30% hexanes in ethyl acetate) afforded the title compound. $^1$H NMR (300 MHz, CD$_3$OD) δ ppm 1.73-1.87 (m, 1H) 1.89-2.05 (m, 2H), 2.09-2.22 (m, 1H), 2.52 (s, 3H), 2.79 (s, 3H), 3.69-3.78 (m, 1H), 3.85-3.94 (m, 1H), 3.88 (s, 3H), 4.21-4.31 (m, 1H), 4.38-4.49 (m, 1H), 4.59 (dd, J=13.9, 3.1 Hz, 1H), 7.10 (d, J=9.2 Hz, 1H), 7.44 (dd, J=8.8, 2.7 Hz, 1H), 7.94 (d, J=2.7 Hz, 1H); MS (DCI/NH$_3$) m/z 409 (M+H)$^+$. Anal. Calculated for C$_{19}$H$_{21}$ClN$_2$O$_4$S.0.12H$_2$O: C, 55.52; H, 5.21; N, 6.81. Found: C, 55.83; H, 5.21; N, 6.41.

Example 239

5-chloro-N-[(2Z)-5-(1-hydroxy-1-methylethyl)-4-methyl-3-[(2R)-tetrahydrofuran-2-ylmethyl]-1,3-thiazol-2(3H)-ylidene]-2-methoxybenzamide To Example 238B (0.11 g, 0.27 mmol) in 5 mL of tetrahydrofuran at –78° C. was added a solution of methyl lithium (1.6 M in ether; 0.50 mL, 0.81 mmol) dropwise over 5 minutes. The mixture stirred at –78° C. for 1 hour and was slowly warmed to ambient temperature and was allowed to stir for 18 hours. The mixture was quenched with 5 mL of NH$_4$Cl and diluted with 5 mL of ethyl acetate. The layers were separated and the aqueous layer was extracted twice with 5 mL of ethyl acetate. The combined organic extracts were dried over anhydrous Na$_2$SO$_4$, filtered and concentrated under reduced pressure. Purification via column chromatography (SiO$_2$, 20% hexanes in ethyl acetate) afforded the title compound. $^1$H NMR (300 MHz, CD$_3$O) δ ppm 1.26 (none, 1H), 1.61 (s, 6H), 1.73-1.85 (m, 1H), 1.88-2.01 (m, 2H), 2.05-2.19 (m, 1H), 2.52 (s, 3H), 3.69-3.78 (m, 1H), 3.85 (s, 3H), 3.87-3.93 (m, 1H), 4.02-4.19 (m, 2H), 4.36-4.45 (m, 1H), 4.50 (dd, J=13.9, 3.1 Hz, 1H), 7.06 (d, J=8.8 Hz, 1H), 7.39 (dd, J=8.8, 2.7 Hz, 1H), 7.83 (d, J=2.7 Hz, 1H); MS (DCI/NH$_3$) m/z 425 (M+H)$^+$. Anal. Calculated for C$_{20}$H$_{25}$ClN$_2$O$_4$S.0.1H$_2$O: C, 56.29; H, 5.95; N, 6.56. Found: C, 55.95; H, 5.87; N, 6.47.

Example 240

N-[(2Z)-5-tert-butyl-3-[(2R)-tetrahydrofuran-2-ylmethyl]-1,3-thiazol-2(3H)-ylidene]-5-chloro-2-methoxybenzamide Example 240A 5-tert-butylthiazol-2-amine To a solution of 3,3-dimethylbutyraldehyde (10 g, 99.8 mmol) in 200 mL of cyclohexane was added pyrrolidine (8.7 mL, 0.11 mol) followed by p-toluenesulfonic acid monohydrate (0.95 g, 5.0 mmol). This reaction flask was equipped with a Dean-Stark trap and the mixture was warmed to reflux and was allowed to stir for 3 hours. The mixture was cooled to ambient temperature, filtered and concentrated under reduced pressure. The residue was dissolved in 75 mL of CH$_3$OH, sulfur was added (3.2 g, 99.8 mmol), and the mixture was cooled to 0° C. Cyanamide (4.2 g, 99.8 mmol) was added portion wise over 10 minutes and the mixture was allowed to warm to ambient temperature and stir for 18 hours. The reaction mixture was concentrated under reduced pressure and purified by column chromatography (SiO$_2$, ethyl acetate then 10% methanol in ethyl acetate) to afford the title compound. MS (DCI/NH$_3$) m/z 157 (M+H)$^+$.

Example 240B (R)-(tetrahydrofuran-2-yl)methyl 4-methylbenzenesulfonate

To a solution of (R)-tetrahydrofurfuryl alcohol (Lancaster, 1.0 g, 9.8 mmol) in 5 mL of CH$_2$Cl$_2$ and 5 mL of pyridine was added p-toluenesulfonyl chloride (2.8 g, 14.7 mmol) in portions over 15 minutes. The mixture was stirred at ambient temperature for 3 hours and was quenched with 5 mL of saturated, aqueous NaHCO$_3$. The layers were separated and the aqueous layer was extracted with three 5 mL of portions of CH$_2$Cl$_2$. The combined organic extracts were dried over anhydrous Na$_2$SO$_4$, filtered and concentrated under reduced pressure to afford the title compound. MS (DCI/NH$_3$) m/z 257 (M+H)$^+$, 274 (M+NH$_4$)$^+$.

Example 240C (R)-5-tert-butyl-3-((tetrahydrofuran-2-yl)methyl) thiazol-2(3H)-imine 4-methylbenzenesulfonate A mixture of Example 240A (9.8 g, 62.7 mmol), Example 240B (23.5 g, 91.7 mmol) and tetrabutylammonium iodide (11.6 g, 31.4 mmol) in 35 mL of N,N-dimethylformamide was warmed to 85° C. and was allowed to stir for 72 hours. The mixture was diluted with 50 mL of CH$_2$Cl$_2$ and the layers were separated. The organic layer was washed with 15 mL of saturated, aqueous NaHCO$_3$ and the combined aqueous layers were extracted with three 10 mL of portions of CH$_2$Cl$_2$. The combined organic extracts were dried over anhydrous Na$_2$SO$_4$, filtered and concentrated under reduced pressure. Purification via column chromatography (SiO$_2$, 10% methanol in ethyl acetate then 9:1:0.1 CH$_2$Cl$_2$:methanol:NH$_4$OH) afforded the title compound. MS (DCI/NH$_3$) m/z 241 (M+H)$^+$.

Example 240D 5-chloro-2-methoxybenzoyl chloride

A solution of 2-methoxy-5-chlorobenzoic acid (6.9 g, 37 mmol) in 15 mL of SOCl$_2$ was warmed to reflux and was allowed to stir for 2 hours. The mixture was cooled to ambient temperature and concentrated tinder reduced pressure. The crude material was diluted with 5 mL of toluene and concentrated tinder reduced pressure. This dilution with toluene and concentration was repeated two additional times to afford the title compound. $^1$H NMR (300 MHz, dimethylsulfoxide-d$_6$) δ ppm 3.82 (s, 3H), 7.16 (d, J=8.8 Hz, 1H), 7.49-7.59 (m, 1H), 7.61 (d, J=2.7 Hz, 1H).

Example 240E

N-[(2Z)-5-tert-butyl-3-[(2R)-tetrahydrofuran-2-ylmethyl]-1,3-thiazol-2(3H)-ylidene]-5-chloro-2-methoxybenzamide To a solution of Example 240C (13.9 g, 34 mmol) in 120 mL of tetrahydrofuran at ambient temperature was added triethylamine (19 mL, 135 mmol) followed by Example 240D (7.6 g, 37 mmol) in 30 mL of tetrahydrofuran via cannula. This mixture was warmed to 60° C. and was allowed to stir for 3 hours and was quenched with 30 mL of NH$_4$Cl and diluted with 50 mL of ethyl acetate. The layers were separated and the aqueous layer was extracted with three 5 mL of portions of ethyl acetate. The combined organic extracts were dried over anhydrous Na$_2$SO$_4$, filtered and concentrated under reduced pressure. Purification via flash column chromatography (SiO$_2$, 50% hexanes:ethyl acetate) afforded the title compound. $^1$H NMR (300 MHz, CDCl$_3$) δ ppm 1.35 (s, 9H), 1.64-1.92 (m, 3H), 2.00-2.14 (m, 1H), 3.72-3.88 (m, 2H), 3.90 (s, 3H), 4.19-4.34 (m, 2H), 4.40 (dd, J=29, 24 Hz, 1H), 6.86 (s, 1H), 6.90 (d, J=9.2 Hz, 1H), 7.32 (dd, J=9.0, 2.9 Hz, 1H), 7.95 (d, J=3.1 Hz, 1H); MS (DCI/NH$_3$) m/z 409 (M+H)$^+$. Anal. Calculated for C$_{20}$H$_{25}$ClN$_2$O$_3$S: C, 58.74; H, 6.16; N, 6.85. Found: C, 58.74; H, 6.27; N, 6.81.

Example 241

N-[(2Z)-5-tert-butyl-3-(1,3-dioxolan-2-ylmethyl)-1,3-thiazol-2(3H)-ylidene]-5-chloro-2-methoxybenzamide Example 241A 3-((1,3-dioxolan-2-yl)methyl)-5-tert-butylthiazol-2(3H)-imine A mixture of Example 240A (0.17 g, 1.1 mmol) and 2-bromomethyl-1,3-dioxolane (0.21 g, 1.2 mmol) was warmed to 85° C. and was allowed to stir for 18 hours. The mixture was cooled to ambient temperature and the crude material was purified via flash column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 243 (M+H)$^+$.

Example 241B

N-[(2Z)-5-tert-butyl-3-(1,3-dioxolan-2-ylmethyl)-1,3-thiazol-2(3H)-ylidene]-5-chloro-2-methoxybenzamide Example 241A (64 mg, 0.26 mmol, triethylamine (0.11 mL, 0.79 mmol) and Example 205B (0.26 mmol) in 2 mL of tetrahydrofuran and 0.5 mL of N,N-dimethylformamide were processed as in Example 208D to afford the title compound. $^1$H NMR (300 MHz, CD$_3$OD) δ ppm 1.38 (s, 9H), 3.86 (s, 3H), 3.88-3.98 (m, 4H), 4.42 (d, J=4.1 Hz, 2H), 5.29 (dd, J=4.1 Hz, 1H), 7.07 (d, J=8.8 Hz, 1H), 7.12 (s, 1H), 7.40 (dd, J=9.0, 2.9 Hz, 1H), 7.87 (d, J=2.7 Hz, 1H); MS (DCI/NH$_3$) m/z 411 (M+H)$^+$. Anal. Calculated for C$_{19}$H$_{23}$ClN$_2$O$_4$S: C, 55.54; H, 5.64; N, 6.82. Found: C, 55.43; H, 5.60; N, 6.62.

Example 242

5-chloro-N-[(2Z)-5-chloro-3-[(2R)-tetrahydrofuran-2-ylmethyl]-1,3-thiazol-2(3H)-ylidene]-2-methoxybenzamide Example 242A 5-chloro-N-(5-chlorothiazol-2-yl)-2-methoxybenzamide A mixture of 2-amino-5-chlorothiazole hydrochloric acid (1.0 g, 5.9 mmol), 5-chloro-2-methoxybenzoic acid (1.3 g, 7.0 mmol), 1-ethyl-(3-dimethylaminopropyl)carbodiimide hydrochloride (Chem-Impex International, 2.2 g, 12 mmol), 1-hydroxybenzotriazole (0.95 g, 7.0 mmol) and 4-dimethylaminopyridine (0.14 g, 1.2 mmol) in 6 mL of pyridine was allowed to stir at ambient temperature for 72 hours. The reaction mixture was concentrated under reduced pressure and 10 mL of H$_2$O was added. The resulting solids were isolated by filtration, washed with 5 mL of H$_2$O and twice with 5 mL of ethyl acetate, and dried to afford the title compound. MS (DCI/NH$_3$) m/Z 303 (M+H)$^+$.

Example 242B 5-chloro-N-[(2Z)-5-chloro-3-[(2R)-tetrahydrofuran-2-ylmethyl]-1,3-thiazol-2(3H)-ylidene]-2-methoxybenzamide To a slurry of sodium hydride (40 mg of a 60% dispersion, 1.0 mmol) in 4 mL of N,N-dimethylformamide at 0° C. was added Example 242A (0.20 g, 0.66 mmol). This mixture was allowed to warm to ambient temperature and stirred for 1 hour. The mixture was cooled to 0° C. and Example 208A (0.19 g, 0.73 mmol) was added. The mixture was warmed to 80° C. and allowed to stir for 24 hours and cooled to ambient temperature. The reaction mixture was quenched with ice and 5 mL of saturated, aqueous NH$_4$Cl and diluted with 5 mL of ethyl acetate. The layers were separated and the aqueous layer was extracted with three 5 mL of portions of ethyl acetate. The combined organic extracts were dried over anhydrous Na$_2$SO$_4$, filtered and concentrated under reduced pressure. Purification via flash column chromatography (SiO$_2$, 50% hexanes:ethyl acetate) afforded the title compound. $^1$H NMR (300 MHz, CD$_3$OD) δ ppm 1.65-1.80 (m, 1H), 1.85-1.97 (m, 2H), 2.02-2.18 (m, 1H) 3.72-3.82 (m, 1H), 3.84-3.94 (m, 1H), 3.87 (s, 3H), 4.21-4.38 (m, 2H), 4.40-4.48 (m, 1H), 7.09 (d, J=8.8 Hz, 1H), 7.43 (dd, J=9.0, 2.9 Hz, 1H), 7.50 (s, 1H), 7.90 (d, J=2.7 Hz, 1H); MS (DCI/NH$_3$) m/z 387 (M+H)$^+$. Anal. Calculated for C$_{16}$H$_{16}$ClN$_2$O$_3$S: C, 49.62; H, 4.16; N, 7.23. Found: C, 50.49; H, 4.03; N, 6.70.

Example 243

5-chloro-N-[(2Z)-5-chloro-3-(tetrahydro-2H-pyran-4-ylmethyl)-1,3-thiazol-2(3H)-ylidene]-2-methoxybenzamide Example 242A (0.20 g, 0.66 mmol), Example 203A (0.20, 0.73 mmol) and NaH (40 mg, 1 mmol) in 4 mL of tetrahydrofuran and 1 mL of N,N-dimethylformamide were processed as in Example 242B to afford the title compound. $^1$H NMR (300 MHz, CD$_3$OD) δ ppm 1.36-1.52 (m, 2H), 1.53-1.61 (m, 2H), 2.19-2.38 (m, 1H), 3.40 (dt, J=11.17, 2.4 Hz, 2H), 3.88 (s, 3H), 3.92-4.00 (m, 2H), 4.19 (d, J=7.1 Hz, 2H), 7.10 (d, J=8.8 Hz, 1H), 7.44 (dd, J=9.0, 2.9 Hz, 1H), 7.55 (s, 1H), 7.91 (d, J=2.7 Hz, 1H); MS (DCI/NH$_3$) m/z 401 (M+H)$^+$.

Example 244

N-[(2Z)-5-tert-butyl-3-[(3-methyl-4,5-dihydroisoxazol-5-yl)methyl]-1,3-thiazol-2(3H)-ylidene]-5-chloro-2-methoxybenzamide Example 244A N-(5-tert-butylthiazol-2-yl)-5-chloro-2-methoxybenzamide To a solution of Example 202A (0.94 g, 6.0 mmol) in tetrahydrofuran (40 mL) was added Example 205B (1.23 g, 6.0 mmol), triethylamine (2.4 mL, 18 mmol), and 4-dimethylaminopyridine (7.5 mg, 0.06 mmol). The reaction mixture was stifled at 60° C. for 14 hours and then cooled to ambient

Example 244B

N-[(2Z)-3-allyl-5-tert-butyl-1,3-thiazol-2(3H)-ylidene]-5-chloro-2-methoxybenzamide To a solution of Example 244A (410 mg, 1.3 mmol) in 5 mL of tetrahydrofuran:N,N-dimethylformamide (4/1) at 0° C. was added potassium tert-butoxide (230 mg, 1.9 mmol). The reaction mixture was stirred for 1 hour then allyl bromide (0.16 mL, 1.9 mmol) was added. The mixture was warmed to 65° C. and stirred overnight. The mixture was cooled to ambient temperature, concentrated, diluted with $CH_2Cl_2$ and washed with water and brine. The organic layer was dried over magnesium sulfate, filtered, and concentrated under reduced pressure. Purification by chromatography (20-50% ethyl acetate/hexane gradient) afforded the title compound. $^1H$ NMR ($CDCl_3$, 300 MHz) δ ppm 1.34 (s, 9H), 3.90 (s, 3H), 4.78-4.85 (m, 3H), 522-5.36 (m, 2H), 5.90-6.09 (m, J=17.0, 10.17 Hz, 1H), 6.62 (s, 1H), 6.90 (d, J=9.2 Hz, 1H), 7.32 (dd, J=8.8, 3.1 Hz, 1H), 8.00 (d, J=2.7 Hz, 1H); MS ($DCI/NH_3$) m/z 365 $(M+H)^+$.

Example 244C

N-[(2Z)-5-tert-butyl-3-[(3-methyl-4,5-dihydroisoxazol-5-yl)methyl]-1,3-thiazol-2(3H)-ylidene]-5-chloro-2-methoxybenzamide Example 244B was processed according to the method of Example 227C to afford the title compound. MS ($DCI/NH_3$) m/z 422 $(M+H)^+$.

Example 245

N-[(2Z)-5-tert-butyl-3-[(2R)-tetrahydrofuran-2-ylmethyl]-1,3-thiazol-2(3H)-ylidene]-2,2-dimethyl-4-oxo-3,4-dihydro-2H-pyran-6-carboxamide To a solution of the product from Example 240C (300 mg, 0.94 mmol) and 2,2-dimethyl-4-oxo-3,4-dihydro-2H-pyran-6-carboxylic acid (180 mg, 1.0 mmol) in 5 mL of N,N-dimethylformamide were added 1-hydroxybenzotriazole hydrate (190 mg, 1.4 mmol), triethylamine (0.30 mL, 2.1 mmol), and 1-ethyl-3-[3-(dimethylamino)propyl]-carbodiimide hydrochloride (260 mg, 1.4 mmol) The mixture was warmed to 65° C. and stirred overnight. The mixture was cooled to ambient temperature, diluted with $CH_2Cl_2$ and washed with water and brine. The organic extract was dried ($MgSO_4$), filtered, and concentrated under reduced pressure. Purification by column chromatography ($SiO_2$, 20-40% ethyl acetate/hexanes gradient) afforded the title compound. $^1H$ NMR (500 MHz, $CDCl_3$) δ ppm 1.34 (s, 9H), 1.57 (s, 6H), 1.72-1.84, (m, 1H), 1.83-1.94 (m, 2H), 2.00-2.12 (m, 2H), 2.55 (s, 2H), 3.73-3.88 (m, 2H), 4.10-4.27 (m, 2H), 4.39 (dd, J=13.7, 2.8 Hz, 1H), 6.48 (s, 1H), 6.91 (s, 1H); MS ($DCI/NH_3$) m/z 393 $(M+H)^+$.

Example 246

N-[(2Z)-5-tert-butyl-3-(tetrahydro-2H-pyran-4-ylmethyl)-1,3-thiazol-2(3H)-ylidene]-5-chloro-2-methoxybenzamide To a solution of Example 244A (10 g, 3.1 mmol) in 4:1 N,N-dimethylformamide/tetrahydrofuran (20 mL) were added potassium tert-butoxide (Aldrich, 0.42 g, 3.7 mmol) and 4-(iodomethyl)tetrahydro-2H-pyran (Maybridge, 0.97 g, 4.3 mmol). The reaction mixture was stirred at 80° C. for 16 hours, cooled to room temperature, quenched with saturated aqueous $NaHCO_3$ (20 mL) and extracted with ethyl acetate (3×20 mL). The combined organic extracts were dried over anhydrous $Na_2SO_4$, filtered and concentrated under reduced pressure. The residue was purified by column chromatography using an Analogix® Intelliflash280™ ($SiO_2$, 0-100% ethyl acetate in hexanes) to afford the title compound. $^1H$ NMR (300 MHz, dimethylsulfoxide-$d_6$) δ ppm 1.21-1.51 (m, 4H), 1.32 (s, 9H), 2.06-2.35 (m, 1H), 3.20-3.30 (m, 2H), 3.79 (s, 3H), 3.80-3.91 (m, J=9.3, 2.2, 2.0 Hz, 2H), 4.06 (d, J=7.1 Hz, 2H), 7.11 (d, J=8.8 Hz, 1H), 7.30 (s, 1H), 7.45 (dd, J=8.8, 3.1 Hz, 1H), 7.64 (d, J=2.7 Hz, 1H); MS (ESI+) m/z 423 $(M+H)^+$; Anal. Calculated for $C_{21}H_{27}ClN_2O_3S$: C, 59.63; H, 6.43; N, 6.62 Found: C, 59.66; H, 6.36; N, 6.56.

Example 247

5-chloro-2-methoxy-N-[(2Z)-3-(tetrahydro-2H-pyran-4-ylmethyl)-4,5,6,7-tetrahydro-1,3-benzothiazol-2(3H)-ylidene]benzamide

Example 247A 5-chloro-2-methoxy-N-(4,5,6,7-tetrahydrobenzo[d]thiazol-2-yl)benzamide Commercially available 4,5,6,7-tetrahydrobenzo[d]thiazol-2-amine (Aldrich) and 5-chloro-2-methoxybenzoic acid (Aldrich) were processed using the method described in Example 58 to afford the title compound MS ($ESI^+$) m/z 323 $(M+H)^+$.

Example 247B 5-chloro-2-methoxy-N-[(2Z)-3-(tetrahydro-2H-pyran-4-ylmethyl)-4,5,6,7-tetrahydro-1,3-benzothiazol-2(3H)-ylidene]benzamide Example 203A and Example 247A were processed using the method described in Example 246 to afford the title compound. $^1H$ NMR (300 MHz, dimethylsulfoxide-$d_6$) δ ppm 1.25-1.55 (m, 4H), 1.69-1.94 (m, 4H), 2.07-2.30 (m, 1H), 2.52-2.59 (m, 2H), 2.58-2.66 (m, 2H), 3.18-3.30 (m, 2H), 3.80 (s, 3H), 3.81-3.89 (m, 2H), 4.03 (d, J=7.1 Hz, 2H), 7.11 (d, J=8.8 Hz, 1H), 7.45 (dd, J=8.8, 2.7 Hz, 1H), 7.69 (d, J=3.1 Hz, 1H); MS ($ESI^+$) m/z 421 $(M+H)^+$.

Example 248

5-chloro-2-methoxy-N-[(2Z)-3-(2-methoxyethyl)-4,4,6,6-tetramethyl-4,6-dihydrofuro[3,4-d][1,3]thiazol-2(3H)-ylidene]benzamide

Example 248A 4-bromo-2,2,5,5-tetramethyldihydrofuran-3(2H)-one

To a solution of commercially available 2,2,5,5-tetramethyldihydrofuran-3(2H)-one (Aldrich, 10.0 g, 0.07 mol) in

--- temperature, diluted with saturated aqueous $NaHCO_3$ (20 mL) and extracted with ethyl acetate (3×30 mL). The combined organic extracts were dried over anhydrous $Na_2SO_4$, filtered and concentrated under reduced pressure. The residue was purified by column chromatography using an Analogix® Intelliflash280™ ($SiO_2$, 0-100% ethyl acetate in hexanes) to afford the title compound. MS (ESI+) m/z 325 $(M+H)^+$.

CH₂Cl₂ (100 mL) was added bromine (Aldrich, 3.6 mL, 0.07 mol) dropwise at room temperature. The reaction mixture was stirred for 2 hours over which time the reaction mixture became clear. Then, the reaction mixture was cooled to 0° C., quenched with NaHCO₃ powder in small portions, filtered and concentrated under reduced pressure to afford the title compound. $^1$H NMR (300 MHz, dimethylsulfoxide-$d_6$) δ ppm 1.26 (s, 3H), 1.27 (s, 3H), 1.30 (s, 3H), 1.39 (s, 3H), 5.22 (s, 1H).

Example 248B 4,4,6,6-tetramethyl-4,6-dihydrofuro[3,4-d]thiazol-2-amine

To a solution of Example 248A (10.0 g, 0.045 mol) in ethanol (100 mL) were added thiourea (3.8 g, 0.05 mol) and triethylamine (6.3 mL, 0.045 mol). The reaction mixture was heated at reflux overnight, then cooled, and concentrated under reduced pressure. The residue was diluted with water (25 mL) and extracted with ethyl acetate (3×50 mL). The combined organic extracts were dried (Na₂SO₄), filtered and concentrated. The residue was purified by column chromatography (SiO₂, 0-5% methanol in CH₂Cl₂) to afford the title compound MS (ESI⁺) m/z 199 (M+H)⁺.

Example 248C 5-chloro-2-methoxy-N-(4,4,6,6-tetramethyl-4,6-dihydrofuro[3,4-d]thiazol-2-yl)benzamide Example 248B and Example 205B were processed using the method described in Example 244A to afford the title compound. MS (ESI⁺) m/z 367 (M+H)⁺.

Example 248D 5-chloro-2-methoxy-N-[(2Z)-3-(2-methoxyethyl)-4,4,6,6-tetramethyl-4,6-dihydrofuro[3,4-d][1,3]thiazol-2(3H)-ylidene]benzamide Example 248C and commercially available 2-bromoethyl methyl ether (Aldrich) were processed using the method described in Example 246 to afford the title compound. $^1$H NMR (300 MHz, dimethylsulfoxide-$d_6$) δ ppm 1.48 (s, 6H), 1.55 (s, 6H), 3.25 (s, 3H), 3.71-3.90 (m, 2H), 3.81 (s, 3H), 4.20 (t, J=5.6 Hz, 2H), 7.13 (d, J=9.2 Hz, 1H), 7.48 (dd, J=9.0, 2.9 Hz, 1H), 7.68 (d, J=2.7 Hz, 1H); MS (ESI⁺) m/z 425 (M+H)⁺.

Example 249

5-chloro-2-methoxy-N-[(2Z)-3-(2-methoxyethyl)-6,6-dimethyl-4-oxo-4,6-dihydrofuro[3,4-d][1,3]thiazol-2(3H)-ylidene]benzamide

Example 249A tert-butyl 6,6-dimethyl-4-oxo-4,6-dihydrofuro[3,4-d]thiazol-2-ylcarbamate To a solution of diisopropylamine (23.5 mL, 165 mmol) in tetrahydrofuran (200 mL) was added butyllithium (103 mL, 1.6 M in hexanes, 165 mmol) dropwise at –78° C. The solution was stirred at –78° C. for 30 minutes then transferred via cannula into a solution of methyl 2-(tert-butoxycarbonylamino)thiazole-4-carboxylate (Combi-Blocks, 14.2 g, 55 mmol) in tetrahydrofuran (300 mL) at –78° C. After stirring at –78° C. for 30 minutes, dry acetone (Acros, 16.2 mL, 220 mmol) was added dropwise and the reaction mixture was allowed to warm to room temperature and stirred overnight. The reaction mixture was quenched with saturated aqueous NH₄Cl solution (200 mL) and the aqueous layer was extracted with ethyl acetate (4×200 mL). The combined organic extracts were dried (Na₂SO₄), filtered and concentrated. The residue was purified by column chromatography (SiO₂, 0-100% ethyl acetate in hexanes) to afford the title compound MS (ESI⁺) m/z 285 (M+H)⁺.

Example 249B 2-amino-6,6-dimethylfuro[3,4-d]thiazol-4(6H)-one

To a solution of Example 249A (7.4 g, 26.0 mmol) in CH₂Cl₂ (20 mL) was added trifluoroacetic acid (20.0 mL, 260 mmol) slowly at 0° C. The reaction mixture was stirred at room temperature for 3 hours, and then concentrated under vacuum. The residue was diluted with ethyl acetate (100 mL) and neutralized with saturated aqueous NaHCO₃ solution. The layers were separated and the aqueous phase was extracted with ethyl acetate (5×100 mL). The combined organic extracts were dried (Na₂SO₄), filtered and concentrated to afford the title compound. MS (ESI⁺) m/z 185 (M+H)⁺.

Example 249C 2-imino-3-(2-methoxyethyl)-6,6-dimethyl-2,3-dihydrofuro[3,4-d]thiazol-4(6H)-one hydrobromide A mixture of Example 249B and commercially available 2-bromoethyl methyl ether (Aldrich) was processed at 120° C. using the method described in Example 12A to afford the title compound. MS (ESI⁺) m/z 243 (M+H)⁺.

Example 249D 5-chloro-2-methoxy-N-[(2Z)-3-(2-methoxyethyl)-6,6-dimethyl-4-oxo-4,6-dihydrofuro[3,4-d][1,3]thiazol-2(3H)-ylidene]benzamide Example 249C and Example 205B were processed using the method described in Example 244A to afford the title compound. $^1$H NMR (300 MHz, dimethylsulfoxide-$d_6$) δ ppm 1.71 (s, 6H), 3.26 (s, 3H), 3.78 (t, J=5.6 Hz, 2H), 3.82 (s, 3H), 4.46 (t, J=5.6 Hz, 2H), 7.17 (d, J=8.8 Hz, 1H), 7.53 (dd, J=9.0, 2.9 Hz, 1H), 7.77 (d, J=2.7 Hz, 1H)); MS (ESI⁺) m/z 411 (M+H)⁺; Anal. Calculated for C₁₈H₁₉ClN₂O₅S: C, 52.62; H, 4.66; N, 6.82. Found: C, 52.72; H, 4.49; N, 6.90.

Example 250

N-[(2Z)-5-acetyl-4-methyl-3-(oxetan-2-ylmethyl)-1,3-thiazol-2(3H)-ylidene]-5-chloro-2-methoxybenzamide Example 238A and Example 211A were processed using the method described in Example 246 to afford the title compound. $^1$H NMR (300 MHz, CDCl₃) δ ppm 2.49 (s, 3H), 2.54-2.67 (m, 1H), 2.74-2.82 (m, 1H), 2.84 (s, 3H), 3.93 (s, 3H), 4.45-4.74 (m, 4H), 5.30 (d, 1H), 6.93 (d, J=9.2 Hz, 1H), 7.38 (dd, J=8.8, 2.7 Hz, 1H), 7.97 (d, J=2.7 Hz, 1H); MS (ESI⁺) m/z 493 (M+H)⁺; Anal. Calculated for C₁₈H₁₉ClN₂O₄S: C, 54.75; H, 4.85; N, 7.09 Found: C, 54.68; M, 4.70; N, 7.07.

Example 251

5-chloro-N-[(2Z)-4,4-dimethyl-1-(oxetan-2-ylmethyl)-1,4,6,7-tetrahydro-2H-pyrano[4,3-d][1,3]thiazol-2-ylidene]-2-methoxybenzamide Example 251A ethyl 2-(2-(tert-butoxycarbonylamino)thiazol-4-yl)acetate The title compound was obtained from commercially available ethyl 2-(2-aminothiazol-4-yl)acetate (Aldrich) as per the procedure described in JP 06345736. MS (ESI⁺) m/z 287 (M+H)⁺.

Example 251B tert-butyl 4-(2-hydroxyethyl)thiazol-2-ylcarbamate

To a cooled solution of Example 251A in tetrahydrofuran (100 mL) was added lithium borohydride (Aldrich, 100 mL, 2 M solution in tetrahydrofuran) at 0° C. The reaction mixture was heated at reflux overnight, then cooled to 0° C., quenched with water and extracted with ethyl acetate (3×100 mL). The combined organic extracts were dried (Na₂SO₄), filtered and concentrated. The residue was purified by column chromatography (SiO₂, 0-5% methanol in CH₂Cl₂) to afford the title compound MS (ESI⁺) m/z 245 (M+H)⁺.

Example 251C tert-butyl 4-(2-(tetrahydro-2H-pyran-2-yloxy)ethyl)thiazol-2-ylcarbamate To a solution of Example 251B (6.3 g, 27.4 mmol) in CH₂Cl₂ (100 mL) was added commercially available 3,4-dihydro-2H-pyran (Aldrich, 21 g, 250 mmol) and pyridinium-p-toluenesulfonic acid (Aldrich, 3.5 g, 14.0 mmol). The reaction mixture was stirred overnight at room temperature and was diluted with CH₂Cl₂, washed with water, dried (Na₂SO₄), filtered and concentrated. The residue was purified by column chromatography (SiO₂, 0-100% ethyl acetate in hexanes) to afford the title compound. MS (ESI⁺) m/z 329 (M+H)⁺.

Example 251D tert-butyl 5-(2-hydroxypropan-2-yl)-4-(2-(tetrahydro-2H-pyran-2-yloxy)ethyl)thiazol-2-ylcarbamate Example 251C, diisopropylamine, butyllithium, and dry acetone (Acros) were processed as described for Example 249A to obtain the title compound. MS (ESI⁺) m/Z 387 (M+H)⁺.

Example 251E 4,4-dimethyl-6,7-dihydro-4H-pyrano[4,3-d]thiazol-2-amine

To a solution of Example 251D (4.6 g, 11 mmol) in tetrahydrofuran was added concentrated HCl (6.9 mL). The reaction mixture was heated at reflux for overnight and then cooled. The mixture was basified with 5N NaOH (17 mL) and extracted with ethyl acetate (3×50 mL). The combined organic extracts were dried (Na₂SO₄), filtered and concentrated. The residue was purified by column chromatography (SiO₂, 0-10% methanol in CH₂Cl₂) to afford the title compound. MS (ESI⁺) m/z 185 (M+H)⁺.

Example 251F 5-chloro-N-(4,4-dimethyl-6,7-dihydro-4H-pyrano[4,3-d]thiazol-2-yl)-2-methoxybenzamide Example 251E and Example 205B were processed using the method described in Example 244A to afford the title compound. MS (ESI⁺) m/z 353 (M+H)⁺.

Example 251G 5-chloro-N-[(2Z)-4,4-dimethyl-1-oxetan-2-ylmethyl)-1,4,6,7-tetrahydro-2H-pyrano[4,3-d][1,3]thiazol-2-ylidene]-2-methoxybenzamide Example 251F and Example 211A were processed using the method described in Example 246 to afford the title compound. ¹H NMR (300 MHz, dimethylsulfoxide-d₆) δ ppm 1.45 (s, 3H), 1.46 (s, 3H), 2.67-2.75 (m, 2H), 2.74-2.83 (m, 2H), 3.79 (s, 3H), 3.90-4.01 (m, 2H), 4.32-4.44 (m, 2H), 4.45-4.58 (m, 2H), 5.06 (d, 1H), 7.11 (d, J=8.8 Hz, 1H), 7.45 (dd, J=8.8, 2.7 Hz, 1H), 7.62 (d, J=2.7 Hz, 1H); MS (ESI⁺) m/z 423 (M+H)⁺; Anal. Calculated for C₂₀H₂₃ClN₂O₄S.0.2C₄H₈O₂: C, 56.71; H, 5.63; N, 6.36. Found: C, 56.33; H, 5.39; N, 6.41.

Example 252

5-chloro-N-{(2Z)-4,4-dimethyl-1-[(2R)-tetrahydrofuran-2-ylmethyl]-1,4,6,7-tetrahydro-2H-pyrano[4,3-d][1,3]thiazol-2-ylidene}-2-methoxybenzamide Example 251F and Example 208A were processed using the method described in Example 246 to afford the title compound. ¹H NMR (300 MHz, dimethylsulfoxide-d₆) δ ppm 1.45 (s, 6H), 1.61-2.04 (m, 4H), 2.71 (t, J=5.8 Hz, 2H) 3.56-3.70 (m, 1H), 3.73-3.84 (m, 1H), 3.79 (s, 3H), 3.96 (t, J=3 Hz, 2H), 4.00-4.05 (m, 1H), 4.20-4.38 (m, 2H), 7.11 (d, J=8.8 Hz, 1H), 7.46 (dd, J=9.0, 2.9 Hz, 1H), 7.66 (d, J=3.1 Hz, 1H); MS (ESI⁺) m/z 437 (M+H)⁺; Anal. Calculated For C₂₁H₂₅ClN₂O₄S: C, 57.72; H, 5.77; N, 6.41 Found: C, 57.58; H, 5.86; N, 6.33.

Example 253

N-[(2Z)-5-acetyl-4-methyl-3-(tetrahydro-2H-pyran-2-ylmethyl)-1,3-thiazol-2(3H)-ylidene]-5-chloro-2-methoxybenzamide Commercially available 2-(bromomethyl)tetrahydro-2H-pyran (Aldrich) and Example 238A were processed using the method described in Example 246 to afford the title compound. ¹H NMR (300 MHz, dimethylsulfoxide-d₆) δ ppm 1.28-1.38 (m, 1H), 1.41-1.52 (m, 3H), 1.62-1.71 (m, 1H), 1.78-1.88 (m, 1H), 2.50 (s, 3H), 2.61-2.84 (m, 3H), 3.64-3.93 (m, 3H), 3.83 (s, 3H), 4.14 (dd, J=14.1, 8.6 Hz, 1H), 4.37 (dd, J=14.2, 3.1 Hz, 1H), 7.16 (d, J=8.8 Hz, 1H) 7.51 (dd, J=9.0, 2.9 Hz, 1H), 7.79 (d, J=2.7 Hz, 1H); MS (ESI⁺) m/z 423

(M+H)+; Anal. Calculated for C$_{20}$H$_{23}$ClN$_2$O$_4$S: C, 56.80; H, 5.48; N, 6.62. Found: C, 56.53; H, 5.27; N, 6.55.

Example 254

N-[(2Z)-5-acetyl-4-methyl-3-(tetrahydro-2H-pyran-3-ylmethyl)-1,3-thiazol-2(3H)-ylidene]-5-chloro-2-methoxybenzamide Example 225A and Example 238A were processed using the method described in Example 246 to afford the title compound. $^1$H NMR (300 MHz, dimethylsulfoxide-d$_6$) δ ppm 1.47 (s, 6H) 1.52 (s, 6H) 3.72 (s, 3H) 5.35 (s, 2H) 7.07 (d, 3H) 7.32 (d, 1H) 7.37 (d, J=2.71 Hz, 1H) 7.40-7.50 (m, J=8.81 Hz, 1H); MS (ESI+) m/z 423 (M+H)+; Anal. Calculated for C$_{20}$H$_{23}$ClN$_2$O$_4$S.0.2H$_2$O: C, 56.32; H, 5.53; N, 6.57. Found: C, 56.19; H, 5.50; N, 6.62.

Example 255

5-chloro-N-[(2Z)-5-(1-hydroxy-1-methylethyl)-4-methyl-3-(tetrahydro-2H-pyran-2-ylmethyl)-1,3-thiazol-2(3H)-ylidene]-2-methoxybenzamide A solution of methyllithium (Aldrich, 1.6 M in diethyl ether, 0.41 mL, 0.66 mmol) was added slowly a solution of Example 253 (0.14 g, 0.33 mmol) in tetrahydrofuran (3 mL) at −78° C. The reaction mixture was stirred at −78° C. for 30 minutes and was allowed to reach room temperature. The reaction mixture was quenched with water (6 mL) and extracted with ethyl acetate (2×10 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-5% methanol in CH$_2$Cl$_2$) to afford the title compound. $^1$H NMR (300 MHz, dimethylsulfoxide-d$_6$) δ ppm 1.21-1.36 (m, 1H), 1.41-1.48 (m, 3H), 1.49 (s, 3H) 1.50 (s, 3H), 1.57-1.67 (m, 1H), 1.74-1.85 (m, 1H), 2.42 (s, 3H), 3.68-3.89 (m, 3H), 3.79 (s, 3H), 3.92-4.09 (m, 1H), 4.17-4.38 (m, 1H), 5.60 (s, 1H), 7.10 (d, J=8.8 Hz, 1H), 7.44 (dd, J=8.8, 2.7 Hz, 1H), 7.68 (d, J=2.7 Hz, 1H); MS (ESI+) m/z 439 (M+H)+; Anal. Calculated for C$_{21}$H$_{27}$ClN$_2$O$_4$S: C, 57.46; H, 6.20; N, 6.38. Found: C, 57.44; H, 5.88; N, 6.06.

Example 256

5-chloro-2-methoxy-N-[(2Z)-4-methyl-3-[(2R)-tetrahydrofuran-2-ylmethyl]-5-[2,2,2-trifluoro-1-hydroxy-1-(trifluoromethyl)ethyl]-1,3-thiazol-2(3H)-ylidene]benzamide Example 256A 2-(2-amino-4-methylthiazol-5-yl)-1,1,1,3,3,3-hexafluoropropan-2-ol The title compound was prepared from commercially available of 4-methylthiazol-2-amine (Aldrich) and hexafluoroacetone trihydrate (Aldrich) using the procedure described in European Journal of Organic Chemistry, (21), 4286-4291; 2003. MS (ESI+) m/z 281 (M+H)+.

Example 256B 5-chloro-N-(5-(1,1,1,3,3,3-hexafluoro-2-hydroxypropan-2-yl)-4-methylthiazol-2-yl)-2-methoxybenzamide Commercially available 5-chloro-2-methoxybenzoic acid (Aldrich) and Example 256A were processed using the method described in Example 58 to afford the title compound. MS (ESI+) m/z 449 (M+H)+.

Example 256C 5-chloro-2-methoxy-N-[(2Z)-4-methyl-3-[(2R)-tetrahydrofuran-2-ylmethyl]-5-[2,2,2-trifluoro-1-hydroxy-1-(trifluoromethyl)ethyl]-1,3-thiazol-2(3H)-ylidene]benzamide Example 256B and Example 208A were processed using the method described in Example 246 to afford the title compound. $^1$H NMR (300 MHz, dimethylsulfoxide-d$_6$) δ ppm 1.62-1.76 (m, 1H), 1.78-1.93 (m, 2H), 1.93-2.09 (m, 1H), 2.57 (s, 3H), 3.57-3.70 (m, 1H), 3.74-3.88 (m, 1H), 3.80 (s, 3H), 4.12-4.26 (m, 1H) 4.39 (d, 2H), 7.14 (d, J=8.8 Hz, 1H), 7.49 (dd, J=8.8, 2.7 Hz, 1H), 7.74 (d, J=2.7 Hz, 1H), 9.34 (s, 1H); MS (ESI+) m/z 533 (M+H)+.

Example 257

5-chloro-N-[(2Z)-5-(1-hydroxy-1-methylethyl)-4-methyl-3-(tetrahydro-2H-pyran-3-ylmethyl)-1,3-thiazol-2(3H)-ylidene]-2-methoxybenzamide Example 254 and commercially available methyllithium (Aldrich, 1.6 M in diethyl ether) were processed using the method described in Example 255 to afford the title compound. $^1$H NMR (300 MHz, dimethylsulfoxide-d$_6$) δ ppm 1.32-1.48 (m, 2H), 1.51 (s, 6H), 1.57-1.80 (m, 2H), 2.02-2.23 (m, 1H), 2.41 (s, 3H), 3.19-3.28 (m, 1H), 3.35-3.43 (m, 1H), 3.55-3.73 (m, 2H), 3.79 (s, 3H), 3.95-4.29 (m, 2H), 5.60 (s, 1H), 7.10 (d, J=8.8 Hz, 1H), 7.44 (dd, J=8.8, 3.1 Hz, 1H), 7.67 (d, J=2.7 Hz, 1H); MS (ESI+) m/z 439 (M+H)+; Anal. Calculated for C$_{21}$H$_{27}$ClN$_2$O$_4$S: C, 57.46; H, 6.20; N, 6.38. Found: C, 57.14; H, 6.23; N, 6.53.

Example 258

5-chloro-N-[(2Z)-3-{[(4R)-2,2-dimethyl-1,3-dioxolan-4-yl]methyl}-5-(1-hydroxy-1-methylethyl)-4-methyl-1,3-thiazol-2(3H)-ylidene]-2-methoxybenzamide Example 258A 5-chloro-N-(5-(2-hydroxypropan-2-yl)-4-methylthiazol-2-yl)-2-methoxybenzamide Example 238A and methyllithium (Aldrich, 1.6M in diethyl ether) were processed using the method described in Example 255 to afford the title compound. MS (ESI+) m/z 341 (M+H)+.

Example 258B 5-chloro-N-[(2Z)-3-{[(4R)-2,2-dimethyl-1,3-dioxolan-4-yl]methyl}-5-(1-hydroxy-1-methylethyl)-4-methyl-1,3-thiazol-2(3H)-ylidene]-2-methoxybenzamide Example 258A and commercially available (S)-(2,2-dimethyl-1,3-dioxolan-4-yl)methyl 4-methylbenzenesulfonate (Aldrich) were processed using the method described in Example 246 to afford the title compound. $^1$H NMR (300 MHz, dimethylsulfoxide-$d_6$) δ ppm 1.25 (s, 3H), 1.31 (s, 3H), 1.50 (s, 6H), 2.45 (s, 3H), 3.78 (s, 3H), 3.84 (dd, J=8.8, 6.1 Hz, 1H), 4.04 (dd, J=8.5, 6.4 Hz, 1H), 4.18-4.29 (m, 1H), 4.32-4.42 (m, 1H), 4.46-4.58 (m, 1H), 5.63 (s, 1H), 7.10 (d, J=8.8 Hz, 1H), 7.43 (dd, J=8.8, 2.7 Hz, 1H), 7.64 (d, J=2.7 Hz, 1H); MS (ESI$^+$) m/z 455 (M+H)$^+$; Anal. Calculated for $C_{21}H_{27}ClN_2O_5S$: C, 55.44; H, 5.98; N, 6.16. Found: C, 55.34; H, 5.79; N, 6.21.

Example 259

5-chloro-N-[(2Z)-6,6-dimethyl-4-oxo-3-[(2R)-tetrahydrofuran-2-ylmethyl]-4,6-dihydrofuro[3,4-d][1,3]thiazol-2(3H)-ylidene]-2-methoxybenzamide

Example 259A 5-chloro-N-(6,6-dimethyl-4-oxo-4,6-dihydrofuro[3,4-d]thiazol-2-yl)-2-methoxybenzamide Example 249B, triethylamine, 4-dimethylaminopyridine, and Example 205B were processed as described for Example 244A to obtain the title compound. MS (ESI$^+$) m/z 353 (M+H)$^+$.

Example 259B 5-chloro-N-[(2Z)-6,6-dimethyl-4-oxo-3-[(2R)-tetrahydrofuran-2-ylmethyl]-4,6-dihydrofuro[3,4-d][1,3]thiazol-2(3H)-ylidene]-2-methoxybenzamide Example 259A and Example 208A were processed using the method described in Example 246 to afford the title compound. $^1$H NMR (300 MHz, dimethylsulfoxide-$d_6$) δ ppm 1.71 (s, 6H), 1.73-2.05 (m, 4H), 3.60-3.69 (m, 1H), 3.72-3.81 (m, 1H), 3.82 (s, 3H), 4.18-4.35 (m, 2H), 4.35-4.47 (m, 1H), 7.17 (d, J=8.8 Hz, 1H), 7.53 (dd, J=8.8, 2.7 Hz, 1H), 7.76 (d, J=2.7 Hz, 1H); MS (ESI$^+$) m/z 437 (M+H)$^+$; Anal. Calculated for $C_{20}H_{21}ClN_2O_5S \cdot 0.4H_2O$: C, 54.09; H, 4.95; N, 6.31. Found: C, 53.81; H, 4.55; N, 5.99.

Example 260

5-chloro-N-[(2Z)-3-{[(4S)-2,2-dimethyl-1,3-dioxolan-4-yl]methyl}-5-(1-hydroxy-1-methylethyl)-4-methyl-1,3-thiazol-2(3H)-ylidene]-2-methoxybenzamide Example 258A and commercially available (R)-(2,2-dimethyl-1,3-dioxolan-4-yl)methyl 4-methylbenzenesulfonate (Aldrich) were processed using the method described in Example 246 to afford the title compound. $^1$H NMR (300 MHz, dimethylsulfoxide-$d_6$) δ ppm 1.25 (s, 3H), 1.31 (s, 3H), 1.50 (s, 6H), 2.45 (s, 3H), 3.78 (s, 3H), 3.84 (dd, J=8.5, 6.1 Hz, 1H), 4.04 (dd, J=8.8, 6.4 Hz, 1H), 4.14-4.30 (m, 1H), 4.32-4.43 (m, 1H), 4.43-4.63 (m, 1H), 5.63 (s, 1H), 7.10 (d, J=9.2 Hz, 1H), 7.43 (dd, J=9.0, 2.9 Hz, 1H), 7.64 (d, J=2.7 Hz, 1H); MS (ESI$^+$) m/z 455 (M+H)$^+$; Anal. Calculated for $C_{21}H_{27}ClN_2O_5S$: C, 55.44; H, 5.98; N, 6.16. Found: C, 55.73; H, 6.07; N, 6.07.

Example 261

N-[(2Z)-5-acetyl-3-(1,4-dioxan-2-ylmethyl)-4-methyl-1,3-thiazol-2(3H)-ylidene]-5-chloro-2-methoxybenzamide Example 238A and commercially available 2-(iodomethyl)-1,4-dioxane (Synchem) were processed using the method described in Example 246 to afford the title compound. $^1$H NMR (300 MHz, dimethylsulfoxide-$d_6$) δ ppm 2.50 (s, 3H), 2.72 (s, 3H), 3.33-3.42 (m, 1H), 3.45-3.56 (m, 2H) 3.59-3.77 (m, 2H), 3.78-3.87 (m, 1H), 3.83 (s, 3H), 4.00-4.11 (m, 1H), 4.12-4.25 (m, 1H), 4.31-4.43 (m, 1H), 7.16 (d, J=8.8 Hz, 1H), 7.52 (dd, J=8.8, 3.1 Hz, 1H), 7.79 (d, J=2.7 Hz, 1H); MS (ESI$^+$) m/z 425 (M+H)$^+$; Anal. Calculated for $C_{19}H_{21}ClN_2O_5S$: C, 53.71; H, 4.98; N, 6.59 Found: C, 53.32; H, 4.73; N, 6.59.

Example 262

5-chloro-N-[(2Z)-5-(1-hydroxy-1-methylethyl)-4-methyl-3-(oxetan-2-ylmethyl)-1,3-thiazol-2(3H)-ylidene]-2-methoxybenzamide Example 258A and Example 211A were processed using the method described in Example 246 to afford the title compound. $^1$H NMR (300 MHz, dimethylsulfoxide-$d_6$) δ ppm 1.50 (s, 6H), 2.47 (s, 3H), 2.59-2.84 (m, 1H), 3.78 (s, 3H), 4.25-4.64 (m, 5H), 5.00-5.19 (m, 1H), 5.63 (s, 1H), 7.09 (d, J=9.2 Hz, 1H), 7.43 (dd, J=8.8, 3.1 Hz, 1H), 7.60 (d, J=2.7 Hz, 1H); MS (ESI$^+$) m/z 411 (M+H)$^+$; Anal. Calculated for $C_{19}H_{23}ClN_2O_4S$: C, 55.54; H, 5.64; N, 6.82. Found: C, 55.41; H, 5.51; N, 6.78.

Example 263

5-chloro-N-[(2Z)-5-(1-hydroxy-1-methylethyl)-4-methyl-3-(tetrahydrofuran-3-ylmethyl)-1,3-thiazol-2(3H)-ylidene]-2-methoxybenzamide Example 258A and Example 162A were processed using the method described in Example 246 to afford the title compound. $^1$H NMR (300 MHz, dimethylsulfoxide-$d_6$) δ ppm 1.51 (s, 6H), 1.65-1.82 (m, 1H), 1.84-2.03 (m, 1H), 2.43 (s, 3H), 2.68-2.89 (m, 1H), 3.48-3.71 (m, 3H), 3.78 (s, 3H), 3.80-3.93 (m, 1H), 4.08-4.34 (m, 2H), 5.62 (s, 1H), 7.09 (d, J=8.8 Hz, 1H), 7.43 (dd, J=8.8, 3.1 Hz, 1H), 7.65 (d, J=2.7 Hz, 1H); MS (ESI$^+$) m/z 425 (M+H)$^+$; Anal. Calculated for $C_{20}H_{25}ClN_2O_4S$: C, 56.53; H, 5.93; N, 6.59. Found: C, 56.35; H, 5.55; N, 6.56.

Example 264

5-chloro-N-[(2Z)-3-(1,4-dioxan-2-ylmethyl)-5-(1-hydroxy-1-methylethyl)-4-methyl-1,3-thiazol-2(3H)-ylidene]-2-methoxybenzamide Example 258A and commercially available 2-(iodomethyl)-1,4-dioxane (Synchem) were processed using the method described in Example 246 to afford the title compound. $^1$H NMR (300 MHz, dimethylsulfoxide-$d_6$) δ ppm 0.93 (t, J=7.46 Hz, 3H) 1.28-1.38 (m, 2H) 1.45 (s, 6H) 1.63-

1.78 (m, 2H) 2.69 (t, J=5.42 Hz, 2H) 3.79 (s, 3H) 3.97 (t, J=5.42 Hz, 2H) 4.07-4.17 (m, 2H) 7.11 (d, J=8.81 Hz, 1H) 7.46 (dd, J=8.81, 2.71 Hz, 1H) 7.69 (d, J=2.71 Hz, 1H); LCMS (ESI+) m/z 441 (M+H)+; Anal. Calculated for $C_{20}H_{25}ClN_2O_5S$: C, 54.48; H, 5.71; N, 6.35. Found: C, 54.54; H, 5.38; N, 6.43.

Example 265

N-[(2Z)-5-tert-butyl-3-[(2R)-tetrahydrofuran-2-ylmethyl]-1,3-thiazol-2(3H)-ylidene]-3-methoxy-2-naphthamide Commercially available 3-methoxy-2-naphthoic acid (Aldrich) and Example 240C were processed using the method described in Example 240E to afford the title compound. $^1$H NMR (300 MHz, dimethylsulfoxide-$d_6$) δ ppm 1.32 (s, 9H), 1.58-1.74 (m, 1H), 1.75-1.88 (m, 2H), 1.88-1.97 (m, 1H), 3.60-3.71 (m, 1H), 3.74-3.85 (m, 1H), 3.88 (s, 3H), 4.15-4.26 (m, 2H), 4.27-4.41 (m, 1H), 7.24 (s, 1H), 7.31-7.43 (m, 2H), 7.45-7.55 (m, 1H), 7.86 (dd, J=13.6, 8.5 Hz, 2H), 8.12 (s, 1H); MS (ESI+) m/z 425 (M+H)+; Anal. Calculated for $C_{20}H_{23}ClN_2O_4S \cdot 0.2C_4H_8O_2 \cdot 0.2H_2O$: C, 66.82; H, 6.78; N, 6.28. Found: C, 66.70; H, 6.65; N, 6.33.

Example 266

N-[(2Z)-5-tert-butyl-3-[(3-methyloxetan-3-yl)methyl]-1,3-thiazol-2(3H)-ylidene]-5-chloro-2-methoxybenzamide To a solution of Example 244A (0.75 g, 2.31 mmol) in N,N-dimethylformamide/tetrahydrofuran (1:4, 20 mL) were added potassium tert-butoxide (0.39 g, 3.46 mmol), tetrabutylammonium iodide (0.09 mg, 0.23 mmol) and commercially available 3-(chloromethyl)-3-methyloxetane (TCI, 0.28 g, 2.31 mmol). The reaction mixture was stirred at 80° C. for 16 hours, cooled, diluted with ethyl acetate (20 mL) and quenched with saturated aqueous $NaHCO_3$ (20 mL). The aqueous layer was extracted with ethyl acetate (2×20 mL). The combined organic layers were washed with water (1×25 mL). The combined organic extracts were dried over anhydrous $Na_2SO_4$, filtered and concentrated under reduced pressure. The residue was purified by column chromatography using an Analogix® Intelliflash280 ™ ($SiO_2$, 0-100% ethyl acetate in hexanes) to afford the title compound. $^1$H NMR (300 MHz, dimethylsulfoxide-$d_6$) δ ppm 1.24 (s, 3H), 1.33 (s, 9H), 3.77 (s, 3H), 4.19 (d, J=6.1 Hz, 2H), 4.38 (s, 2H), 4.69 (d, J=6.1 Hz, 2H), 7.10 (d, J=9.2 Hz, 1H), 7.29 (s, 1H), 7.44 (dd, J=9.0, 2.9 Hz, 1H), 7.58 (d, J=2.7 Hz, 1H); MS (ESI+) m/z 409 (M+H)+; Anal. Calculated for $C_{20}H_{25}ClN_2O_3S$: C, 58.74; H, 6.16; N, 6.85. Found: C, 58.92; H, 6.04; N, 6.84.

Example 267

5-chloro-2-methoxy-N-[(2Z)-3-(tetrahydrofuran-2-ylmethyl)-3,4,5,6-tetrahydro-2H-cyclopenta[d][1,3]thiazol-2-ylidene]benzamide Example 267A 5,6-dihydro-4H-cyclopenta[d]thiazol-2-amine A mixture of 2-chlorocyclopentanone (5.0 g, 40 mmol) and thiourea (3.0 g, 40 mmol) was heated at 70° C. for 3 hours. After cooling, the solid was triturated with ethanol and collected by filtration to afford the title compound. MS (ESI) m/z 141 (M+H)+.

Example 267B

Example 267A and 5-chloro-2-methoxybenzoic acid were processed using the method described in Example 223A to afford the title compound. MS (ESI) m/z 309 (M+H)+.

Example 267C 5-chloro-2-methoxy-N-[(2Z)-3-(tetrahydrofuran-2-ylmethyl)-3,4,5,6-tetrahydro-2H-cyclopenta[d][1,3]thiazol-2-ylidene]benzamide Example 267B (150 mg, 0.49 mmol) in tetrahydrofuran/ N,N-dimethylformamide (2:1)(10 mL) was treated with NaH (60%) (24 mg, 0.58 mmol). After 10 minutes, 2-(bromomethyl)tetrahydrofuran (96 mg, 0.58 mmol) was added and the mixture was heated at 95° C. for 12 hours. After cooling to ambient temperature, the mixture was diluted with water, and extracted with ethyl acetate. The organic extract was dried ($Na_2SO_4$), filtered and concentrated. Purification by chromatography afforded the title compound. $^1$H NMR (400 MHz, dimethylsulfoxide-$d_6$) δ ppm 1.62-1.73 (m, 1H) 1.79-1.88 (m, 2H) 1.91-2.02 (m, 1H) 2.35-2.44 (m, 2H) 2.77-2.91 (m, 4H) 3.64 (dd, J=14.7, 7.1 Hz, 1H) 3.74-3.81 (m, 1H) 3.79 (s, 3H) 4.00 (dd, J=13.5, 8.0 Hz, 1H) 4.23 (dd, J=13.5, 3.7 Hz, 1H) 4.26-4.33 (m, 1H) 7.11 (d, J=8.9 Hz, 1H) 7.44 (dd, J=8.9, 2.8 Hz, 1H) 7.68 (d, J=2.8 Hz, 1H); MS (ESI) m/z 393 (M+H)+.

Example 268

5-chloro-2-methoxy-N-[(2Z)-3-(tetrahydro-2H-pyran-4-ylmethyl)-3,4,5,6-tetrahydro-2H-cyclopenta[d][1,3]thiazol-2-ylidene]benzamide Example 267B and 4-(bromomethyl)tetrahydro-2H-pyran were processed using the method described in Example 267C to afford the title compound. $^1$H NMR (500 MHz, dimethylsulfoxide-$d_6$) δ ppm 1.33 (ddd, J=24.7, 11.90, 4.3 Hz, 2H) 1.40-1.54 (m, 2H) 1.83-1.86 (m, 1H) 2.15-2.26 (m, 1H) 2.36-2.45 (m, 2H) 2.82 (dt, J=20.8, 6.7 Hz, 4H) 3.26 (td, J=1.9, 1.8 Hz, 1H) 3.80 (s, 3H) 3.84 (dd, J=11.6, 2.4 Hz, 2H) 3.99 (d, J=7.3 Hz, 2H) 7.11 (d, J=8.9 Hz, 1H) 7.45 (dd, J=8.9, 2.8 Hz, 1H) 7.70 (d, J=2.8 Hz, 1H); MS (ESI) m/z 407 (M+H)+.

Example 269

N-[(2Z)-4,5-dimethyl-3-(tetrahydro-2H-pyran-4-ylmethyl)-1,3-thiazol-2(3H)-ylidene]-2,2-dimethyltetrahydro-2H-pyran-4-carboxamide Example 269A A mixture of 4,5-dimethylthiazol-2-amine (Aldrich) and 2,2-dimethyltetrahydro-2H-pyran-4-carboxylic acid (Chembridge Building Block Library) were processed using the method described in Example 223A to afford the title compound. MS (ESI) m/z 269 (M+H)+.

Example 269B

N-[(2Z)-4,5-dimethyl-3-(tetrahydro-2H-pyran-4-ylmethyl)-1,3-thiazol-2(3H)-ylidene]-2,2-dimethyltetrahydro-2H-pyran-4-carboxamide Example 269A and 4-(bromomethyl)tetrahydro-2H-pyran were processed using the method described in Example 267C to afford the title compound. $^1$H NMR (300 MHz, dimethylsulfoxide d$_6$) δ ppm 1.11-1.14 (m, 3H) 1.15-1.18 (m, 3H) 1.30-1.43 (m, 4H) 1.43-1.56 (m, 2H) 1.68-1.80 (m, 2H) 2.14-2.18 (m, 3H), 2.19-2.23 (m, 3H) 2.55-2.71 (m, 1H) 3.16-3.26 (m, 2H) 3.35-3.41 (m, 1H) 3.60 (dd, J=11.9, 2.4 Hz, 1H) 3.63-3.68 (m, 1H) 3.79-3.83 (m, 1H) 3.83-3.87 (m, 1H) 4.01-4.03 (m, 1H) 4.03-4.06 (m, 1H); MS (ESI) m/z 376 (M+H)$^+$.

Example 270

N-[(2Z)-5-tert-butyl-3-(oxetan-2-ylmethyl)-1,3-thiazol-2(3H)-ylidene]-5-chloro-2-methoxybenzamide Example 244A and the product from Example 211A were processed using the method described in Example 244B to afford the title compound. $^1$H NMR (400 MHz, CDCl$_3$) δ ppm 1.35 (s, 9H) 2.39-2.56 (m, 1H) 2.68-2.83 (m, 1H) 3.86-3.90 (s, 3H) 4.34-4.38 (m, 1H) 4.37-4.43 (m, 1H) 4.55 (dd, J=14.1, 5.8 Hz, 1H) 4.62-4.68 (m, 1H) 5.15-5.22 (m, 1H) 6.89 (d, J=8.9 Hz, 1H) 6.93-6.94 (m, 1H) 7.31 (dd, J=8.9, 2.8 Hz, 1H) 7.89 (d, J=2.8 Hz, 1H); MS (ESI) m/z 395 (M+H)$^+$.

Example 271

N-[(2Z)-5-tert-butyl-3-(tetrahydro-2H-pyran-2-ylmethyl)-1,3-thiazol-2(31)-ylidene]-5-chloro-2-methoxybenzamide Example 244A and 2-(bromomethyl)tetrahydro-2H-pyran were processed using the method described in Example 246 to afford the title compound. $^1$H NMR (500 MHz, CDCl$_3$) δ ppm 1.20-1.34 (m, 2H) 1.34 (s, 9H) 1.51-1.55 (m, 2H) 1.71 (dt, J=12.8, 1.8 Hz, 1H) 1.85-1.92 (m, 1H) 3.39 (td, J=14.3, 11.3, 3.4 Hz, 1H) 3.70-3.77 (m, 1H) 3.90 (s, 3H) 3.94-4.00 (m, 2H) 4.40 (dd, J=14.0, 3.0 Hz, 1H) 6.78 (s, 1H) 6.90 (d, J=8.9 Hz, 1H) 7.32 (dd, J=8.9, 2.8 Hz, 1H) 7.95 (d, J=2.8 Hz, 1H); MS (ESI) m/z 423 (M+H)$^+$.

Example 272

N-[(2Z)-5-tert-butyl-3-(1,4-dioxan-2-ylmethyl)-1,3-thiazol-2(3H)-ylidene]-5-chloro-2-methoxybenzamide Example 244A and 2-(iodomethyl)-1,4-dioxane were processed using the method described in Example 246 to afford the title compound. $^1$H NMR (500 MHz, CDCl$_3$) δ ppm 1.34 (s, 9H) 3.32 (dd, J=111.60, 10.1 Hz, 1H) 3.52-3.62 (m, 1H) 3.68-3.76 (m, 2H) 3.80 (dd, J=11.0, 2.8 Hz, 1H) 3.85-3.91 (m, 1H) 3.90 (s, 3H) 4.00-4.06 (m, 1H) 4.05 (dd, J=19.5, 6.71 Hz, 1H) 4.33 (dd, J=10.7, 3.1 Hz, 1H) 6.74 (s, 1H) 6.90 (d, J=8.9 Hz, 1H) 7.33 (dd, J=8.9, 2.8 Hz, 1H) 7.92 (d, J=2.8 Hz, 1H); MS (ESI) m/z 425 (M+H)$^+$.

Example 273

N-[(2Z)-5-tert-butyl-3-{[(4S)-2,2-dimethyl-1,3-dioxolan-4-yl]methyl}-1,3-thiazol-2(3H)-ylidene]-5-chloro-2-methoxybenzamide Example 244A and (R)-(2,2-dimethyl-1,3-dioxolan-4-yl) methyl 4-methylbenzenesulfonate were processed using the method described in Example 246 to afford the title compound. $^1$H NMR (500 MHz, CDCl$_3$) δ ppm 1.34 (s, 9H) 1.36 (s, 3H) 1.37 (s, 3H) 3.76 (dd, J=8.9, 6.7 Hz, 1H) 3.90 (s, 3H) 4.11 (dd, J=8.9, 6.4 Hz, 1H) 4.31-4.42 (m, 2H) 4.47-4.53 (m, 1H) 6.80 (s, 1H) 6.90 (d, J=8.9 Hz, 1H) 7.32 (dd, J=8.9, 2.75 Hz, 1H) 7.90 (d, J=3.1 Hz, 1H); MS (ESI) m/z 439 (M+H)$^+$.

Example 274

N-[(2Z)-5-tert-butyl-3-{[(4R)-2,2-dimethyl-1,3-dioxolan-4-yl]methyl}-1,3-thiazol-2(3H)-ylidene]-5-chloro-2-methoxybenzamide Example 244A and (S)-(2,2-dimethyl-1,3-dioxolan-4-yl) methyl 4-methylbenzenesulfonate were processed using the method described in Example 246 to afford the title compound. $^1$H NMR (500 MHz, CDCl$_3$) δ ppm 1.35 (s, 9H) 1.36 (s, 3H) 1.37 (s, 3H) 3.76 (dd, J=8.9, 6.71 Hz, 1H) 3.90 (s, 3H) 4.11 (dd, J=8.9, 6.4 Hz, 1H) 4.33-4.43 (m, 2H) 4.48-4.54 (m, 1H) 6.81 (s, 1H) 6.90 (d, J=8.9 Hz, 1H) 7.33 (dd, J=8.9, 2.8 Hz, 1H) 7.89 (d, J=2.8 Hz, 1H); MS (ESI) m/z 439 (M+H)$^+$.

Example 275

N-[(2Z)-5-tert-butyl-3-(tetrahydrofuran-3-ylmethyl)-1,3-thiazol-2(3H)-ylidene]-5-chloro-2-methoxybenzamide Example 244A and the product from Example 162A were processed using the method described in Example 246 to afford the title compound. $^1$H NMR (500 MHz, CDCl$_3$) δ ppm 1.35 (s, 9H) 1.71-1.79 (m, 1H) 1.98-2.10 (m, 1H) 2.90-3.02 (m, 1H) 3.64 (dd, J=9.15, 5.19 Hz, 1H) 3.76-3.83 (m, 2H) 3.90 (s, 3H) 3.95-4.01 (m, 1H) 4.08 (dd, J=13.43, 7.93 Hz, 1H) 4.24 (dd, J=13.12, 7.32 Hz, 1H) 6.63 (s, 1H) 6.91 (d, J=8.85 Hz, 1H) 7.33 (dd, J=8.85, 3.05 Hz, 1H) 7.97 (d, J=3.05 Hz, 1H); MS (ESI) m/z 409 (M+H)$^+$.

Example 276

N-[(2Z)-5-tert-butyl-3-(tetrahydro-2H-pyran-3-ylmethyl)-1,3-thiazol-2(3H)-ylidene]-5-chloro-2-methoxybenzamide Example 244A and the product from Example 225A were processed using the method described in Example 246 to afford the title compound. $^1$H NMR (500 MHz, CDCl$_3$) δ ppm 1.34 (s, 9H) 1.39-1.48 (m, 1H) 1.56-1.67 (m, 1H) 1.69-1.77 (m, 1H) 1.78-1.89 (m, 1H) 2.23-2.34 (m, 1H) 3.34 (dd, J=11.0, 8.2 Hz, 1H) 3.53 (ddd, J=9.2, 3.1 Hz, 1H) 3.74-3.85 (m, 2H) 3.90 (s, 3H) 4.04-4.16 (m, 2H) 6.60 (s, 1H) 6.90 (d, J=8.9 Hz, 1H) 7.33 (dd, J=8.9, 2.75 Hz, 1H) 7.98 (d, J=2.8 Hz, 1H); MS (ESI) m/z 423 (M+H)$^+$.

Example 277

N-[(2Z)-5-tert-butyl-3-{[(2S)-5-oxotetrahydrofuran-2-yl]methyl}-1,3-thiazol-2(3H)-ylidene]-5-chloro-2-methoxybenzamide

Example 277A (S)-(5-oxotetrahydrofuran-2-yl)methyl 4-methylbenzenesulfonate

A mixture of (S)-5-(hydroxymethyl)dihydrofuran-2(3H)-one, para-toluenesulfonyl chloride and pyridine were processed using the method described in Example 162A to afford the title compound MS (ESI) m/z 288 (M+18)⁺.

Example 277B

N-[(2Z)-5-tert-butyl-3-{[(2S)-5-oxotetrahydrofuran-2-yl]methyl}-1,3-thiazol-2(3H)-ylidene]-5-chloro-2-methoxybenzamide Example 244A and the product from Example 277A were processed using the method described in Example 246 to afford the title compound. $^1$H NMR (400 MHz, CDCl$_3$) δ ppm 1.34 (s, 9H) 2.07-2.20 (m, 1H) 2.34-2.48 (m, 2H) 2.49-2.61 (m, 1H) 3.90 (s, 3H) 4.39 (dd, J=14.4, 6.1 Hz, 1H) 4.55 (dd, J=14.4, 3.1 Hz, 1H) 4.92-5.01 (m, 1H) 6.75 (s, 1H) 6.92 (d, J=8.9 Hz, 1H) 7.35 (dd, J=8.9, 2.8 Hz, 1H) 7.92 (d, J=2.8 Hz, 1H); MS (ESI) m/z 423 (M+H)⁺.

Example 278

N-[(2Z)-5-acetyl-4-methyl-3-[(2R)-tetrahydrofuran-2-ylmethyl]-1,3-thiazol-2(3H)-ylidene]-1-benzofuran-5-carboxamide

Example 278A (R)-1-((tetrahydrofuran-2-yl)methyl)thiourea

To a 0° C. solution of (R)-(tetrahydrofuran-2-yl)methanamine (5.0 g, 49.5 mmol) and triethylamine (690 uL, 4.95 mmol) in tetrahydrofuran (100 mL) was added carbon disulfide (5.65 g, 74.3 mmol). Stirring was continued for 0.5 hour followed by the dropwise addition of 30% hydrogen peroxide (5.6 g, 49.5 mmol) so that the temperature was maintained below 40° C. The reaction mixture was poured into water, and extracted with ethyl acetate. The organic extract was dried (Na$_2$SO$_4$), filtered and concentrated to afford an oil. The residue was dissolved in tetrahydrofuran, and treated with 7 N ammonia in methanol (14.3 mL, 100 mmol). The precipitate was collected by filtration and washed with water to afford the title compound.

Example 278B (R)-1-(2-imino-4-methyl-3-((tetrahydrofuran-2-yl)methyl)-2,3-dihydrothiazol-5-yl)ethanone To a solution of pentane-2,4-dione (451 mg, 4.5 mmol) and the product from Example 278A (786 mg, 4.5 mmol) in tetrahydrofuran (5 mL) was added a mixture of dimethylsulfoxide (0.64 mL, 9.0 mmol) and concentrated HCl (0.75 mL, 9.0 mmol). The reaction mixture was heated at 40° C. for 12 hours. After cooling to ambient temperature, the mixture was diluted with ethyl acetate and washed with saturated aqueous NaHCO$_3$. The organic extract was dried (Na$_2$SO$_4$), filtered and concentrated to afford the title compound. MS (ESI) m/z 241 (M+H)⁺.

Example 278C

N-[(2Z)-5-acetyl-4-methyl-3-[(2R)-tetrahydrofuran-2-ylmethyl]-1,3-thiazol-2(3H)-ylidene]-1-benzofuran-5-carboxamide Example 298B and benzofuran-5-carboxylic acid were processed using the method described in Example 223A to afford the title compound. $^1$H NMR (400 MHz, CDCl$_3$) δ ppm 1.73-1.84 (m, 1H) 1.91-2.03 (m, 2H) 2.16-2.26 (m, 1H) 2.50 (s, 3H) 2.81 (s, 3H) 3.75 (dd, J=14.12, 6.44 Hz, 1H) 3.90 (dd, J=14.1, 7.4 Hz, 1H) 4.16 (dd, J=13.9, 8.0 Hz, 1H) 4.41-4.51 (m, 1H) 4.71 (dd, J=13.8, 3.4 Hz, 1H) 6.88 (s, 1H) 7.55 (d, J=8.6 Hz, 1H) 7.68 (t, J=2.2 Hz, 1H) 8.30 (dt, J=8.6, 1.5 Hz, 1H) 8.57-8.59 (m, 1H); MS (ESI) m/z 385 (M+H)⁺.

Example 279

N-[(2Z)-5-(1-hydroxy-1-methylethyl)-4-methyl-3-[(2R)-tetrahydrofuran-2-ylmethyl]-1,3-thiazol-2(3H)-ylidene]-1-benzofuran-5-carboxamide Example 278C (300 mg, 0.78 mmol) in tetrahydrofuran (20 mL) was treated with a solution of methyllithium in diethyl ether (1.56 mL, 1.56 mmol) at −78° C. The reaction mixture was stirred at −78° C. for 4 hours and quenched with saturated aqueous NH$_4$Cl, warmed to ambient temperature and extracted with ethyl acetate. The organic extract was dried (Na$_2$SO$_4$), filtered and concentrated. Purification by reverse phase HPLC afforded the title compound. $^1$H NMR (500 MHz, CDCl$_3$) δ ppm 1.65 (s, 3H) 1.67 (s, 3H) 1.74-1.84 (m, 1H) 1.89-2.00 (m, 2H) 1.99-2.02 (m, 1H) 2.12-2.22 (m, 1H) 2.55 (s, 3H) 3.76 (dd, J=14.3, 7.6 Hz, 1H) 3.90 (dd, J=15.0, 6.7 Hz, 1H) 4.06 (dd, J=13.7, 7.3 Hz, 1H) 4.40-4.49 (m, 1H) 4.64 (dd, J=14.0, 3.7 Hz, 1H) 6.85 (dd, J=2.1, 0.9 Hz, 1H) 7.52 (d, J=8.5 Hz, 1H) 7.66 (d, J=2.1 Hz, 1H) 8.30 (dd, J=8.5, 1.5 Hz, 1H) 8.57 (d, J=1.5 Hz, 1H); MS (ESI) m/z 401 (M+H)⁺.

Example 280

N-[(2Z)-5-acetyl-4-methyl-3-[(2R)-tetrahydrofuran-2-ylmethyl]-1,3-thiazol-2(3H)-ylidene]-5-chloro-2-(2,2,2-trifluoroethoxy)benzamide

Example 280A

N-((2Z)-5-acetyl-4-methyl-3-(((2R)-tetrahydrofuran-2-yl)methyl)thiazol-2(3H)-ylidene)-5-chloro-2-fluorobenzamide Example 278B and 5-chloro-2-fluorobenzoic acid were processed using the method described in Example 223A to afford the title compound. MS (ESI) m/z 397 (M+H)⁺.

Example 280B

N-[(2Z)-5-acetyl-4-methyl-3-[(2R)-tetrahydrofuran-2-ylmethyl]-1,3-thiazol-2(3H)-ylidene]-5-chloro-2-(2,2,2-trifluoroethoxy)benzamide To the solution of the product from Example 280A (360 mg, 0.91 mmol) in tetrahydrofuran (4 mL) was added 2,2,2-trifluoroethanol (227 mg, 2.27 mmol) and a 1.0 M solution of potassium tert-butoxide in tetrahydrofuran (2.27 mL, 2.27 mmol). The reaction mixture was stirred at room temperature for 24 hours. The mixture was diluted with water, and extracted with ethyl acetate. The organic extract was dried (Na$_2$SO$_4$), filtered and concentrated. Purification by reverse phase HPLC afforded the title compound. $^1$H NMR (500 MHz, CDCl$_3$) δ ppm 1.64-1.75 (m, 1H) 1.90-2.00 (m, 2H) 2.10-2.20 (m, 1H) 2.51 (s, 3H) 2.80 (s, 3H) 3.73 (dd, J=1.59, 7.3 Hz, 1H) 3.88 (dd, J=15.3, 6.7 Hz, 1H) 4.07 (dd, J=13.7, 8.2 Hz, 1H) 4.33-4.41 (m, 1H) 4.47 (dd, J=16.8, 8.2 Hz, 2H)

4.62 (dd, J=13.7, 2.8 Hz, 1H) 7.03 (d, J=8.5 Hz, 1H) 7.39 (dd, J=8.5, 2.8 Hz, 1H) 8.02 (d, J=2.8 Hz, 1H); MS (ESI) m/z 477 (M+H)⁺.

Example 281

N-[(2Z)-5-tert-butyl-3-[(5-methyltetrahydrofuran-2-yl)methyl]-1,3-thiazol-2(3H)-ylidene]-5-chloro-2-methoxybenzamide

Example 281A hex-5-en-2-ol

A solution of hex-5-en-2-one (10 g, 102 mmol) in ether (60 mL) was treated with lithium aluminum hydride (4.0 g, 110 mmol) and the mixture was stirred at room temperature for 1 hour. The reaction mixture was quenched with saturated aqueous $NH_4Cl$, and extracted with ether. The organic extract was dried ($Na_2SO_4$), filtered and concentrated to afford the title compound.

Example 281B 2-(bromomethyl)-5-methyltetrahydrofuran

A solution of the product from Example 281A (6.9 g, 69 mmol in $CH_2Cl_2$ (100 mL) was treated with N-bromosuccinimide (14.7, 83 mmol). The reaction mixture was stirred at room temperature for 48 hours, poured into water, and extracted with $CH_2Cl_2$. The organic extract was dried ($Na_2SO_4$), filtered and concentrated to afford the title compound. MS (ESI) m/z 179 (M+H)⁺.

Example 281C

N-[(2Z)-5-tert-butyl-3-[(5-methyltetrahydrofuran-2-yl)methyl]-1,3-thiazol-2(3H)-ylidene]-5-chloro-2-methoxybenzamide Example 244A and the product from Example 281B were processed using the method described in Example 246 to afford the title compound. ¹H NMR (500 MHz, CDCl₃) δ ppm 1.22 (d, J=6.1 Hz, 3H) 1.33-1.37 (m, 9H) 1.46-1.54 (m, 2H) 1.67-1.76 (m, 1H) 1.91-2.00 (m, 1H) 3.90 (s, 3H) 4.01-4.08 (m, 1H) 4.29-4.34 (m, 2H) 4.39-4.46 (m, 1H) 6.89-6.90 (m, 1H) 6.90-6.91 (m, 1H) 7.32 (dd, J=8.5, 3.1 Hz, 1H) 7.94 (d, J=2.8 Hz, 1H); MS (ESI) m/z 423 (M+H)⁺.

Example 282

N-[(2Z)-5-tert-butyl-3-[(5,5-dimethyltetrahydrofuran-2-yl)methyl]-1,3-thiazol-2(3H)-ylidene]-5-chloro-2-methoxybenzamide

Example 282A 2-methylhex-5-en-2-ol

A 0° C. solution of hex-5-en-2-one (10 g, 102 mmol) in ether (200 mL) was treated dropwise with a 3.0 M solution of methylmagnesium iodide in ether (102 mL, 306 mmol) over 20 minutes. The reaction mixture was gradually warmed to room temperature, and stirred for 1 hour, quenched with water, and filtered through Celite (ether wash). The filtrate was concentrated and the resulting residue was distilled (27-30° C. at 5 mm Hg) to afford the title compound. ¹H NMR (500 MHz, CDCl₃) δ ppm 1.23 (s, 6H) 1.54-1.62 (m, 2H) 2.11-2.19 (m, 2H) 4.96 (dq, J=11.29, 1.83, 1.22 Hz, 1H) 5.05 (dq, J=17.39, 1.53 Hz, 1H) 5.80-5.91 (m, 1H).

Example 282B 5-(bromomethyl)-2,2-dimethyltetrahydrofuran

The product from 282A was processed using the method described in Example 281B to afford the title compound. ¹H NMR (400 MHz, CDCl₃) δ ppm 1.23 (s, 3H) 1.29 (s, 3H) 1.73-1.82 (m, 2H) 1.81-1.91 (m, 1H) 2.10-2.22 (m, 1H) 3.32 (dd, J=10.13, 7.06 Hz, 1H) 3.43 (dd, J=9.82, 4.60 Hz, 1H) 4.16-4.27 (m, 1H).

Example 282C

N-[(2Z)-5-tert-butyl-3-[(5,5-dimethyltetrahydrofuran-2-yl)methyl]-1,3-thiazol-2(3H)-ylidene]-5-chloro-2-methoxybenzamide Example 244A and the product from Example 282B were processed using the method described in Example 246 to afford the title compound. ¹H NMR (400 MHz, dimethylsulfoxide-d₆) δ ppm 1.13 (s, 3H) 1.17 (s, 3H) 1.31 (s, 9H) 1.54-1.62 (m, 1H) 1.64-1.72 (m, 1H) 1.72-1.80 (m, 1H) 1.93-2.04 (m, 1H) 3.78 (s, 3H) 4.12 (dd, J=15.34, 6.75 Hz, 1H) 4.29-4.39 (m, 2H) 7.10 (d, J=8.59 Hz, 1H) 7.20 (s, 1H) 7.44 (dd, J=8.59, 2.76 Hz, 1H) 7.64 (d, J=2.76 Hz, 1H); MS (ESI) m/z 437 (M+H)⁺.

Example 283

N-[(2Z)-5-tert-butyl-3-[(2R)-tetrahydrofuran-2-ylmethyl]-1,3-thiazol-2(3H)-ylidene]-5-chloro-2-(2-methoxyethoxy)benzamide

Example 283A

Example 240C and 5-chloro-2-fluorobenzoic acid were processed using the method described in Example 223A to afford the title compound. MS (ESI) ml/z 397 (M+H)⁺.

Example 283B

N-[(2Z)-5-tert-butyl-3-[(2R)-tetrahydrofuran-2-ylmethyl]-1,3-thiazol-2(3H)-ylidene]-5-chloro-2-(2-methoxyethoxy)benzamide Example 283A and 2-methoxyethanol were processed using the method described in Example 280B to afford the title compound. ¹H NMR (500 MHz, CDCl₃) δ ppm 1.36 (s, 9H) 1.62-1.71 (m, 1H) 1.74-1.83 (m, 1H) 1.84-1.93 (m, 1H) 2.02-2.11 (m, 1H) 3.42 (s, 3H) 3.77 (m, 3H) 3.84 (dd, J=15.0, 6.71 Hz, 1H) 4.21 (t, J=5.2 Hz, 2H) 4.22-4.31 (m, 2H) 4.43 (dd, J=10.4 Hz, 1H) 6.90 (s, 1H) 6.97 (d, J=8.9 Hz, 1H) 7.30 (dd, J=8.5, 2.8 Hz, 1H) 7.89 (d, J=2.8 Hz, 1H) MS (ESI) m/z 477 (M+H)⁺.

Example 284

N-[(2Z)-5-tert-butyl-3-[(2R)-tetrahydrofuran-2-ylmethyl]-1,3-thiazol-2(3H)-ylidene]-6-chloroquinoline-8-carboxamide Example 240C and 6-chloroquinoline-8-carboxylic acid were processed using the method described in Example 223A to afford the title compound. $^1$H NMR (400 MHz, CDCl$_3$) δ ppm 1.38 (s, 9H) 1.63-1.74 (m, 1H) 1.74-1.83 (m, 1H) 1.82-1.93 (m, 1H) 1.98-2.08 (m, 1H) 3.72-3.88 (m, 2H) 4.18-4.30 (m, 2H) 4.40 (dd, J=13.2, 2.5 Hz, 1H) 6.90 (s, 1H) 7.40 (dd, J=8.3, 4.0 Hz, 1H) 7.82 (d, J=2.5 Hz, 1H) 7.99 (d, J=2.2 Hz, 1H) 8.06 (dd, J=8.3, 1.84 Hz, 1H) 9.02 (dd, J=4.3, 1.84 Hz, 1H); MS (ESI) m/z 430 (M+H)$^+$.

Example 285

5-chloro-2-methoxy-N-[(2Z)-5-(1-methylcyclopropyl)-3-[(2R)-tetrahydrofuran-2-ylmethyl]-1,3-thiazol-2(3H)-ylidene]benzamide Example 285A 2-(2-aminothiazol-5-yl)propane-2-ol To a −78° C. solution of thiazol-2-amine (7.0 g, 69.9 mmol) in tetrahydrofuran (200 ml) was added a 10.0 M solution of butyllithium in hexane (14 mL, 140 mmol). The mixture was stirred at −78° C. for 1 hour and chlorotrimethylsilane (15.2 g, 140 mmol) was added dropwise. The mixture was allowed to warm up to −40° C., cooled to −78° C. and a 10.0 M solution of butyllithium in hexane (7.0, 70 mmol) was added After 10 minutes, propan-2-one (8.12 g, 140 mmol) was added and the mixture was stirred for 12 hours. The reaction mixture was quenched with saturated aqueous NH$_4$Cl and extracted with ether. The organic extract was dried (Na$_2$SO$_4$), filtered and concentrated. The residue was purified by column chromatography using an Analogix® Intelliflash280™ (SiO$_2$, 0-100% ethyl acetate in hexanes) to afford the title compound. $^1$H NMR (500 MHz, CDCl$_3$) δ ppm 1.61 (s, 6H) 5.04-5.19 (brs, 2H) 6.89 (s, 1H); MS (ESI) m/z 159 (M+H)$^+$.

Example 285B (R)-5-(prop-1-en-2-yl)-3-((tetrahydrofuran-2-yl)methyl)thiazol-2(3H)-imine Example 285A and the product from Example 208A were processed using the method described in Example 240C to afford the title compound. MS (ESI) m/z 225 (M+H)$^+$.

Example 285C (R,Z)-5-chloro-2-methoxy-N-(5-(prop-1-en-2-yl)-3-((tetrahydrofuran-2-yl)methyl)thiazol-2(3H)-ylidene)benzamide Example 285B and the product from Example 205B were processed using the method described in Example 223A to afford the title compound. MS (ESI) m/z 393 (M+H)$^+$.

Example 285D 5-chloro-2-methoxy-N-[(2Z)-5-(1-methylcyclopropyl)-3-[(2R)-tetrahydrofuran-2-ylmethyl]-1,3-thiazol-2(3H)-ylidene]benzamide A 20 mL vial was charged with 1 mL of CH$_2$Cl$_2$ and 1,2-dimethoxyethane (110 mg, 1.22 mmol). The solution was cooled to −10° C. and diethylzinc (151 mg, 1.22 mmol) was added. To this mixture was added dropwise diiodomethane (654 mg, 2.44 mmol). After the addition was complete, the resulting clear solution was stirred for 10 minutes at −10° C. A solution of Example 285C (80 mg, 0.204 mmol) was added. The mixture was allowed to warm to room temperature, stirred for 16 hours, then concentrated. Purification by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow Tate of 40 mL/minutes) afforded the title compound for Example 285D and the title compound for Example 286. Characterization for Example 285D: $^1$H NMR (400 MHz, CDCl$_3$) δ ppm 0.97-1.02 (m, 2H) 1.02-1.08 (m, 2H) 1.50 (s, 3H) 1.62-1.72 (m, 1H) 1.82-1.91 (m, 1H) 1.93-2.04 (m, 1H) 2.21-2.31 (m, 1H) 3.72-3.86 (m, 2H) 4.04 (s, 3H) 4.29-4.39 (m, 1H) 4.48-4.61 (m, 1H) 4.80-4.93 (m, 1H) 7.02 (d, J=9.2 Hz, 1H) 7.54 (dd, J=8.9, 2.8 Hz, 1H) 7.53-7.55 (m, 1H) 8.04 (d, J=2.8 Hz, 1H); MS (ESI) m/z 407 (M+H)$^+$.

Example 286

5-chloro-N-[(2Z)-5-(1-hydroxy-3-iodo-1-methylpropyl)-3-[(2R)-tetrahydrofuran-2-ylmethyl]-1,3-thiazol-2(3H)-ylidene]-2-methoxybenzamide See Example 285D for experimental details: $^1$H NMR (500 MHz, CDCl$_3$) δ ppm 1.61 (d, J=1.53 Hz, 3H) 1.63-1.72 (m, 1H) 1.79-1.96 (m, 2H) 2.03-2.14 (m, 2H) 2.40-2.47 (m, 2H) 3.02-3.11 (m, 1H) 3.19 (dd, J=17.4, 9.2 Hz, 1H) 3.78 (dd, J=15.0, 7.0 Hz, 1H) 3.83-3.89 (m, 1H) 3.91 (s, 3H) 4.15-4.22 (m 1H) 4.25-4.31 (m, 1H) 6.91 (d, J=8.9 Hz, 1H) 7.11 (d, J=5.5 Hz, 1H) 7.34 (dd, J=8.5, 3.1 Hz, 1H) 7.96 (d, J=2.8 Hz, 1H); MS (ESI) m/z 550 (M+H)$^+$.

Example 287

N-[(2Z)-5-tert-butyl-3-[(2R)-tetrahydrofuran-2-ylmethyl]-1,3-thiazol-2(3H)-ylidene]-5-chloro-2-[(1-methylcyclopropyl)methoxy]benzamide The product from 283A and (1-methylcyclopropyl)methanol were processed using the method described in Example 280B to afford the title compound. $^1$H NMR (500 MHz, CDCl$_3$) δ ppm 0.36 (t, J=4.8 Hz, 2H) 0.55 (t, J=4.6 Hz, 2H) 1.22 (s, 3H) 1.36 (s, 9H) 1.61-1.70 (m, 1H) 1.74-1.83 (m, 1H) 1.83-1.92 (m, 1H) 2.01-2.10 (m, 1H) 3.77 (dd, J=14.3, 7.6 Hz, 1H) 3.81 (s, 2H) 3.84 (dd, J=15.9, 8.2 Hz, 1H) 4.21 (dd, J=13.4, 6.41 Hz, 1H) 4.23-4.29 (m, 1H) 4.42 (dd, J=13.4, 2.4 Hz, 1H) 6.86 (d, J=9.5 Hz, 1H) 6.87-6.88 (m, 1H) 7.26 (dd, J=7.9, 3.7 Hz, 1H) 7.81 (d, J=2.8 Hz, 1H); MS (ESI) m/z 463 (M+H)$^+$.

Example 288

N-[(2Z)-5-tert-butyl-3-[(2R)-tetrahydrofuran-2-ylmethyl]-1,3-thiazol-2(3H)-ylidene]-5-chloro-2-isopropoxybenzamide Example 283A and propan-2-ol were processed using the method described in Example 280B to afford the title compound. $^1$H NMR (500 MHz, CDCl$_3$) δ ppm 1.35 (s, 9H) 1.35 (d, J=5.8 Hz, 6H) 1.63-1.71 (m, 1H) 1.75-1.82 (m, 1H) 1.83-1.92 (m, 1H) 2.01-2.10 (m, 1H) 3.77 (dd, J=14.65, 7.32 Hz, 1H) 3.85 (dd, J=14.7, 6.7 Hz, 1H) 4.20 (dd, J=13.7, 6.4 Hz, 1H) 4.24-4.30 (m, 1H) 4.42 (dd, J=13.4, 2.8 Hz, 1H) 4.49-4.57 (m, 1H) 6.86 (s, 1H) 6.89 (d, J=8.9 Hz, 1H) 7.26 (dd, J=8.9, 2.8 Hz, 1H) 7.84 (d, J=2.8 Hz, 1H); MS (ESI) m/z 437 (M+H)$^+$.

Example 289

N-[(2Z)-5-tert-butyl-3-[(2R)-tetrahydrofuran-2-ylmethyl]-1,3-thiazol-2(3H)-ylidene]-5-chloro-2-ethoxybenzamide Example 283A and ethanol were processed using the method described in Example 280B to afford the title compound. $^1$H NMR (500 MHz, CDCl$_3$) δ ppm 1.35 (s, 9H) 1.44 (t, J=7.02 Hz, 3H) 1.62-1.73 (m, 1H) 1.75-1.83 (m, 1H) 1.84-1.92 (m, 1H) 2.01-2.11 (m, 1H) 3.77 (dd, J=13.7, 7.6 Hz, 1H) 3.84 (dd, J=14.7, 6.7 Hz, 1H) 4.13 (dd, J=14.0, 7.2 Hz, 2H) 4.22 (dd, J=3.4, 6.0 Hz, 1H) 4.25-4.31 (m, 1H) 4.41 (dd, J=13.4, 2.8 Hz, 1H) 6.86 (s, 1H) 6.89 (d, J=8.9 Hz, 1H) 7.29 (dd, J=8.9, 2.8 Hz, 1H) 7.91 (d, J=2.8 Hz, 1H); MS (ESI) m/z 423 (M+H)$^+$.

Example 290

N-[(2Z)-5-tert-butyl-3-[(2R)-tetrahydrofuran-2-ylmethyl]-1,3-thiazol-2(3H)-ylidene]-5-chloro-2-(tetrahydrofuran-3-yloxy)benzamide Example 283A and tetrahydrofuran-3-ol were processed using the method described in Example 280B to afford the title compound. $^1$H NMR (500 MHz, CDCl$_3$) δ ppm $^1$H NMR (500 MHz, CDCl$_3$) δ ppm 1.36 (s, 9H) 1.61-1.70 (m, 1H) 1.76-1.83 (m, 1H) 1.84-1.93 (m, 1H) 2.03-2.10 (m, 1H) 2.11-2.25 (m, 2H) 3.77 (dd, J=14.0, 7.3 Hz, 1H) 3.82-3.91 (m, 2H) 3.98 (dd, J=15.3, 8.5 Hz, 1H) 4.02 (d, J=3.7 Hz, 2H) 4.20 (ddd, J=6.4, 1.5 Hz, 1H) 4.23-4.30 (m, 1H) 4.41 (dd, J=13.7, 3.1 Hz, 1H) 4.88-5.00 (m, 1H) 6.83 (dd, J=8.9, 0.6 Hz, 1H) 6.88 (d, J=0.9 Hz, 1H) 7.28 (dd, J=8.9, 2.75 Hz, 1H) 7.87 (t, J=3.1 Hz, 1H); MS (ESI) m/z 423 (M+H)$^+$.

Example 291

N-[(2)-5-tert-butyl-3-[(2R)-tetrahydrofuran-2-ylmethyl]-1,3-thiazol-2(3H)-ylidene]-5-chloro-2-[(2-methoxyethyl)methyl)amino]benzamide A mixture of the product from Example 283A (120 mg, 0.3 mmol), 2-methoxy-N-methylethanamine (54 mg, 0.6 mmol) and triethylamine (127 ul, 0.91 mmol) in tetrahydrofuran (1 mL) was heated at 120° C. in a microwave (CEM) for 2 hours. The reaction mixture was diluted with water and extracted with ethyl acetate. The organic extract was died (Na$_2$SO$_4$), filtered, and concentrated. Purification by reverse phase preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes) to afford the title compound afforded the title compound. $^1$H NMR (500 MHz, CDCl$_3$) δ ppm 1.36 (s, 9H) 1.62-1.71 (m, 1H) 1.78-1.86 (m, 1H) 1.86-1.93 (m, 1H) 2.01-2.11 (m, 1H) 2.89 (s, 3H) 3.26 (s, 3H) 3.29 (t, J=6.1 Hz, 2H) 3.54 (t, J=6.4 Hz, 2H) 3.78 (dd, J=14.7, 7.3 Hz, 1H) 3.85 (dd, J=15.0, 8.2 Hz, 1H) 4.18 (dd, J=13.7, 6.4 Hz, 1H) 4.23-4.30 (m, 1H) 4.40 (dd, J=13.7, 3.1 Hz, 1H) 6.85 (s, 1H) 6.92 (d, J=8.9 Hz, 1H) 7.20 (dd, J=8.9, 2.8 Hz, 1H) 7.67 (d, J=2.4 Hz, 1H); MS (ESI) m/z 466 (M+H)$^+$.

Example 292

N-[(2Z)-5-tert-butyl-3-[(2R)-tetrahydrofuran-2-ylmethyl]-1,3-thiazol-2(3H)-ylidene]-5-chloro-2-(difluoromethoxy)benzamide Example 240C and 5-chloro-2-(difluoromethoxy)benzoic acid were processed using the method described in Example 223A to afford the title compound. $^1$H NMR (500 MHz, CDCl$_3$) δ ppm 1.36 (s, 9H) 1.60-1.69 (m, 1H) 1.76-1.84 (m, 1H) 1.85-1.93 (m, 1H) 2.02-2.12 (m, 1H) 3.78 (dd, J=13.7, 7.3 Hz, 1H) 3.85 (dd, J=15.0, 6.7 Hz, 1H) 4.20 (dd, J=13.4, 6.4 Hz, 1H) 4.24-4.30 (m, 1H) 4.44 (dd, J=13.7, 2.8 Hz, 1H) 6.73 (t, J=6.3 Hz, 1H) 6.91 (s, 1H) 7.17 (d, J=8.5 Hz, 1H) 7.38 (dd, J=8.5, 2.8 Hz, 1H) 8.05 (d, J=2.8 Hz, 1H); MS (ESI) m/z 445 (M+H)$^+$.

Example 293

N-[(2Z)-5-tert-butyl-3-[(2R)-tetrahydrofuran-2-ylmethyl]-1,3-thiazol-2(3H)-ylidene]-5-chloro-2-(trifluoromethoxy)benzamide Example 240C and 5-chloro-2-(trifluoromethoxy)benzoic acid were processed using the method described in Example 223A to afford the title compound. $^1$H NMR (500 MHz, CDCl$_3$) δ ppm 1.36 (s, 9H) 1.58-1.67 (m, 1H) 1.75-1.83 (m, 1H) 1.84-1.93 (m, 1H) 2.01-2.11 (m, 1H) 3.77 (dd, J=13.7, 6.4 Hz, 1H) 3.84 (dd, J=15.0, 6.7 Hz, 1H) 4.18 (dd, J=13.7, 6.7 Hz, 1H) 4.22-4.29 (m, 1H) 4.46 (dd, J=13.7, 2.8 Hz, 1H) 6.91 (s, 1H) 7.23 (dd, J=8.5, 1.2 Hz, 1H) 7.40 (dd, J=8.9, 2.8 Hz, 1H) 8.06 (d, J=2.8 Hz, 1H); MS (ESI) m/z 463 (M+H)$^+$.

Example 294

N-[(2Z)-5-tert-butyl-3-[(2R)-tetrahydrofuran-2-ylmethyl]-1,3-thiazol-2(3H)-ylidene]-5-chloro-2-(2,2,2-trifluoroethoxy)benzamide The product from 283A and 2,2,2-trifluoroethanol were processed using the method described in Example 280B to afford the title compound. $^1$H NMR (500 MHz, CDCl$_3$) δ ppm 1.37 (s, 9H) 1.60-1.69 (m, 1H) 1.76-1.84 (m, 1H) 1.85-1.93 (m, 1H) 2.02-2.11 (m, 1H) 3.78 (dd, J=13.7, 7.3 Hz, 1H) 3.85 (dd, J=15.0, 7.0 Hz, 1H) 4.21 (dd, J=13.4, 6.4 Hz, 1H) 4.24-4.29 (m, 1H) 4.43 (dd, J=11.0, 2.8 Hz, 1H) 4.47 (dd, J=17.1, 8.5 Hz, 2H) 6.91 (s, 1H) 7.01 (d, J=8.9 Hz, 1H) 7.33 (dd, J=8.5, 2.8 Hz, 1H) 7.99 (d, J=2.8 Hz, 1H); MS (ESI) m/z 477 (M+H)$^+$.

Example 295

N-[(2Z)-5-tert-butyl-3-[(2R)-tetrahydrofuran-2-ylmethyl]-1,3-thiazol-2(3H)-ylidene]-5-chloro-2-[3-(dimethylamino)propoxy]benzamide The product from 283A and 3-(dimethylamino)propan-1-ol were processed using the method described in Example 280B to afford the title compound. $^1$H NMR (500 MHz, CDCl$_3$) δ ppm 1.38 (s, 9H) 1.62-1.71 (m, 1H) 1.84-1.91 (m, 1H) 1.91-1.98 (m, 1H) 2.09-2.19 (m, 1H) 2.29-2.36 (m, 2H) 3.04-3.09 (m, J=4.9 Hz, 2H) 3.81 (dd, J=13.7, 6.4 Hz, 1H) 3.87 (dd, J=15.0, 7.0 Hz, 1H) 4.25-4.34 (m, 4H) 4.51 (d, J=2.8 Hz, 1H) 6.93 (d, J=9.2 Hz, 1H) 7.00-7.02 (m, 1H) 7.44 (dd, J=8.9, 2.9 Hz, 1H) 8.20 (d, J=2.8 Hz, 1H) 10.35-10.51 (m, 1H); MS (ESI) m/z 480 (M+H)$^+$.

Example 296

5,6-dichloro-N-[(2Z)-4,5-dimethyl-3-(tetrahydrofuran-2-ylmethyl)-1,3-thiazol-2(3H)-ylidene]quinoline-8-carboxamide A mixture of Example 186A (145 mg), 5,6-dichloroquinoline-8-carboxylic acid (99.65 mg) (Bailey J. Heterocycl.

Chem. 1974, 11, 229), 1-hydroxybenzotriazole hydrate (55 mg), 1-ethyl-3-[3-(dimethylamino)propyl]-carbodiimide hydrochloride (79 mg) and triethylamine (0.14 mL) in tetrahydrofuran (3 mL) was heated at 70° C. on a shaker overnight, cooled, quenched in saturated NaHCO$_3$ and extracted with ethyl acetate (2×). The organic extracts were dried (Na$_2$SO$_4$), filtered and the solvent was evaporated. The crude material was purified by reverse phase preparative HPLC on a Waters Symmetry C8 column (25 mm×100 mm, 7 μm particle size) using a gradient of 10% to 100% acetonitriile:10 mM ammonium acetate over 8 minutes (10 minutes run time) at a flow rate of 40 mL/minutes) to afford the title compound. $^1$H NMR (300 MHz, CDCl$_3$) δ ppm 1.62-1.75 (m, 1H), 1.85-1.95 (m, 2H), 2.0-2.1 (m, 1H), 2.26 (s, 3H), 2.30 (s, 3H), 3.70-3.77 (m, 1H), 3.83-3.90 (m, 1H), 3.97 (dd, 1H), 4.35-4.42 (m, 1H), 4.55 (dd, 1H), 7.53 (dd, 1H), 8.60 (dd, 1H), 9.07 (m, 1H); MS (DCI/NH$_3$) m/z 436, 438 (M+H)$^+$.

Example 297

6-chloro-N-[(2Z)-4,5-dimethyl-3-(tetrahydrofuran-2-ylmethyl)-1,3-thiazol-2(3H)-ylidene]quinoline-8-carboxamide A mixture of Example 186A (106 mg), 6-chloro-quinoline-8-carboxylic acid (73 mg) (Weyer et al, *Arzneim. Forsch* 1974, 24, 269), 1-hydroxybenzotriazole hydrate (47 mg), 1-ethyl-3-[3-(dimethylamino)propyl]-carbodiimide hydrochloride (69 mg), and triethylamine (0.15 mL) in tetrahydrofuran (2 mL) was heated to 70° C. on a shaker overnight, cooled, poured into saturated NaHCO$_3$ and extracted with ethyl acetate (2×). The organic extracts were dried (Na$_2$SO$_4$), filtered and the solvent was evaporated. The crude material was dissolved in warm methanol and allowed to cool overnight. The solid precipitate was discarded, the filtrate was concentrated to dryness, triturated with cold methanol, and collected to afford the title compound. $^1$H NMR (300 MHz, dimethylsulfoxide-d$_6$) δ ppm 1.56-1.64 (m, 1H), 1.70-1.95 (m, 3H), 2.26 (s, 3H), 2.27 (s, 3H), 3.57-3.65 (m, 1H), 3.73-3.80 (m, 1H), 3.97-4.05 (m, 1H), 4.24-4.35 (m, 2H), 7.60 (dd, 1H), 7.78 (d, 1H), 8.15 (d, 1H), 8.38 (dd, 1H), 8.91 (dd, 1H); MS (DCI/NH$_3$) m/z 402 (M+H)$^+$.

Example 298

6-chloro-N-[(2Z)-5-methyl-3-(tetrahydrofuran-2-ylmethyl)-1,3-thiazol-2(3H)-ylidene]quinoline-8-carboxamide A mixture of Example 149A (142 mg), 6-chloro-quinoline-8-carboxylic acid (105 mg) (Weyer et al, *Arzneim Forsch* 1974, 24, 269), 1-hydroxybenzotriazole hydrate (67 mg), 1-ethyl-3-[3-(dimethylamino)propyl]-carbodiimide hydrochloride (94 mg), and triethylamine (0.15 mL) in tetrahydrofuran (3 mL) was heated to 70° C. for 24 hours, cooled, poured into saturated NaHCO$_3$ and extracted with ethyl acetate (2×). The organic extracts were dried (Na$_2$SO$_4$), filtered and the solvent was evaporated. The crude material was purified by reverse phase preparative HPLC on a Waters Symmetry C8 column (25 mm×100 mm, 7 μm particle size) using a gradient of 10% to 100% acetonitrile: 10 mM ammonium acetate over 8 minutes (10 minutes run time) at a flow rate of 40 mL/minutes) to afford the title compound. $^1$H NMR (300 MHz, CDCl$_3$) δ ppm 1.65-1.72 (m, 1H), 1.80-1.95 (m, 2H), 2.0-2.1 (m, 1H), 2.34 (d, J=1.4 Hz, 3H), 3.74-3.90 (m, 2H), 4.14 (dd, 1H), 4.2-4.3 (m, 1H), 2.34 (d, J=1.4 Hz, 3H), 3.74-3.90 (m, 2H), 4.14 (dd, 1H), 4.2-4.3 (m, 1H), 4.47 (dd, 1H), 6.95 (q, J=1.4 Hz, 1H), 7.42 (dd, 1H), 7.84 (d, 1H), 8.03 (d, 1H), 8.08 (dd, 1H), 9.04 (dd, 1H); MS (DCI/NH$_3$) m/z 388 (M+H)$^+$.

Example 299

5,6-dichloro-N-[(2Z)-5-methyl-3-(tetrahydrofuran-2-ylmethyl)-1,3-thiazol-2(3H)-ylidene]quinoline-8-carboxamide A mixture of Example 149A (117 mg), 5,6-dichloroquinoline-8-carboxylic acid (71 mg), 1-hydroxybenzotriazole hydrate (51 mg), 1-ethyl-3-[3-(dimethylamino)propyl]-carbodiimide hydrochloride (79 mg) and triethylamine (0.15 mL) in tetrahydrofuran was processed and purified according to the method of Example 298 to afford the title compound. $^1$H NMR (300 MHz, CDCl$_3$) δ ppm 1.6-1.71 (m, 1H), 1.78-1.95 (m, 2H), 2.0-2.1 (m, 1H), 2.34 (d, J=1.4 Hz, 3H), 3.72-3.90 (m, 2H), 4.12 (dd, 1H), 4.2-4.3 (m, 1H), 4.46 (dd, 1H), 6.94 (q, J=1.4 Hz, 1H), 7.53 (dd, 1H), 8.60 (dd, 1H), 9.06 (dd, 1H); MS (DCI/NH$_3$) m/z 422 (M+H)$^+$.

Example 300

3-methoxy-N-[(2Z)-5-methyl-3-(tetrahydrofuran-2-ylmethyl)-1,3-thiazol-2(3H)-ylidene]-2-naphthamide A mixture of Example 149A (113 mg), 3-methoxy-2-naphthoic acid (Aldrich) (69 mg), 1-hydroxybenzotriazole hydrate (50 mg), 1-ethyl-3-[3-(dimethylamino)propyl]-carbodiimide hydrochloride (79 mg) and triethylamine (0.15 mL) in tetrahydrofuran (2 mL) was shaken over the weekend at room temperature, poured into saturated NaHCO$_3$ and extracted with ethyl acetate (2×). The organic extracts were dried (Na$_2$SO$_4$), filtered and the solvent was evaporated. The crude material was purified by flash chromatography over silica gel eluting with ethyl acetate:hexane (7:3) to afford the title compound. $^1$H NMR (300 MHz, CDCl$_3$) δ ppm 1.64-1.78 (m, 1H), 1.80-1.95 (m, 2H), 2.02-2.15 (m, 1H), 2.32 (d, J=1.4 Hz, 3H), 3.74-3.92 (m, 2H), 4.01 (s, 3H), 4.2 (dd, 1H), 4.27-4.35 (m, 1H), 4.51 (d, 1H), 6.91 (br s, 1H), 7.20 (s, 1H), 7.33 (m, 1H), 7.46 (m, 1H), 7.73 (d, 1H), 7.81 (d, 1H), 8.42 (s, 1H); MS (DCI/NH$_3$) m/z 383 (M+H)$^+$.

Example 301

N-[(2Z)-5-tert-butyl-3-[(cis)-(3-methoxycyclobutyl) methyl]-1,3-thiazol-2(3H)-ylidene]-5-chloro-2-methoxybenzamide Example 301A cis-3-benzyloxymethylcyclobutanol methyl ether To a solution of cis-3-benzyloxymethylcyclobutanol (Albany Molecular Research Institute, 1.0 g, 5.2 mmol) in 10 mL of tetrahydrofuran at 0° C. was added NaH (0.62 g, 15.6 mmol). The mixture stirred for 15 minutes and iodomethane (0.49 mL, 7.8 mmol) was added and the mixture was allowed to warm to ambient temperature and stirred for 16 hours. Some starting material remained by TLC so additional NaH (0.21, 5.2 mmol) and iodomethane (0.32 mL, 5.2 mmol) were added and the mixture stirred for an additional 2 hours. The mixture was quenched with 10 mL of NH$_4$Cl and diluted with 10 mL of ethyl acetate. The layers were separated and the aqueous layer was extracted twice with 5 mL portions of ethyl acetate. The combined organic extracts were dried over anhydrous Na$_2$SO$_4$, filtered and concentrated under reduced pressure. Purification via column chromatography (SiO$_2$, 75% hexanes in ethyl acetate) afforded the title compound. MS (DCI/NH$_3$) m/z 207 (M+H)$^+$.

Example 301B

(cis-3-methoxycyclobutyl)methanol

A solution of Example 301A (1.05 g, 5.2 mmol) in 10 mL of ethanol was degassed and the flask was filled with N$_2$. This was repeated two additional times. Pd/C (0.1 g, 10 wt %) was added and the mixture was degassed again and flushed with N$_2$. This was repeated two additional times and the flask was put under 1 atm of H$_2$ and the mixture was allowed to stir at ambient temperature for 72 hours. The mixture was degassed and the flask was filled with N$_2$. The reaction mixture was filtered, concentrated under reduced pressure and purified by column chromatography (SiO$_2$, 25% hexanes in ethyl acetate) to afford the title compound. MS (DCI/NH$_3$) m/z 134 (M+NH$_4$)$^+$.

Example 301C

(cis-3-methoxycyclobutyl)methyl 4-methylbenzenesulfonate

Example 301B (0.49 g, 4.2 mmol) and p-toluenesulfonyl chloride (0.80 g, 4.2 mmol) in 5 mL of CH$_2$Cl$_2$ and 5 mL of pyridine were processed as in Example 203A to afford the title compound. MS (DC/NH$_3$) m/z 288 (M+NH$_4$)$^+$.

Example 301D

5-tert-butyl-3-((cis-3-methoxycyclobutyl)methyl) thiazol-2(3H)-imine

Example 240A (0.25 g, 1.6 mmol), Example 301C (0.44 g, 1.6 mmol) and tetrabutylammonium iodide (0.30 g, 0.81 mmol) in 0.5 mL of N,N-dimethylformamide were processed as in Example 240C to afford the title compound. MS (DCI/NH$_3$) m/z 266 (M+H)$^+$.

Example 301E

N-[(2Z)-5-tert-butyl-3-[(cis)-(3-methoxycyclobutyl) methyl]-1,3-thiazol-2(3H)-ylidene]-5-chloro-2-methoxybenzamide Example 301D (0.19 g, 0.75 mmol), triethylamine (0.31 mL, 2.2 mmol) and Example 205B (0.75 mmol) in 10 mL of tetrahydrofuran were processed as in Example 208D to afford the title compound (0.105 g, 0.25 mmol, 33% yield). $^1$H NMR (300 MHz, CD$_3$OD) δ ppm 1.38 (s, 9H), 1.71-1.84 (m, 2H), 2.31-2.47 (m, 3H), 3.21 (s, 3H), 3.71-3.83 (m, 1H), 3.86 (s, 3H), 4.29 (d, J=6.4 Hz, 2H), 7.07 (d, J=8.8 Hz, 1H), 7.14 (s, 1H), 7.40 (dd, J=8.8, 3.1 Hz, 1H), 7.83 (d, J=2.7 Hz, 1H); MS (DCI/NH$_3$) m/z 423 (M+H)$^+$. Anal. Calculated for C$_{21}$H$_{27}$ClN$_2$O$_3$S: C, 59.63; H, 6.43; N, 6.62. Found: C, 59.66; H, 6.28; N, 6.44.

Example 302

N-[(2Z)-5-tert-butyl-3-[(cis)-(3-hydroxycyclobutyl) methyl]-1,3-thiazol-2(3H)-ylidene]-5-chloro-2-methoxybenzamide

Example 302A

(cis-3-(benzyloxymethyl)cyclobutoxy)(tert-butyl) dimethylsilane

To a solution of cis-3-benzyloxymethylcyclobutanol (Albany Molecular Research Institute, 1.0 g, 5.2 mmol) in 50 mL of CH$_2$Cl$_2$ was added imidazole (2.7 g, 39 mmol) followed by tert-butyldimethylsilyl chloride (3.9 g, 26 mmol). This mixture stirred at ambient temperature for 2 hours and was quenched with 10 mL of saturated aqueous NH$_4$Cl. The layers were separated and the aqueous layer was extracted with three 5 mL of portions of CH$_2$Cl$_2$. The combined organic extracts were dried over anhydrous Na$_2$SO$_4$, filtered and concentrated under reduced pressure. Purification via column chromatography (SiO$_2$, 75% hexanes in ethyl acetate) afforded the title compound. MS (DCI/NH$_3$) m/z 307 (M+H)$^+$.

Example 302B

(cis-3-(tert-butyldimethylsilyloxy)cyclobutyl)methanol

A solution of Example 302A (3.7 g, 12 mmol) in 20 mL of ethanol was degassed and the flask was flushed with N$_2$. This was repeated two additional times Pd/C (0.37 g, 10 wt %) was added and the mixhtre was degassed again and flushed with N$_2$. This was repeated two additional times then the flask was put under 1 atm of H$_2$ and the reaction mixture was allowed to stir at ambient temperature for 48 hours. The mixture was degassed and the flask was filled with N$_2$ then the reaction mixture was filtered, concentrated under reduced pressure and purified by column chromatography (SiO$_2$, 50% hexanes in ethyl acetate) to afford the title compound. MS (DCI/NH$_3$) m/z 217 (M+NH$_4$)$^+$.

Example 302C

(cis-3-(tert-butyldimethylsilyloxy)cyclobutyl)methyl 4-methylbenzenesulfonate Example 302B (1.2 g, 5.5 mmol and p-toluenesulfonyl chloride (1.1 g, 5.5 mmol) in 7 mL of CH$_2$Cl$_2$ and 7 mL of pyridine were processed as in Example 203A to afford the title compound. MS (DCI/NH$_3$) m/z 371 (M+H)$^+$, 388 (M+NH$_4$)$^+$.

Example 302D

5-tert-butyl-3-((cis-3-(tert-butyldimethylsilyloxy) cyclobutyl)methyl)thiazol-2(3H)-imine Example 240A (0.72 g, 4.6 mmol), Example 302C (1.7 g, 4.6 mmol) and tetrabutylammonium iodide (0.85 g, 2.3 mmol) in 1.5 mL of N,N-dimethylformamide were processed as in Example 240C to afford the title compound. MS (DCI/NH$_3$) m/z 355 (M+H)$^+$.

Example 302E (Z)—N-(5-tert-butyl-3-((cis-3-(tert-butyldimethylsilyloxy)cyclobutyl)methyl)thiazol-2(3H)-ylidene)-5-chloro-2-methoxybenzamide Example 302D (0.57 g, 1.6 mmol), triethylamine (0.67 mL, 4.8 mmol) and Example 205B (1.6 mmol) in 10 mL of tetrahydrofuran were processed as in Example 208D to afford the title compound. MS (DCI/NH$_3$) m/z 523 (M+H)$^+$.

Example 302F

N-[(2Z)-5-tert-butyl-3-[(cis)-(3-hydroxycyclobutyl)methyl]-1,3-thiazol-2(3H)-ylidene]-5-chloro-2-methoxybenzamide To Example 302E (0.78 g, 1.5 mmol) in 10 mL of tetrahydrofuran at ambient temperature was added tetrabutylammonium fluoride (1 M in tetrahydrofuran, 1.8 mL, 1.8 mmol) dropwise via syringe pump over 30 minutes. The reaction mixture was stirred at ambient temperature for 2 hours and was concentrated under reduced pressure and purified by column chromatography (SiO$_2$, 50% hexanes in ethyl acetate then 100% ethyl acetate) to afford the title compound. $^1$H NMR (300 MHz, CD$_3$OD) δ ppm 1.38 (s, 9H), 1.70-1.82 (m, 2H), 2.25-2.42 (m, 3H), 3.86 (s, 3H), 4.00-4.10 (m, 1H), 4.28 (d, J=6.4 Hz, 2H), 7.07 (d, J=9.2 Hz, 1H), 7.12 (s, 1H), 7.39 (dd, J=8.8, 2.7 Hz, 1H), 7.80 (d, J=2.7 Hz, 1H); MS (DCI/NH$_3$) m/z 409 (M+H)$^+$.

Example 303

N-[(2Z)-5-tert-butyl-3-[((cis)-3-hydroxy-3-methylcyclobutyl)methyl]-1,3-thiazol-2(3H)-ylidene]-5-chloro-2-methoxybenzamide

Example 303A (Z)—N-(5-tert-butyl-3-((3-oxocyclobutyl)methyl)thiazol-2(3H)-ylidene)-5-chloro-2-methoxybenzamide To Example 302F (0.57 g, 1.4 mmol) in 15 mL of CH$_2$Cl$_2$ was added 4-methylmorpholine N-oxide (0.82 g, 7.0 mmol) followed by approximately 0.5 g powdered 4 Å molecular sieves. This mixture was stirred at ambient temperature for 15 minutes and was cooled to 0° C. and tetrapropylammonium perruthenate (49 mg, 0.14 mmol) was added in portions over 5 minutes. The mixture was stirred at 0° C. for 5 minutes and was allowed to warm to ambient temperature and stirred for an additional 90 minutes. The mixture was filtered through Celite, concentrated under reduced pressure and purified by column chromatography (SiO$_2$, 20% hexanes in ethyl acetate) to afford the title compound. MS (DCI/NH$_3$) m/z 407 (M+H)$^+$.

Example 303B

N-[(2Z)-5-tert-butyl-3-[((cis)-3-hydroxy-3-methylcyclobutyl)methyl]-1,3-thiazol-2(3H)-ylidene]-5-chloro-2-methoxybenzamide To Example 302A (0.21 g, 0.52 mmol) in 10 mL of tetrahydrofuran at −78° C. was added a 1.6 M solution of methyllithium in diethyl ether (1.0 mL, 1.6 mmol) dropwise over 5 minutes. The mixture was stirred at −78° C. for 2 hours and was slowly warmed to ambient temperature and was allowed to stir for 18 hours. The mixture was quenched with 5 mL of saturated aqueous NH$_4$Cl and diluted with 5 mL of ethyl acetate. The layers were separated and the aqueous layer was extracted twice with 5 mL of ethyl acetate. The combined organic extracts were dried over anhydrous Na$_2$SO$_4$, filtered and concentrated under reduced pressure. Purification via column chromatography (SiO$_2$, 30% hexanes in ethyl acetate) afforded the title compound. $^1$H NMR (300 MHz, CD$_3$OD) δ ppm 1.32 (s, 3H), 1.38 (s, 9H), 1.90-2.00 (m, 2H), 2.06-2.16 (m, 2H) 2.35-2.52 (m, 1H), 3.86 (s, 3H) 4.30 (d, J=7.1 Hz, 2H), 7.07 (d, J=8.8 Hz, 1H), 7.12 (s, 1H), 7.39 (dd, J=8.8, 2.7 Hz, 1H), 7.80 (d, J=3.1 Hz, 1H); MS (DCI/NH$_3$) m/z 423 (M+H)$^+$. Anal. Calculated for C$_{21}$H$_{27}$ClN$_2$O$_3$S.0.1H$_2$O: C, 59.38; H, 6.45; N, 6.59. Found: C, 59.17; H, 6.62; N, 6.28.

Example 304

5-chloro-N-[(2Z)-5-(1-hydroxy-1-methylethyl)-3-[((cis)-3-methoxycyclobutyl)methyl]-4-methyl-1,3-thiazol-2(3H)-ylidene]-2-methoxybenzamide

Example 304A (Z)—N-(5-acetyl-3-(((cis)-3-methoxycyclobutyl)methyl)-4-methylthiazol-2(3H)-ylidene)-5-chloro-2-methoxybenzamide Example 238A (0.57 g, 1.8 mmol), Example 301C (0.48 g, 1.8 mmol) and potassium tert-butoxide (0.42 g, 3.5 mmol) were processed as described in the procedure for Example 238B to afford the title compound. MS (DCI/NH$_3$) m/z 423 (M+H)$^+$.

Example 304B 5-chloro-N-[(2Z)-5-(1-hydroxy-1-methylethyl)-3-[((cis)-3-methoxycyclobutyl)methyl]-4-methyl-1,3-thiazol-2(3H)-ylidene]-2-methoxybenzamide Example 304A (20 mg, 0.047 mmol) and methyllithium (1.6 M in ether, 88 μL, 0.14 mmol) in 1 mL of tetrahydrofuran were processed as described in Example 239 to afford the title compound. $^1$H NMR (300 MHz, CD$_3$OD) δ ppm 1.61 (s, 6H), 1.80-1.87 (m, 2H), 2.32-2.43 (m, 2H), 2.49 (s, 3H), 3.20-3.24 (m, 1H), 3.20 (s, 3H), 3.34-3.41 (m, 1H), 3.68-3.78 (m, 1H), 3.86 (s, 3H), 4.38 (d, J=6.1 Hz, 2H), 7.06 (d, J=8.8 Hz, 1H), 7.39 (dd, J=8.8, 2.7 Hz, 1H), 7.86 (d, J=2.7 Hz, 1H) MS (DCI/NH$_3$) m/z 439 (M+H)$^+$.

Example 305

N-[(2Z)-5-tert-butyl-3-[2-(2-methoxyethoxy)ethyl]-1,3-thiazol-2(3H)-ylidene]-5-chloro-2-methoxybenzamide

Example 305A 5-tert-butyl-3-(2-(2-methoxyethoxy)ethyl)thiazol-2(3H)-imine hydrobromide A mixture of Example 240A (0.20 g, 1.3 mmol) and 1-bromo-2-(2-methoxyethoxy)ethane (0.27 g, 1.4 mmol) was warmed to 85° C. and was allowed to stir for 24 hours. The mixture was cooled to ambient temperature and the crude solids were triturated with ethanol and ether to afford the title compound. MS (DCI/NH$_3$) m/z 259 (M+H)$^+$.

Example 305B

N-[(2Z)-5-tert-butyl-3-[2-(2-methoxyethoxy)ethyl]-1,3-thiazol-2(3H)-ylidene]-5-chloro-2-methoxybenzamide Example 305A (0.3 g, 0.88 mmol), triethylamine (0.49 mL, 3.5 mmol) and Example 205B (0.88 mmol) in 10 mL of tetrahydrofuran and 1.5 mL of N,N-dimethylformamide were processed as described in Example 208D to afford the title compound. $^1$H NMR (300 MHz, CD$_3$OD) δ ppm 1.38 (s, 9H), 3.31 (s, 3H), 3.47-3.52 (m, 2H), 3.59-3.65 (m, 2H), 3.87 (dd, J=5.4 Hz, 2H), 3.86 (s, 3H), 4.42 (dd, J=5.1 Hz, 2H), 7.07 (d, J=8.8 Hz, 1H), 7.18 (s, 1H), 7.39 (dd, J=8.8, 2.7 Hz, 1H), 7.82 (d, J=2.7 Hz, 1H); MS (DCI/NH$_3$) m/z 427 (M+H)$^+$. Anal. Calculated for C$_{20}$H$_{27}$ClN$_2$O$_4$S: C, 56.26; H, 6.37; N, 6.56. Found: C, 56.06; H, 5.50; N, 6.43.

Example 306

N-[(2Z)-5-tert-butyl-3-(3-methoxypropyl)-1,3-thiazol-2(3H)-ylidene]-5-chloro-2-methoxybenzamide Example 306A 5-tert-butyl-3-(3-methoxypropyl)thiazol-2(3H)-imine A mixture of Example 240A (0.20 g, 1.3 mmol) and 1-bromo-3-methoxypropane (0.22 g, 1.4 mmol) was warmed to 85° C. and was allowed to stir for 24 hours. The mixture was cooled to ambient temperature, concentrated under reduced pressure and purified via column chromatography (SiO$_2$, 10% methanol in ethyl acetate then 9:1:0.1 CH$_2$Cl$_2$:methanol:NH$_4$OH) to afford the title compound MS (DCI/NH$_3$) m/z 229 (M+H)$^+$.

Example 306B

N-[(2Z)-5-tert-butyl-3-(3-methoxypropyl)-1,3-thiazol-2(3H)-ylidene]-5-chloro-2-methoxybenzamide Example 306A (0.25 g, 0.81 mmol), triethylamine (0.34 mL, 2.4 mmol) and Example 205B (0.81 mmol) in 10 mL of tetrahydrofuran and 1 mL of N,N-dimethylformamide were processed as in Example 208D to afford the title compound. $^1$H NMR (300 MHz, CD$_3$OD) δ ppm 1.38 (s, 9H), 2.05-2.17 (m, 2H), 3.32 (s, 3H), 3.41 (t, J=5.9 Hz, 2H), 3.86 (s, 3H), 4.33 (t, J=7.0 Hz, 2H), 7.07 (d, J=8.8 Hz, 1H), 7.11 (s, 1H), 7.40 (dd, J=9.0, 2.9 Hz, 1H), 7.89 (d, J=2.7 Hz, 1H); MS (DCI/NH$_3$) m/z 397 (M+H)$^+$. Anal. Calculated for C$_{19}$H$_{25}$ClN$_2$O$_3$S: C, 57.49; H, 6.35; N, 7.06. Found: C, 57.18; H, 6.21; N, 6.94.

Example 307

N-[(2Z)-5-tert-butyl-3-(2-ethoxyethyl)-1,3-thiazol-2(3H)-ylidene]-5-chloro-2-methoxybenzamide Example 307A 5-tert-butyl-3-(2-ethoxyethyl)thiazol-2(3H)-imine A mixture of Example 240A (0.17 g, 1.1 mmol) and 2-(bromoethyl)ether (0.20 g, 1.2 mmol) was warmed to 85° C. and was allowed to stir for 24 hours. The mixture was cooled to ambient temperature, concentrated and purified via column chromatography (SiO$_2$, 10% methanol in ethyl acetate then 9.1:0.1 CH$_2$Cl$_2$:methanol:NH$_4$OH) to afford the title compound. MS (DCI/NH$_3$) m/z 229 (M+H)$^+$.

Example 307B

N-[(2Z)-5-tert-butyl-3-(2-ethoxyethyl)-1,3-thiazol-2(3H)-ylidene]-5-chloro-2-methoxybenzamide Example 307A (0.24 g, 1.05 mmol), triethylamine (0.44 mL, 3.2 mmol) and Example 205B (1.05 mmol) in 15 mL of tetrahydrofuran were processed as in Example 208D to afford the title compound. $^1$H NMR (300 MHz, CD$_3$OD) δ ppm 1.14 (t, J=7.0 Hz, 3H), 1.38 (s, 9H), 3.52 (q, J=6.9 Hz, 2H), 3.81 (t, J=5.3 Hz, 2H), 3.86 (s, 3H), 4.41 (t, J=5.3 Hz, 2H), 7.07 (d, J=8.8 Hz, 1H), 7.14 (s, 1H), 7.39 (dd, J=8.8, 2.7 Hz, 1H), 7.83 (d, J=3.1 Hz, 1H); MS (DCI/NH$_3$) m/z 397 (M+H)$^+$. Anal. Calculated for C$_{19}$H$_{25}$ClN$_2$O$_3$S: C, 57.49; H, 6.35; N, 7.06. Found: C, 57.34; H, 6.04; N, 6.94.

Example 308

N-[(2Z)-5-tert-butyl-3-(3-hydroxy-3-methylbutyl)-1,3-thiazol-2(3H)-ylidene]-5-chloro-2-methoxybenzamide Example 308A 3-hydroxy-3-methylbutyl 4-methylbenzenesulfonate To a solution of 3-methylbutane-1,3-diol (2.13 mL, 20 mmol) in pyridine (20 mL) at 0° C. was added para-toluenesulfonyl chloride (3.8 g, 20 mmol) in pyridine (10 mL) dropwise over 15 minutes. This mixture stirred at ambient temperature for 3 hours and 35 mL H$_2$O was added and the mixture was extracted with ethyl acetate (2×50 mL). The combined organics were washed with H$_2$O (2×50 mL), dried over MgSO$_4$, filtered, concentrated tinder reduced pressure and dried under vacuum (~1 mm Hg) to afford the title compound. MS (ESI) m/z 276 (M+18)$^+$.

Example 308B

N-[(2Z)-5-tert-butyl-3-(3-hydroxy-3-methylbutyl)-1,3-thiazol-2(3H)-ylidene]-5-chloro-2-methoxybenzamide A solution of Example 244A (75 mg, 0.23 mmol) in N,N-dimethylformamide (2 mL) was treated with NaH 60% dispersion in oil (9.5 mg, 0.23 mmol) followed by Example 308A (60 mg, 0.23 mmol). The reaction mixture was stirred at room temperature for 18 hours, poured into water and extracted with ethyl acetate. The organic layer was washed with H$_2$O (2×50 mL), dried over MgSO$_4$, filtered, concentrated under reduced pressure and dried under vacuum (~1 mm Hg) to afford the title compound. $^1$H NMR (300 MHz, dimethylsulfoxide-d$_6$) δ ppm 1.17 (s, 6H), 1.32 (s, 9H), 1.76-1.91 (m, 2H), 3.79 (s, 3H), 4.14-4.31 (m, 2H), 4.43 (s, 1H), 7.10 (d, J=8.8 Hz, 1H), 7.31 (s, 1H), 7.44 (dd, J=9.0, 2.9 Hz, 1H), 7.76 (d, J=3.1 Hz, 1H); MS (ESI) m/z 411 (M+H)+. Anal. Calculated for $C_{20}H_{27}ClN_2O_3S$ C, 58.45; H, 6.62; N, 6.82. Found C, 58.30; H, 6.51; N, 6.71.

Example 309

N-[(2Z)-5-tert-butyl-3-(3-hydroxy-3-methylbutyl)-4-methyl-1,3-thiazol-2(3H)-ylidene]-5-chloro-2-methoxybenzamide Example 309A (Z)—N-(5-tert-butyl-4-methylthiazol-2(3H)-ylidene)-5-chloro-2-methoxybenzamide A mixture of 5-tert-butyl-4-methylthiazol-2(3H)-imine (250 mg, 1.5 mmol) in tetrahydrofuran (10 mL) was treated with triethylamine (0.25 mL, 1.8 mmol) and 5-chloro-2-methoxybenzoylchloride (307 mg, 1.5 mmol). The reaction mixture was stirred at 60° C. for 18 hours then concentrated under, reduced pressure. The residue was diluted with ethyl acetate and $H_2O$. The organic extract was dried over $MgSO_4$, filtered, concentrated under reduced pressure and dried under vacuum to afford the title compound (490 mg, 96% yield). MS (ESI) m/z 339 (M+H)+.

Example 309B

N-[(2Z)-5-tert-butyl-3-(3-hydroxy-3-methylbutyl)-4-methyl-1,3-thiazol-2(3H)-ylidene]-5-chloro-2-methoxybenzamide Example 308A and Example 309A were processed using the method described in Example 308B to afford the title compound. $^1$H NMR (300 MHz, dimethylsulfoxide-$d_6$) δ ppm 1.19 (s, 6H), 1.38 (s, 9H), 1.65-1.81 (m, 2H), 2.41 (s, 3H), 3.78 (s, 3H), 4.17-4.33 (m, 2H), 4.49 (s, 1H), 7.09 (d, J=8.8 Hz, 1H), 7.43 (dd, J=8.8, 3.1 Hz, 1H), 7.78 (d, J=2.7 Hz, 1H). MS (ESI) m/z 425 (M+H)+. Anal. Calculated for $C_{21}H_{29}ClN_2O_3S$ C, 59.35; H, 6.88; N, 6.55. Found C, 58.83; H, 7.13; N, 6.41.

Example 310

N-[(2Z)-5-tert-butyl-3-(2-methoxyethyl)-1,3-thiazol-2(3H)-ylidene]-5-chloro-2-methoxybenzamide Commercially available 2-bromoethyl methyl ether (Aldrich) and Example 244A were processed using the method described in Example 246 to afford the title compound. $^1$H NMR (300 MHz, dimethylsulfoxide-$d_6$) δ ppm 1.35 (s, 9H), 3.36 (s, 3H), 3.68-3.84 (m, 2H), 3.90 (s, 3H), 4.36 (t, J=5.1 Hz, 2H), 6.77 (s, 1H), 6.90 (d, J=8.8 Hz, 1H), 7.32 (dd, J=8.8, 2.7 Hz, 1H), 7.95 (d, J=2.7 Hz, 1H); MS (ESI+) m/z 383 (M+H)+; Anal. Calculated for $C_{18}H_{23}ClN_2O_3S$: C, 56.46; H, 6.05; N, 7.32. Found: C, 56.69; H, 6.02; N, 7.42.

Example 311

5-chloro-N-[(2Z)-5-(1-hydroxy-1-methylethyl)-3-(2-methoxyethyl)-4-methyl-1,3-thiazol-2(3H)-ylidene]-2-methoxybenzamide Example 311A (Z)—N-(5-acetyl-3-(2-methoxyethyl)-4-methylthiazol-2(3H)-ylidene)-5-chloro-2-methoxybenzamide Commercially available 2-bromoethyl methyl ether (Aldrich) and Example 238A were processed using the method described in Example 246 to afford the title compound. MS (ESI+) m/z 383 (M+H)+.

Example 311B 5-chloro-N-[(2Z)-5-(1-hydroxy-1-methylethyl)-3-(2-methoxyethyl)-4-methyl-1,3-thiazol-2(3H)-ylidene]-2-methoxybenzamide Example 311A and commercially available methyllithium (Aldrich, 1.6 M in diethyl ether) were processed using the method described in Example 255 to afford the title compound. $^1$H NMR (300 MHz, dimethylsulfoxide-$d_6$) δ ppm 1.50 (s, 6H), 2.42 (s, 3H), 3.25 (s, 3H), 3.68 (t, J=5.4 Hz, 2H), 3.78 (s, 3H), 4.30 (t, J=5.4 Hz, 2H), 5.62 (s, 1H), 7.09 (d, J=9.2 Hz, 1H), 7.43 (dd, 1H), 7.63 (d, J=2.7 Hz, 1H); MS (ESI+) m/z 399 (M+H)+; Anal. Calculated for $C_{18}H_{23}ClN_2O_4S$: C, 54.20; H, 5.81; N, 7.02. Found: C, 54.30; H, 5.68; N, 6.91.

Example 312

N-[(2Z)-5-tert-butyl-3-(2-methoxy-2-methylpropyl)-1,3-thiazol-2(3H)-ylidene]-5-chloro-2-methoxybenzamide Example 244A and 1-bromo-2-methoxy-2-methylpropane were processed using the method described in Example 246 to afford the title compound. $^1$H NMR (500 MHz, CDCl$_3$) δ ppm 1.23 (s, 6H) 1.36 (s, 9H) 3.22 (s, 3H) 3.89 (s, 3H) 4.32 (s, 2H) 6.89 (s, 1H) 6.91 (s, 1H) 7.33 (dd, J=8.9, 2.8 Hz, 1H) 7.92 (d, J=2.8 Hz, 1H); MS (ESI) m/z 411 (M+H)+.

Example 313

N-[(2Z)-3-butyl-5-(1-hydroxy-1-methylethyl)-4-methyl-1,3-thiazol-2(3H)-ylidene]-5-chloro-2-methoxybenzamide Example 313A (Z)—N-(5-acetyl-3-butyl-4-methylthiazol-2(3H)-ylidene)-5-chloro-2-methoxybenzamide A mixture of Example 238A (0.40 g, 1.2 mmol), 1-bromobutane (0.16 mL, 1.5 mmol), and potassium t-butoxide (0.22 g, 1.9 mmol) in 5 mL N,N-dimethylformamide was warmed to 65° C. and stirred for 20 hours. The mixture was cooled to ambient temperature quenched with 5 mL of saturated aqueous NH$_4$Cl and diluted with 5 mL of ethyl acetate. The layers were separated and the aqueous phase was extracted twice with 5 mL of ethyl acetate. The combined organic extracts were dried over anhydrous Na$_2$SO$_4$, filtered and concentrated under reduced pressure. Purification via column chromatography (SiO$_2$, 40% hexanes in ethyl acetate) afforded the title compound. $^1$H NMR (300 MHz, CD$_3$OD) δ ppm 1.04 (t, J=7.3 Hz, 3H), 1.42-1.55 (m, 2H), 1.77-1.90 (m, 2H), 2.51 (s, 3H), 2.76 (s, 3H), 3.889 (s, 3H), 4.32-4.41 (m, 2H), 7.10 (d, J=8.8 Hz, 1H), 7.45 (dd, J=8.8, 2.7 Hz, 1H), 7.99 (d, J=3.1 Hz, 1H); MS (DCI/NH$_3$) m/z 381 (M+H)$^+$. Anal. Calculated for C$_{18}$H$_{21}$ClN$_2$O$_3$S: C, 56.76; H, 5.56, N, 7.35. Found: C, 56.68; H, 5.49; N, 7.26.

Example 313B

N-[(2Z)-3-butyl-5-(1-hydroxy-1-methylethyl)-4-methyl-1,3-thiazol-2(3H)-ylidene]-5-chloro-2-methoxybenzamide To the product of Example 313A (90 mg, 0.24 mmol in 5 mL of THF at −78° C. was added a solution of methyllithium (1.6 M in diethyl ether, 0.44 mL, 0.71 mmol) dropwise over 5 minutes. The mixture was stirred at −78° C. for 4 hours and was slowly warmed to ambient temperature and allowed to stir for 12 hours. The mixture was quenched with 3 mL of saturated aqueous NH$_4$Cl and diluted with 5 mL of ethyl acetate. The layers were separated and the aqueous phase was extracted twice with 5 mL ethyl acetate. The combined organic extracts were dried over anhydrous Na$_2$SO$_4$, filtered and concentrated under reduced pressure. Purification via column chromatography (SiO$_2$, 20% hexanes in ethyl acetate) afforded the title compound. $^1$H NMR (300 MHz, CD$_3$OD) δ ppm 1.02 (t, J=7.3 Hz, 3H), 1.39-1.54 (m, 2H), 1.61 (s, 6H), 1.71-1.84 (m, 2H), 2.51 (s, 3H), 3.85 (s, 3H), 4.23-4.31 (m, 2H), 7.06 (d, J=8.8 Hz, 1H), 7.39 (dd, J=9.0, 2.9 Hz, 1H), 7.87 (d, J=3.1 Hz, 1H); MS (DCI/NH$_3$) m/z 397 (M+H)$^+$. Anal. Calculated for C$_{19}$H$_{25}$ClN$_2$O$_3$S: C, 57.49; H, 6.35; N, 7.06. Found: C, 57.36; H, 6.33; N, 6.85.

Example 314

(5-chloro-N-[(2Z)-3-(cyclobutylmethyl)-5-(1-hydroxy-1-methylethyl-4-methyl-1,3-thiazol-2(3H)-ylidene]-2-methoxybenzamide Example 314A (Z)—N-(5-acetyl-3-(cyclobutylmethyl)-4-methylthiazol-2(3H)-ylidene)-5-chloro-2-methoxybenzamide A mixture of the product of Example 238A (0.75 g, 2.3 mmol), (bromomethyl)cyclobutane (0.31 mL, 2.8 mmol), and potassium t-butoxide (0.41 g, 3.5 mmol) in 7 mL N,N-dimethylformamide was warmed to 65° C. and stirred for 16 hours. The mixture was cooled to ambient temperature, quenched with 5 mL of saturated aqueous NH$_4$Cl and diluted with 10 mL of ethyl acetate. The layers were separated and the aqueous phase was extracted twice with 7 mL of ethyl acetate. The combined organic extracts were dried over anhydrous Na$_2$SO$_4$, filtered and concentrated under reduced pressure. Purification via column chromatography (SiO$_2$, 40% hexanes in ethyl acetate) afforded the title compound. $^1$H NMR (300 MHz, CD$_3$OD) δ ppm 1.88-2.15 (m, 6H), 2.51 (s, 3H), 2.75 (s, 3H) 2.83-2.96 (m, 1H), 3.89 (s, 3H), 4.46 (d, J=7.5 Hz, 2H), 7.11 (d, J=9.2 Hz, 1H), 7.45 (dd, J=8.8, 2.7 Hz, 1H), 7.99 (d, J=3.1 Hz, 1H); MS (DCI/NH$_3$) m/z 393 (M+H)$^+$. Anal. Calculated for C$_{19}$H$_{21}$ClN$_2$O$_3$S: C, 58.08; H, 5.39; N, 7.13. Found: C, 58.06; H, 5.20; N, 7.06

Example 314B (5-chloro-N-[(2Z)-3-(cyclobutylmethyl)-5-(1-hydroxy-1-methylethyl)-4-methyl-1,3-thiazol-2(3H)-ylidene]-2-methoxybenzamide To the product of Example 314A (0.13 g, 0.33 mmol) in 5 mL of tetrahydrofuran at −78° C. was added a solution of methyllithium (1.6 M in diethyl ether, 0.62 mL, 0.99 mmol) dropwise over 5 minutes. The mixture was stirred at −78° C. for 1 hour then slowly warmed to ambient temperature and allowed to stir for 16 hours. The mixture was quenched with 5 mL of saturated aqueous NH$_4$Cl and diluted with 5 mL of ethyl acetate. The layers were separated and the aqueous phase was extracted twice with 5 mL ethyl acetate. The combined organic extracts were dried over anhydrous Na$_2$SO$_4$, filtered and concentrated under reduced pressure. Purification via column chromatography (SiO$_2$, 30% hexanes in ethyl acetate) afforded the title compound. $^1$H NMR (300 MHz, CD$_3$OD) δ ppm 1.61 (s, 6H), 1.86-2.13 (m, 6H), 2.49 (s, 3H), 2.79-2.93 (m, 1H) 3.86 (s, 3H), 4.37 (d, J=7.1 Hz, 2H), 7.06 (d, J=8.8 Hz, 1H), 7.39 (dd, J=8.8, 2.7 Hz, 1H), 7.87 (d, J=2.7 Hz, 1H); MS (DCI/NH$_3$) m/z 409 (M+H)$^+$. Anal. Calculated for C$_{20}$H$_{25}$ClN$_2$O$_3$S: C, 58.74; H, 6.16; N, 6.85. Found: C, 58.70; H, 6.12; N, 6.74.

In Vitro Methods

The CB$_1$ and CB$_2$ radioligand binding assays described herein are utilized to ascertain the selectivity of compounds of the present application for binding to CB$_2$ relative to CB$_1$ receptors.

Human CB$_2$ Radioligand Binding Assays:

HEK293 cells stably expressing human CB$_2$ receptors were grown until a confluent monolayer was formed. Briefly, the cells were harvested and homogenized in TE buffer (50 mM Tris-HCl, 1 mM MgCl$_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM MgCl$_2$, and 1 mM EDTA and 10% sucrose) and frozen at −78° C. until used. Saturation binding reactions were initiated by the addition of membrane preparation (protein concentration of 5 µg/well for human CB$_2$) into wells of a deep well plate containing ([$^3$H] CP-55,940 (120 Ci/mmol, a nonselective CB agonist commercially available from Tocris) in assay buffer (50 mM Tris, 2.5 mM EDTA, 5 mM MgCl$_2$, and 0.5 mg/mL fatty acid free BSA, pH 7.4). After 90 min incubation at 30° C., binding reaction was terminated by the addition of 300 µl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations (1 nM to 10 µM) of displacing ligands. The addition of 10 µM unlabeled CP-55,940 (Tocris, Ellisville, Mo.) was used to assess nonspecific binding.

The majority of the compounds of the present application bound to CB$_2$ receptors with K$_i$ of less than about 1,000 nM, preferably less than 400 nM, more preferably less than 200 nM, and most preferably lower than 100 nM.

Human CB$_1$ Radioligand Binding Assay:

HEK293 human CB$_1$ membranes were purchased from Perkin Elmer. Binding was initiated by the addition of membranes (8-12 µg per well) into wells (Scienceware 96-well DeepWell plate, VWR, West Chester, Pa.) containing [$^3$H]

CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 µL. After incubation (30° C. for 90 minutes), binding was terminated by the addition of 300 µL per well of cold assay buffet and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 µM) of displacing ligands. The addition of 10 µM unlabeled CP-55,940 (Tocris, Ellisville, Mo.) was used to assess nonspecific binding. The majority of the compounds of the present application tested for $CB_1$ binding, bound to $CB_1$ receptors with $K_i$ 10×-1000× higher than the $K_i$ for $CB_2$. These results show that the compounds of the present application preferably bind to $CB_2$ receptors, therefore are selective ligands for the $CB_2$ receptor.

In Vivo Methods:

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

Incision Model of Postoperative Pain

A skin incision model of postoperative pain was produced using the procedures previously described (Brennan et al., 1996, Pain, 64, 493). All rats were anesthetized with isoflurane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as previously described (Chaplan, S. R., F. W. Bach, J. W. Pogrel, J. M. Chung and T. L. Yaksh, 1994, Quantitative assessment of tactile allodynia in the rat paw, J. Neurosci. Methods, 53, 55). Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev Pharmacol. Toxicol. 20, 441).

Representative compounds of the present application showed a statistically significant change in paw withdrawal latency versus a saline vehicle at less than about 300 micromoles/kg in the incision model of postoperative pain. In a more preferred embodiment, compounds of the present application showed efficacy at less than about 50 micromoles/kg in the incision model of postoperative pain.

Complete Freund's Adjuvant (CFA) Model of Inflammatory Pain

Chronic inflammatory thermal hyperalgesia was induced by injection of 150 µl of a 50% solution o CFA in phosphate buffered saline (PBS) into the plantar surface of the right hind paw in rats; control animals received only PBS treatment. Thermal hyperalgesia was assessed 48 hours post CFA injection. Thermal hyperalgesia was determined using a commercially available thermal paw stimulator (University Anesthesiology Research and Development Group (UARDG), University of California, San Diego, Calif.) described by Hargreaves et al. (Hargreaves, et. al., 1988, Pain 32, 77). Rats were placed into individual plastic cubicles mounted on a glass surface maintained at 30° C., and allowed a 20 min habituation period. A thermal stimulus, in the form of radiant heat emitted from a focused projection bulb, was then applied to the plantar surface of each hind paw. The stimulus current was maintained at 4.50±0.05 amp, and the maximum time of exposure was set at 20.48 sec to limit possible tissue damage. The elapsed time until a brisk withdrawal of the hind paw from the thermal stimulus was recorded automatically using photodiode motion sensors. The right and left hind paw of each rat was tested in three sequential trials at approximately 5-minute intervals. Paw withdrawal latency (PWL) was calculated as the mean of the two shortest latencies.

Representative compounds of the present invention showed a statistically significant change in paw withdrawl latency versus a saline vehicle at less than about 300 micromoles/kg in the Complete Freund's Adjuvant (CFA) model of inflammatory pain. In a more preferred embodiment, compounds of the present invention showed efficacy at less than about 50 micromoles/kg in the Complete Freund's Adjuvant (CFA) model of inflammatory pain.

Spinal Nerve Ligation Model of Neuropathic Pain

A model of spinal nerve ligation-induced (SNL model) neuropathic pain was produced using the procedure originally described by Kim and Chung (Kim, S. H. and J. M. Chung, 1992, An experimental model for peripheral neuropathy produced by segmental spinal nerve ligation in the rat, Pain 50, 355). The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as previously described (Chaplan, S. R., F. W. Bach, J. W. Pogrel, J. M. Chung and T. L. Yaksh, 1994, Quantitative assessment of tactile allodynia in the rat paw, J. Neurosci. Methods 53, 55). Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol Toxicol. 20, 441). Only rats with a baseline threshold score of less that 4.25 g were used in this study, and animals demonstrating motor deficit were excluded. Tactile allodynia thresholds were also assessed in several control groups, including naive, sham-operated, and saline infused animals a well as in the contralateral paws of nerve-injured rats.

Representative compounds of the present invention showed efficacy at less than about 300 micromoles/kg in the spinal nerve ligation model of neuropathic pain. In a more preferred embodiment, compounds of the present invention showed efficacy at less than about 100 micromoles/kg in the spinal nerve ligation model of neuropathic pain.

The data contained herein demonstrates that compounds of the present invention bind to the $CB_2$ receptor. Certain compounds of the present invention were shown to have an analgesic effect in two types of animal pain models relating to neuropathic and nociceptive pain.

In addition to the data contained herein, several lines of evidence support the assertion that $CB_2$ receptors play a role in analgesia. For example, Zimmer et al. have reported that the nonselective cannabinioid agonist $\Delta^9$-THC retains some analgesic efficacy in $CB_1$ receptor knockout mice (Zimmer, A., et al., Proc. Nat. Acad. Sci., 1999, 96, 5780-5785). HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260). The analgesic effects induced by these $CB_2$-selective ligands are blocked by $CB_2$ and not by $CB_1$ receptor antagonists. Furthermore, at fully efficacious doses, AM-1241 and GW405833 are devoid of typical $CB_1$ receptor-mediated CNS side effects, providing evidence that modulation of $CB_2$ receptors can produce broad-spectrum pain relief with reduced side-effect liability.

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators are useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. They are quiescent and resting having a ramified morphology as long as the CNS is healthy. Microglia express a variety of receptors enabling them to survey the CNS and respond to pathological events. Insult or injury to the CNS leads to microglial cell activation, which is characterized by various morphological changes allowing response to the lesion. Ramifications are retracted and microglia are transformed into amoeboid-like cells with phagocytic function. They can proliferate, rapidly migrate to the site of injury, and produce and release cytokines, chemokines and complement components (Watkins L. R., et al., Trends in Neuroscience., 2001, 24(8), 450; Kreutzberg, G. W., Trends Neurosci., 1996, 19, 312-318). $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. It is conceivable that $CB_2$ receptors may be more susceptible to pharmacological effects during neuroinflammation (Walter, L., Stella, N., Br. J. Pharmacol. 2004, 141, 775-785). Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

$CB_2$ receptor expression has been detected in perivascular microglial cells within normal, healthy human cerebellum (Nunez, E., et al., Synapse, 2004, 58, 208-213). Perivascular cells are immunoregulatory cells located adjacent to CNS blood vessels and, along with parenchymal microglia and astrocytes, they play a pivotal role in maintaining CNS homeostasis and blood-brain barrier functionality (Williams, K., et al., Glia, 2001, 36, 156-164). $CB_2$ receptor expression has also been detected on cerebromicrovascular endothelial cells, which represent a main component of the blood-brain barrier (Golech, S. A., et al., Mol. Brain Res., 2004, 132, 87-92). A recent report demonstrated that $CB_2$ receptor expression is up-regulated in the brains of macaques with simian immunodeficiency virus-induced encephalitis (Benito, C., et al., J. Neurosci. 2005, 25(10), 2530-2536). Thus, compounds that affect $CB_2$ signaling may protect the blood-brain barrier and be clinically useful in the treatment of neuroinflammation and a variety of neuroinflammatory disorders including retroviral encephalitis, which occurs with human immunodeficiency virus (HIV) infection in the CNS.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators provide a unique treatment for demyeliniating pathologies.

Alzheimer's disease is a chronic neurodegenerative disorder accounting for the most common form of elderly dementia Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators represents a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators represents a unique approach for the treatment of liver fibrosis.

$CB_2$ receptors are involved in the neuroprotective and anti-inflammatory mechanisms induced by the interleukin-1 receptor antagonist (IL-1ra) (Molina-Holgado, F., et al., J. Neurosci., 2003, 23(16), 6470-6474). IL-1ra is an important anti-inflammatory cytokine that protects against ischemic, excitotoxic, and traumatic brain insults. $CB_2$ receptors play a role in mediating these neuroprotective effects indicating that $CB_2$ ligands are useful in the treatment of traumatic brain injury, stroke, and in mitigating brain damage.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators have utility as antitussive agents for the treatment pulmonary inflammation, chronic cough, and a variety of airway inflammatory diseases including but not limited to asthma, chronic obstructive pulmonary disease, and pulmonary fibrosis.

Osteoporosis is a disease characterized by reduced bone mass, which leads to deterioration of bone microstructure and increased susceptibility to fracture. Age is associated with bone loss and it is estimated that 50% of all Caucasian women will have osteoporosis by the age of 80 (Ralston, S. H., Curr. Opin. Pharmacol., 2003, 3, 286-290). There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371) Cannabinioid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators are useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor are clinically useful for the treatment of atheroscelorsis.

CB$_2$ receptors are expressed on malignant cells of the immune system and targeting CB$_2$ receptors to induce apoptosis may constitute a novel approach to treating malignancies of the immune system. Selective CB$_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lynphomas (McKallip, R. J., et al., Blood, 2002, 15(2), 637-634). Thus, CB$_2$ modulators have utility as anticancer agents against tumors of immune origin.

Activation of CB$_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453459). Thus, CB$_2$ modulators have utility for the treatment or prophylaxis of cardiovascular disease and the development of myocardial infarction.

The present invention also provides pharmaceutical compositions that comprise compounds of the present invention. The pharmaceutical compositions comprise compounds of the present invention formulated together with one or more non-toxic pharmaceutically acceptable carriers.

The pharmaceutical compositions of this invention can be administered to humans and other mammals orally, rectally, parenterally, intracisternally, intravaginally, topically (as by powders, ointments or drops), bucally or as an oral or nasal spray. The term "parenterally," as used herein, refers to modes of administration that include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants, which may be required. Opthalmic formulations, eye ointments, powders and solutions are also contemplated as being within the scope of this invention.

Actual dosage levels of active ingredients in the pharmaceutical compositions of this invention can be varied so as to obtain an amount off the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutically acceptable salt," as used herein, means acid addition salts or basic addition salts. The salts can be prepared in situ during the final isolation and purification of the compounds of the present application or separately by reacting the free base of the compounds of of the present invention with an inorganic or organic acid. Representative acid addition salts include, but are not limited to, acetate, adipate, alginate, citrate, aspartate, benzoate, benzenesulfonate, bisulfate, butyrate, camphorate, camphor-sulfonate, digluconate, glycerophosphate, hemisulfate, heptanoate, hexanoate, fumarate, hydrochloride, hydrobromide, hydroiodide, 2-hydroxyethansulfonate (isethionate), lactate, malate, maleate, fumarate, methanesulfonate, nicotinate, 2-naphthalenesulfonate, oxalate, pamoate, pectinate, persulfate, 3-phenylpropionate, picrate, pivalate, propionate, succinate, sulfate, (L) tartrate, (D) tartrate, (DL) tartrate, thiocyanate, phosphate, glutamate, bicarbonate, p-toluenesulfonate, and undecanoate.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the lice. Prodrugs of the present invention may be rapidly transformed in vivo to compounds of the invention, for example, by hydrolysis in blood.

The present invention contemplates compounds of the invention formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others, are equivalent to the unsolvated forms for the purposes of the invention.

The total daily dose of the compounds of this invention administered to a human or lower animal may range from about 0.003 to about 30 mg/kg/day. For purposes of oval administration, more preferable doses can be in the range of from about 0.01 to about 10 mg/kg/day. If desired, the effective daily dose can be divided into multiple doses for purposes of administration; consequently, single dose compositions may contain such amounts or submultiples thereof to make up the daily dose.

What is claimed is:

1. A compound according to formula (I),

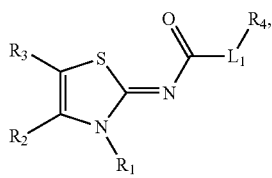

(I)

or a pharmaceutically acceptable salt, prodrug, salt of a prodrug, or a combination thereof,
wherein
$R_1$ is A-alkylene-;
$R_2$ is hydrogen;
$R_3$ is hydrogen or alkyl
$R_4$ is phenyl, wherein the phenyl is unsubstituted or substituted with 1-5 substituents selected from the group consisting of alkenyl, alkoxy, alkoxyalkoxy, alkoxyalkoxyalkyl, alkoxyalkyl, alkyl, alkylcarbonyl, alkylcarbonylalkyl, alkylcarbonyloxy, alkyl-S—, alkyl-S-alkyl, alkynyl, cyano, cyanoalkyl, formyl, formylalkyl, halogen, haloalkyl, hydroxy, hydroxyalkyl, —SH, $N(O)_2$, and —$NZ_1Z_2$, wherein $NZ_1Z_2$ means two groups $Z_1$ and $Z_2$ which are appended to the parent molecular moiety through a nitrogen atom, and wherein $Z_1$ and $Z_2$ are each independently hydrogen, alkyl, alkylcarbonyl, or formyl, or wherein $Z_1$ and $Z_2$ taken together with the nitrogen atom to which they are attached form a heterocyclic ring, optionally substituted with 1, 2, or 3 substituents selected from the group consisting of alkyl, hydroxy, and haloalkyl;
A is a 4-, 5-, 6-, or 7-membered monocyclic heterocycle containing zero or one double bond, and one or two oxygen, and zero or one nitrogen as ring atoms wherein each A is independently unsubstituted or substituted with 1, 2, or 3 substituents independently selected from the group consisting of oxo, alkyl, —OH, and —O(alkyl); and
$L_1$ is a single bond.

2. The compounds of claim 1, or a pharmaceutically acceptable salt, prodrug, salt of a prodrug, or a combination thereof, wherein A is (i), (ii), (iii), (iv), (v), or (vi)

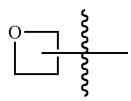

(i)

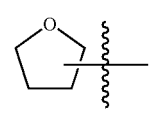

(ii)

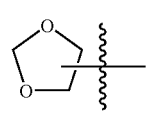

(iii)

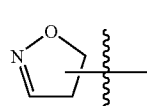

(iv)

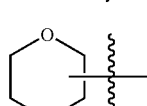

(v)

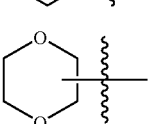

(vi)

3. The compound of claim 1 selected from the group consisting of
2,3-dichloro-N-[(2Z)-5-methyl-3-(tetrahydrofuran-2-ylmethyl)-1,3-thiazol-2(3H)-ylidene]benzamide;
2,3-dichloro-N-[(2Z)-5-methyl-3-(tetrahydro-2H-pyran-2-ylmethyl)-1,3-thiazol-2(3H)-ylidene]benzamide;
2-ethoxy-N-[(2Z)-5-methyl-3-(tetrahydro-2H-pyran-2-ylmethyl)-1,3-thiazol-2(3H)-ylidene]benzamide;
5-chloro-2-methoxy-N-[(2Z)-5-methyl-3-(tetrahydrofuran-2-ylmethyl)-1,3-thiazol-2(3H)-ylidene]benzamide;
5-chloro-2-methoxy-N-[(2Z)-5-methyl-3-(tetrahydro-2H-pyran-2-ylmethyl)-1,3-thiazol-2(3H)-ylidene]benzamide;
2-ethoxy-N-[(2Z)-5-methyl-3-(tetrahydrofuran-2-ylmethyl)-1,3-thiazol-2(3H)-ylidene]benzamide;
5-chloro-2-methoxy-N-[(2Z)-5-methyl-3-(tetrahydrofuran-3-ylmethyl)-1,3-thiazol-2(3H)-ylidene]benzamide;
2-ethoxy-N-[(2Z)-5-methyl-3-(tetrahydrofuran-3-ylmethyl)-1,3-thiazol-2(3H)-ylidene]benzamide;
2-methoxy-N-[(2Z)-5-methyl-3-(tetrahydrofuran-2-ylmethyl)-1,3-thiazol-2(3H)-ylidene]benzamide;
2-ethoxy-N-[(2Z)-5-methyl-3-(tetrahydro-2H-pyran-4-ylmethyl)-1,3-thiazol-2(3H)-ylidene]benzamide;
2,4-dimethoxy-N-[(2Z)-5-methyl-3-(tetrahydrofuran-2-ylmethyl)-1,3-thiazol-2(3H)-ylidene]benzamide;
5-chloro-2-methoxy-N-[(2Z)-5-methyl-3-(tetrahydro-2H-pyran-4-ylmethyl)-1,3-thiazol-2(3H)-ylidene]benzamide;
5-chloro-2-methoxy-N-[(2Z)-3-(tetrahydro-2H-pyran-2-ylmethyl)-1,3-thiazol-2(3H)-ylidene]benzamide;
5-chloro-2-methoxy-N-[(2Z)-5-methyl-3-[(2R)-tetrahydrofuran-2-ylmethyl]-1,3-thiazol-2(3H)-ylidene]benzamide;
5-chloro-2-methoxy-N-[(2Z)-5-methyl-3-[(2S)-tetrahydrofuran-2-ylmethyl]-1,3-thiazol-2(3H)-ylidene]benzamide;
5-chloro-2-methoxy-N-[(2Z)-5-methyl-3-(oxetan-2-ylmethyl)-1,3-thiazol-2(3H)-ylidene]benzamide;
5-chloro-N-[(2Z)-3-(1,3-dioxolan-2-ylmethyl)-5-methyl-1,3-thiazol-2(3H)-ylidene]2-methoxybenzamide;
5-chloro-N-[(2Z)-3-[2-(1,3-dioxolan-2-yl)ethyl]-5-methyl-1,3-thiazol-2(3H)-ylidene]2-methoxybenzamide;

N-[(2Z)-3-(1,3-dioxolan-2-ylmethyl)-5-methyl-1,3-thiazol-2(3H)-ylidene]-2-ethoxybenzamide;

5-bromo-2-ethoxy-N-[(2Z)-5-methyl-3-[(2R)-tetrahydrofuran-2-ylmethyl]-1,3-thiazol-2(3H)-ylidene]benzamide;

5-chloro-2-ethoxy-N-[(2Z)-5-methyl-3-[(2R)-tetrahydrofuran-2-ylmethyl]-1,3-thiazol-2(3H)-ylidene]benzamide;

4-chloro-2-methoxy-N-[(2Z)-5-methyl-3-(tetrahydrofuran-2-ylmethyl]-1,3-thiazol-2(3H)-ylidene]benzamide;

5-bromo-2-methoxy-N-[(2Z)-5-methyl-3-[(2R)-tetrahydrofuran-2-ylmethyl]-1,3-thiazol-2-ylidene]benzamide;

5-chloro-2-methoxy-N-[(2Z)-5-methyl-3-(2-tetrahydro-2H-pyran-4-ylethyl)-1,3-thiazol-2-ylidene]benzamide;

5-chloro-N-[(2Z)-5-ethyl-3-(tetrahydrofuran-2-ylmethyl)-1,3-thiazol-2(3H)-ylidene]-2-methoxybenzamide;

5-chloro-2-methoxy-N-[(2Z)-5-propyl-3-(tetrahydrofuran-2-ylmethyl)-1,3-thiazol-2(3H)-ylidene]benzamide;

4,5-dichloro-2-methoxy-N-[(2Z)-5-methyl-3-[(2R)-tetrahydrofuran-2-ylmethyl]-1,3-thiazol-2(3H)-ylidene]benzamide;

5-chloro-2-methoxy-N-[(2Z)-5-methyl-3-(tetrahydro-2H-pyran-3-ylmethyl)-1,3-thiazol-2(3H)-ylidene]benzamide;

5-chloro-2-methoxy-N-[(2Z)-5-methyl-3-[(3-methyl-4,5-dihydroisoxazol-5-yl)methyl]-1,3-thiazol-2(3H)-ylidene]benzamide;

5-bromo-N-[(2Z)-5-tert-butyl-3-[(2R)-tetrahydrofuran-2-ylmethyl]-1,3-thiazol-2(3H)-ylidene]-2-methoxybenzamide;

5-chloro-N-[(2Z)-3-(1,4-dioxan-2-ylmethyl)-5-methyl-1,3-thiazol-2(3H)-ylidene]-2-methoxybenzamide;

N-[(2Z)-5-tert-butyl-3-[(2R)-tetrahydrofuran-2-ylmethyl]-1,3-thiazol-2(3H)-ylidene]-5-chloro-2-methoxybenzamide;

N-[(2Z)-5-tert-butyl-3-(1,3-dioxolan-2-ylmethyl)-1,3-thiazol-2(3H)-ylidene]-5-chloro-2-methoxybenzamide;

N-[(2Z)-5-tert-butyl-3-[(3-methyl-4,5-dihydroisoxazol-5-yl)methyl]-1,3-thiazol-2(3H)-ylidene]-5-chloro-2-methoxybenzamide;

N-[(2Z)-5-tert-butyl-3-(tetrahydro 2H-pyran-4-ylmethyl]-1,3-thiazol-2(3H)-ylidene]-5-chloro-2-methoxybenzamide;

N-[(2Z)-5-tert-butyl-3-[(3-methyloxetan-3-yl)methyl]-1,3-thiazol-2(3H)-ylidene]-5-chloro-2-methoxybenzamide;

N-[(2Z)-5-tert-butyl-3-(oxetan-2-ylmethyl)-1,3-thiazol-2(3H)-ylidene]-5-chloro-2-methoxybenzamide;

N-[(2Z)-5-tert-butyl-3-(tetrahydro-2H-pyran-2-ylmethyl)-1,3-thiazol-2(3H)-ylidene]-5-chloro-2-methoxybenzamide;

N-[(2Z)-5-tert-butyl-3-(1,4-dioxan-2-ylmethyl)-1,3-thiazol-2(3H)-ylidene]-5-chloro-2-methoxybenzamide;

N-[(2Z)-5-tert-butyl-3-{[(4S)-2,2-dimethyl-1,3-dioxolan-4-yl]methyl}-1,3-thiazol-2(3H)-ylidene]-5-chloro-2-methoxybenzamide;

N-[(2Z)-5-tert-butyl-3-{[(4R)-2,2-dimethyl-1,3-dioxolan-4-yl]methyl}-1,3-thiazol-2(3H)-ylidene]-5-chloro-2-methoxybenzamide;

N-[(2Z)-5-tert-butyl-3-(tetrahydrofuran-3-ylmethyl)-1,3-thiazol-2(3H)-ylidene]-5-chloro-2-methoxybenzamide;

N-[(2Z)-5-tert-butyl-3-(tetrahydro-2H-pyran-3-ylmethyl)-1,3-thiazol-2(3H)-ylidene]-5-chloro-2-methoxybenzamide;

N-[(2Z)-5-tert-butyl-3-{[(2S)-5-oxotetrahydrofuran-2-yl]methyl}-1,3-thiazol-2(3H)-ylidene]-5-chloro-2-methoxybenzamide;

N-[(2Z)-5-tert-butyl-3-[(5-methyltetrahydrofuran-2-yl)methyl]-1,3-thiazol-2(3H)-ylidene]-5-chloro-2-methoxybenzamide;

N-[(2Z)-5-tert-butyl-3-[(5,5-dimethyltetrahydrofuran-2-yl)methyl]-1,3-thiazol-2(3H)-ylidene]-5-chloro-2-methoxybenzamide;

N-[(2Z)-5-tert-butyl-3-[(2R)-tetrahydrofuran-2-ylmethyl]-1,3-thiazol-2(3H)-ylidene]-5-chloro-2-(2-methoxyethoxy)benzamide;

N-[(2Z)-5-tert-butyl-3-[(2R)-tetrahydrofuran-2-ylmethyl]-1,3-thiazol-2(3H)-ylidene]-5-chloro-2-isopropoxybenzamide; and N-[(2Z)-5-tert-butyl-3-[(2R)-tetrahydrofuran-2-ylmethyl]-1,3-thiazol-2(3H)-ylidene]-5-chloro-2-ethoxybenzamide;

or a pharmaceutically acceptable salt thereof.

4. A pharmaceutical composition comprising therapeutically effective amount of a compound of claim 1 of formula (I) or a pharmaceutically acceptable salt thereof, in combination with a pharmaceutically acceptable carrier.

5. A method of treating neuropathic pain, nociceptive pain, and inflammatory pain in a mammal in need of such treatment comprising administering to the mammal a therapeutically effective amount of a compound of claim 1 of formula (I) or a pharmaceutically acceptable salt thereof.

\* \* \* \* \*